US012686707B2

(12) United States Patent
Bosco et al.

(10) Patent No.: US 12,686,707 B2
(45) Date of Patent: Jul. 21, 2026

(54) ANTI-STEAP2 CHIMERIC ANTIGEN RECEPTORS AND USES THEREOF

(71) Applicant: MEDIMMUNE, LLC, Gaithersburg, MD (US)

(72) Inventors: Emily Bosco, Wilmington, DE (US); Dewald Van Dyk, Wilmington, DE (US); Gordon Moody, Wilmington, DE (US); Christine Fazenbaker, Gaithersburg, MD (US); Chien-Ying Chang, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 645 days.

(21) Appl. No.: 18/046,728

(22) Filed: Oct. 14, 2022

(65) Prior Publication Data

US 2023/0192803 A1     Jun. 22, 2023

Related U.S. Application Data

(60) Provisional application No. 63/262,602, filed on Oct. 15, 2021.

(51) Int. Cl.
| | |
|---|---|
| *C07K 14/705* | (2006.01) |
| *A61P 35/04* | (2006.01) |
| *C12N 15/86* | (2006.01) |

(52) U.S. Cl.
CPC ............ *C07K 14/705* (2013.01); *A61P 35/04* (2018.01); *C12N 15/86* (2013.01); *C07K 2319/03* (2013.01); *C07K 2319/30* (2013.01)

(58) Field of Classification Search
CPC combination set(s) only.
See application file for complete search history.

(56) References Cited

U.S. PATENT DOCUMENTS

| | | |
|---|---|---|
| 2011/0082054 A1 | 4/2011 | Ladner |
| 2012/0316071 A1 | 12/2012 | Smider et al. |
| 2020/0038442 A1 | 2/2020 | Rossi et al. |
| 2021/0213119 A1 | 7/2021 | Wang et al. |
| 2021/0332105 A1 | 10/2021 | Moody et al. |

FOREIGN PATENT DOCUMENTS

| | | |
|---|---|---|
| WO | 2005079490 A2 | 9/2005 |
| WO | 2018058001 A1 | 3/2018 |
| WO | 2024013702 A2 | 1/2024 |

OTHER PUBLICATIONS

Int'l Search Rpt. and Written Opin. for PCT/IB22/59885 mailed Mar. 2, 2023.
Hawkins E.R., et al., "Armored CAR T-Cells: The Next Chapter in T-Cell Cancer Immunotherapy", Biologics: Targets and Therapy, vol. 15, Apr. 1, 2021, pp. 95-105, XP093024991, ISSN: 1177-5475, DOI: 10.2147/BTT.S291768, Retrieved from the Internet: URL: https://www.dovepress.com/getfile.php?fileID=68487 the whole document.
Supplementary European Search Report in European Patent Application No. 22880526.3, dated Sep. 9, 2025, 8 Pages.
Zanvit P., et al., "Antitumor Activity of AZD0754, a dnTGFbetaRII-Armored, STEAP2-Targeted CAR-T Cell Therapy, in Prostate Cancer", The Journal of Clinical Investigation, vol. 133, No. 22, E169655, Nov. 15, 2023, XP093227036, ISSN: 1558-8238, DOI: 10.1172/JCI169655, pp. 1-17, the whole document.

*Primary Examiner* — Misook Yu
*Assistant Examiner* — James Lyle McLellan

(57) ABSTRACT

The disclosure provides chimeric antigen receptors and antibodies that comprise antigen-binding domains that specifically bind human STEAP2, nucleotides that encode the same, cells comprising the same, and methods of using the same in the treatment of cancer (e.g., prostate cancer).

40 Claims, 58 Drawing Sheets

Specification includes a Sequence Listing.

CaP = carcinoma of the prostate; cDNA = complementary DNA; CRPC = castration-resistant prostate cancer;
FFPE = formalin-fixed paraffin-embedded; GAPDH = glyceraldehyde 3-phosphate dehydrogenase;
PCR = polymerase chain reaction; STEAP2 = six transmembrane epithelial antigen of prostate 2.

| Disease Subset | % with >50% membrane staining |
|---|---|
| Primary (n=36) | 89% |
| CRPC, Primary (n=28) | 100% |
| Lymph Node Metastasis (n=16) | 94% |
| Bone Metastasis (n=11) | 82% |

*Bone Metastasis*

*CRPC*

| ISH/IHC score | Criteria |
|---|---|
| 0 | Negative |
| 1 | Low |
| 2 | Medium |
| 3 | High |

|  | ISH | IHC+, membrane stain |
|---|---|---|
| Heart | 0 | 0 |
| Kidney cortex | 0.5 | 0 |
| Kidney medulla | 0.5 | 0 |
| Lung parenchyma | 2 | 0 |
| Cerebellum cortex | 0 | 0 |
| Cerebrum | 0 | 0 |
| Liver | 0.5 | 0 |
| Ileum | 0.5 | 0 |
| Colon descendens | 2 | 0 |
| Skin | 0 | 0 |
| Stomach fundus | 0.5 | 0 |
| Stomach muscular | 1 | 0 |
| Gallbladder | 0 | 0 |
| Spleen | 0 | 0 |
| Adrenal gland | 0 | 0 |
| Thymus | 0 | 0 |
| Thyroid | 0.5 | 0 |
| Myometrium | 0 | 0 |
| Exocervix | 0.5 | 0 |
| Breast glands | 2 | 0 |
| Endocervix | 1 | 0 |
| Endometrium | 1 | 0 |
| Ovary | 1 | 0 |
| Fallopian Tube | 0.5 | 0 |
| Placenta early | 0.5 | 0 |
| Prostate | 2 | 3 |
| Testis | 1 | 0 |

FIG. 1G

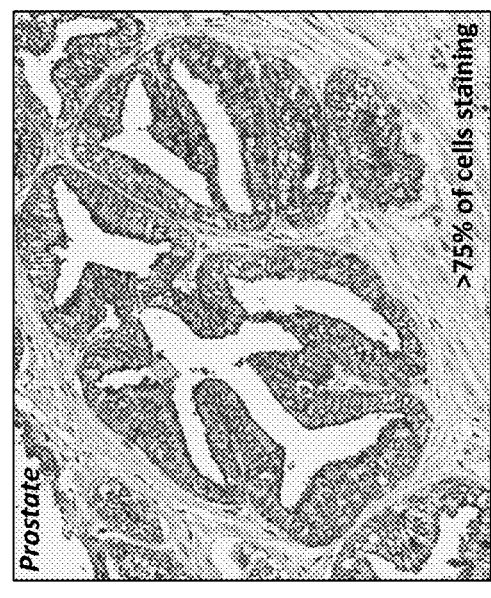

Prostate

>75% of cells staining

FIG. 1H

(1) TCM
(2) TEFF
(3) TEM
(4) TSCM

40A3Bz dnTGFβRII

40A3Bz

Untransduced

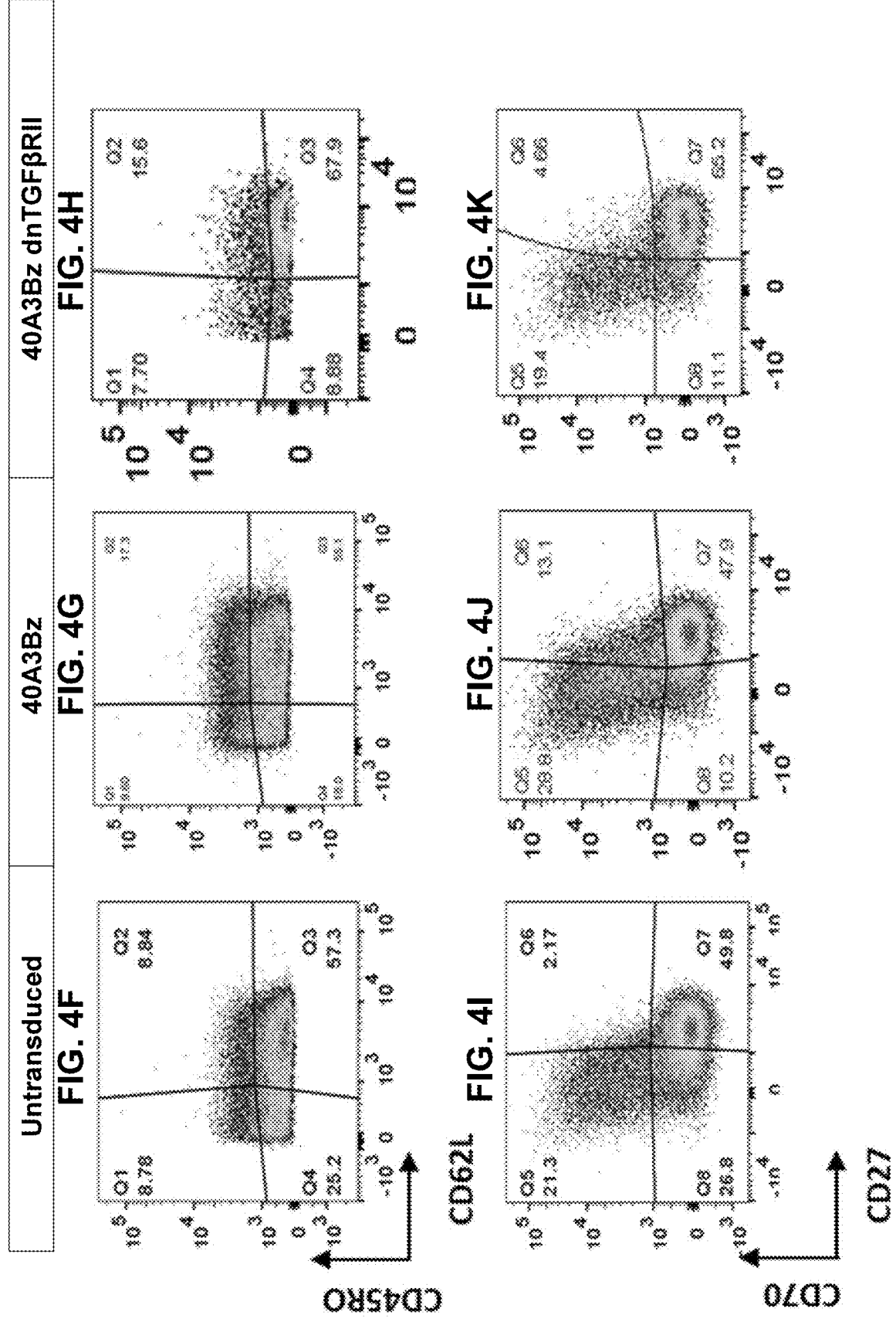

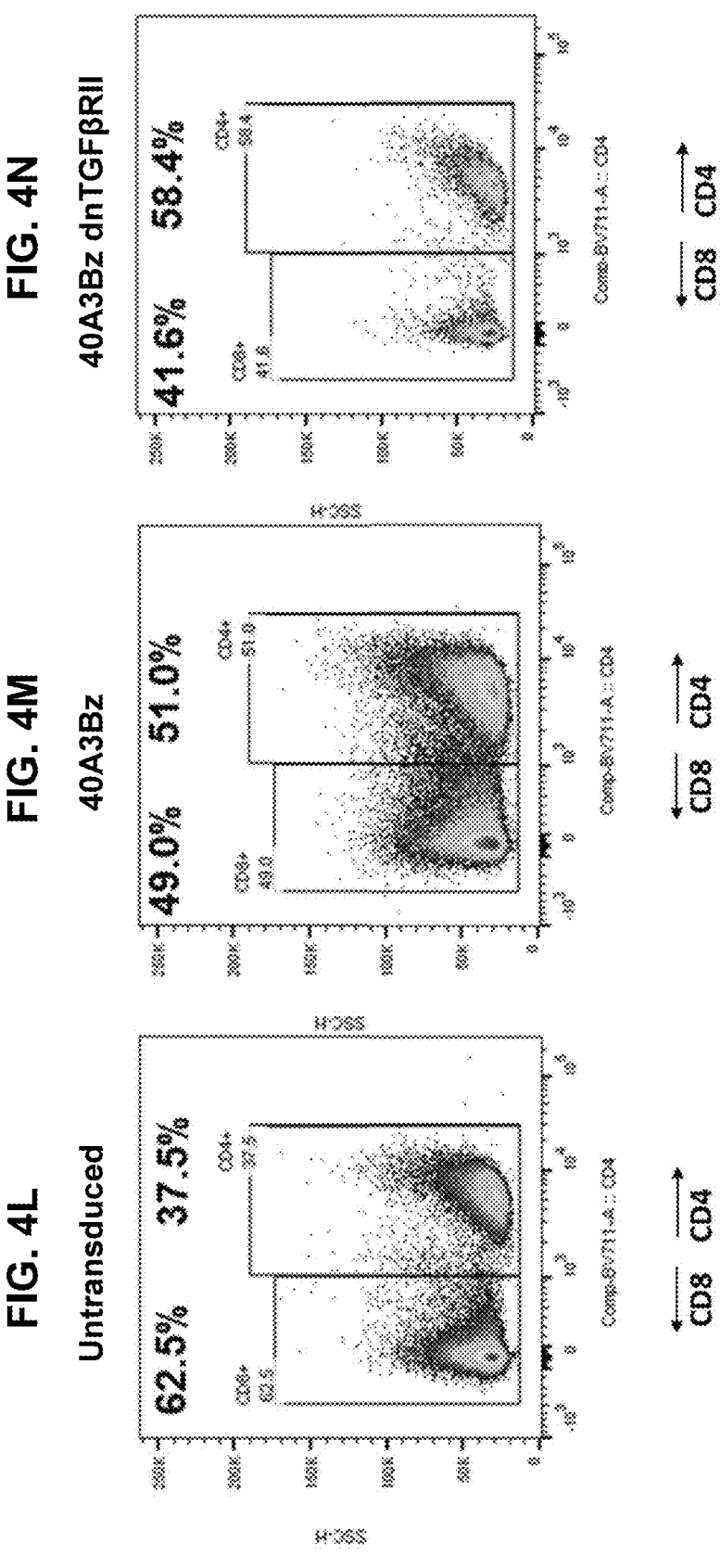

STEAP2 ISH

STEAP2 IHC

STEAP2 ISH

STEAP2 IHC

Ad293

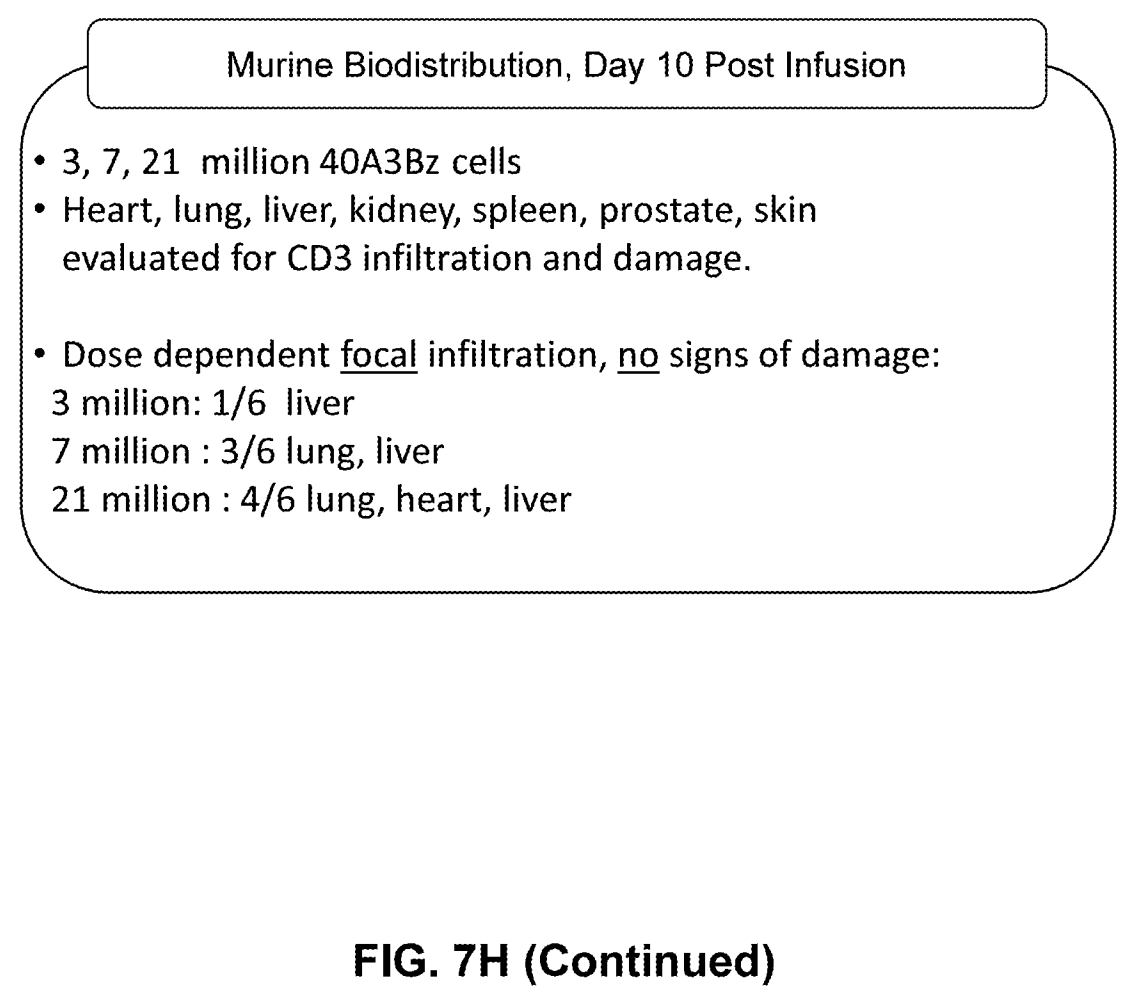

Murine Biodistribution, Day 10 Post Infusion

- 3, 7, 21 million 40A3Bz cells
- Heart, lung, liver, kidney, spleen, prostate, skin evaluated for CD3 infiltration and damage.

- Dose dependent focal infiltration, no signs of damage:

3 million: 1/6 liver 7 million : 3/6 lung, liver 21 million : 4/6 lung, heart, liver

Figures 7A, 7B:
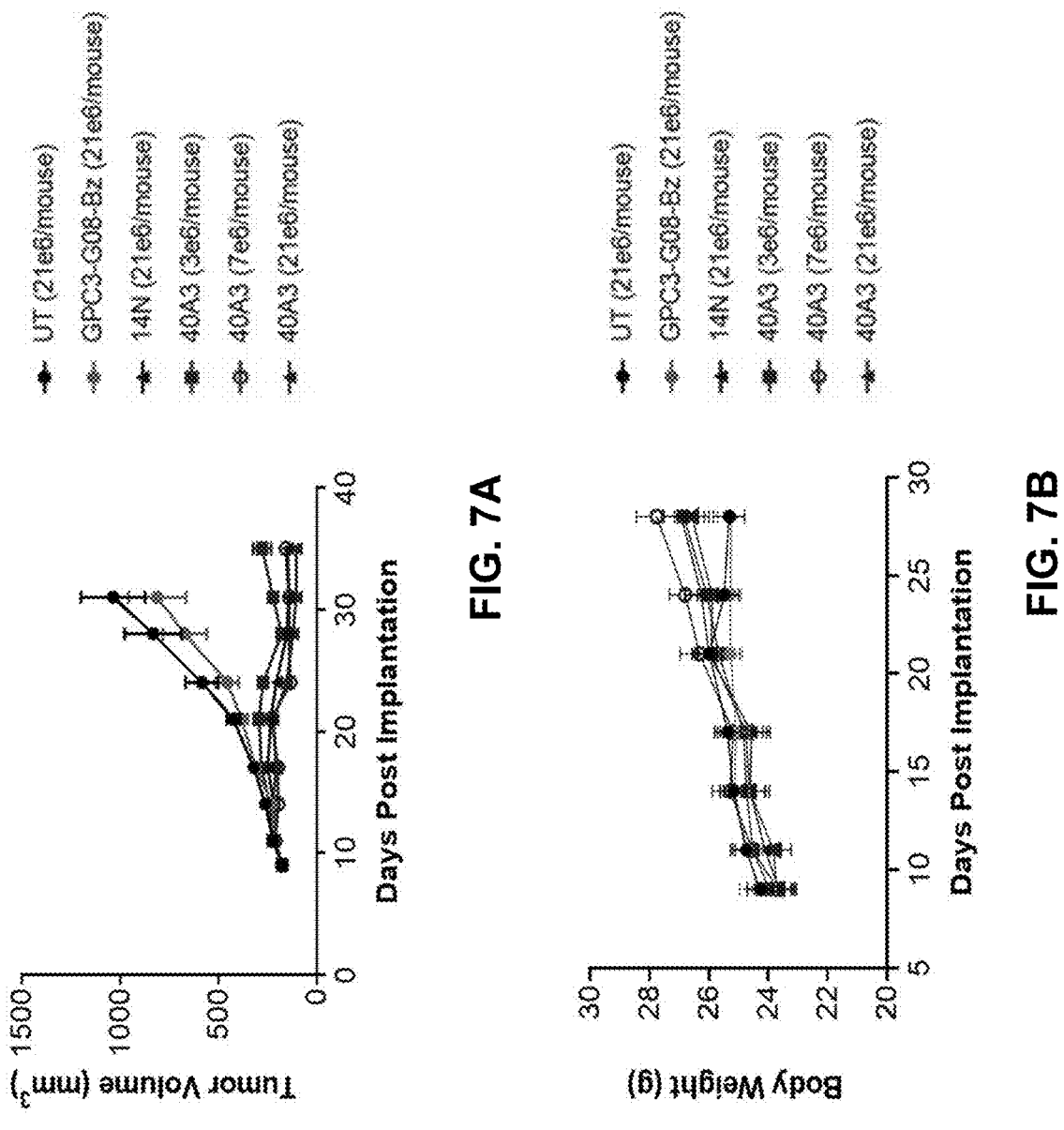
Figure 7C:
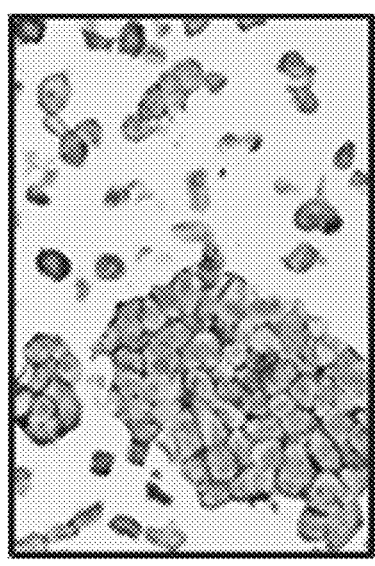
Figure 7D:
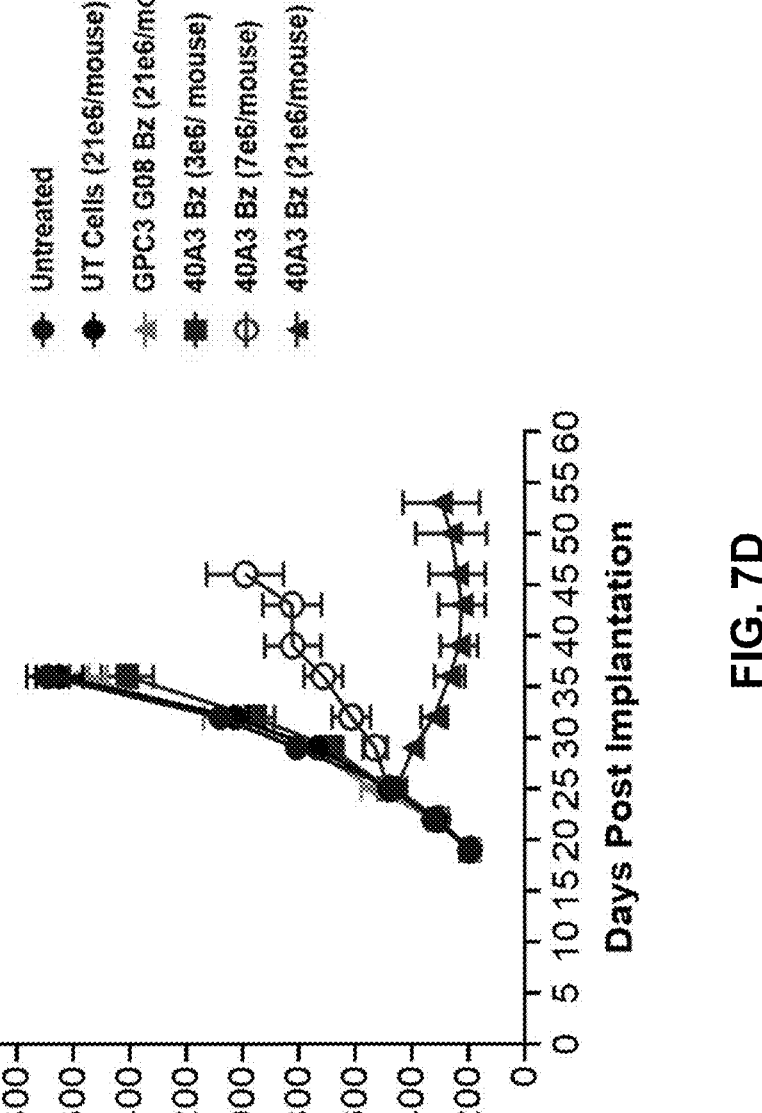
Figure 7E:
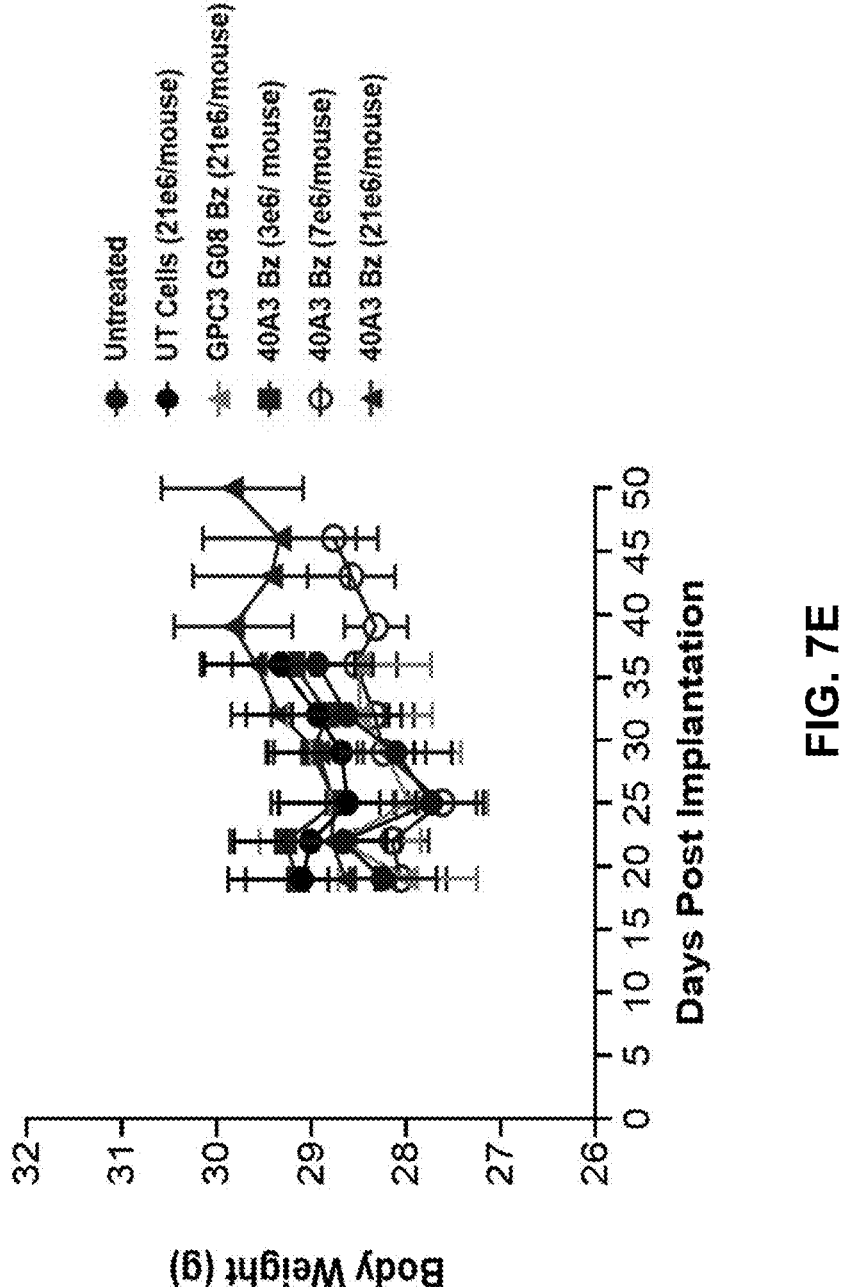
Figure 7F:
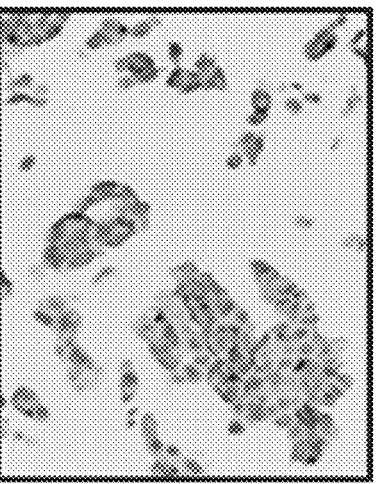
Figure 7G:
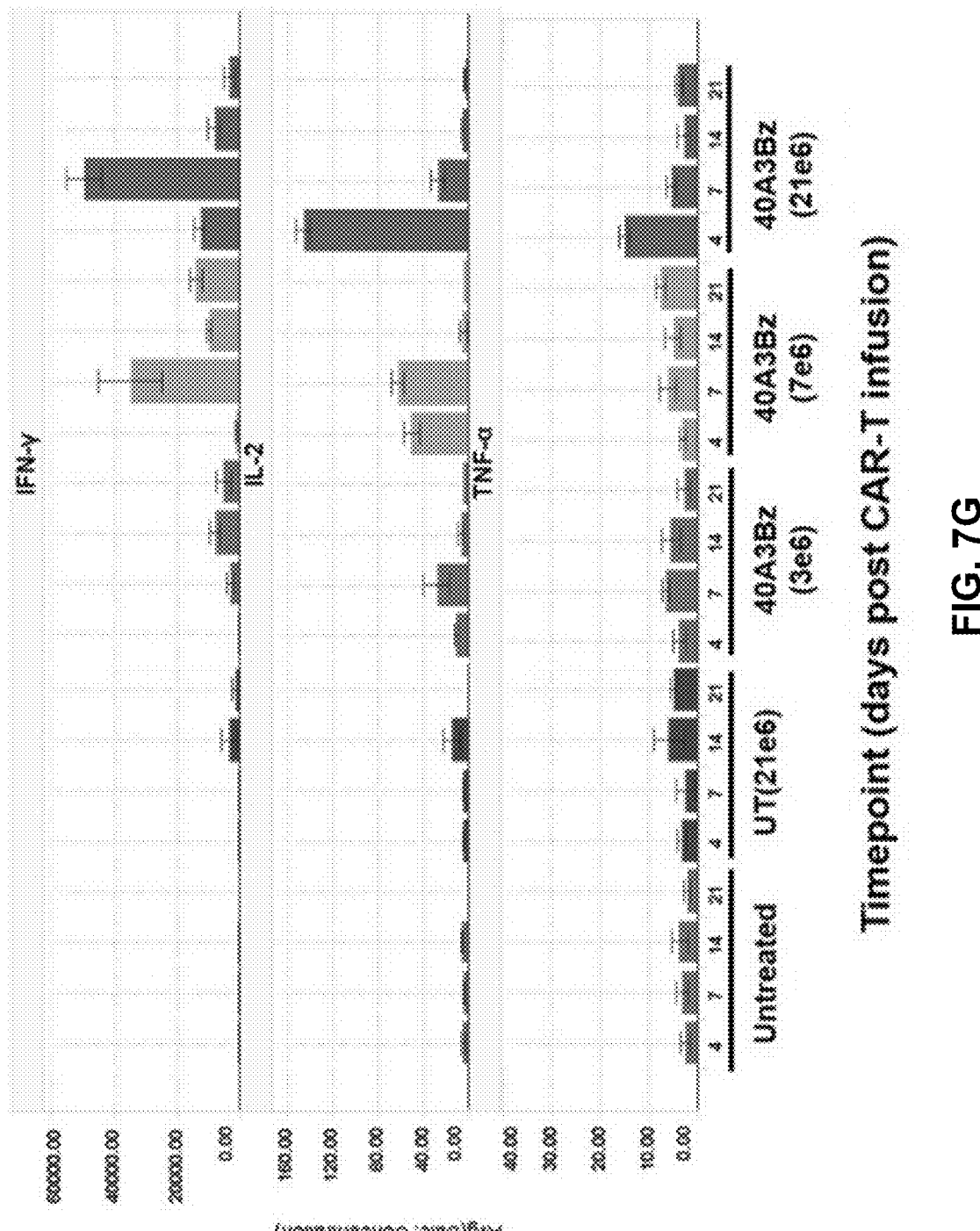
Figure 7H:

FIG. 7H (Continued)

Murine Heart

H&E

Human CD3

40A3 (21e6 at Day 10 post infusion harvest)

Murine Skin

H&E

Human CD3

40A3 (21e6 at Day 10 post infusion harvest)

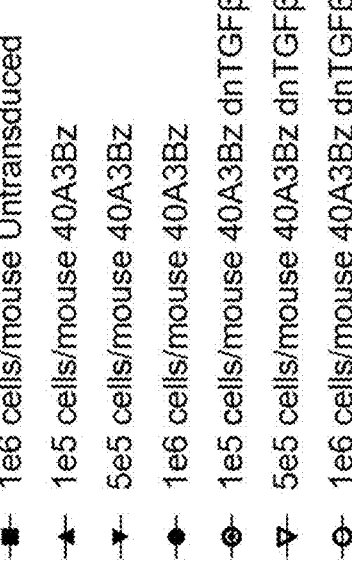
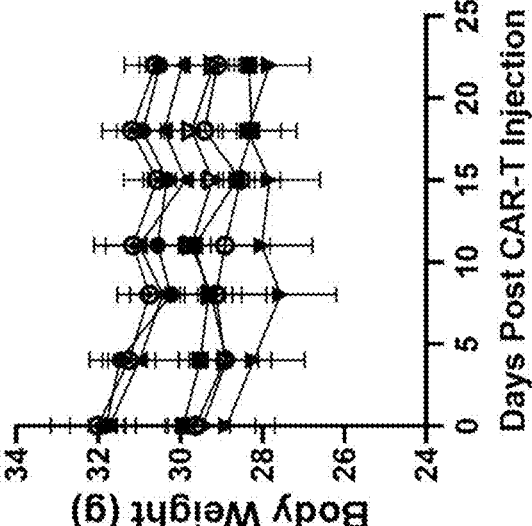
FIG. 8I

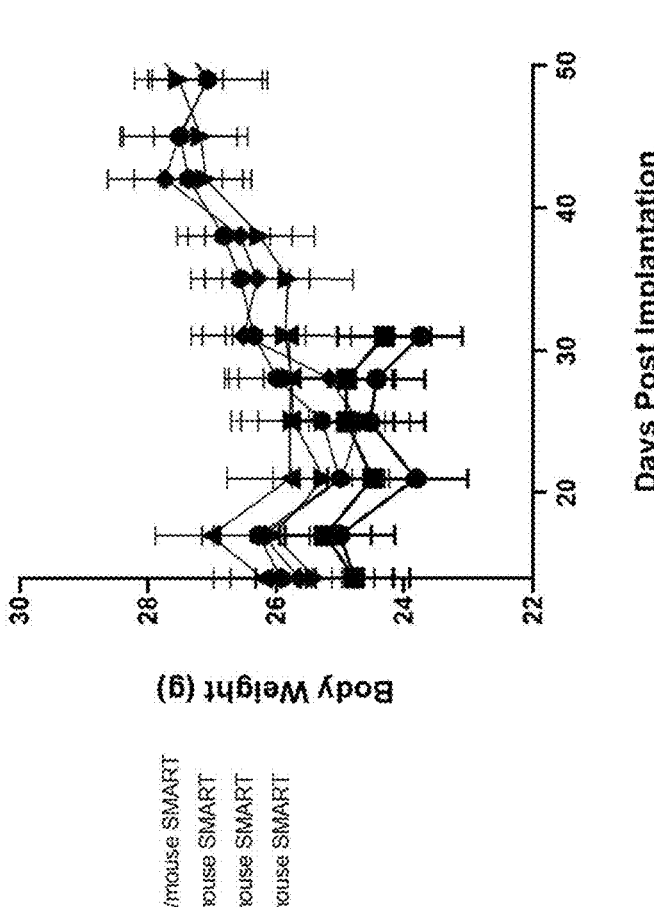
- Untreated
- UT 6e6/mouse SMART
- 40A3Bz dnTGFβRII 0.3e6/mouse SMART
- 40A3Bz dnTGFβRII 1e6/mouse SMART
- 40A3Bz dnTGFβRII 3e6/mouse SMART
- 40A3Bz dnTGFβRII 6e6/mouse SMART
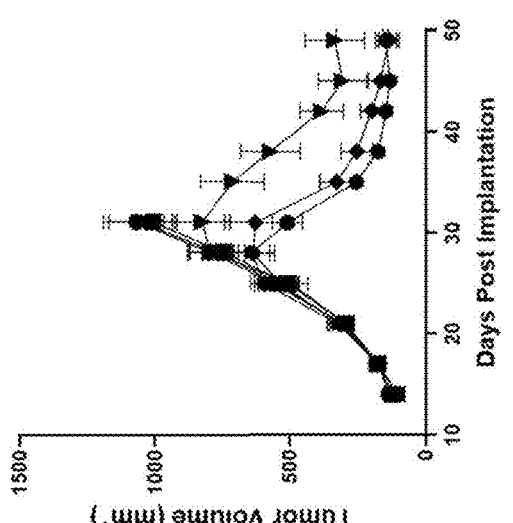
FIG. 9B

ANTI-STEAP2 CHIMERIC ANTIGEN RECEPTORS AND USES THEREOF

CROSS-REFERENCE TO RELATED APPLICATION

This application claims the priority benefit of U.S. Provisional Application No. 63/262,602, filed Oct. 15, 2021, which is incorporated herein by reference in its entirety.

REFERENCE TO SEQUENCE LISTING SUBMITTED ELECTRONICALLY VIA EFS WEB

The content of the electronically submitted sequence listing (CARTSTEAP2-100-US-NP.xml; Size: 144,479 bytes; and Date of Creation: Oct. 13, 2022) submitted in this application is incorporated herein by reference in its entirety.

BACKGROUND OF THE DISCLOSURE

Immunotherapy has emerged as a powerful tool in the fight against various types of diseases, including cancer. Immunotherapies harness the power of the patient's own immune system to combat various types of tumors.

Chimeric antigen receptor (CAR) T cell therapy is a specific form of cell-based immunotherapy that uses engineered T cells to fight cancer. In CAR-T cell therapy, T cells are harvested from a patient's blood, engineered ex vivo to express CARs containing both antigen-binding and T cell-activating domains, expanded into a larger population, and administered to the patient. The CAR-T cells act as a living drug, binding to cancer cells and bringing about their destruction. When successful, the effects of CAR-T cell treatment tend to be long lasting, as evidenced by detection of CAR-T cell persistence and expansion in the patients long after clinical remission.

Though several promising CAR-therapies have been approved for use, there remains a need to develop CARs against novel targets to expand the number of indications that can be treated using this therapy. Described herein are novel CARs directed to human STEAP2 and methods of using the same in the treatment of cancer, e.g., prostate cancer.

SUMMARY OF THE DISCLOSURE

Some aspects of the present disclosure are directed to a polynucleotide comprising a nucleotide sequence encoding a chimeric antigen receptor (CAR), wherein the CAR comprises: (i) an antigen-binding domain that binds an epitope on human six transmembrane epithelial antigen of prostate-2 (STEAP2); (ii) a transmembrane domain; and (iii) an intracellular domain. In some aspects, the antigen-binding domain binds an epitope on an extracellular loop of human STEAP2.

In some aspects, the antigen-binding domain comprises an Fab, Fab', F(ab')2, Fd, Fv, single-chain fragment variable (scFv), single chain antibody, V_HH, vNAR, nanobody (single-domain antibody), or any combination thereof. In some aspects, the antigen-binding domain comprises a scFv.

In some aspects, the antigen-binding domain comprises a variable heavy chain region (VH) and a variable light chain region (VL), wherein the VH comprises a VH complementarity determining region (CDR) 1, a VH-CDR2, a VH-CDR3; and wherein the VL comprises a VL-CDR1, a VL-CDR2, and VL-CDR3.

In some aspects, the antigen-binding domain comprises a VH-CDR3 comprising an amino acid sequence selected from SEQ ID NOs: 6, 16, 26, 36, 46, and 96. In some aspects, the antigen-binding domain comprises a VH-CDR2 comprising an amino acid sequence selected from SEQ ID NOs: 5, 15, 25, 35, 45, and 95. In some aspects, the antigen-binding domain comprises a VH-CDR1 comprising an amino acid sequence selected from SEQ ID NOs: 4, 14, 24, 34, 44, and 94. In some aspects, the antigen-binding domain comprises a VL-CDR3 comprising an amino acid sequence selected from SEQ ID NOs: 3, 13, 23, 33, 43, and 93. In some aspects, the antigen-binding domain comprises a VL-CDR2 comprising an amino acid sequence selected from SEQ ID NOs: 2, 12, 22, 32, 42, and 92. In some aspects, the antigen-binding domain comprises a VL-CDR1 comprising an amino acid sequence selected from SEQ ID NOs: 1, 11, 21, 31, 41, and 91.

In some aspects, the antigen-binding domain comprises: (a) a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (b) a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (c) a VL-CDR1 comprising the amino acid sequence set forth in SEQ ID NO: 21, a VL-CDR2 comprising the amino acid sequence set forth in SEQ ID NO: 22, a VL-CDR3 comprising the amino acid sequence set forth in SEQ ID NO: 23, a VH-CDR1 comprising the amino acid sequence set forth in SEQ ID NO: 24, a VH-CDR2 comprising the amino acid sequence set forth in SEQ ID NO: 25, a VH-CDR3 comprising the amino acid sequence set forth in SEQ ID NO: 26; (d) a VL-CDR1 comprising the amino acid sequence set forth in SEQ ID NO: 31, a VL-CDR2 comprising the amino acid sequence set forth in SEQ ID NO: 32, a VL-CDR3 comprising the amino acid sequence set forth in SEQ ID NO: 33, a VH-CDR1 comprising the amino acid sequence set forth in SEQ ID NO: 34, a VH-CDR2 comprising the amino acid sequence set forth in SEQ ID NO: 35, a VH-CDR3 comprising the amino acid sequence set forth in SEQ ID NO: 36; (e) a VL-CDR1 comprising the amino acid sequence set forth in SEQ ID NO: 41, a VL-CDR2 comprising the amino acid sequence set forth in SEQ ID NO: 42, a VL-CDR3 comprising the amino acid sequence set forth in SEQ ID NO: 43, a VH-CDR1 comprising the amino acid sequence set forth in SEQ ID NO: 44, a VH-CDR2 comprising the amino acid sequence set forth in SEQ ID NO: 45, a VH-CDR3 comprising the amino acid sequence set forth in SEQ ID NO: 46; or (f) a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 7, 17, 27, 37, 47, and 97. In some aspects, the antigen-binding domain comprises a VH comprising an amino acid sequence selected from SEQ ID NOs: 7, 17, 27, 37, 47, and 97.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 8, 18, 28, 38, 48, and 98. In some aspects, the antigen-binding domain comprises a VL comprising an amino acid sequence selected from SEQ ID NOs: 8, 18, 28, 38, 48, and 98.

In some aspects, the antigen-binding domain comprises: (a) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (b) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (c) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28; (d) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38; (e) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48; or (f) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88.

In some aspects, the antigen-binding domain comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97.

In some aspects, the antigen-binding domain comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, the antigen-binding domain comprises: (a) a VH comprising the amino acid sequence set forth in SEQ ID NO: 7, and a VL comprising the amino acid sequence set forth in SEQ ID NO: 8; (b) a VH comprising the amino acid sequence set forth in SEQ ID NO: 17, and a VL comprising the amino acid sequence set forth in SEQ ID NO: 18; (c) a VH comprising the amino acid sequence set forth in SEQ ID NO: 27, and a VL comprising the amino acid sequence set forth in SEQ ID NO: 28; (d) a VH comprising the amino acid sequence set forth in SEQ ID NO: 37, and a VL comprising the amino acid sequence set forth in SEQ ID NO: 38; (e) a VH comprising the amino acid sequence set forth in SEQ ID NO: 47, and a VL comprising the amino acid sequence set forth in SEQ ID NO: 48; (f) a VH comprising the amino acid sequence set forth in SEQ ID NO: 57, and a VL comprising the amino acid sequence set forth in SEQ ID NO: 58; (g) a VH comprising the amino acid sequence set forth in SEQ ID NO: 67, and a VL comprising the amino acid sequence set forth in SEQ ID NO: 68; (h) a VH comprising the amino acid sequence set forth in SEQ ID NO: 77, and a VL comprising the amino acid sequence set forth in SEQ ID NO: 78; or (i) a VH comprising the amino acid sequence set forth in SEQ ID NO: 87, and a VL comprising the amino acid sequence set forth in SEQ ID NO: 88; or (j) a VH comprising the amino acid sequence set forth in SEQ ID NO: 97, and a VL comprising the amino acid sequence set forth in SEQ ID NO: 98.

In some aspects, the antigen-binding domain comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9. In some aspects, the antigen-binding domain comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99.

In some aspects, the intracellular domain comprises a costimulatory domain or a portion thereof. In some aspects, the intracellular domain comprises a costimulatory domain selected from the group consisting of the intracellular domain of CD3z, a CD28 co-stimulatory domain, a CD27 co-stimulatory domain, a 4-1BB co-stimulatory domain, an ICOS co-stimulatory domain, an OX-40 co-stimulatory domain, a GITR co-stimulatory domain, a CD2 co-stimulatory domain, an IL-2Rβ co-stimulatory domain, an MyD88/CD40a CD28 co-stimulatory domain, and any combination thereof. In some aspects, the intracellular domain comprises a 4-1BB co-stimulatory domain. In some aspects, the intracellular domain comprises the intracellular domain of CD3z and a CD28 co-stimulatory domain. In some aspects, the intracellular domain comprises the intracellular domain of CD3z and a 4-1BB co-stimulatory domain. In some aspects, the intracellular domain of CD3z comprises SEQ ID NO: 131 and the 4-1BB co-stimulatory domain comprises SEQ ID NO: 130. In some aspects, the intracellular domain comprising the intracellular domain of CD3z and the 4-1BB co-stimulatory domain comprises SEQ ID NO: 130. In some aspects, the intracellular domain comprises the intracellular domain of CD3z, a CD28 co-stimulatory domain, and a 4-1BB co-stimulatory domain.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10.

In some aspects, the transmembrane domain comprises a transmembrane domain selected from the transmembrane domain of CD4, CD8a, or CD28. In some aspects, the transmembrane domain comprises the transmembrane domain of CD28. In some aspects, the transmembrane domain of CD28 comprises SEQ ID NO: 129.

In some aspects, the CAR further comprises a hinge/spacer domain. In some aspects, the hinge/spacer domain comprises an immunoglobulin hinge/spacer. In some aspects, the hinge/spacer domain comprises an IgG hinge domain. In some aspects, the hinge/spacer domain comprise an IgG1 hinge domain, and IgG2 hinge domain, an IgG3 hinge domain, or an IgG4 hinge domain. In some aspects, the hinge/spacer domain comprises an IgG4 hinge domain. In some aspects, the IgG4 hinge domain comprises SEQ ID NO: 128.

In some aspects, the polynucleotide further encodes an armoring molecule, wherein the armoring molecule counters immunosuppression of a cell in a tumor microenvironment when expressed on a surface of the cell. In some aspects, the armoring molecule comprises a dominant-negative TGF-β receptor type 2 (TGFβRIIDN). In some aspects, the armoring molecule comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the armoring molecule comprises the amino acid sequence set forth in SEQ ID NO: 105.

In some aspects, the nucleotide sequence encoding the CAR has at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 101 or 103. In some aspects, the nucleotide sequence encoding the CAR comprises the nucleotide sequence set forth in SEQ ID NO: 101 or 103.

In some aspects, the polynucleotide further comprises a second nucleotide sequence encoding an armoring molecule, wherein the second nucleotide sequence has at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 104. In some aspects, the second nucleotide comprises the nucleotide sequence set forth in SEQ ID NO: 104. In some aspects, the nucleotide sequence encoding the CAR comprises the nucleotide sequence set forth in SEQ ID NO: 101, and the second nucleotide sequence comprises the nucleotide sequence set forth in SEQ ID NO: 104. In some aspects, the nucleotide sequence encoding the CAR comprises the nucleotide sequence set forth in SEQ ID NO: 103, and the second nucleotide sequence comprises the nucleotide sequence set forth in SEQ ID NO: 104.

In some aspects, the nucleotide sequence encoding the CAR and the second nucleotide sequence are linked by a third nucleotide sequence, wherein the third nucleotide sequence encodes a cleavable peptide linker. In some aspects, the cleavable peptide linker is a self-cleaving peptide linker. In some aspects, the cleavable peptide linker comprises a T2A peptide. In some aspects, the cleavable peptide linker comprises SEQ ID NO: 126.

In some aspects, the polynucleotide comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 107. In some aspects, the polynucleotide comprises the nucleotide sequence set forth in SEQ ID NO: 107.

Some aspects of the present disclosure are directed to a vector or a set of vectors comprising a polynucleotide disclosed herein. In some aspects, the vector is a viral vector.

Some aspects of the present disclosure are directed to a cell comprising a polynucleotide disclosed herein or a vector or a set of vectors disclosed herein. In some aspects, the cell is an immune cell. In some aspects, the cell is selected from the group consisting of a T cell, a Natural Killer (NK) cell, a cytotoxic T lymphocyte (CTL), a regulatory T cell, a tumor infiltrating lymphocyte, and any combination thereof.

Some aspects of the present disclosure are directed to a cell comprising (i) a polynucleotide encoding a chimeric antigen receptor (CAR) that binds human STEAP2 and (ii) a polynucleotide encoding an armoring molecule. In some aspects, the cell is an immune cell. In some aspects, the cell is selected from the group consisting of a T cell, a Natural Killer (NK) cell, a cytotoxic T lymphocyte (CTL), a regulatory T cell, a tumor infiltrating lymphocyte, and any combination thereof. In some aspects, the cell is a human cell.

In some aspects, the CAR comprises an antigen-binding domain comprising a VH and a VL, wherein the VH comprises a VH-CDR1, a VH-CDR2, a VH-CDR3, and wherein the VL comprises a VL-CDR1, a VL-CDR2, and VL-CDR3; and wherein (a) the VL-CDR1 comprises the amino acid sequence set forth in SEQ ID NO: 1, the VL-CDR2 comprises the amino acid sequence set forth in SEQ ID NO: 2, the VL-CDR3 comprises the amino acid sequence set forth in SEQ ID NO: 3, the VH-CDR1 comprises the amino acid sequence set forth in SEQ ID NO: 4, the VH-CDR2 comprises the amino acid sequence set forth in SEQ ID NO: 5, and the VH-CDR3 comprises the amino acid sequence set forth in SEQ ID NO: 6; (b) the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 14, the VH-CDR2 comprises the amino acid sequence set forth in SEQ ID NO: 15, and the VH-CDR3 comprises the amino acid sequence set forth in SEQ ID NO: 16; (c) the VL-CDR1 comprises the amino acid sequence set forth in SEQ ID NO: 21, the VL-CDR2 comprises the amino acid sequence set forth in SEQ ID NO: 22, the VL-CDR3 comprises the amino acid sequence set forth in SEQ ID NO: 23, the VH-CDR1 comprises the amino acid sequence set forth in SEQ ID NO: 24, the VH-CDR2 comprises the amino acid sequence set forth in SEQ ID NO: 25, and the VH-CDR3 comprises the amino acid sequence set forth in SEQ ID NO: 26; (d) the VL-CDR1 comprises the amino acid sequence set forth in SEQ ID NO: 31, the VL-CDR2 comprises the amino acid sequence set forth in SEQ ID NO: 32, the VL-CDR3 comprises the amino acid sequence set forth in SEQ ID NO: 33, the VH-CDR1 comprises the amino acid sequence set forth in SEQ ID NO: 34, the VH-CDR2 comprises the amino acid sequence set forth in SEQ ID NO: 35, and the VH-CDR3 comprises the amino acid sequence set forth in SEQ ID NO: 36; (e) the VL-CDR1 comprises the amino acid sequence set forth in SEQ ID NO: 41, the VL-CDR2 comprises the amino acid sequence set forth in SEQ ID NO: 42, the VL-CDR3 comprises the amino acid sequence set forth in SEQ ID NO: 43, the VH-CDR1 comprises the amino acid sequence set forth in SEQ ID NO: 44, the VH-CDR2 comprises the amino acid sequence set forth in SEQ ID NO: 45, and the VH-CDR3 comprises the amino acid sequence set forth in SEQ ID NO: 46; or (f) the VL-CDR1 comprises the amino acid sequence set forth in SEQ ID NO: 91, the VL-CDR2 comprises the amino acid sequence set forth in SEQ ID NO: 92, the VL-CDR3 comprises the amino acid sequence set forth in SEQ ID NO: 93, the VH-CDR1 comprises the amino acid sequence set forth in SEQ ID NO: 94, the VH-CDR2 comprises the amino acid sequence set forth in SEQ ID NO: 95, and the VH-CDR3 comprises the amino acid sequence set forth in SEQ ID NO: 96.

In some aspects, (a) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (b) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (c) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28; (d) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38; (e) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48; or (f) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, provided is a cell comprising: (a) the VH comprises the amino acid sequence set forth in SEQ ID NO: 7, and the VL comprises the amino acid sequence set forth in SEQ ID NO: 8; (b) the VH comprises the amino acid sequence set forth in SEQ ID NO: 17, and the VL comprises the amino acid sequence set forth in SEQ ID NO: 18; (c) the VH comprises the amino acid sequence set forth in SEQ ID NO: 27, and the VL comprises the amino acid sequence set forth in SEQ ID NO: 28; (d) the VH comprises the amino acid sequence set forth in SEQ ID NO: 37, and the VL comprises the amino acid sequence set forth in SEQ ID NO: 38; (e) the VH comprises the amino acid sequence set forth in SEQ ID NO: 47, and the VL comprises the amino acid sequence set forth in SEQ ID NO: 48; (f) the VH comprises the amino acid sequence set forth in SEQ ID NO: 57, and the VL comprises the amino acid sequence set forth in SEQ ID NO: 58; (g) the VH comprises the amino acid sequence set forth in SEQ ID NO: 67, and the VL comprises the amino acid sequence set forth in SEQ ID NO: 68; (h) the VH comprises the amino acid sequence set forth in SEQ ID NO: 77, and the VL comprises the amino acid sequence set forth in SEQ ID NO: 78; (i) the VH comprises the amino acid sequence set forth in SEQ ID NO: 87, and the VL comprises the amino acid sequence set forth in SEQ ID NO: 88; or (j) the VH comprises the amino acid sequence set forth in SEQ ID NO: 97, and the VL comprises the amino acid sequence set forth in SEQ ID NO: 98.

In some aspects, the armoring molecule comprises a dominant-negative TGF-β receptor type 2 (TGFβRIIDN). In some aspects, the armoring molecule comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the armoring molecule comprises the amino acid sequence set forth in SEQ ID NO: 105.

In some aspects, the polynucleotide encoding the CAR comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 101 or 103. In some aspects, the polynucleotide encoding the CAR comprises the nucleotide sequence set forth in SEQ ID NO: 101 or 103.

In some aspects, the polynucleotide encoding the armoring molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 104. In some aspects, the polynucleotide encoding the armoring molecule comprises the nucleotide sequence set forth in SEQ ID NO: 104.

In some aspects, the polynucleotide encoding the CAR comprises the nucleotide sequence set forth in SEQ ID NO: 101, and the polynucleotide encoding the armoring molecule comprises the nucleotide sequence set forth in SEQ ID NO: 104.

In some aspects, the polynucleotide encoding the CAR comprises the nucleotide sequence set forth in SEQ ID NO: 103, and the polynucleotide encoding the armoring molecule comprises the nucleotide sequence set forth in SEQ ID NO: 104.

In some aspects, the polynucleotide encoding the CAR and the polynucleotide encoding the armoring molecule are operably linked under the control of a single promoter. In some aspects, the polynucleotide encoding the CAR and the polynucleotide encoding the armoring molecule are operably linked by an IRES. In some aspects, the polynucleotide encoding the CAR and the polynucleotide encoding the armoring molecule are linked by a nucleotide sequence encoding a cleavable peptide linker. In some aspects, the cleavable peptide linker is a self-cleaving peptide linker. In some aspects, the cleavable peptide linker comprises a T2A peptide. In some aspects, the cleavable peptide linker comprises SEQ ID NO: 126.

Some aspects of the present disclosure are directed to an antibody or an antigen-binding portion thereof that specifically binds human STEAP2, comprising a variable heavy chain region (VH) and a variable light chain region (VL), wherein the VH comprises a VH complementarity determining region (CDR) 1, a VH-CDR2, a VH-CDR3; and wherein the VL comprises a VL-CDR1, a VL-CDR2, and VL-CDR3, wherein (i) the VL-CDR1 comprises an amino acid sequence selected from SEQ ID NOs: 1, 11, 21, 31, 41, and 91; (ii) the VL-CDR2 comprises an amino acid sequence selected from SEQ ID NOs: 2, 12, 22, 32, 42, and 92; (iii) the VL-CDR3 comprises an amino acid sequence selected from SEQ ID NOs: 3, 13, 23, 33, 43, and 93; (iv) the VH-CDR1 comprises an amino acid sequence selected from SEQ ID NOs: 4, 14, 24, 34, 44, and 94; (v) the VH-CDR2 comprises an amino acid sequence selected from SEQ ID NOs: 5, 15, 25, 35, 45, and 95; and (vi) the VH-CDR3 comprises an amino acid sequence selected from SEQ ID NOs: 6, 16, 26, 36, 46, and 96.

In some aspects, (a) the VL-CDR1 comprises the amino acid sequence set forth in SEQ ID NO: 1, the VL-CDR2 comprises the amino acid sequence set forth in SEQ ID NO: 2, the VL-CDR3 comprises the amino acid sequence set forth in SEQ ID NO: 3, the VH-CDR1 comprises the amino acid sequence set forth in SEQ ID NO: 4, the VH-CDR2 comprises the amino acid sequence set forth in SEQ ID NO: 5, and the VH-CDR3 comprises the amino acid sequence set forth in SEQ ID NO: 6; (b) the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 14, the VH-CDR2 comprises the amino acid sequence set forth in SEQ ID NO: 15, and the VH-CDR3 comprises the amino acid sequence set forth in SEQ ID NO: 16; (c) the VL-CDR1 comprises the amino acid sequence set forth in SEQ ID NO: 21, the VL-CDR2 comprises the amino acid sequence set forth in SEQ ID NO: 22, the VL-CDR3 comprises the amino acid sequence set forth in SEQ ID NO: 23, the VH-CDR1 comprises the amino acid sequence set forth in SEQ ID NO: 24, the VH-CDR2 comprises the amino acid sequence set forth in SEQ ID NO: 25, and the VH-CDR3 comprises the amino acid sequence set forth in SEQ ID NO: 26; (d) the VL-CDR1 comprises the amino acid sequence set forth in SEQ ID NO: 31, the VL-CDR2 comprises the amino acid sequence set forth in SEQ ID NO: 32, the VL-CDR3 comprises the amino acid sequence set forth in SEQ ID NO: 33, the VH-CDR1 comprises the amino acid sequence set forth in SEQ ID NO: 34, the VH-CDR2 comprises the amino acid sequence set forth in SEQ ID NO: 35, and the VH-CDR3 comprises the amino acid sequence set forth in SEQ ID NO: 36; (e) the VL-CDR1 comprises the amino acid sequence set forth in SEQ ID NO: 41, the VL-CDR2 comprises the amino acid sequence set forth in SEQ ID NO: 42, the VL-CDR3 comprises the amino acid sequence set forth in SEQ ID NO: 43, the VH-CDR1 comprises the amino acid sequence set forth in SEQ ID NO: 44, the VH-CDR2 comprises the amino acid sequence set forth in SEQ ID NO: 45, and the VH-CDR3 comprises the amino acid sequence set forth in SEQ ID NO: 46; or (f) the VL-CDR1 comprises the amino acid sequence set forth in SEQ ID NO: 91, the VL-CDR2 comprises the amino acid sequence set forth in SEQ ID NO: 92, the VL-CDR3 comprises the amino acid sequence set forth in SEQ ID NO: 93, the VH-CDR1 comprises the amino acid sequence set forth in SEQ ID NO: 94, the VH-CDR2 comprises the amino acid sequence set forth in SEQ ID NO: 95, and the VH-CDR3 comprises the amino acid sequence set forth in SEQ ID NO: 96.

In some aspects, the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 7, 17, 27, 37, 47, 57, 67, 77, 87, and 97. In some aspects, the VH comprises an amino acid sequence selected from SEQ ID NOs: 7, 17, 27, 37, 47, 57, 67, 77, 87, and 97.

In some aspects, the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 8, 18, 28, 38, 48, 58, 68, 78, 88, and 98. In some aspects, the VL comprises an amino acid sequence selected from SEQ ID NOs: 8, 18, 28, 38, 48, 58, 68, 78, 88, and 98.

In some aspects, (a) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (b) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (c) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28; (d) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38; (e) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48; (f) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58; (g) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68; (h) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78; (i) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88; or (j) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, (a) the VH comprises the amino acid sequence set forth in SEQ ID NO: 7, and the VL comprises the amino acid sequence set forth in SEQ ID NO: 8; (b) the VH comprises the amino acid sequence set forth in SEQ ID NO: 17, and the VL comprises the amino acid sequence set forth in SEQ ID NO: 18; (c) the VH comprises the amino acid sequence set forth in SEQ ID NO: 27, and the VL comprises the amino acid sequence set forth in SEQ ID NO: 28; (d) the VH comprises the amino acid sequence set forth in SEQ ID NO: 37, and the VL comprises the amino acid sequence set forth in SEQ ID NO: 38; (e) the VH comprises the amino acid sequence set forth in SEQ ID NO: 47, and the VL comprises the amino acid sequence set forth in SEQ ID NO: 48; (f) the VH comprises the amino acid sequence set forth in SEQ ID NO: 57, and the VL comprises the amino acid sequence set forth in SEQ ID NO: 58; (g) the VH comprises the amino acid sequence set forth in SEQ ID NO: 67, and the VL comprises the amino acid sequence set forth in SEQ ID NO: 68; (h) the VH comprises the amino acid sequence set forth in SEQ ID NO: 77, and the VL comprises the amino acid sequence set forth in SEQ ID NO: 78; (i) the VH comprises the amino acid sequence set forth in SEQ ID NO: 87, and the VL comprises the amino acid sequence set forth in SEQ ID NO: 88; or (j) the VH comprises the amino acid sequence set forth in SEQ ID NO: 97, and the VL comprises the amino acid sequence set forth in SEQ ID NO: 98.

Some aspects of the present disclosure are directed to a pharmaceutical composition comprising a polynucleotide disclosed herein, a vector of disclosed herein, a cell disclosed herein, or an antibody or an antigen-binding portion disclosed herein, and a pharmaceutically acceptable excipient.

Some aspects of the present disclosure are directed to a method of treating a disease or condition in a subject in need thereof, comprising administering to the subject a polynucleotide disclosed herein, a vector of disclosed herein, a cell disclosed herein, an antibody or an antigen-binding portion disclosed herein, or a pharmaceutical composition disclosed herein. In some aspects, the disease or condition comprises a cancer.

Some aspects of the present disclosure are directed to a method of treating a cancer in a subject in need thereof, comprising administering to the subject a polynucleotide disclosed herein, a vector of disclosed herein, a cell disclosed herein, an antibody or an antigen-binding portion disclosed herein, or a pharmaceutical composition disclosed herein. In some aspects, the cancer comprises a prostate cancer. In some aspects, the prostate cancer is metastatic, recurrent, or relapsed.

Some aspects of the present disclosure are directed to the use of a polynucleotide disclosed herein, a vector of disclosed herein, a cell disclosed herein, an antibody or an antigen-binding portion disclosed herein, or a pharmaceutical composition disclosed herein in the treatment of a disease or condition in a subject in need thereof. In some aspects, the disease or condition comprises a cancer.

Some aspects of the present disclosure are directed to the use of a polynucleotide disclosed herein, a vector of disclosed herein, a cell disclosed herein, an antibody or an antigen-binding portion disclosed herein, or a pharmaceutical composition disclosed herein in the treatment of a cancer in a subject in need thereof. In some aspects, the cancer comprises a prostate cancer. In some aspects, the prostate cancer is metastatic, recurrent, or relapsed.

BRIEF DESCRIPTION OF THE DRAWINGS/FIGURES

Figure 1A:
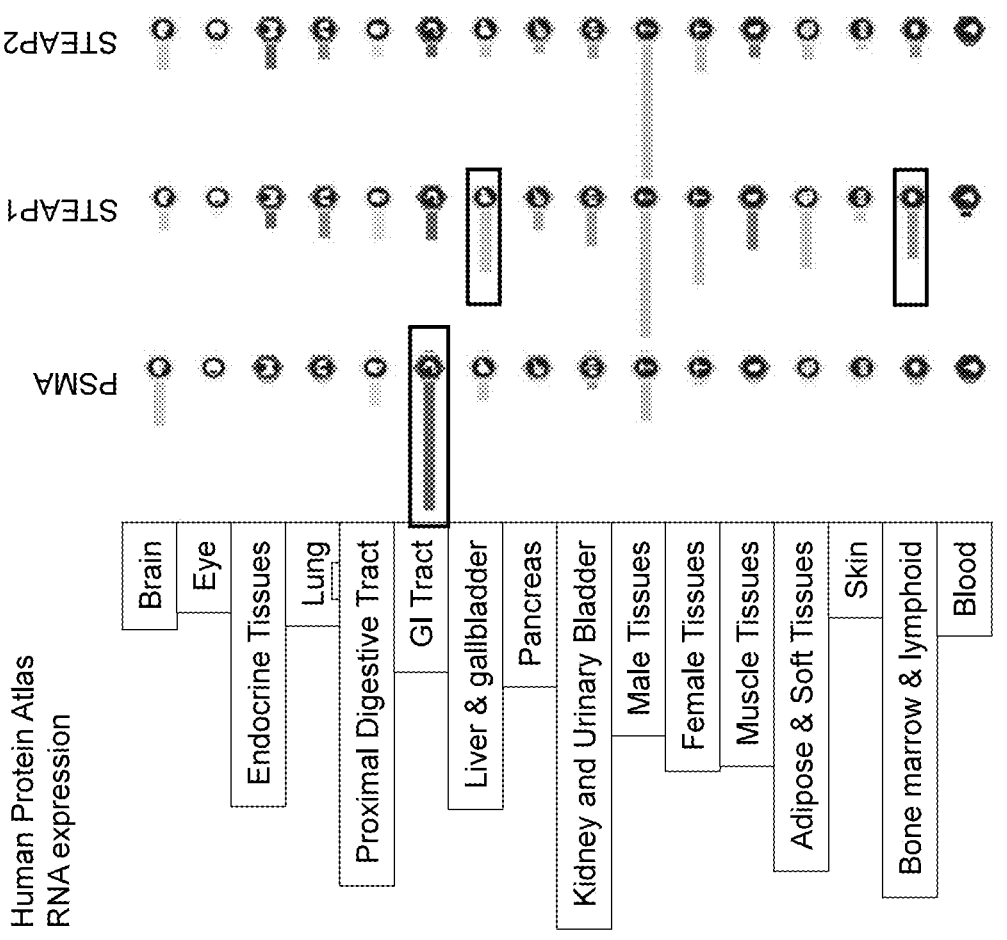
Figure 1B:
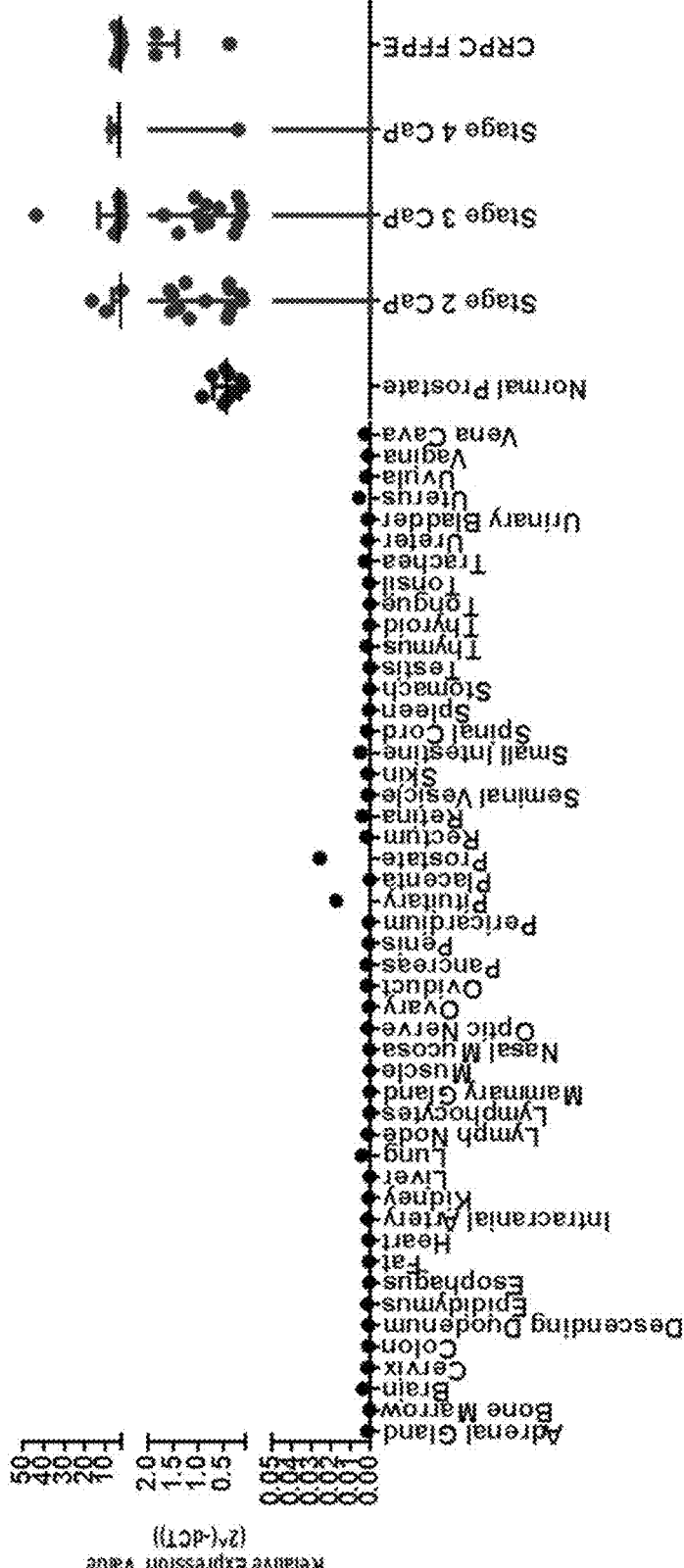
Figure 1C:
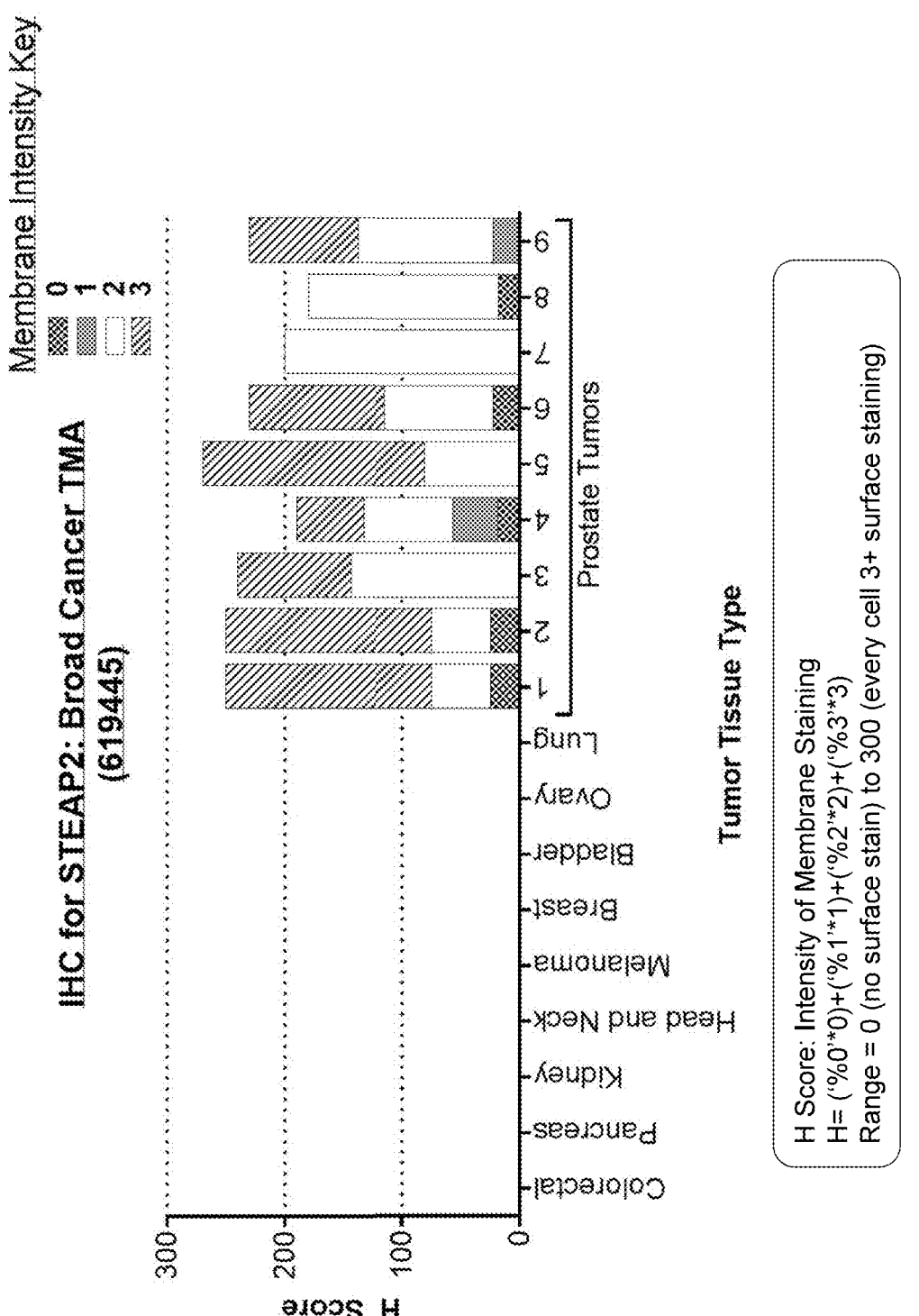
Figures 1D, 1E, 1F:
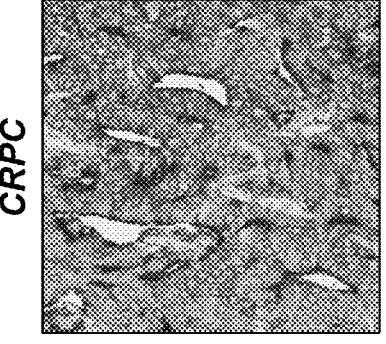

FIGS. 1A-1C show STEAP2 expression and localization across various tumor types according to the genomic Human Protein Atlas database (FIG. 1A), cDNA array gene expression profiling (FIG. 1B), and cell surface protein expression according to immunohistochemistry (IHC) with a custom polyclonal antibody (FIG. 1C). IHC on tissue microarrays containing primary prostate cancer, castrate-resistant prostate cancer (CRPC), and prostate lymph node metastases as well as decalcified full face sections of prostate cancer bone metastases for STEAP2 membrane expression (FIG. 1D), with representative images of STEAP2 in a CRPC (FIG. 1E) and a bone metastasis (FIG. 1F). Summary of STEAP2 IHC and in-situ hybridization (ISH) in normal human tissue microarray and scoring criteria (FIG. 1G). Example of a STEAP2 IHC stain in normal prostate tissue (FIG. 1H).

Figures 2A, 2B:
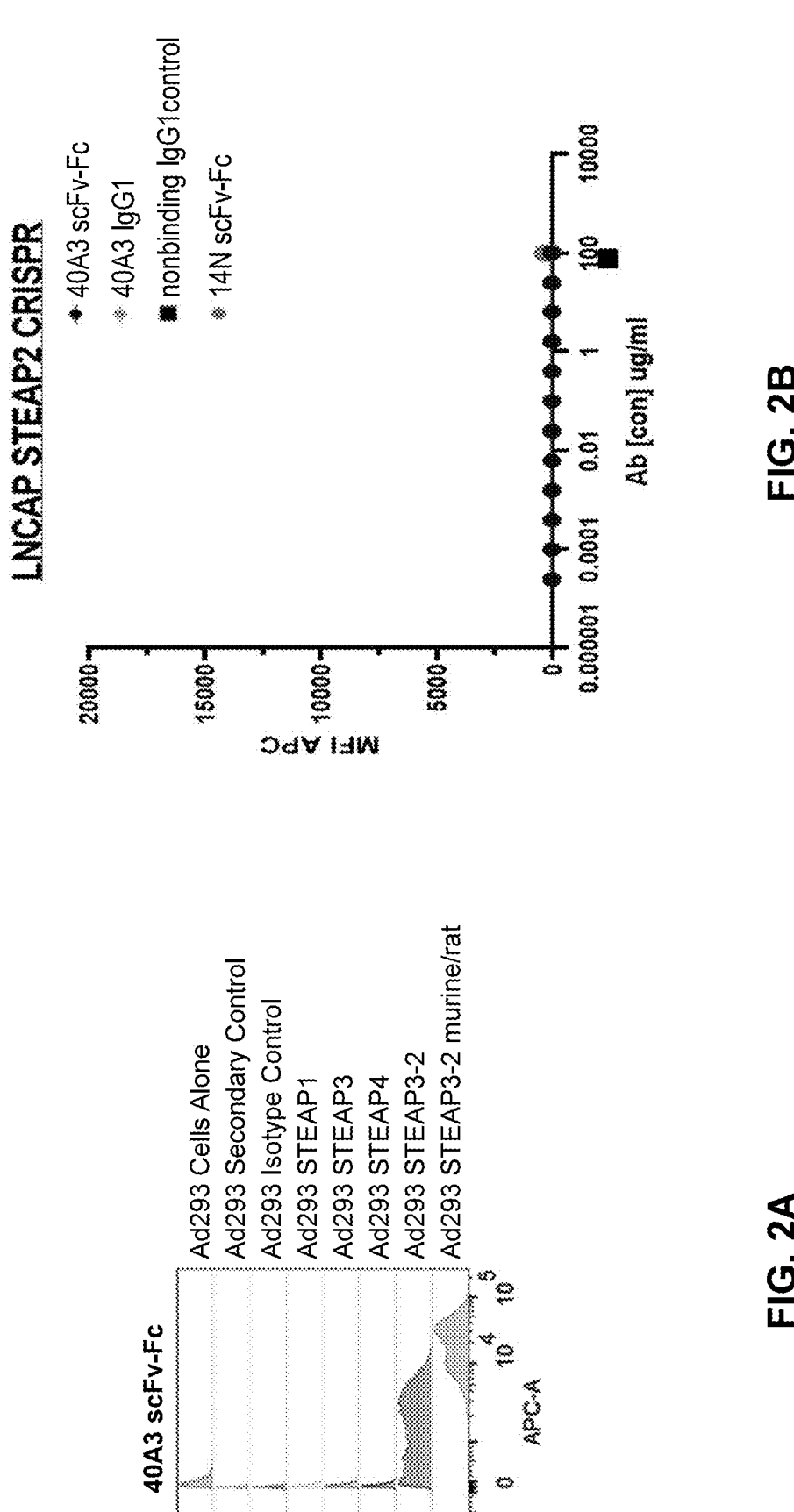
Figure 2C:
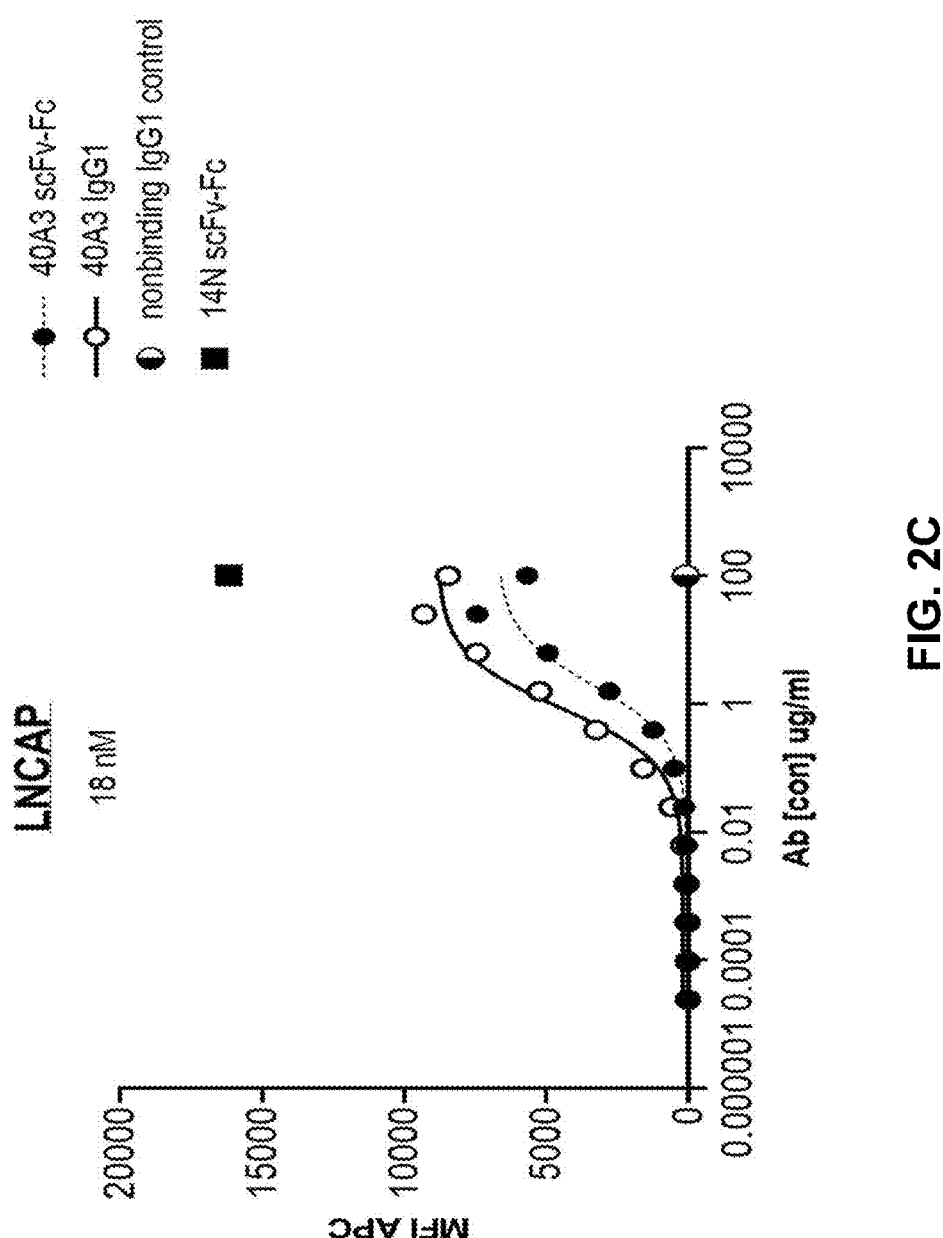
Figure 2D:
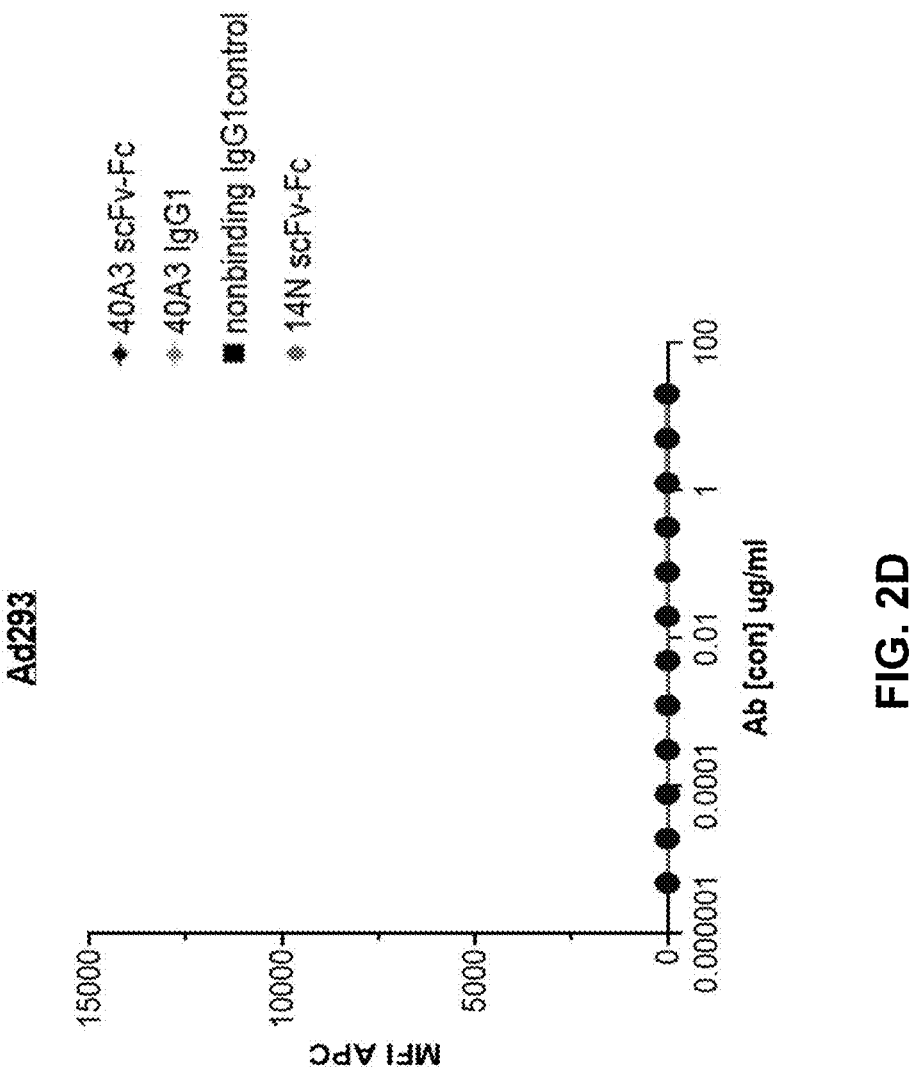
Figures 2E, 2F:
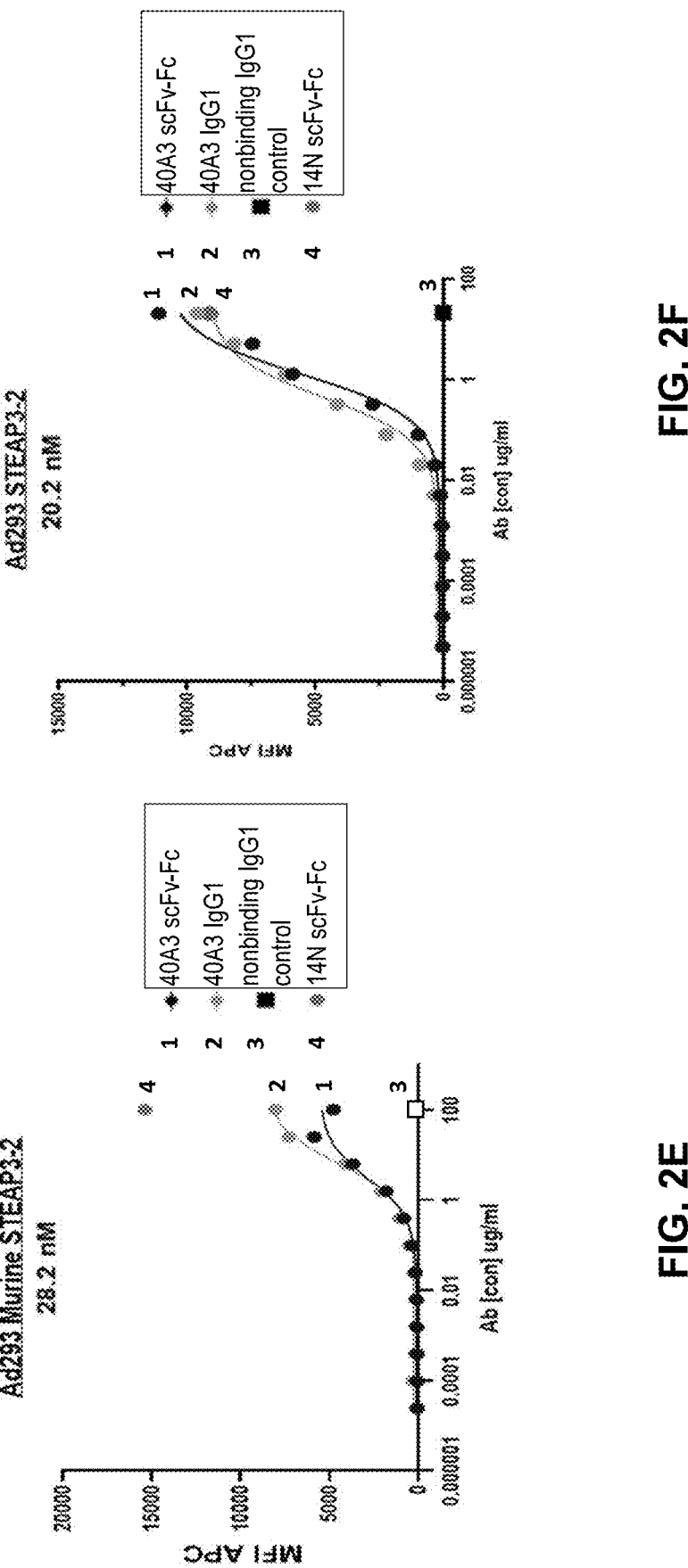

FIGS. 2A-2F. FIG. 2A shows that the 40A3 scFv-Fc was tested for binding to human STEAP family members (STEAP 1, 2, 3, and 4) and murine STEAP2. The 40A3 scFv-Fc affinity was calculated from the EC50 values on a sigmoidal dose response in Graph Pad Prism and converted to molarity. FIGS. 2B-2F show the results of multiple scFv-Fcs and full-length IgG1 antibodies screened for binding to antigen positive cell lines: Ad293 STEAP3-2 (FIG. 2F), Ad293 STEAP3-2 murine (FIG. 2E), and LNCAP (FIG. 2C) cells and antigen negative cell lines: Ad293 (FIG. 2D) and LNCAP STEAP2 CRISPR (FIG. 2B). STEAP2 expression in the LNCAP cell line "LNCAP STEAP2 CRISPR" has been eliminated via CRISPR knockout, and STEAP3-2 cells are a chimeric cell line with the STEAP2 extracellular loops grafted onto the backbone of the STEAP3 protein to exploit the cell surface localization of STEAP3, yet trigger the immune responses against STEAP2. FIGS. 2B-2F show binding curves for the 40A3 scFv-Fc, 40A3 IgG1, and 14N scFv, a known binder for STEAP2 as a positive control, as well as nonbinding IgG1 as a negative control. Alexa fluor 647 conjugated anti-human Fc secondary antibodies were used for detection of scFv-Fc or IgG1 binding to cells by flow cytometry.

Figure 3A:
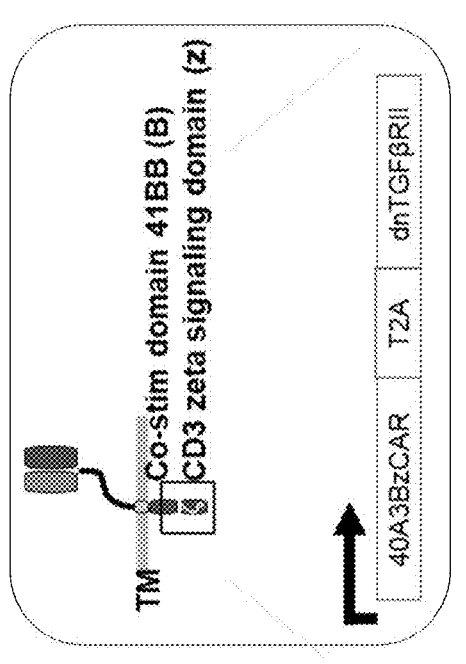
Figures 3B, 3C, 3D:
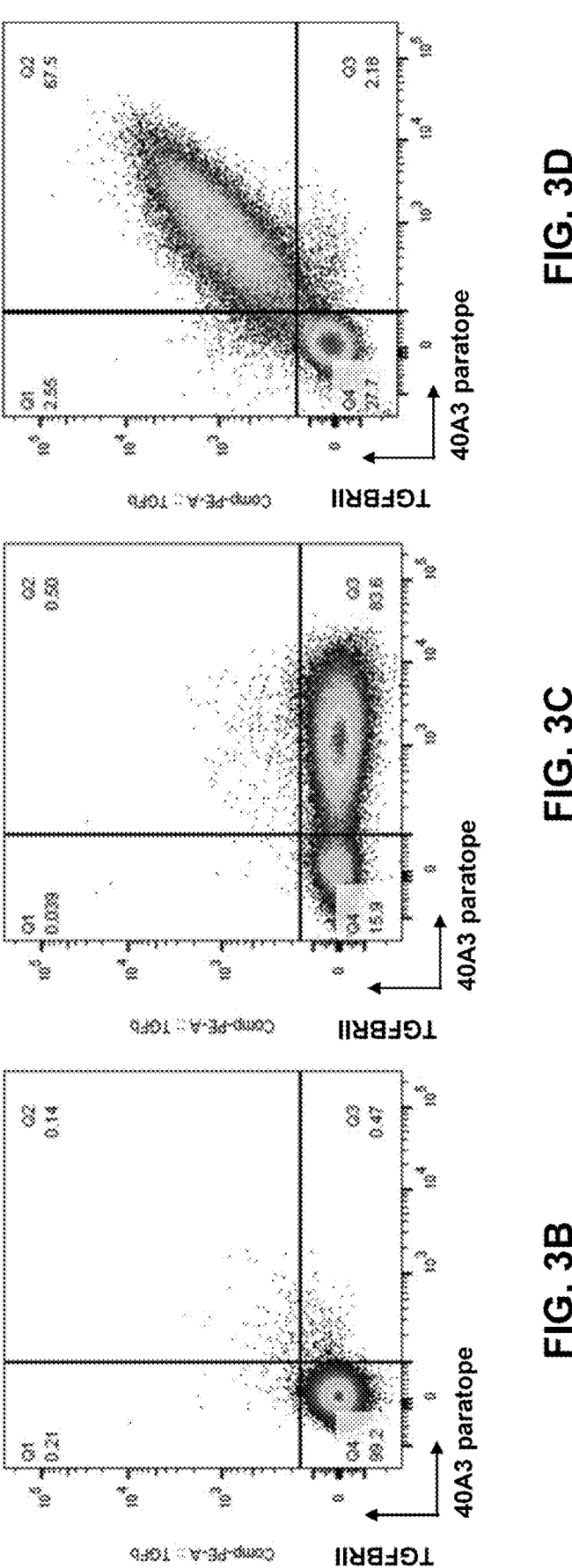
Figure 3E:
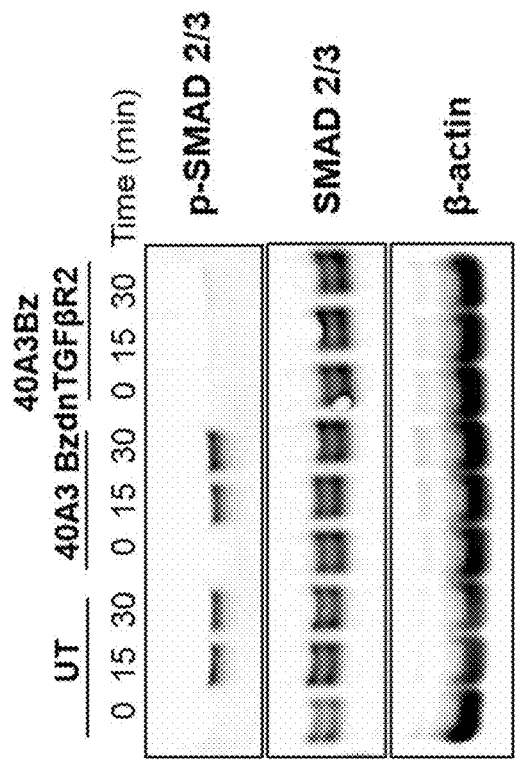

FIGS. 3A-3E. FIG. 3A shows the CAR design including armoring strategy. FIGS. 3B-3D show untransduced (FIG. 3B), 40A3Bz (FIG. 3C), and 40A3Bz dnTGFβRII (FIG. 3D) transduced cell populations at day 10. FIG. 3E shows a western blot of pSMAD 2/3 and total SMAD 2/3 as indicators of acute signaling downstream of the native TGFβRII in 40A3Bz and 40A3Bz dnTGFβRII CAR-T cells. A significant abrogation of TGFβ-mediated signaling in dnTGFβRII (40A3Bz) CAR-T cells compared to 40A3Bz CAR or Untransduced cells alone was confirmed (FIG. 3E).

Figure 4A:
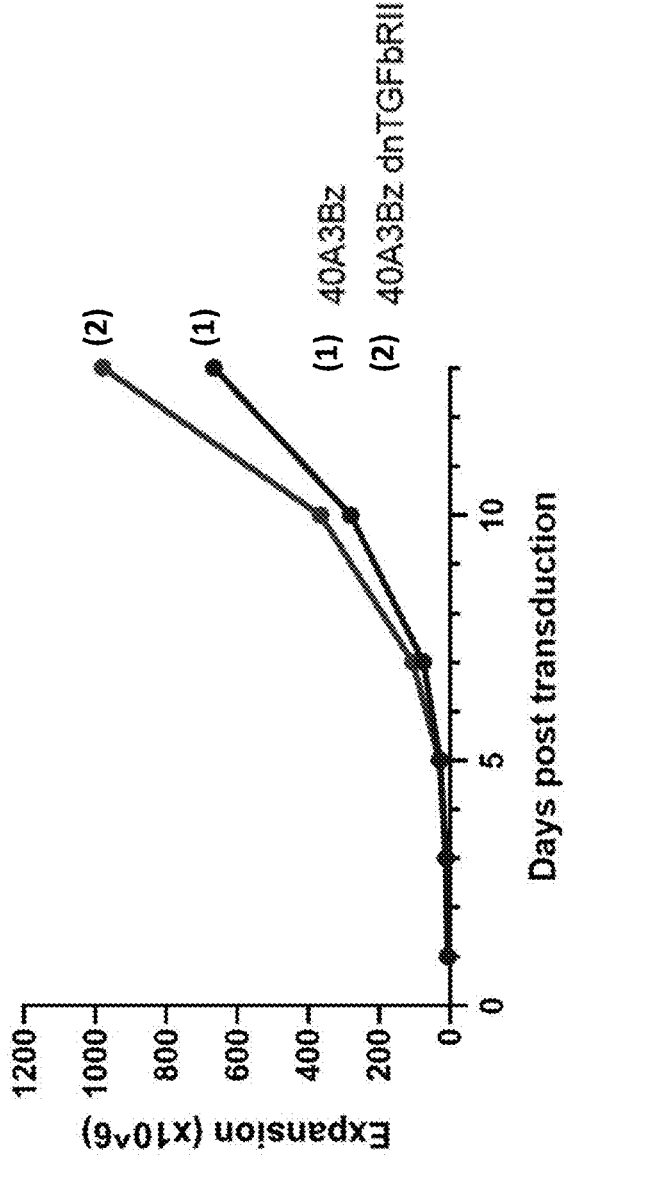
Figures 4B, 4C, 4D:
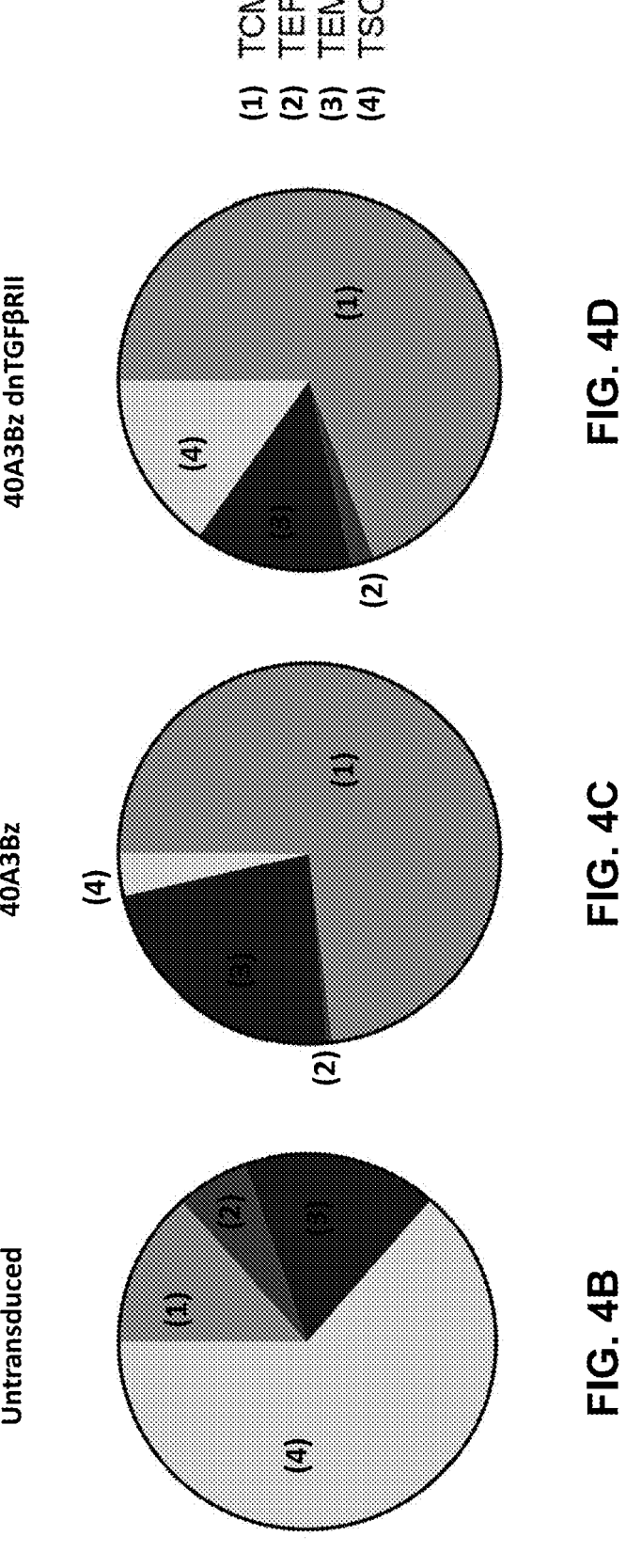
Figure 4E:
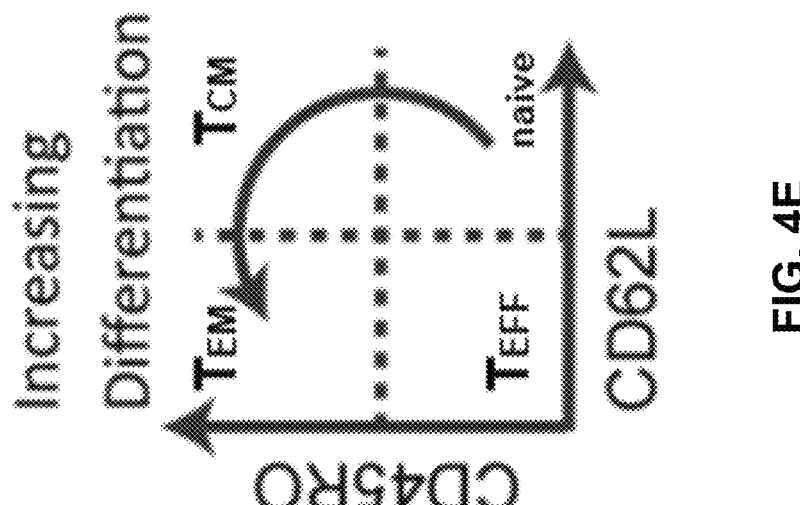
Figure 40:
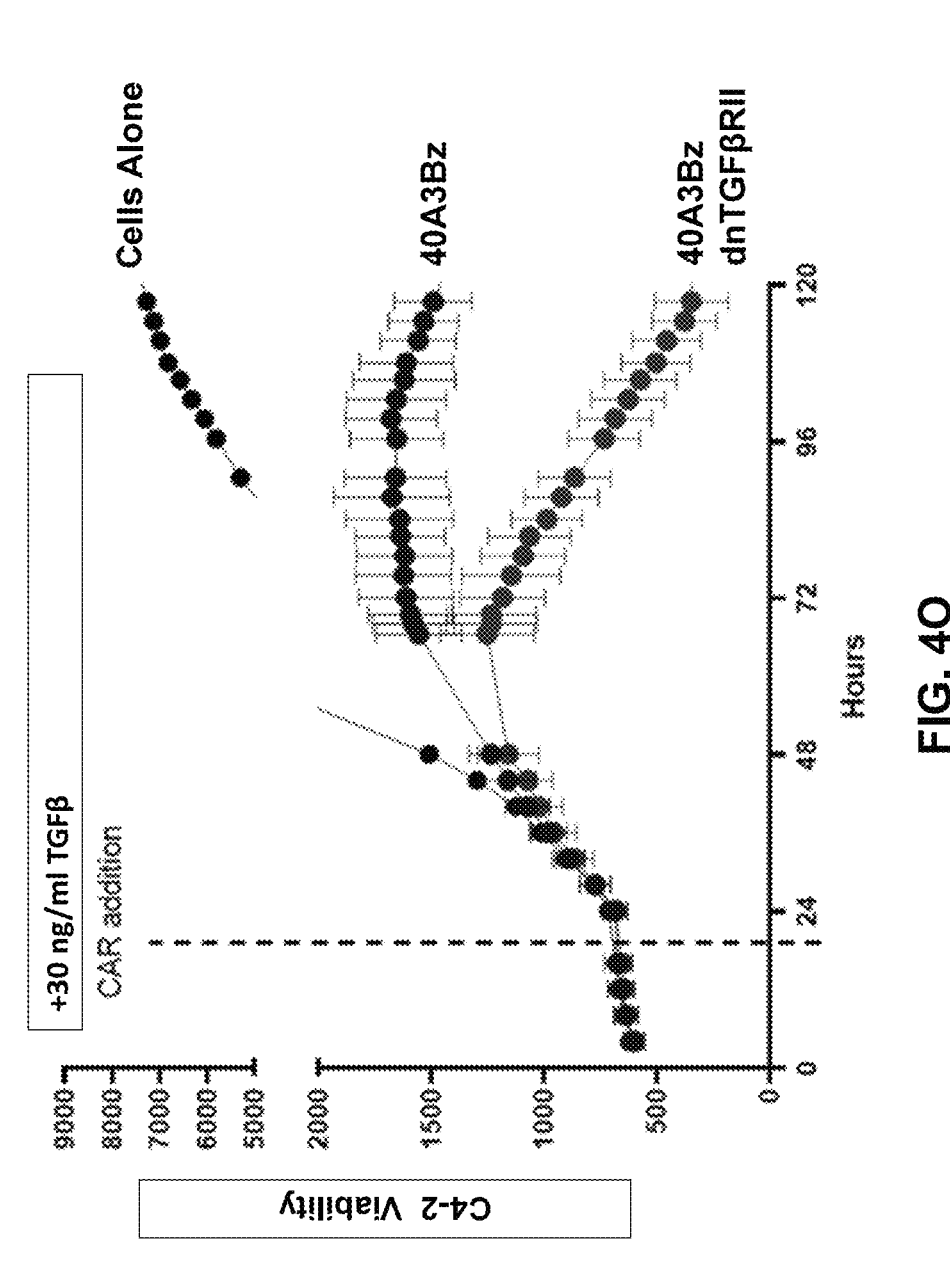
Figure 4P:
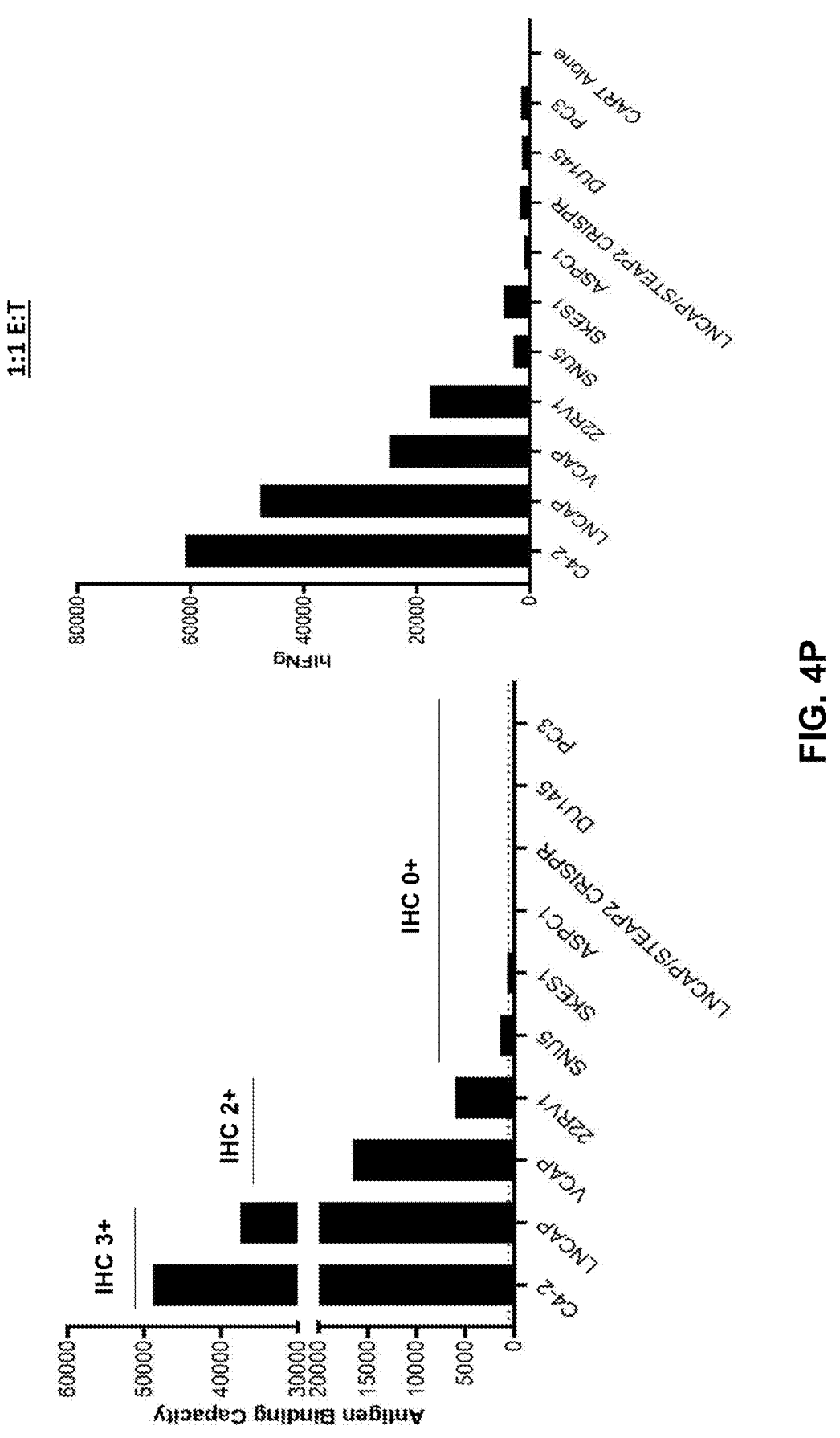

FIGS. 4A-4N. FIG. 4A shows robust CAR-T expansion after transformation. FIG. 4B-4E show that the CD8+ CAR-T cells maintain a Naïve/Stem-Like Phenotype. FIGS. 4F-4K show 40A3Bz STEAP2 CAR-T cells and 40A3Bz dnTGFβRII STEAP2 CAR-T cells from the same donor cells stained for phenotypic surface markers including CD45RO/CD62L/CD70/CD27 and analyzed using flow cytometry and FlowJo. Key=Naïve (CD45RO−CD62L+), Central memory (CD45RO+CD62L+), Effector Memory (CD45RO+CD62L−) and Effector (CD45RO−CD62L−). CAR=chimeric antigen receptor; dnTGFβRII=dominant-negative transforming growth factor beta receptor II; FACS=fluorescence-activated cell sorting; STEAP2=six transmembrane epithelial antigen of the prostate 2; TGFβ=transforming growth factor beta. FIGS. 4L-4N that 40A3Bz CAR-T and 40A3Bz dnTGFβRII CAR-T cells display a mixed CD4:CD8 ratio. FIG. 4O shows that dnTGFβRII armoring enables CAR-T activity in the presence of TGFβ as demonstrated by C4-2 tumor cell killing. FIG. 4P shows a range of tumor cell lines profiled by FACS with an anti-STEAP2 antibody-alexa fluor 647 conjugate for antibody binding capacity using the Bang's beads quantum simply cellular kit and assessment of STEAP2 cell surface IHC (FIG. 4P, left panel). The tumor cell lines were co-cultured with 40A3Bz dnTGFβRII CAR-T cells at an E:T ratio of 1:1 and the media analyzed at 24 hours for the levels of IFNγ released from the CAR T-cells. 40A3Bz dnTGFβRII CAR-T induced substantial IFNγ release in co-cultures with C4-2, LNCAP, VCAP, 22RV1 tumor cell lines (FIG. 4P, right panel).

Figure 5B:
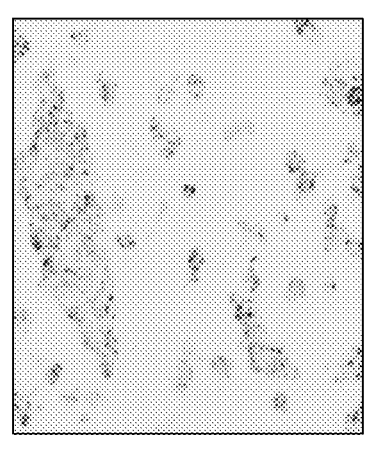
Figure 5A:
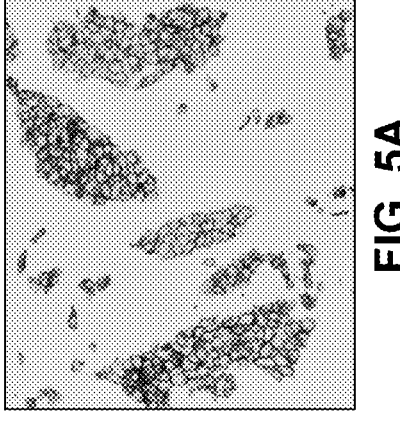
Figure 5C:
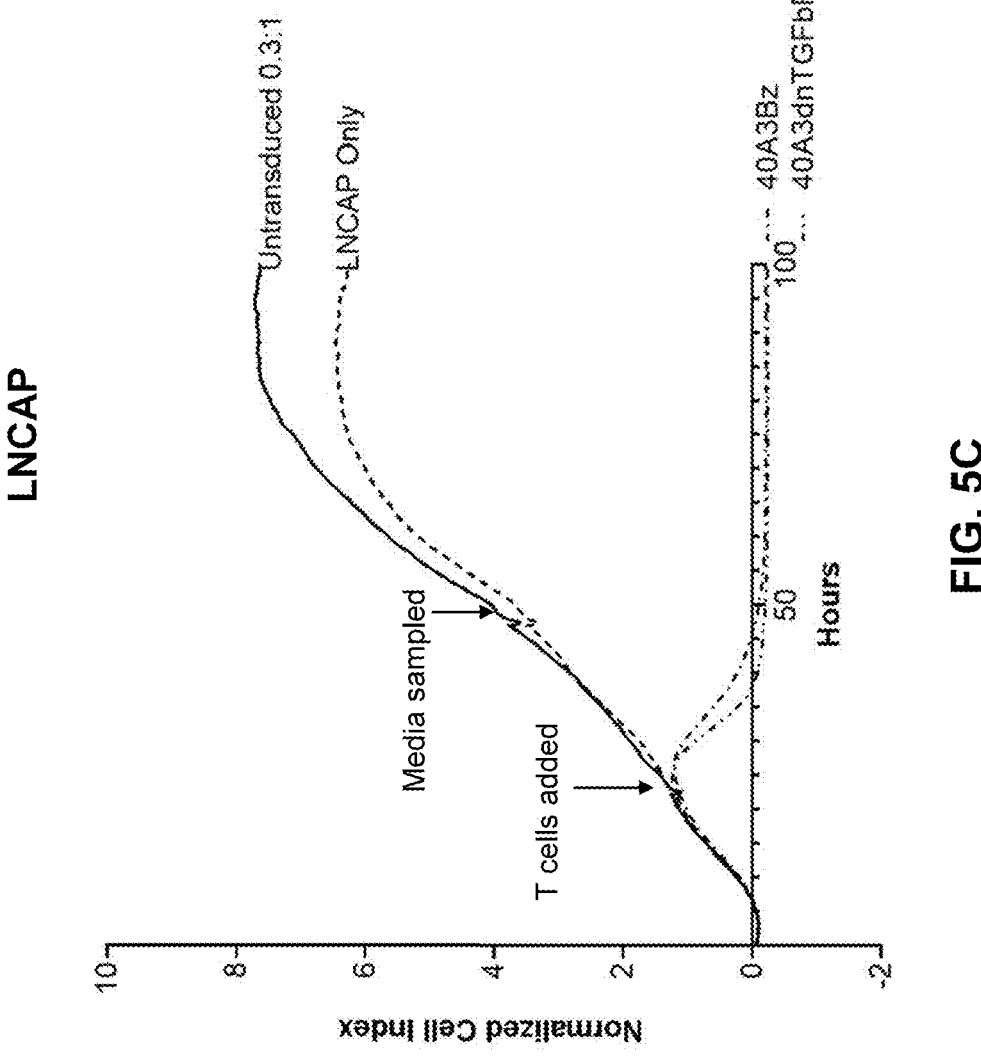
Figure 5E:
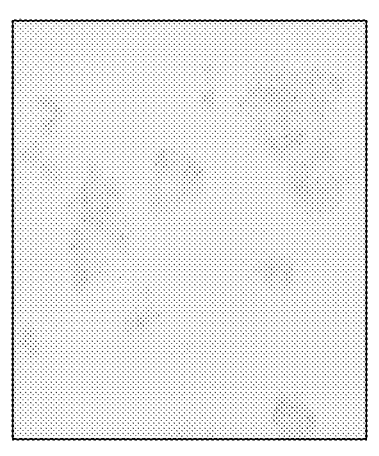
Figure 5D:
Figure 5F:
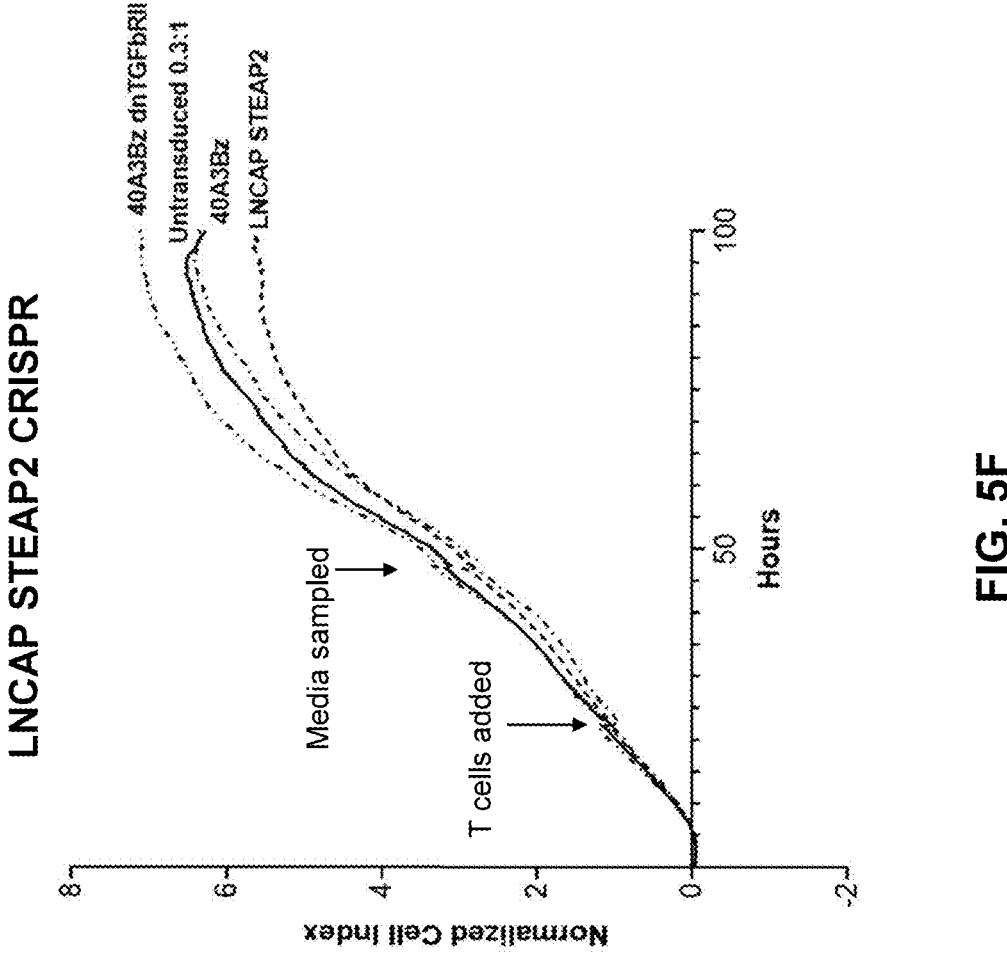
Figure 5G:
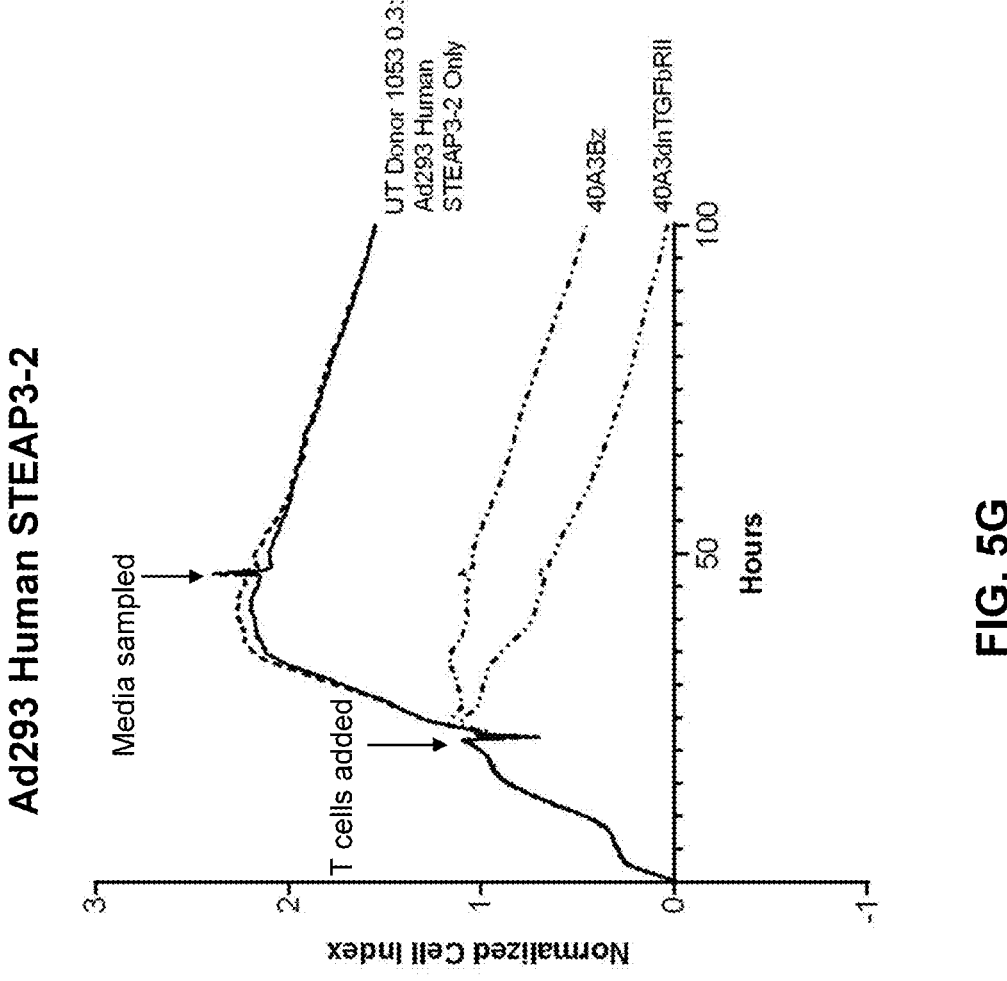
Figure 5H:
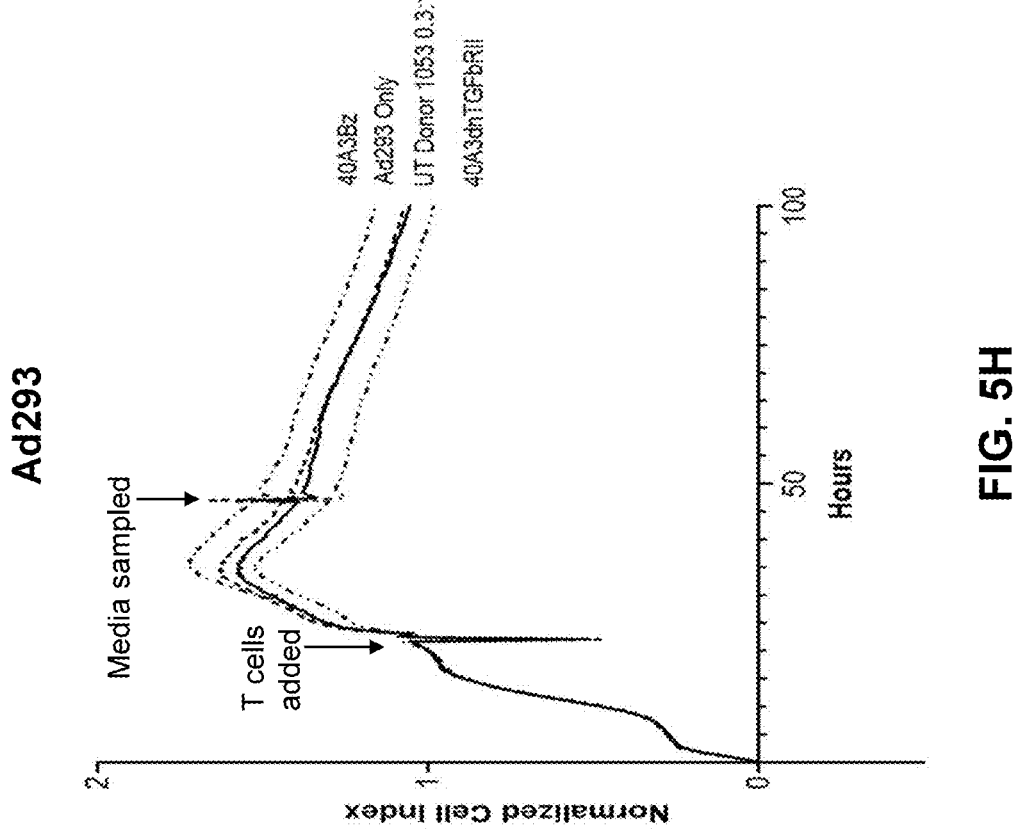
Figure 5I:
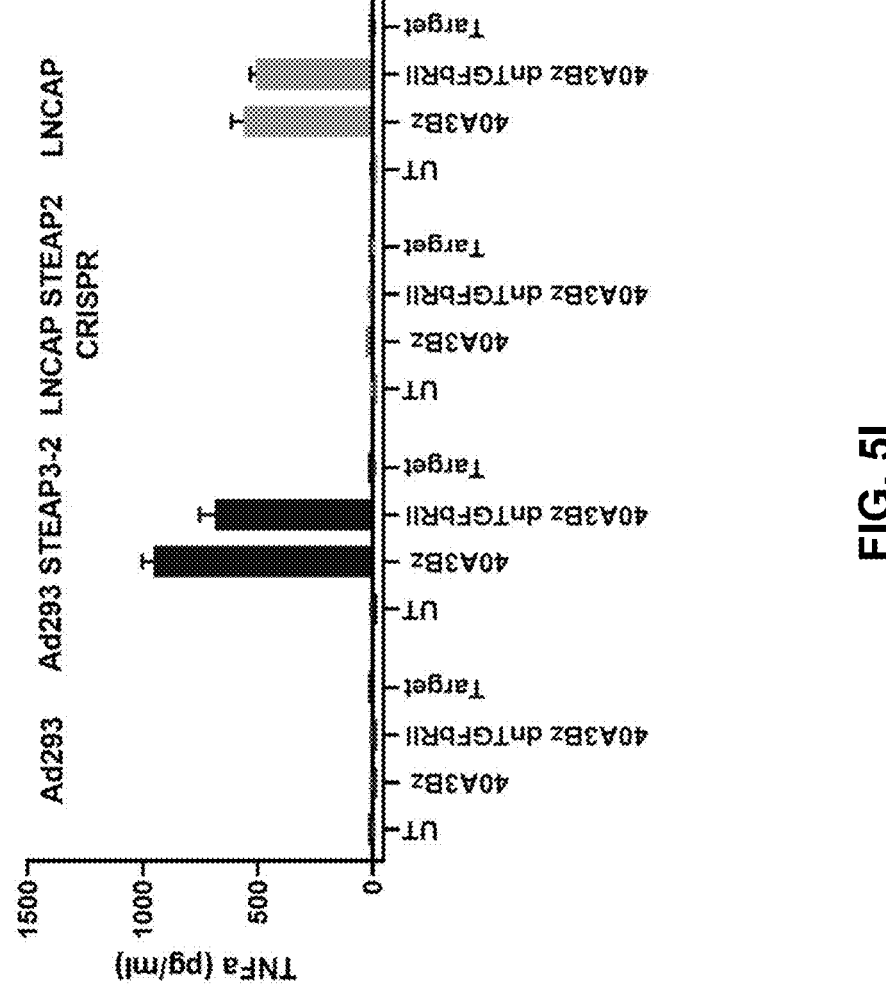
Figure 5J:
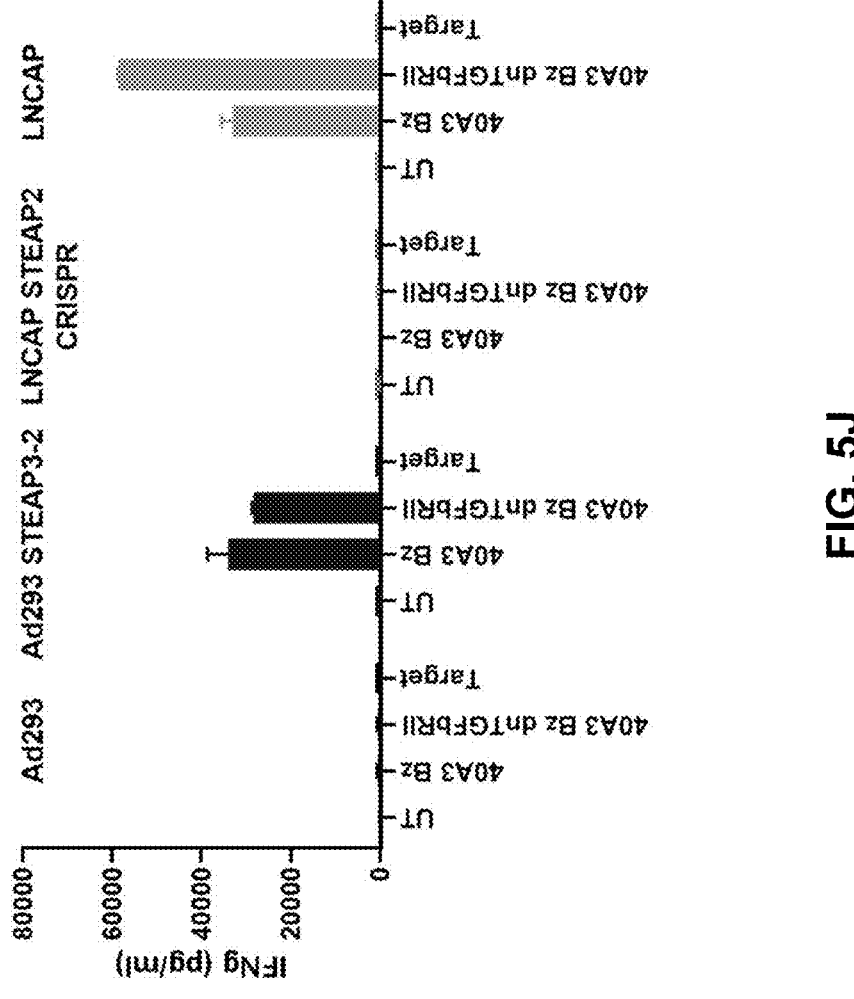
Figure 5K:
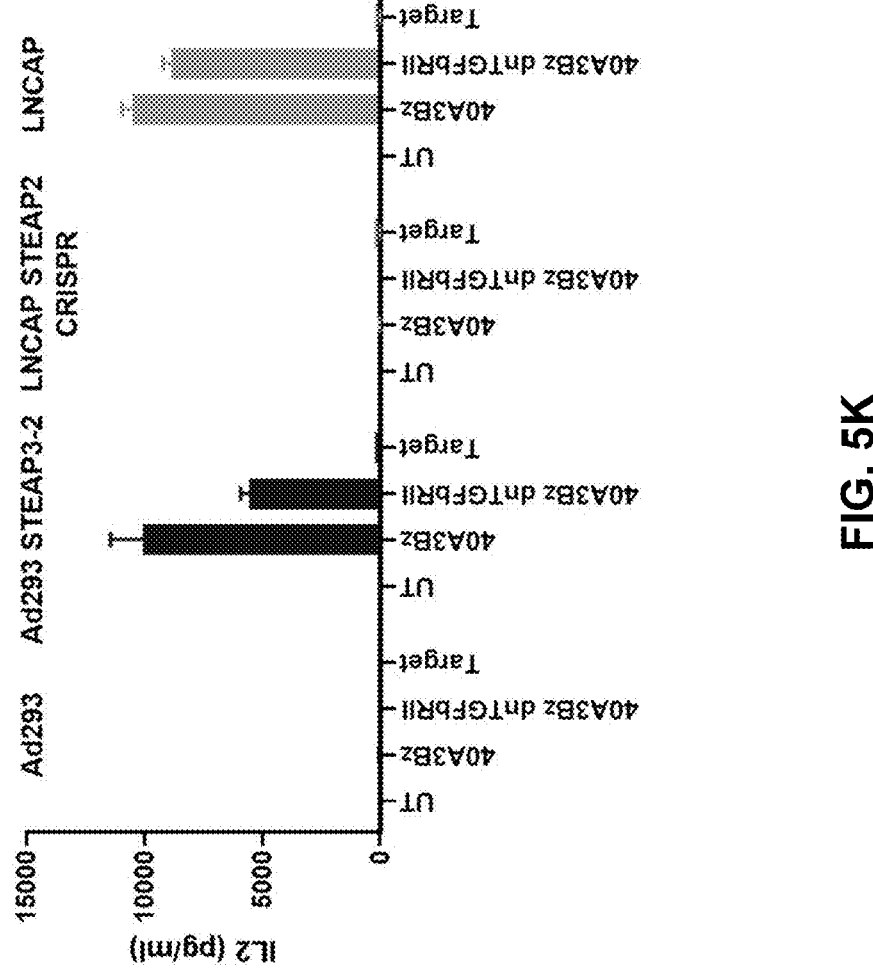

FIGS. 5A-5K. FIGS. 5A-5B and 5D-5E show STEAP2 expression in LNCAP STEAP2 CRISPR (FIGS. 5D-5E) and LNCAP (FIGS. 5A-5B) cellular populations as determined by IHC (FIGS. 5A and 5D) and ISH (FIGS. 5B and 5E). 40A3Bz STEAP2 CAR-T and 40A3Bz dnTGFβRII STEAP2 CAR-T cells were co-cultured with antigen-positive cell lines ("Ad293 STEAP3-2", and "LNCAP") and antigen-negative cell lines ("Ad293" cells and "LNCAP STEAP2 CRISPR" cells). Dominant-negative 40A3Bz TGFβRII STEAP2 CAR-T cells expanded in human T-cell media (AIM-V media supplemented with 5% Human AB Heat Inactivated Serum and 300 U/mL IL-2) for 10 days were shown to kill antigen-positive target cells in a similar fashion to unarmored STEAP2 CAR-T cells as shown for LNCAP (FIG. 5C) and Ad293 STEAP3-2 (FIG. 5G), in contrast to LNCAP STEAP2 CRISPR (FIG. 5F) and Ad293 cells (FIG. 5H). Killing of target cells was measured over 100 hours using an xCELLigence impedance assay. FIGS. 5I-5K show supernatants from the same co-culture experiments taken 24 hours post addition of CAR-T cells and cytokines (IFNγ, TNFα, and IL-2) measured using MSD ECL Assay: TNFα (FIG. 5I), IFNγ (FIG. 5J), IL-2 (FIG. 5K).

Figure 6:
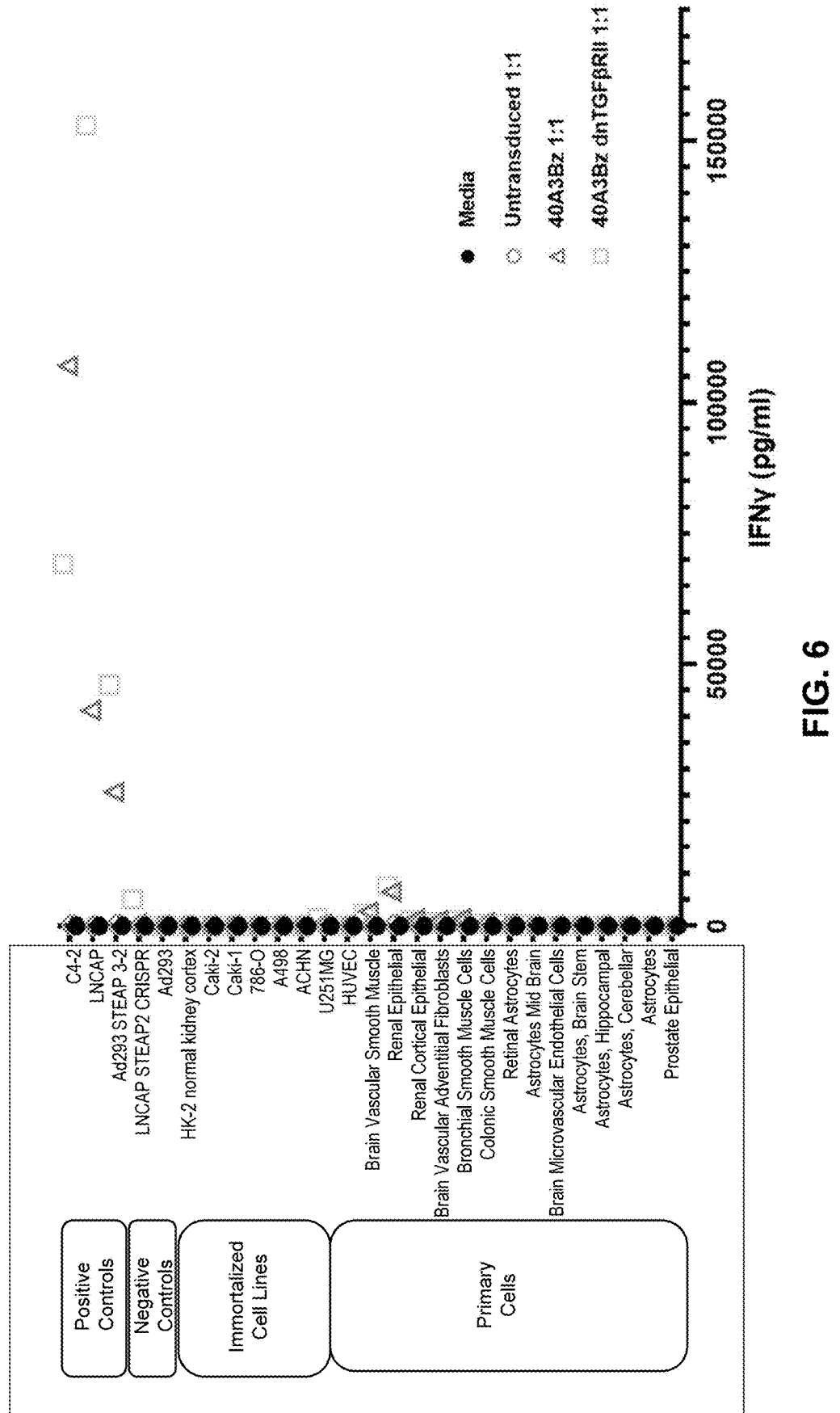

FIG. 6 shows that the tested STEAP2 CAR-T constructs demonstrate minimal on-target, off-tumor activity as evaluated through IFNγ secretion after 24 hours of coculture.

Figure 7K:
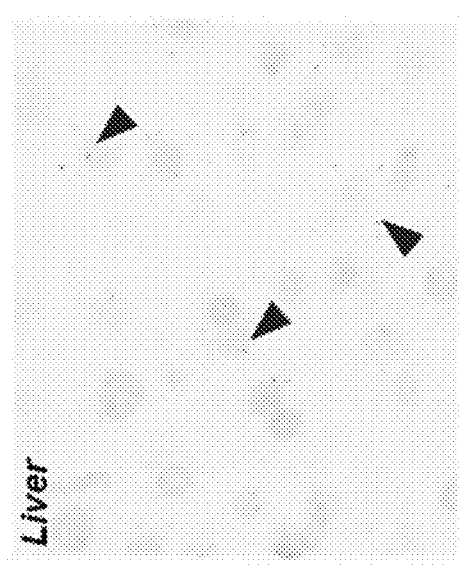
Figure 7J:
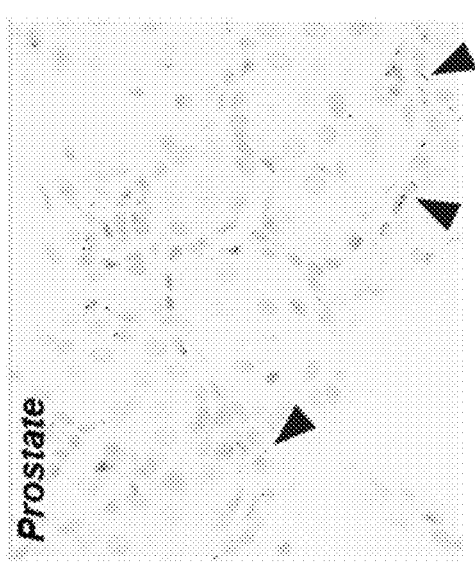
Figure 7I:
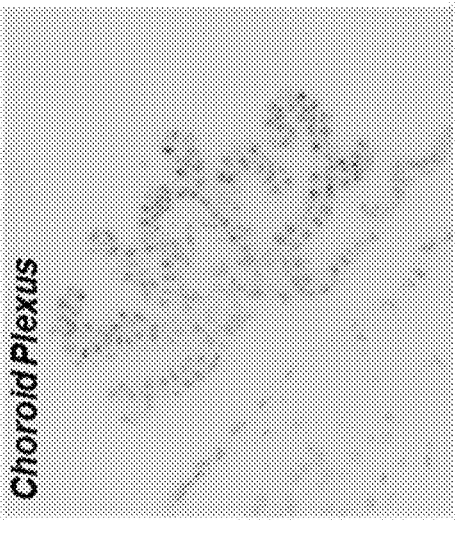
Figures 7L, 7M, 7N, 7O:
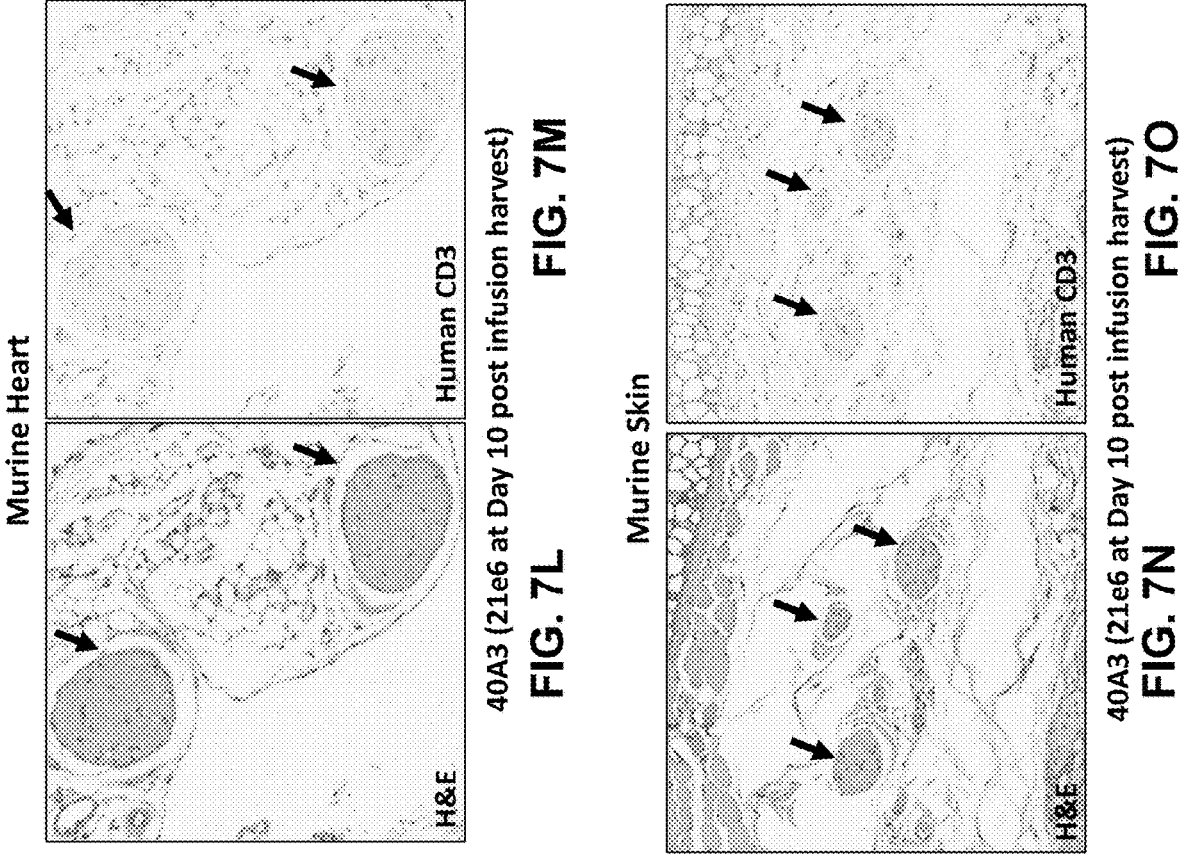
Figures 7P, 7Q, 7R:
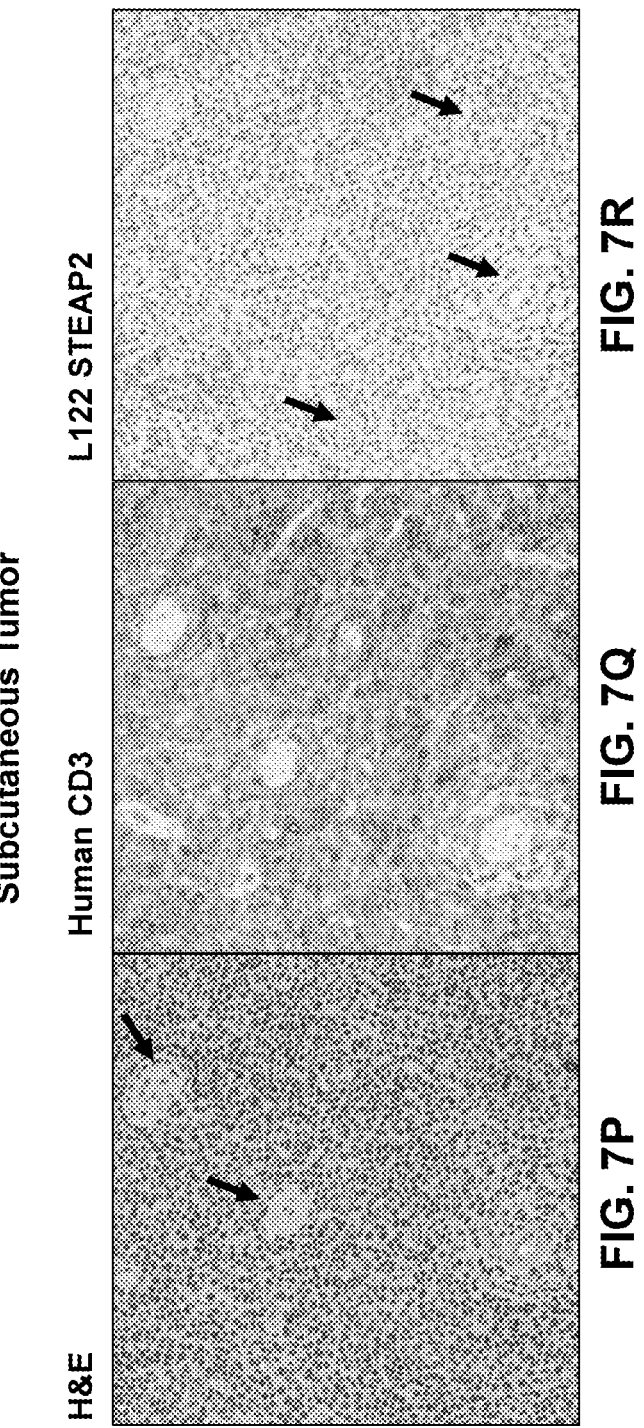

FIGS. 7A-7R. FIGS. 7A-7C show in vivo results where unarmored STEAP2 CAR-T cells were administered at 3 dose levels ($3/7/21 \times 10^6$ cells) via tail vein injection into NSG mice engrafted with prostate cancer cell lines. Tumors were implanted 1:1 in Cultrex BME on the flank. Tumor volume (FIG. 7A) was measured for 35 days post implantation in mice bearing the STEAP2 high expressing cell line C4-2. Mice were randomized when tumors reached 175 $mm^3$ and T cells were administered. Body weight (FIG. 7B) of the mice was measured up to Day 28 post transplantation with the C4-2 cell line. FIG. 7C shows STEAP2 expression as determined by IHC in the C4-2 model. FIGS. 7D-7F show tumor volume measured (FIG. 7D) for 53 days post implantation in mice bearing the cell line 22RV1 with intermediate STEAP2 expression. Mice were randomized when tumors reached 175 $mm^3$ and T cells were administered. Body weight (FIG. 7E) of the mice was measured up to Day 50 post transplantation with the 22RV1 cell line. FIG. 7F shows STEAP2 expression as determined by IHC in the 22RV1 xenograft model. FIG. 7G shows results where 22RV1 tumor bearing mice were bled at Days 4, 7, 14, and 21 post dosing with CAR-T cells. Sera samples were run using an Electrochemiluminescence (ECL) Assay to evaluate cytokine production over time in vivo. FIG. 7H shows a Genevestigator analysis of 40A3Bz murine biodistribution. FIGS. 7I-7K show STEAP2 expression 10 days post infusion as evaluated via ISH, with dose dependent focal infiltration and no signs of damage. FIGS. 7L-7M show no evidence of CD3+ CAR-T infiltration into nerves at the base of heart ($21e^6$ cell dose at Day 10 post infusion harvest). FIGS. 7N-7O show no evidence of CD3+ CAR-T infiltration into peripheral subcutaneous nerves ($21e^6$ cell dose at Day 10 post infusion harvest). FIGS. 7P-7R show subcutaneous tumor sample analysis after 40A3 CAR-T cells were administered at a concentration of $8e^6$ and evaluated at day 14 post infusion harvest. Two small intact and non-infiltrated peripheral nerves entrapped within the dense CAR-T infiltrate are seen (FIG. 7P, arrows). Also present are several small blood vessels with minimal to mild STEAP2 staining (FIG. 7R, arrows). Despite very dense CD3+ CAR-T infiltrate, the nerves are intact and do not appear to be affected (FIG. 7Q).

Figure 8A:
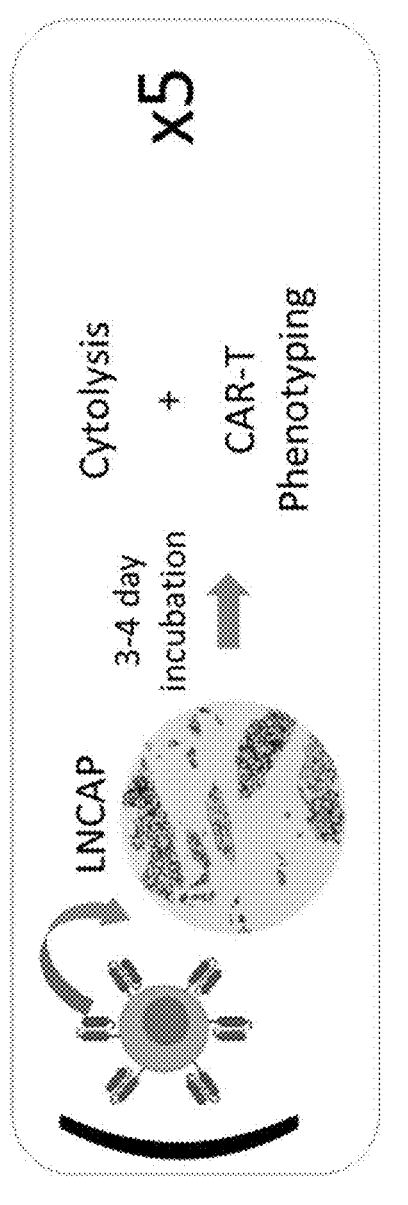
Figure 8B:
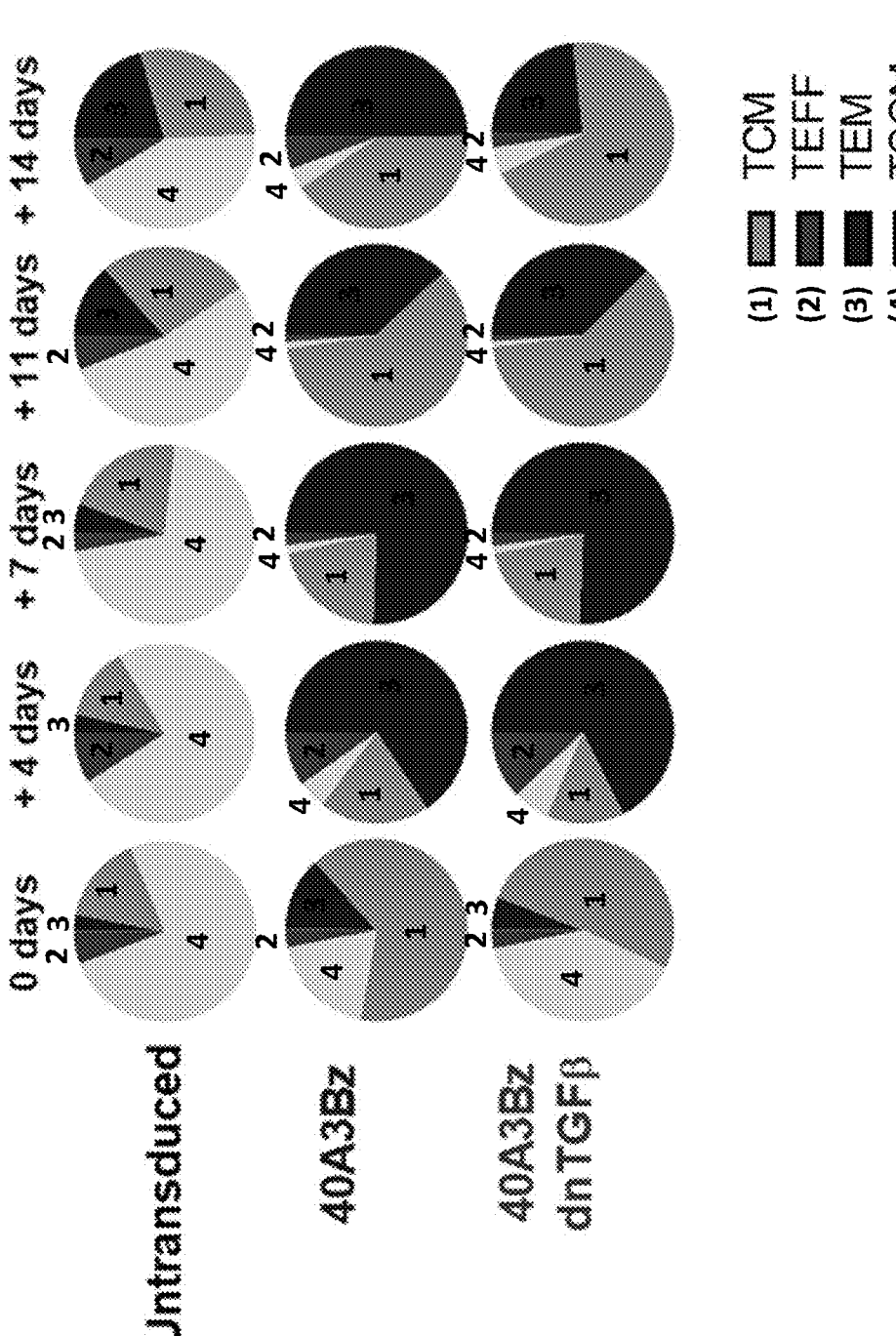
Figure 8D:
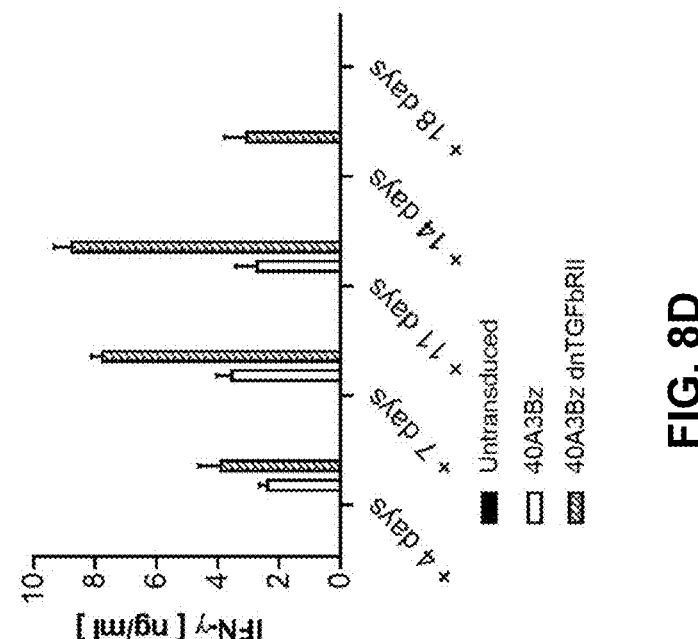
Figure 8C:
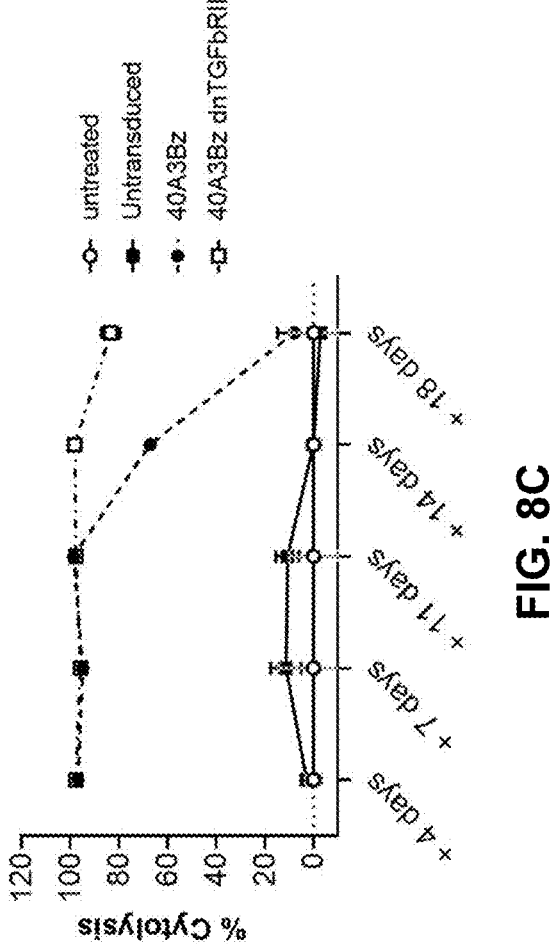
Figure 8E:
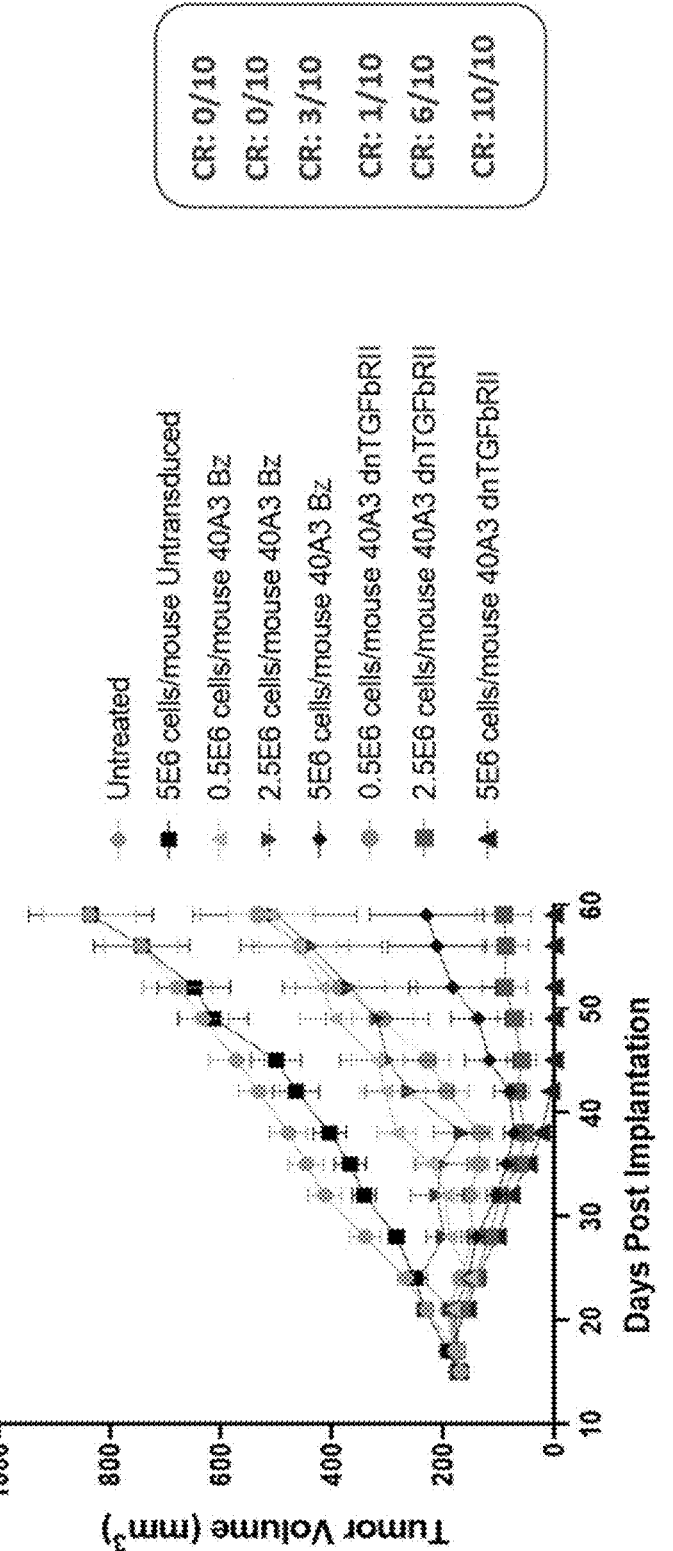
Figure 8F:
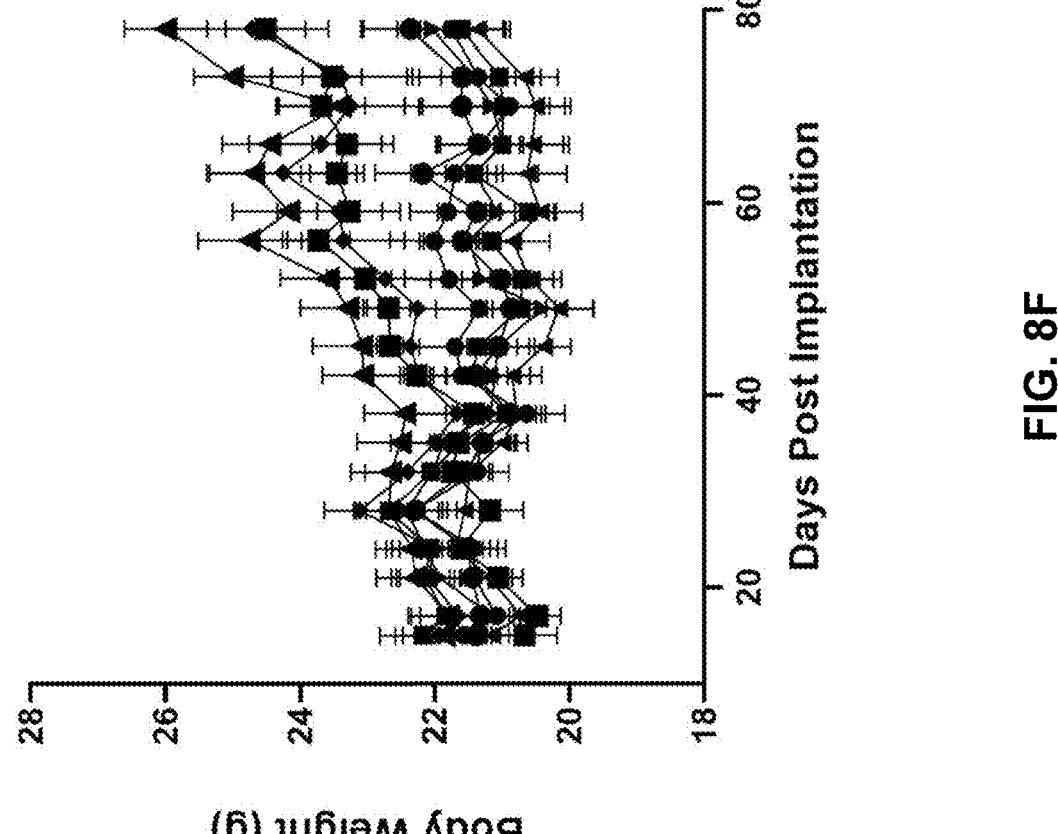
Figure 8G:
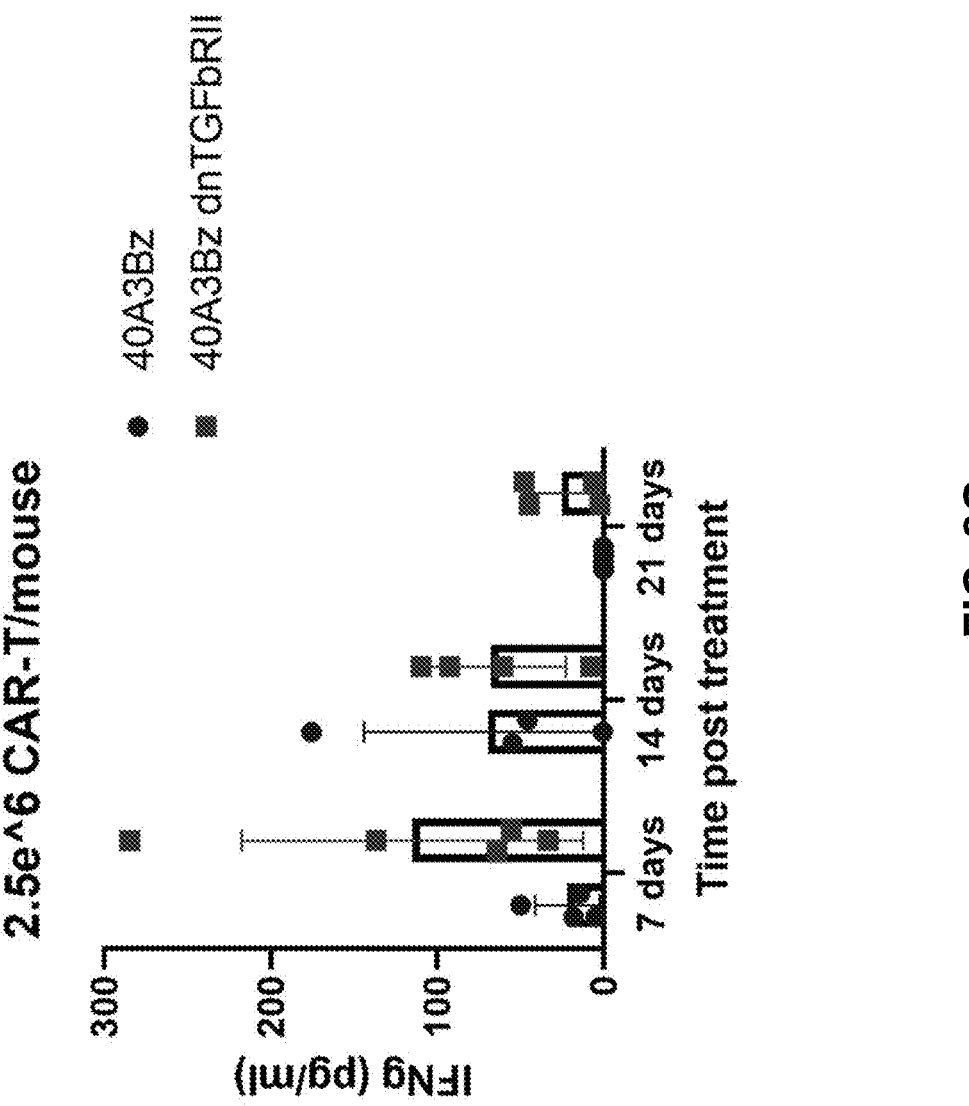
Figure 8H:
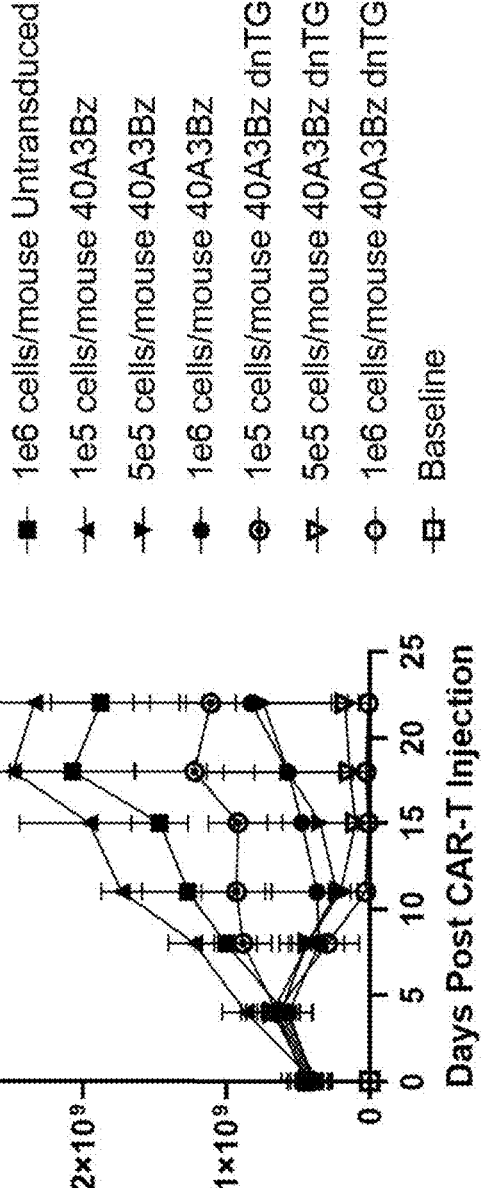

FIGS. 8A-8F show that STEAP2 armored CAR-T cells demonstrate superior persistence and differentiation profiles, including with respect to cytolysis and IFN-γ production. FIG. 8A shows a schematic of five rounds of serial killing. FIG. 8B shows phenotypes of T cells following treatment with 40A3Bz dnTGFβRII armored, 40A3Bz unarmored CAR-T cells and control T cells. FIG. 8C shows cytolytic activity of 40A3Bz dnTGFβRII armored, 40A3Bz unarmored CAR-T cells and control T cells. FIG. 8D shows cytokine release of 40A3Bz dnTGFβRII armored, 40A3Bz unarmored CAR-T cells and control T cells FIG. 8E shows tumor volumes and FIG. 8F shows body weight of mice treated with 40A3Bz dnTGFβRII armored, 40A3Bz unarmored CAR-T and control T cells. FIG. 8G shows cytokine release in mice treated with 2.5 e^6 40A3Bz dnTGFβRII armored, 40A3B unarmored CAR-T cells and control T cells per mouse. FIG. 8H shows fluorescent signals in mice implanted with C4-2 luciferase expressing tumor cells and treated with untransduced T cells, 40A3Bz dnTGFβRII armored CAR-T cells, or 40A3Bz unarmored CAR-T cells. FIG. 8I shows body weight of the mice measured up to Day 22 post transplantation with the luciferase expressing C4-2 cells.

Figure 9A:
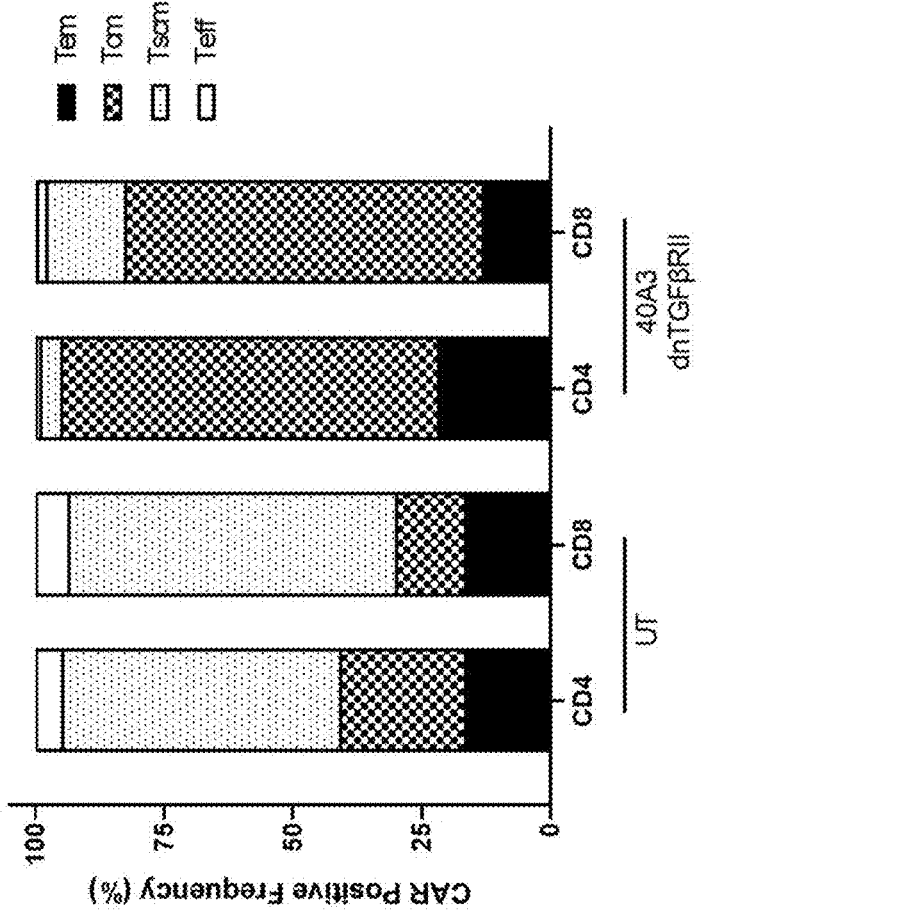
Figure 9C:
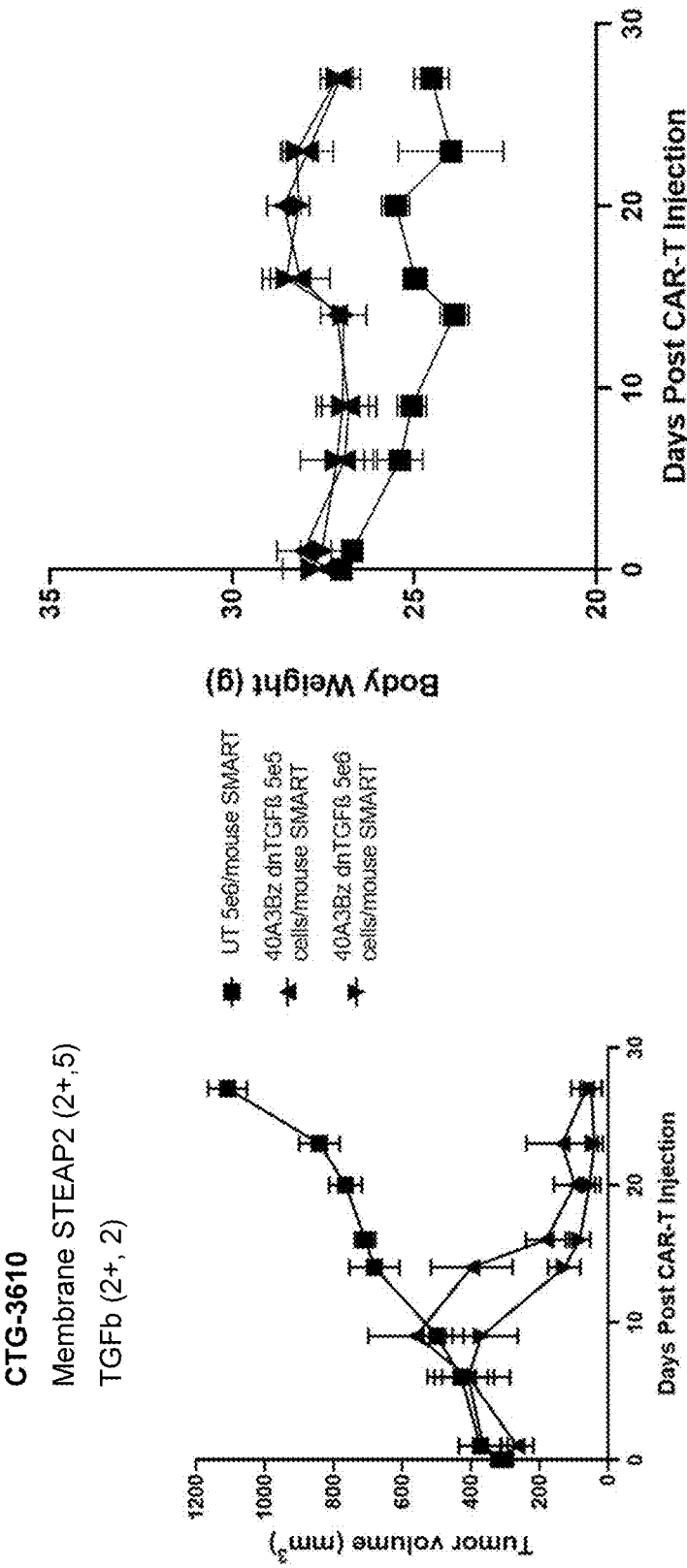
Figure 9D:
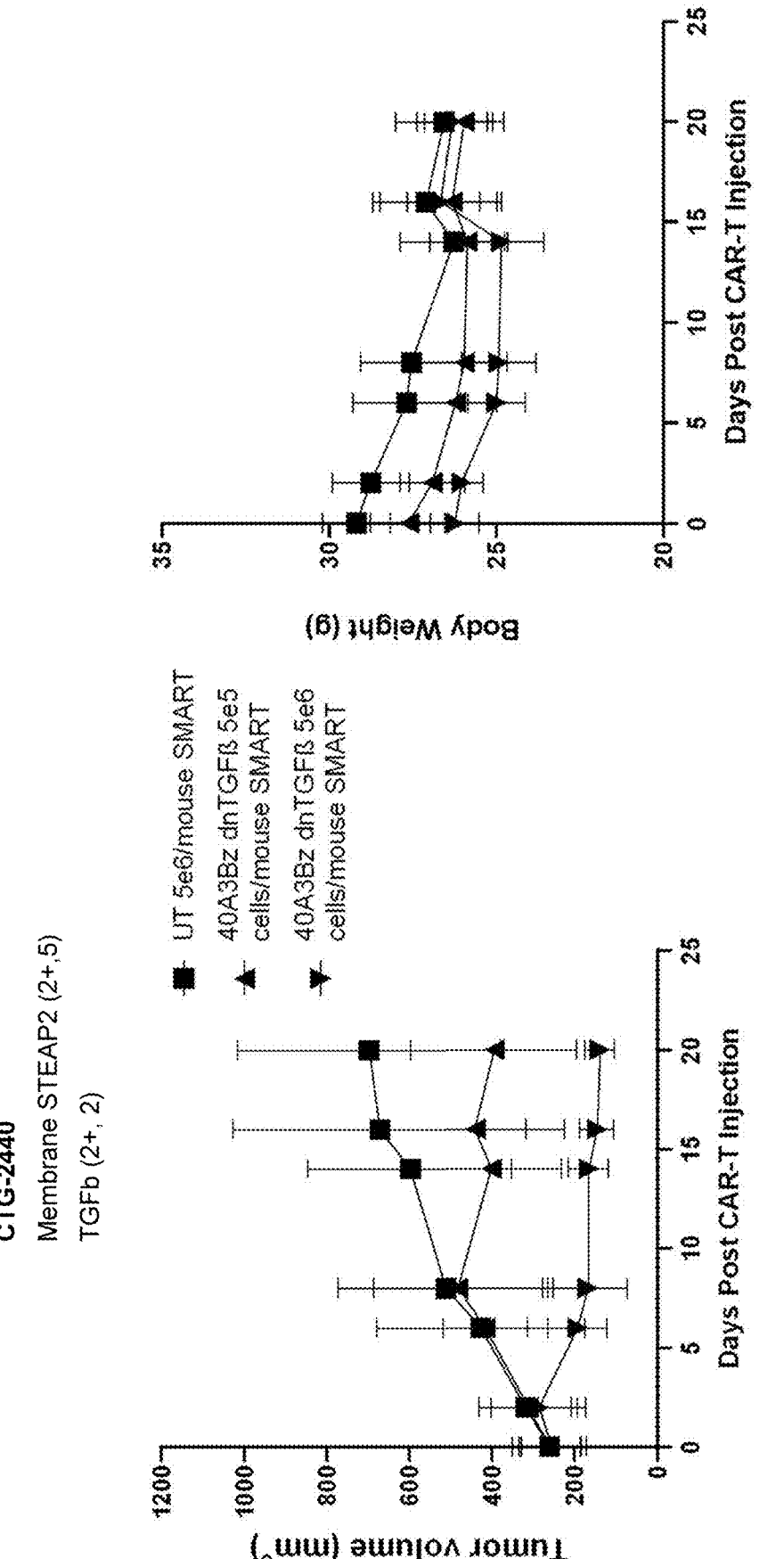
Figure 9E:
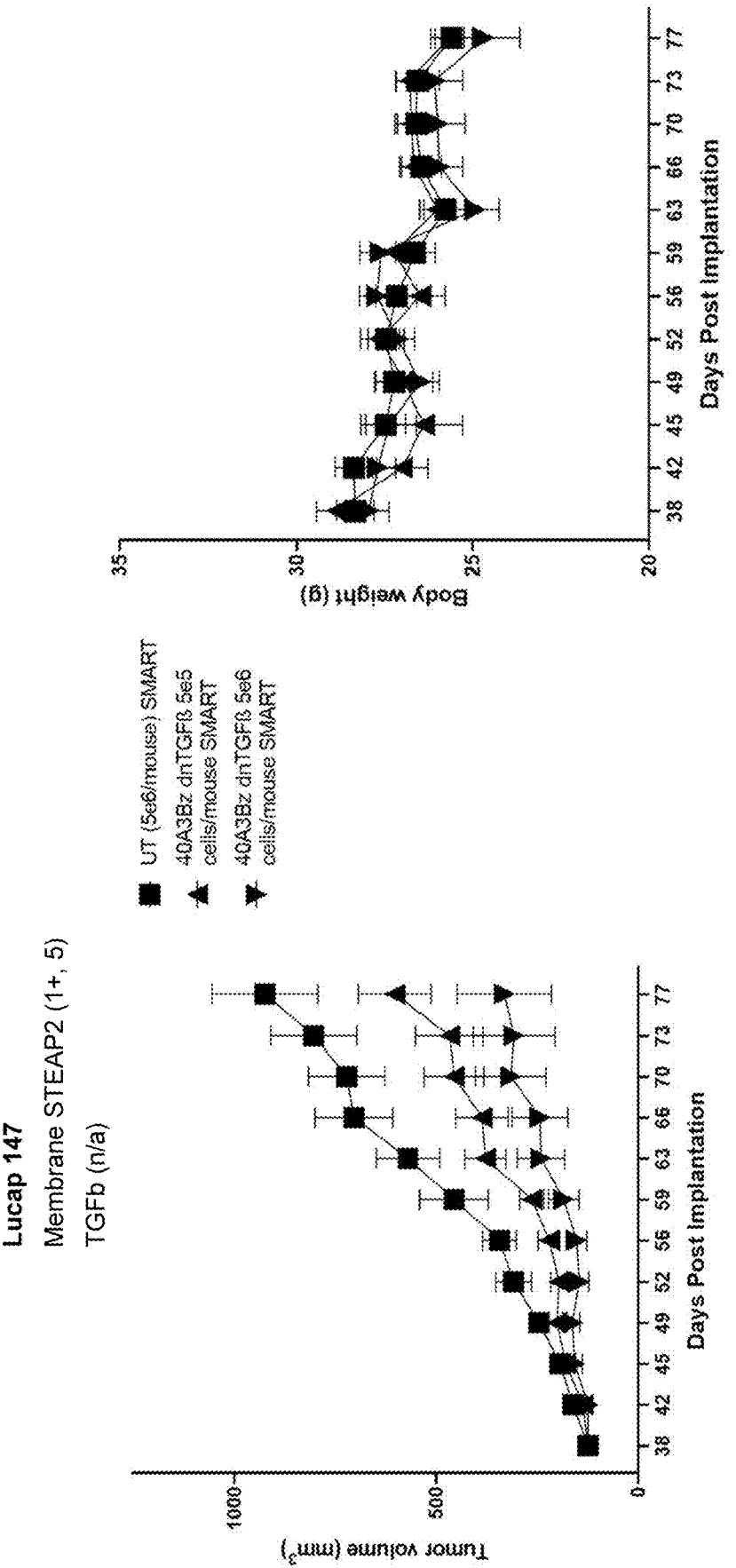
Figure 9F:
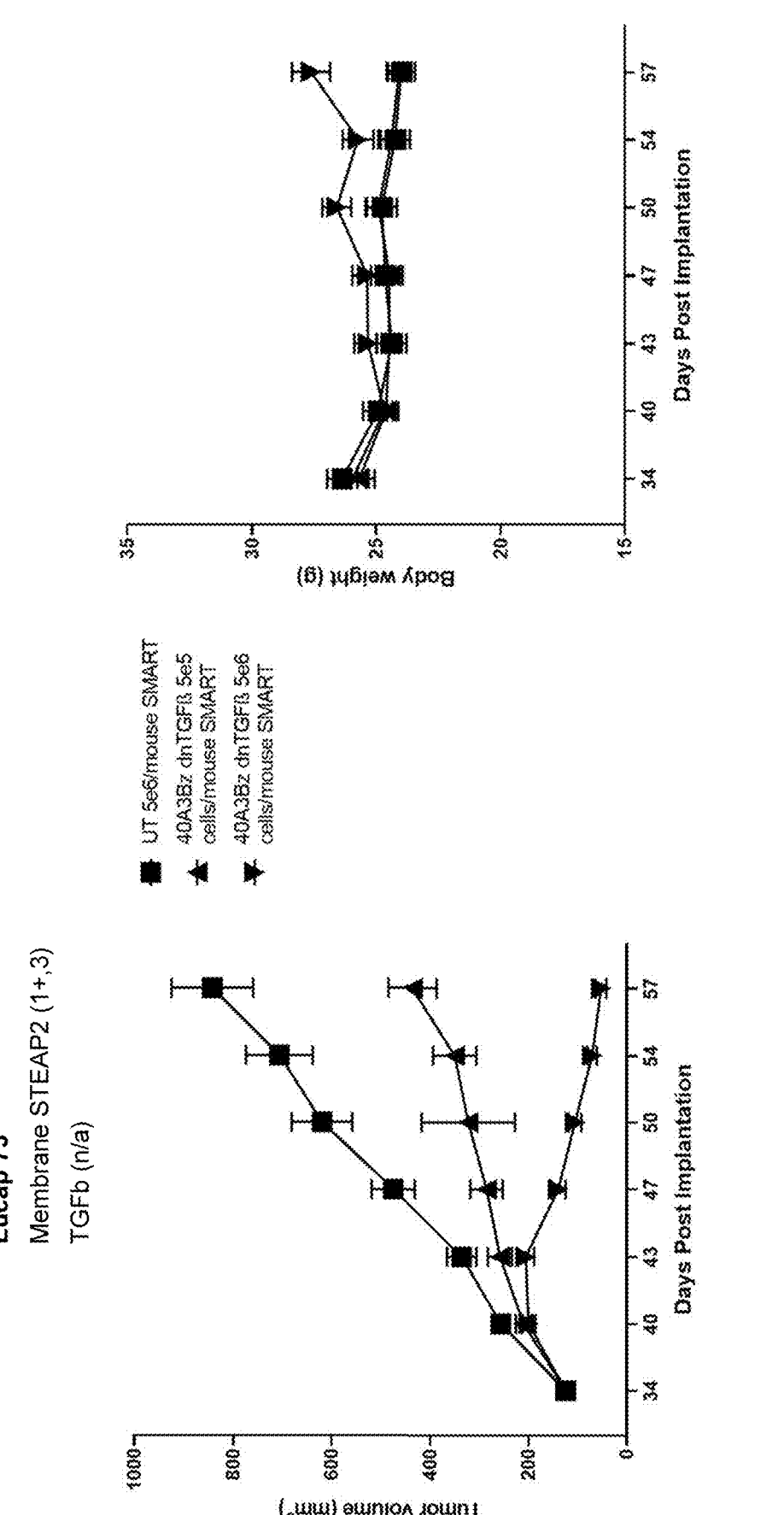

FIG. 9A-9C show that enhanced CAR-T manufacturing augments anti-tumor activity. FIG. 9A shows 40A3Bz dnTGFβRII CAR-T cells manufactured according to the SMART process and phenotyped at expansion Day 4 as compared to untransduced T cells (UT) from the same donor. FIG. 9B shows tumor volume (top) and body weight (bottom) measured out to 50 days post implantation of 22Rv1 tumor cells overexpressing TGFβ into NSG MHC class 1 class 2 knockout mice treated with 40A3Bz dnTGFβRII SMART CAR-T cells dosed at 4 concentrations (0.3, 1, 3, 6×e6 CAR positive cells). FIG. 9C shows tumor volume (top) and body weight (bottom) of NSG class 1 class 2 knockout mice implanted with PDX fragments from frozen stocks of CTG-3610 prostate cancer cells, randomized when tumor volumes ranged from 125-250 $mm^3$ and dosed as in B with 0.5e6 or 5e6 40A3Bz dnTGFβRII SMART CAR-T cells compared to 5e6 UT SMART controls. The IHC intensity and proportion scores for membrane STEAP2 and TGFβ of the CTG-3610 tumor cells are displayed. FIG. 9D shows tumor volume (top) and body weight (bottom) of NSG class 1 class 2 knockout mice implanted with PDX fragments from frozen stocks of CTG-2440 prostate cancer cells, randomized when tumor volumes ranged from 125-250 $mm^3$ and dosed as in B with 0.5e6 or 5e6 40A3Bz dnTGFβRII SMART CAR-T cells compared to 5e6 UT SMART controls. The IHC intensity and proportion scores for membrane STEAP2 and TGFβ of the CTG-2440 cells are displayed. FIG. 9E shows tumor volume (top) and body weight (bottom) of NSG class 1 class 2 knockout mice implanted with PDX fragments from frozen stocks of Lucap 147 prostate cancer cells, randomized when tumor volumes ranged from 125-250 $mm^3$ and dosed as in B with 0.5e6 or 5e6 40A3Bz dnTGFβRII SMART CAR-T cells compared to 5e6 UT SMART controls. The IHC intensity and proportion scores for membrane STEAP2 and TGFβ of Lucap 147 cells are displayed. FIG. 9F shows tumor volume (top) and body weight (bottom) of NSG class 1 class 2 knockout mice implanted with PDX fragments from frozen stocks of Lucap 73 prostate cancer cells, randomized when tumor volumes ranged from 125-250 $mm^3$ and dosed as in B with 0.5e6 or 5e6 40A3Bz dnTGFβRII SMART CAR-T cells compared to 5e6 UT SMART controls. The IHC intensity and proportion scores for membrane STEAP2 and TGFβ of Lucap 73 cells are displayed.

Figure 10A:
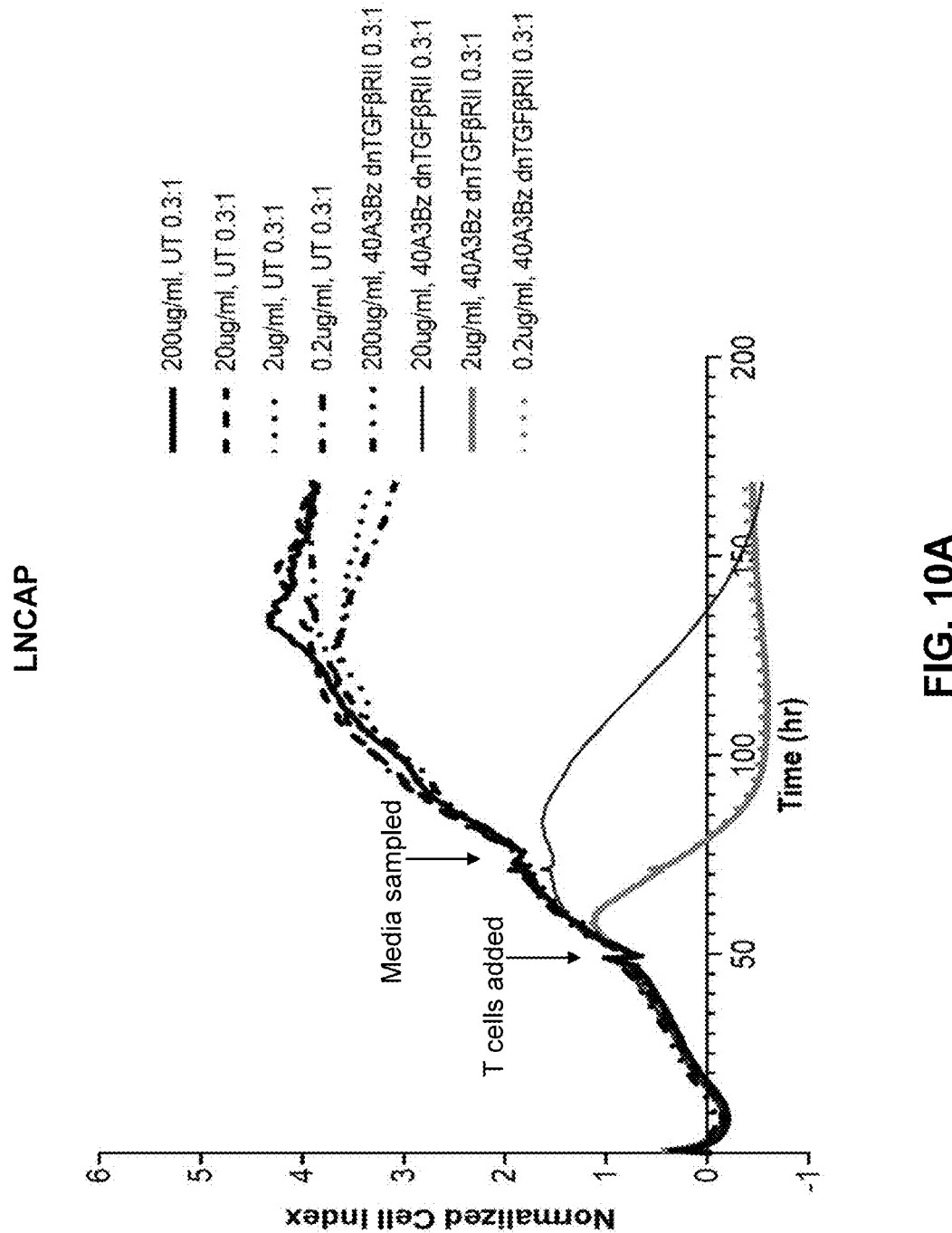
Figure 10B:
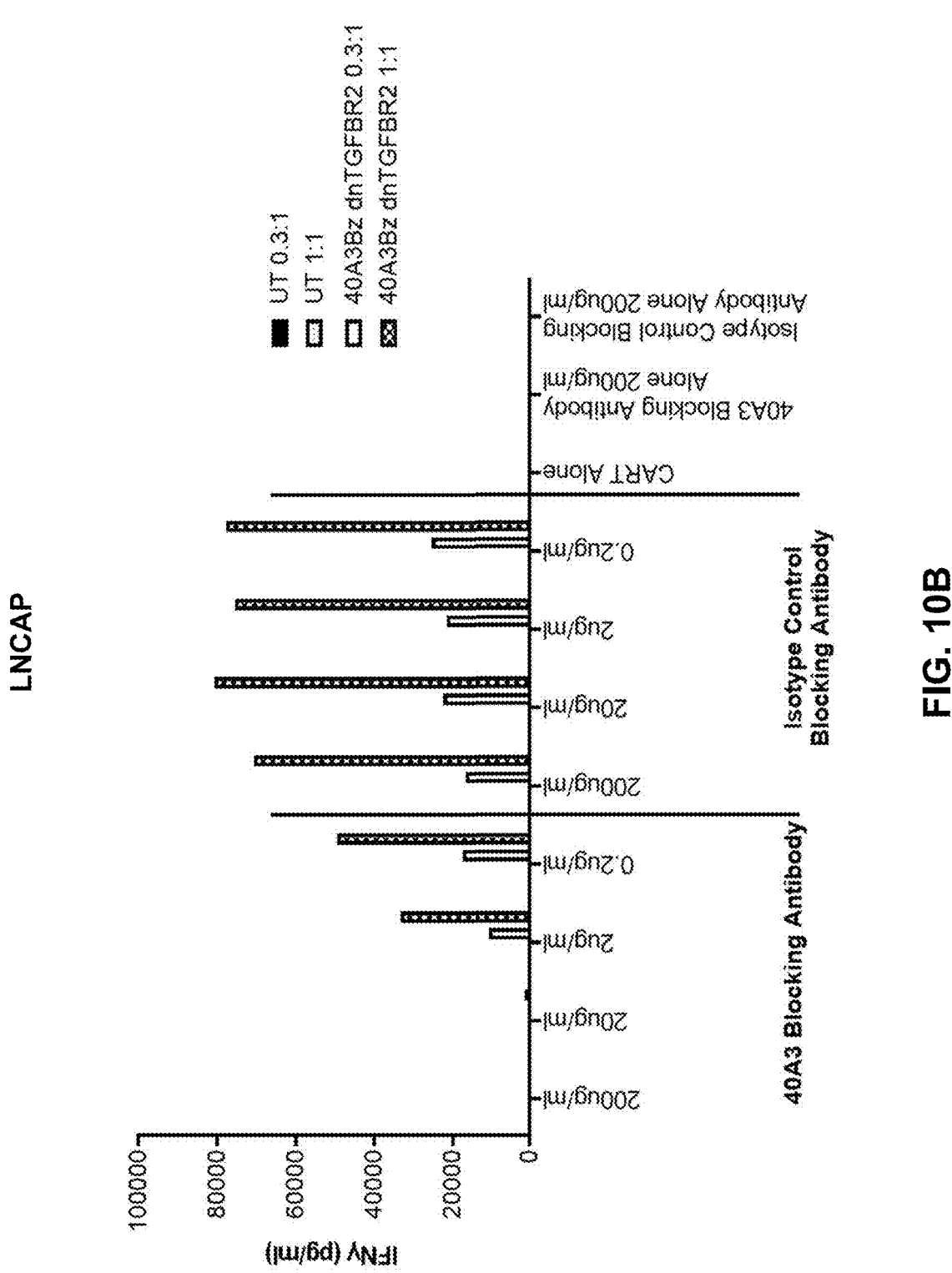
Figure 10C:
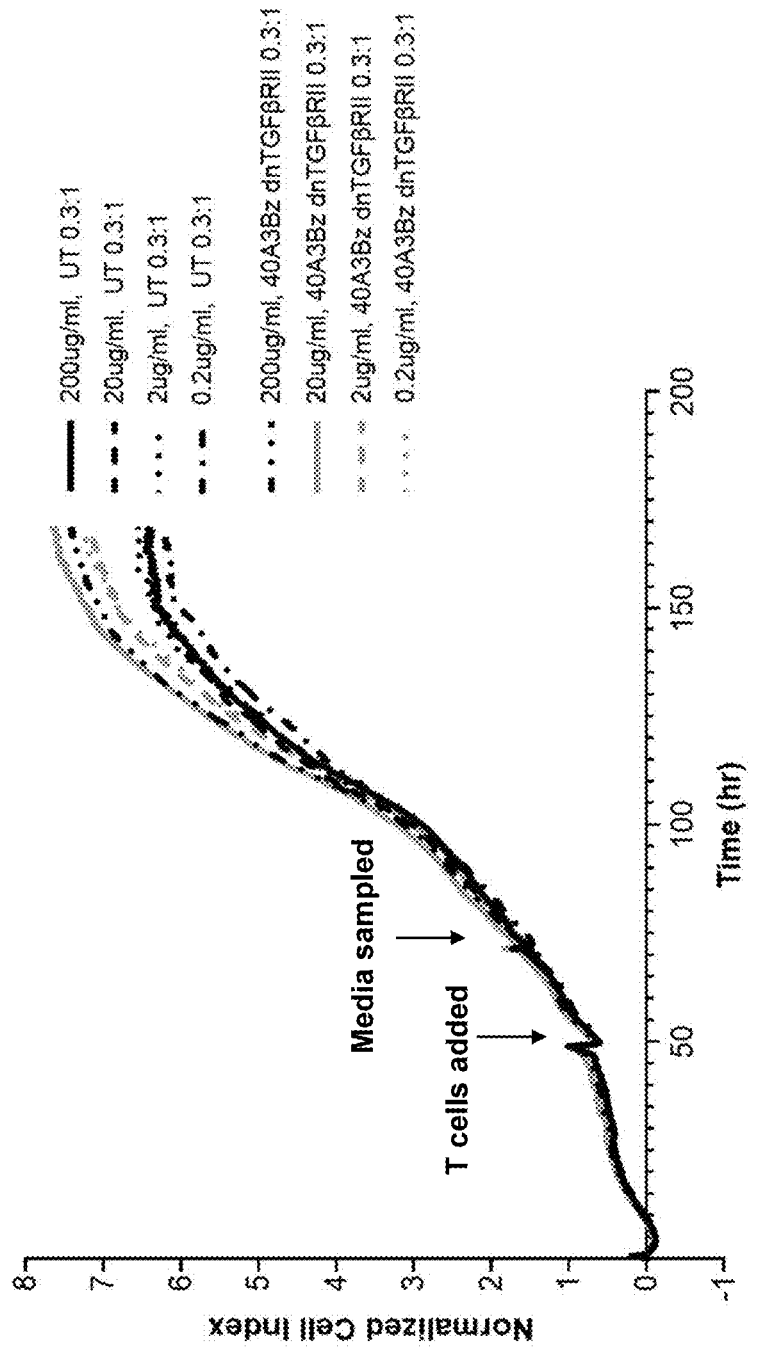
Figure 10D:
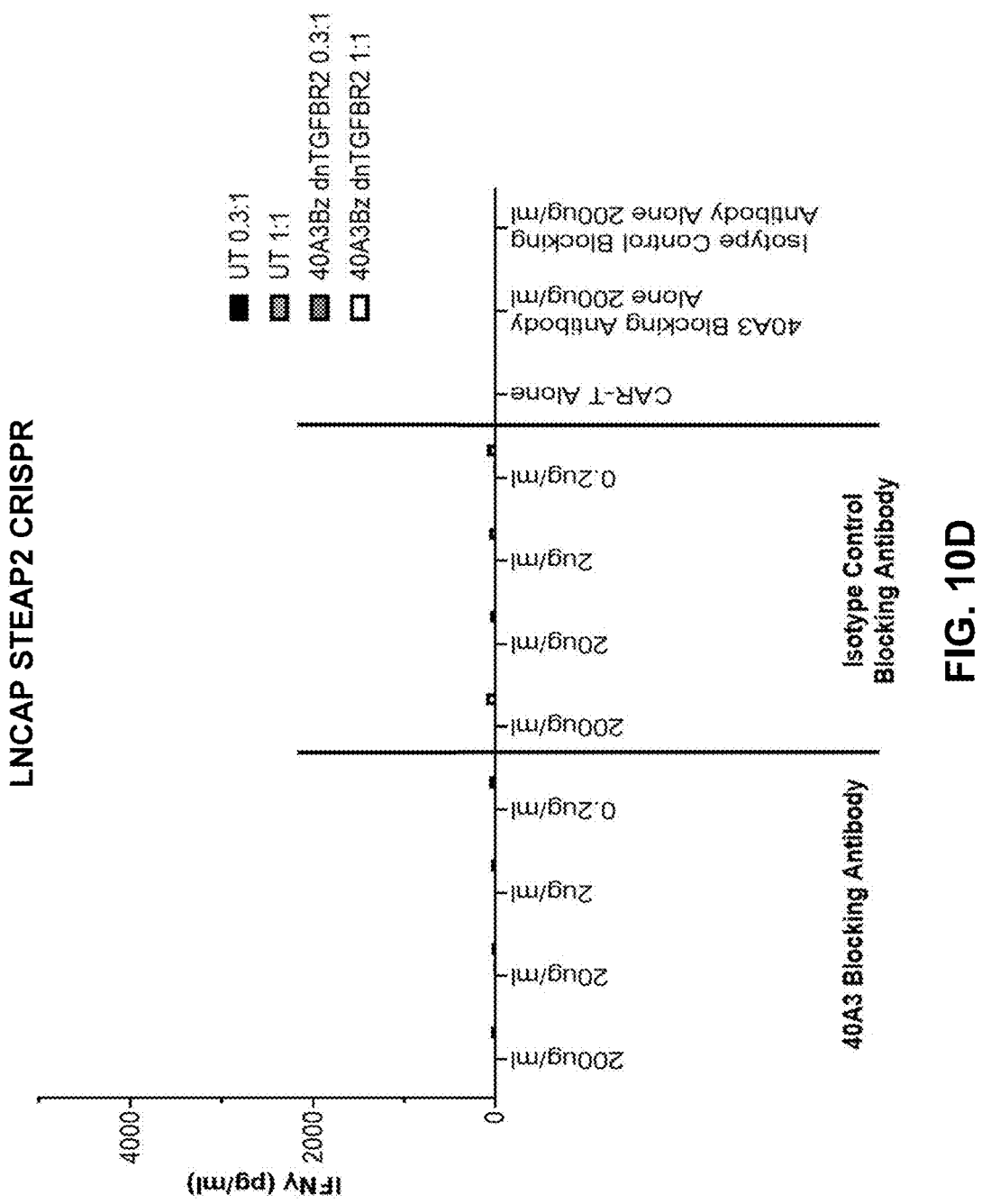

FIG. 10A shows tumor cell line growth of co-cultures of LNCAP tumor cells and 40A3Bz dnTGFβRII CAR-T cells at E:T ratios of 0.3:1 or untransduced T cells in the presence of blocking anti-STEAP2 antibodies (0.2, 2, 20, or 200 µg/ml). FIG. 10B shows IFNγ levels determined by MSD ECL Assay in supernatants of co-cultures of LNCAP tumor cells and 40A3Bz dnTGFβRII CAR-T cells at E:T ratios of
0.3:1 or 1:1 or untransduced T cells in the presence of
blocking anti-STEAP2 antibodies or isotype blocking anti-
bodies (0.2, 2, 20, or 200 μg/ml). FIG. 10C shows tumor cell
line growth of co-cultures of LNCAP STEAP2 CRISPR
tumor cells and 40A3Bz dnTGFβRII CAR-T cells at E:T
ratios of 0.3:1 or untransduced T cells in the presence of
blocking anti-STEAP2 antibodies (0.2, 2, 20, or 200 μg/ml).
FIG. 10D shows IFNγ levels determined by MSD ECL
Assay in supernatants of co-cultures of LNCAP STEAP2
CRISPR tumor cells and 40A3Bz dnTGFβRII CAR-T cells
at E:T ratios of 0.3:1 or 1:1 or untransduced T cells in the
presence of blocking anti-STEAP2 antibodies or isotype
blocking antibodies (0.2, 2, 20, or 200 μg/ml).

DETAILED DESCRIPTION OF DISCLOSURE

The present disclosure relates to antigen-binding moieties
that specifically bind an epitope on human six transmem-
brane epithelial antigen of prostate-2 (STEAP2). Some
aspects of the present disclosure are directed to polynucle-
otides comprising a nucleotide sequence encoding a chime-
ric antigen receptor (CAR), wherein the CAR comprises an
antigen-binding domain that binds an epitope on human
STEAP2. Some aspects of the present disclosure are
directed to a host cell comprising the polynucleotide. Other
aspects of the present disclosure are directed to antibodies or
antigen-binding portions thereof that specifically bind an
epitope on human STEAP2. In some aspects, the antigen-
binding domain binds an epitope on an extracellular loop of
human STEAP2. Further aspects of the present disclosure
are directed to methods of treating a subject in need thereof
comprising administering the polynucleotide, the cell, and/
or the antibody or antigen-binding portion thereof to the
subject. In some aspects, the subject is afflicted with a
prostate cancer or a tumor derived from a prostate cancer.

I. Terms

In order that the present description can be more readily
understood, certain terms are first defined. Additional defi-
nitions are set forth throughout the detailed description.

It is to be noted that the term "a" or "an" entity refers to
one or more of that entity; for example, "a nucleotide
sequence," is understood to represent one or more nucleo-
tide sequences. As such, the terms "a" (or "an"), "one or
more," and "at least one" can be used interchangeably
herein.

Furthermore, "and/or" where used herein is to be taken as
specific disclosure of each of the two specified features or
components with or without the other. Thus, the term
"and/or" as used in a phrase such as "A and/or B" herein is
intended to include "A and B," "A or B," "A" (alone), and
"B" (alone). Likewise, the term "and/or" as used in a phrase
such as "A, B, and/or C" is intended to encompass each of
the following aspects: A, B, and C; A, B, or C; A or C; A or
B; B or C; A and C; A and B; B and C; A (alone); B (alone);
and C (alone).

It is understood that wherever aspects are described herein
with the language "comprising," otherwise analogous
aspects described in terms of "consisting of" and/or "con-
sisting essentially of" are also provided. As used herein, the
terms "comprise" and "include" and variations thereof (e.g.,
"comprises," "comprising," "includes," and "including")
will be understood to indicate the inclusion of a stated
component, feature, element, or step or group of compo-
nents, features, elements or steps but not the exclusion of any other component, feature, element, or step or group of
components, features, elements, or steps. Any of the terms
"comprising," "consisting essentially of" and "consisting
of" may be replaced with either of the other two terms, while
retaining their ordinary meanings.

Unless defined otherwise, all technical and scientific
terms used herein have the same meaning as commonly
understood by one of ordinary skill in the art to which this
disclosure is related. For example, the Concise Dictionary of
Biomedicine and Molecular Biology, Juo, Pei-Show, 2nd
ed., 2002, CRC Press; The Dictionary of Cell and Molecular
Biology, 3rd ed., 1999, Academic Press; and the Oxford
Dictionary Of Biochemistry And Molecular Biology,
Revised, 2000, Oxford University Press, provide one of skill
with a general dictionary of many of the terms used in this
disclosure.

Units, prefixes, and symbols are denoted in their Système
International de Unites (SI) accepted form. Numeric ranges
are inclusive of the numbers defining the range. Unless
otherwise indicated, nucleotide sequences are written left to
right in 5' to 3' orientation. Amino acid sequences are written
left to right in amino to carboxy orientation. The headings
provided herein are not limitations of the various aspects of
the disclosure, which can be had by reference to the speci-
fication as a whole. Accordingly, the terms defined imme-
diately below are more fully defined by reference to the
specification in its entirety.

The term "about" is used herein to mean approximately,
roughly, around, or in the regions of. When the term "about"
is used in conjunction with a numerical range, it modifies
that range by extending the boundaries above and below the
numerical values set forth. In general, the term "about" can
modify a numerical value above and below the stated value
by a variance of, e.g., 10 percent, up or down (higher or
lower).

The term "antibody" refers, in some aspects, to a protein
comprising at least two heavy (H) chains and two light (L)
chains inter-connected by disulfide bonds. Each heavy chain
is comprised of a heavy chain variable region (abbreviated
herein as VH) and a heavy chain constant region (abbrevi-
ated herein as CH). In some antibodies, e.g., naturally-
occurring IgG antibodies, the heavy chain constant region is
comprised of a hinge and three domains, CH1, CH2 and
CH3. In some antibodies, e.g., naturally-occurring IgG
antibodies, each light chain is comprised of a light chain
variable region (abbreviated herein as VL) and a light chain
constant region. The light chain constant region is comprised
of one domain (abbreviated herein as CL). The VH and VL
regions can be further subdivided into regions of hypervari-
ability, termed complementarity determining regions
(CDR), interspersed with regions that are more conserved,
termed framework regions (FR). Each VH and VL is com-
posed of three CDRs and four FRs, arranged from amino-
terminus to carboxy-terminus in the following order: FR1,
CDR1, FR2, CDR2, FR3, CDR3, and FR4. The variable
regions of the heavy and light chains contain a binding
domain that interacts with an antigen. The constant regions
of the antibodies can mediate the binding of the immuno-
globulin to host tissues or factors, including various cells of
the immune system (e.g., effector cells) and the first com-
ponent (C1q) of the classical complement system. A heavy
chain may have the C-terminal lysine or not. Unless speci-
fied otherwise herein, the amino acids in the variable regions
are numbered using the Kabat numbering system and those
in the constant regions are numbered using the EU system.

An immunoglobulin can be from any of the commonly
known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In some aspects, the antibodies described herein are of the IgG1 subtype. Immunoglobulins, e.g., IgG1, exist in several allotypes, which differ from each other in at most a few amino acids. "Antibody" includes, by way of example, both naturally-occurring and non-naturally-occurring antibodies; monoclonal and polyclonal antibodies; chimeric and humanized antibodies; human and nonhuman antibodies and wholly synthetic antibodies.

The term "antigen-binding portion" of an antibody, as used herein, refers to one or more fragments of an antibody that retain the ability to specifically bind to an antigen (e.g., human STEAP2). The antigen-binding function of an antibody can be performed by fragments of a full-length antibody. Examples of binding fragments encompassed within the term "antigen-binding portion" of an antibody, e.g., an anti-STEAP2 antibody described herein, include (i) a Fab fragment (fragment from papain cleavage) or a similar monovalent fragment consisting of the $V_L$, $V_H$, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR) and (vii) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "chimeric antigen receptor" or "CAR," as used herein, refers to an engineered antigen-binding polypeptide, comprising an antigen-binding domain, a transmembrane domain, and an intracellular signaling domain. Expression of a CAR on the surface of a cell, e.g., an immune cell, allows the cell to target and bind a particular antigen. In some aspects, the CAR is expressed by an immune cell, e.g., a T cell. In some aspects, the antigen binding domain comprises an Fab, Fab', F(ab')2, Fd, Fv, single-chain fragment variable (scFv), single chain antibody, VHH, vNAR, nanobody (single-domain antibody), or any combination thereof. In some aspects, the transmembrane domain comprises a transmembrane domain selected from the transmembrane domain of CD4, CD8α, or CD28. In some aspects, the intracellular domain comprises a costimulatory domain or a portion thereof. In some aspects, the intracellular domain comprises a costimulatory domain selected from the group consisting of the intracellular domain of CD3z, a CD28 co-stimulatory domain, a CD27 co-stimulatory domain, a 4-1BB co-stimulatory domain, an ICOS co-stimulatory domain, an OX-40 co-stimulatory domain, a GITR co-stimulatory domain, a CD2 co-stimulatory domain, an IL-2Rβ co-stimulatory domain, an MyD88/CD40a CD28 co-stimulatory domain, and any combination thereof. A CAR can further comprise a "hinge" or "spacer" domain. Non-limiting examples of hinge/spacer domains include immunoglobulin hinge/spacer domains, such as an IgG1 hinge domain, and IgG2 hinge domain, an IgG3 hinge domain, or an IgG4 hinge domain.

As used herein, the term "armoring" refers to molecular manipulation of a CAR-expressing cell (e.g., a CAR-T cell) to further express one or more "armoring molecules" that can counter immunosuppression. For example, investigators recently reported modifying CAR-T cells to secrete PD-1-blocking single-chain variable fragments (scFv), which improved CAR-T cell anti-tumor activity in mouse models of PD-L1+ hematologic and solid tumors (Rafiq, S., Yeku, O., Jackson, H. et al. Targeted delivery of a PD-1-blocking scFv by CAR-T cells enhances anti-tumor efficacy in vivo. Nat Biotechnol 36, 847-856 (2018)). Others studies have demonstrated the effectiveness of armoring T cells with a dominant-negative TGF-β receptor type 2 (TGFβRIIDN) armoring molecule to neutralize the suppressive effects of TGF-β on T cells (Bollard et al., Tumor-Specific T-Cells Engineered to Overcome Tumor Immune Evasion Induce Clinical Responses in Patients With Relapsed Hodgkin Lymphoma, J Clin Oncol 36(11):1128-1139 (2018)). Currently, at least one clinical study is investigating the effectiveness of armoring anti-PSMA-CAR-T cells with a TGFβRIIDN armoring molecule for treating castrate-resistant prostate cancer (NCT03089203).

As used herein, the term "affinity" refers to a measure of the strength of the binding of an antigen or target (such as an epitope) to its cognate binding domain (such as a paratope). As used herein, the term "avidity" refers to the overall stability of the complex between a population of epitopes and paratopes (i.e., antigens and antigen binding domains).

The term "epitope" refers to a site on an antigen (e.g., STEAP2) to which a chimeric antigen receptor, immunoglobulin, or antibody specifically binds, e.g., as defined by the specific method used to identify it. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation.

The term "binds to the same epitope" with reference to two or more antigen-binding moieties means that the antigen-binding moieties bind to the same segment of amino acid residues. Antigen-binding moieties that "compete with another antibody for binding to a target" refer to antigen-binding moieties that inhibit (partially or completely) the binding of the other antibody to the target.

As used herein, the terms "specific binding," "selective binding," "selectively binds," and "specifically binds," refer to an antigen-binding moiety (e.g., a CAR or an antibody) binding to an epitope on a predetermined antigen. Typically, the antigen-binding moiety (e.g., a CAR or an antibody) (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., human STEAP2, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antigen-binding moiety (e.g., a CAR or an antibody) that "specifically binds to human STEAP2" refers to an antigen-binding moiety (e.g., a CAR or an antibody) that binds to human STEAP2 with a $K_D$ of $10^{-7}$M or less, such as approximately less than $10^{-8}$M, $10^{-9}$M or $10^{-10}$ M or even lower.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some aspects, a predicted nonessential amino acid residue in a STEAP2-binding moiety (e.g., an anti-STEAP2 CAR or antibody) is replaced with another amino acid residue from the same side chain family.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

"Immunotherapy" refers to the treatment of a subject afflicted with, or at risk of contracting or suffering a recurrence of, a disease by a method comprising inducing, enhancing, suppressing or otherwise modifying the immune system or an immune response.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the terms "treat," "treatment," or "treatment of" when used in the context of treating cancer refer to reducing disease pathology, reducing or eliminating disease symptoms, promoting increased survival rates, and/or reducing discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

As used herein, "cancer" refers a broad group of diseases characterized by the uncontrolled growth of abnormal cells in the body. Unregulated cell division can result in the formation of malignant tumors or cells that invade neighboring tissues and can metastasize to distant parts of the body through the lymphatic system or bloodstream.

As used herein, the term an "effective amount" or a "therapeutically effective amount" of an administered therapeutic substance, such as a CAR-T cell, is an amount sufficient to carry out a specifically stated or intended purpose, such as treating or treatment of cancer. An "effective amount" can be determined empirically in a routine manner in relation to the stated purpose.

As used herein, the terms "subject," "individual," or "patient," refer to any subject, particularly a mammalian subject, for whom diagnosis, prognosis, or therapy is desired. Mammalian subjects include, for example, humans, non-human primates, dogs, cats, guinea pigs, rabbits, rats, mice, horses, cattle, bears, and so on.

As used herein, the terms "ug" and "uM" are used interchangeably with "µg" and "µM," respectively.

Various aspects described herein are described in further detail in the following subsections.

I. Polynucleotides of the Disclosure

Some aspects of the present disclosure are directed to polynucleotides comprising a nucleotide sequence encoding a CAR that specifically binds human STEAP2. In some aspects, the CAR comprises (i) an antigen-binding domain that binds an epitope on STEAP2, (ii) a transmembrane domain, and (iii) an intracellular domain. In some aspects, the CAR further comprises a hinge/spacer domain. In some aspects, the hinge/spacer domain is positioned between the antigen-binding domain and the transmembrane domain.

In some aspects, the polynucleotide further comprises a nucleotide sequence encoding an armoring molecule. In some aspects, the nucleotide sequence encoding the CAR and the nucleotide sequence encoding the armoring moiety are expressed under the control of the same promoter. In some aspects, the nucleotide sequence encoding the CAR and the nucleotide sequence encoding the armoring moiety are expressed under the control of two promoter. In some aspects, the two promoters are different promoters. In some aspects, the nucleotide sequence encoding the CAR and the nucleotide sequence encoding the armoring moiety are expressed as a single contiguous polypeptide. In some aspects, the nucleotide sequence encoding the CAR and the nucleotide sequence encoding the armoring moiety are expressed as two separate polypeptides. In some aspects, the CAR and the nucleotide sequence encoding the armoring moiety are linked by a nucleotide sequence encoding a linker. In some aspects, the linker is a peptide linker. In some aspects, the linker is a cleavable linker. In some aspects, the linker is a self-cleaving peptide linker, e.g., comprising a T2A peptide.

I.A. Antigen-Binding Domain

Disclosed herein are polynucleotides comprising a nucleotide sequence encoding a CAR, wherein the CAR comprises (i) an antigen-binding domain that binds an epitope on human STEAP2, (ii) an intracellular signaling domain, and (iii) a transmembrane domain. Any antigen-binding domain can be used in the compositions disclosed herein. In some aspects, the antigen-binding domain comprises an Fab, Fab', F(ab')2, Fd, Fv, single-chain fragment variable (scFv), single chain antibody, VHH, vNAR, nanobody (single-domain antibody), or any combination thereof. In some aspects, the antigen-binding domain comprises a scFv.

In some aspects, the antigen-binding domain of the CAR comprises a variable heavy chain region (VH) and a variable light chain region (VL), wherein the VH comprises a VH complementarity determining region (CDR) 1, a VH-CDR2, a VH-CDR3; and wherein the VL comprises a VL-CDR1, a VL-CDR2, and VL-CDR3. In some aspects, the antigen-binding domain comprises a VH-CDR3 comprising an amino acid sequence selected from SEQ ID NOs: 6, 16, 26, 36, 46, and 96. In some aspects, the antigen-binding domain comprises a VH-CDR2 comprising an amino acid sequence selected from SEQ ID NOs: 5, 15, 25, 35, 45, and 95. In some aspects, the antigen-binding domain comprises a VH-CDR1 comprising an amino acid sequence selected from SEQ ID NOs: 4, 14, 24, 34, 44, and 94.

In some aspects, the antigen-binding domain comprises a VL-CDR3 comprising an amino acid sequence selected from SEQ ID NOs: 3, 13, 23, 33, 43, and 93. In some aspects, wherein the antigen-binding domain comprises a VL-CDR2 comprising an amino acid sequence selected from SEQ ID NOs: 2, 12, 22, 32, 42, and 92. In some aspects, the antigen-binding domain comprises a VL-CDR1 comprising an amino acid sequence selected from SEQ ID NOs: 1, 11, 21, 31, 41, and 91.

In some aspects, the antigen binding domain comprises a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6.

In some aspects, the antigen binding domain comprises a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16.

In some aspects, the antigen binding domain comprises a VL-CDR1 comprising the amino acid sequence set forth in SEQ ID NO: 21, a VL-CDR2 comprising the amino acid sequence set forth in SEQ ID NO: 22, a VL-CDR3 comprising the amino acid sequence set forth in SEQ ID NO: 23, a VH-CDR1 comprising the amino acid sequence set forth in SEQ ID NO: 24, a VH-CDR2 comprising the amino acid sequence set forth in SEQ ID NO: 25, a VH-CDR3 comprising the amino acid sequence set forth in SEQ ID NO: 26.

In some aspects, the antigen binding domain comprises a VL-CDR1 comprising the amino acid sequence set forth in SEQ ID NO: 31, a VL-CDR2 comprising the amino acid sequence set forth in SEQ ID NO: 32, a VL-CDR3 comprising the amino acid sequence set forth in SEQ ID NO: 33, a VH-CDR1 comprising the amino acid sequence set forth in SEQ ID NO: 34, a VH-CDR2 comprising the amino acid sequence set forth in SEQ ID NO: 35, a VH-CDR3 comprising the amino acid sequence set forth in SEQ ID NO: 36.

In some aspects, the antigen binding domain comprises a VL-CDR1 comprising the amino acid sequence set forth in SEQ ID NO: 41, a VL-CDR2 comprising the amino acid sequence set forth in SEQ ID NO: 42, a VL-CDR3 comprising the amino acid sequence set forth in SEQ ID NO: 43, a VH-CDR1 comprising the amino acid sequence set forth in SEQ ID NO: 44, a VH-CDR2 comprising the amino acid sequence set forth in SEQ ID NO: 45, a VH-CDR3 comprising the amino acid sequence set forth in SEQ ID NO: 46.

In some aspects, the antigen binding domain comprises the VL-CDR1, VL-CDR2, and VL-CDR3 present in the VL region having the amino acid sequence set forth in SEQ ID NO: 58; and the VH-CDR1, VH-CDR2, and VH-CDR3 present in the VH region having the amino acid sequence set forth in SEQ ID NO: 57.

In some aspects, the antigen binding domain comprises the VL-CDR1, VL-CDR2, and VL-CDR3 present in the VL region having the amino acid sequence set forth in SEQ ID NO: 68; and the VH-CDR1, VH-CDR2, and VH-CDR3 present in the VH region having the amino acid sequence set forth in SEQ ID NO: 67.

In some aspects, the antigen binding domain comprises the VL-CDR1, VL-CDR2, and VL-CDR3 present in the VL region having the amino acid sequence set forth in SEQ ID NO: 78; and the VH-CDR1, VH-CDR2, and VH-CDR3 present in the VH region having the amino acid sequence set forth in SEQ ID NO: 77.

In some aspects, the antigen binding domain comprises the VL-CDR1, VL-CDR2, and VL-CDR3 present in the VL region having the amino acid sequence set forth in SEQ ID NO: 88; and the VH-CDR1, VH-CDR2, and VH-CDR3 present in the VH region having the amino acid sequence set forth in SEQ ID NO: 87.

In some aspects, the antigen binding domain comprises the VL-CDR1, VL-CDR2, and VL-CDR3 present in the VL region having the amino acid sequence set forth in SEQ ID NO: 98; and the VH-CDR1, VH-CDR2, and VH-CDR3 present in the VH region having the amino acid sequence set forth in SEQ ID NO: 97.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 7, 17, 27, 37, 47, 57, 67, 77, 87, and 97. In some aspects, the antigen-binding domain comprises a VH comprising an amino acid sequence selected from SEQ ID NOs: 7, 17, 27, 37, 47, 57, 67, 77, 87, and 97.

In some aspects, the CAR comprises an antigen-binding domain comprising a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 8, 18, 28, 38, 48, 58, 68, 78, 88, and 98. In some aspects, the antigen-binding domain comprises a VL comprising an amino acid sequence selected from SEQ ID NOs: 8, 18, 28, 38, 48, 58, 68, 78, 88, and 98.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the CAR comprises an antigen-binding domain comprising a VH comprising the amino acid sequence set forth in SEQ ID NO: 7, and a VL comprising the amino acid sequence set forth in SEQ ID NO: 8.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the CAR comprises an antigen-binding domain comprising a VH comprising the amino acid sequence set forth in SEQ ID NO: 17, and a VL comprising the amino acid sequence set forth in SEQ ID NO: 18.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28. In some aspects, the CAR comprises an antigen-binding domain comprising a VH comprising the amino acid sequence set forth in SEQ ID NO: 27, and a VL comprising the amino acid sequence set forth in SEQ ID NO: 28.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38. In some aspects, the CAR comprises an antigen-binding domain comprising a VH comprising the amino acid sequence set forth in SEQ ID NO: 37, and a VL comprising the amino acid sequence set forth in SEQ ID NO: 38.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48. In some aspects, the CAR comprises an antigen-binding domain comprising a VH comprising the amino acid sequence set forth in SEQ ID NO: 47, and a VL comprising the amino acid sequence set forth in SEQ ID NO: 48.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and a VL comprising an amino acid sequence having at least about 70%, at least about 75%, at least about 80%, at least about 85%, at least about 90%, at least about 95%, at least about 86%, at least about 97%, at least about 98%, at least about 99% sequence identity to the amino acid sequence set forth in SEQ ID NO: 58. In some aspects, the CAR comprises an antigen-binding domain comprising a VH comprising the amino acid sequence set forth in SEQ ID NO: 57, and a VL comprising the amino acid sequence set forth in SEQ ID NO: 58.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68. In some aspects, the CAR comprises an antigen-binding domain comprising a VH comprising the amino acid sequence set forth in SEQ ID NO: 67, and a VL comprising the amino acid sequence set forth in SEQ ID NO: 68.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78. In some aspects, the CAR comprises an antigen-binding domain comprising a VH comprising the amino acid sequence set forth in SEQ ID NO: 77, and a VL comprising the amino acid sequence set forth in SEQ ID NO: 78.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88. In some aspects, the CAR comprises an antigen-binding domain comprising a VH comprising the amino acid sequence set forth in SEQ ID NO: 87, and a VL comprising the amino acid sequence set forth in SEQ ID NO: 88.

In some aspects, the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the CAR comprises an antigen-binding domain comprising a VH comprising the amino acid sequence set forth in SEQ ID NO: 97, and a VL comprising the amino acid sequence set forth in SEQ ID NO: 98.

In some aspects, the CAR comprises an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9. In some aspects, the CAR comprises an antigen-binding domain comprising the amino acid sequence set forth in SEQ ID NO: 9.

In some aspects, the CAR comprises an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99. In some aspects, the CAR comprises an antigen-binding domain comprising the amino acid sequence set forth in SEQ ID NO: 99.

I.B. Intracellular Domain

Disclosed herein are polynucleotides comprising a nucleotide sequence encoding a CAR, wherein the CAR comprises (i) an antigen-binding domain that binds an epitope on human STEAP2, (ii) an intracellular signaling domain, and (iii) a transmembrane domain. Any intracellular signaling domain can be used in the compositions disclosed herein. In some aspects, the intracellular signaling domain comprises a costimulatory domain or a portion thereof.

In some aspects, the intracellular domain comprises a costimulatory domain selected from the group consisting of the intracellular domain of CD3z, a CD28 co-stimulatory domain, a CD27 co-stimulatory domain, a 4-1BB co-stimu-latory domain, an ICOS co-stimulatory domain, an OX-40 co-stimulatory domain, a GITR co-stimulatory domain, a CD2 co-stimulatory domain, an IL-2Rβ co-stimulatory domain, an MyD88/CD40a CD28 co-stimulatory domain, and any combination thereof.

In some aspects, the intracellular domain comprises a 4-1BB co-stimulatory domain. In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (ii) a 4-1BB costimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; and (ii) a 4-1BB co-stimulatory domain comprising the amino acid sequence set forth in SEQ ID NO: 130.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; and (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain compris-ing the amino acid sequence set forth in SEQ ID NO: 9; and (ii) a 4-1BB co-stimulatory domain comprising the amino acid sequence set forth in SEQ ID NO: 130.

In some aspects, the intracellular domain comprises the intracellular domain of CD3z and a CD28 co-stimulatory domain. In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (ii) the intracellular domain of CD3z and a CD28 co-stimulatory domain. In some aspects, the CAR comprises (i) an antigen-binding domain compris-ing a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; and (ii) the intracellular domain of CD3z comprising the amino acid sequence set forth in SEQ ID NO: 131 and a CD28 co-stimulatory domain comprising the amino acid sequence set forth in SEQ ID NO: 133.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133. In some aspects, the CAR comprises (i) an antigen-binding domain comprising the amino acid sequence set forth in SEQ ID NO: 9; and (ii) the intracellular domain of CD3z comprising the amino acid sequence set forth in SEQ ID NO: 131 and a CD28 co-stimulatory domain comprising the amino acid sequence set forth in SEQ ID NO: 133.

In some aspects, the intracellular domain comprises the intracellular domain of CD3z and a 4-1BB co-stimulatory domain. In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (ii) the intracellular domain of CD3z and a 4-1BB co-stimulatory domain. In some aspects, the CAR comprises (i) an antigen-binding domain comprising a VH comprising an amino acid sequence having at least about 70%, at least about 75%, at least least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; and (ii) the intracellular domain of CD3z comprising the amino acid sequence set forth in SEQ ID NO: 131 and a 4-1BB co-stimulatory domain comprising the amino acid sequence set forth in SEQ ID NO: 130.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising the amino acid sequence set forth in SEQ ID NO: 9; and (ii) the intracellular domain of CD3z comprising the amino acid sequence set forth in SEQ ID NO: 131 and a 4-1BB co-stimulatory domain: comprising the amino acid sequence set forth in SEQ ID NO: 130.

In some aspects, the intracellular domain comprises the intracellular domain of CD3z, a CD28 co-stimulatory domain, and a 4-1BB co-stimulatory domain. In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (ii) the intracellular domain of CD3z, a CD28 co-stimulatory domain, and a 4-1BB co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; and (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising the amino acid sequence set forth in SEQ ID NO: 9; and (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130.

In some aspects, the intracellular domain comprises a 4-1BB co-stimulatory domain. In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (ii) a 4-1BB costimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; and (ii) a 4-1BB co-stimulatory domain comprising the amino acid sequence set forth in SEQ ID NO: 130.

In some aspects, the intracellular domain comprises the intracellular domain of CD3z and a CD28 co-stimulatory domain. In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (ii) the intracellular domain of CD3z and a CD28 co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; and (ii) the intracellular domain of CD3z comprising the amino acid sequence set forth in SEQ ID NO: 131 and a CD28 co-stimulatory domain comprising the amino acid sequence set forth in SEQ ID NO: 133.

In some aspects, the intracellular domain comprises the intracellular domain of CD3z and a 4-1BB co-stimulatory domain. In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (ii) the intracellular domain of CD3z and a 4-1BB co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; and (ii) the intracellular domain of CD3z comprising the amino acid sequence set forth in SEQ ID NO: 131 and a 4-1BB co-stimulatory domain comprising the amino acid sequence set forth in SEQ ID NO: 130.

In some aspects, the intracellular domain comprises the intracellular domain of CD3z, a CD28 co-stimulatory domain, and a 4-1BB co-stimulatory domain. In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (ii) the intracellular domain of CD3z, a CD28 co-stimulatory domain, and a 4-1BB co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; and (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130.

In some aspects, the intracellular domain comprises a 4-1BB co-stimulatory domain. In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (ii) a 4-1BB costimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98 and (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; and (ii) a 4-1BB co-stimulatory domain comprising the amino acid sequence set forth in SEQ ID NO: 130.

In some aspects, the intracellular domain comprises the intracellular domain of CD3z and a CD28 co-stimulatory domain. In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (ii) the intracellular domain of CD3z and a CD28 co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; and (ii) the intracellular domain of CD3z comprising the amino acid sequence set forth in SEQ ID NO: 131 and a CD28 co-stimulatory domain comprising the amino acid sequence set forth in SEQ ID NO: 133.

In some aspects, the intracellular domain comprises the intracellular domain of CD3z and a 4-1BB co-stimulatory domain. In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (ii) the intracellular domain of CD3z and a 4-1BB co-stimulatory domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; and (ii) the intracellular domain of CD3z comprising the amino acid sequence set forth in SEQ ID NO: 131 and a 4-1BB co-stimulatory domain comprising the amino acid sequence set forth in SEQ ID NO: 130.

In some aspects, the intracellular domain comprises the intracellular domain of CD3z, a CD28 co-stimulatory domain, and a 4-1BB co-stimulatory domain. In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; and (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10. In some aspects, the CAR comprises the amino acid sequence set forth in SEQ ID NO: 10.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 108. In some aspects, the CAR comprises the amino acid sequence set forth in SEQ ID NO: 108.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 109. In some aspects, the CAR comprises the amino acid sequence set forth in SEQ ID NO: 109.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 110. In some aspects, the CAR comprises the amino acid sequence set forth in SEQ ID NO: 110.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 111. In some aspects, the CAR comprises the amino acid sequence set forth in SEQ ID NO: 111.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 112. In some aspects, the CAR comprises the amino acid sequence set forth in SEQ ID NO: 112.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 113. In some aspects, the CAR comprises the amino acid sequence set forth in SEQ ID NO: 113.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 114. In some aspects, the CAR comprises the amino acid sequence set forth in SEQ ID NO: 114.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 115. In some aspects, the CAR comprises the amino acid sequence set forth in SEQ ID NO: 115.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 116. In some aspects, the CAR comprises the amino acid sequence set forth in SEQ ID NO: 116.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 118. In some aspects, the CAR comprises the amino acid sequence set forth in SEQ ID NO: 118.

In some aspects, the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 119. In some aspects, the CAR comprises the amino acid sequence set forth in SEQ ID NO: 119.

I.C. Transmembrane Domain

Disclosed herein are polynucleotides comprising a nucleotide sequence encoding a CAR, wherein the CAR comprises (i) an antigen-binding domain that binds an epitope on human STEAP2, (ii) an intracellular signaling domain, and (iii) a transmembrane domain. Any transmembrane domain can be used in the compositions disclosed herein. In some aspects, the transmembrane domain comprises a transmembrane domain selected from the transmembrane domain of CD4, CD8α, or CD28. In some aspects, the transmembrane domain comprises a CD28 transmembrane domain.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) a 4-1BB costimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising the amino acid sequence set forth in SEQ ID NO: 9; (ii) a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z and a CD28 co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z comprising the amino acid sequence set forth in SEQ ID NO: 131 and a CD28 co-stimulatory domain comprising the amino acid sequence set forth in SEQ ID NO: 133; and (iii) a transmembrane domain comprising the amino acid sequence set forth in SEQ ID NO: 129.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; and (iii) a transmembrane domain comprising the transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising the amino acid sequence set forth in SEQ ID NO: 9; (ii) the intracellular domain of CD3z comprising the amino acid sequence set forth in SEQ ID NO: 131 and a CD28 co-stimulatory domain comprising the amino acid sequence set forth in SEQ ID NO: 133; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z comprising the amino acid sequence set forth in SEQ ID NO: 131 and a 4-1BB co-stimulatory domain comprising the amino acid sequence set forth in SEQ ID NO: 130; and (iii) a trans-membrane domain comprising the amino acid sequence set forth in SEQ ID NO: 129.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising the amino acid sequence set forth in SEQ ID NO: 9; (ii) the intracellular domain of CD3z comprising the amino acid sequence set forth in SEQ ID NO: 131 and a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z, a CD28 co-stimulatory domain, and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising the amino acid sequence set forth in SEQ ID NO: 9; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) a 4-1BB costimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z and a CD28 co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) the intracellular domain of CD3z comprising the amino acid sequence set forth in SEQ ID NO: 131 and a CD28 co-stimulatory domain comprising the amino acid sequence set forth in SEQ ID NO: 133; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) the intracellular domain of CD3z comprising the amino acid sequence set forth in SEQ ID NO: 131 and a 4-1BB co-stimulatory domain comprising the amino acid sequence set forth in SEQ ID NO:130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z, a CD28 co-stimulatory domain, and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) a 4-1BB costimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z and a CD28 co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 97 and a VL comprising the amino acid sequence set forth in SEQ ID NO: 18; (ii) the intracellular domain of CD3z comprising the amino acid sequence set forth in SEQ ID NO: 131 and a CD28 co-stimulatory domain comprising the amino acid sequence set forth in SEQ ID NO: 133; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z comprising the amino acid sequence set forth in SEQ ID NO: 131 and a 4-1BB co-stimulatory domain comprising the amino acid sequence set forth in SEQ ID NO:130; and (iii) a transmembrane domain comprising the amino acid sequence set forth in SEQ ID NO: 129.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z, a CD28 co-stimulatory domain, and a 4-1BB co-stimulatory domain; and (iii) a transmembrane domain comprising the transmembrane domain of CD28. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; and (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; and (iii) a transmembrane domain comprising the amino acid sequence set forth in SEQ ID NO: 129.

In some aspects, the CAR comprises an amino acid sequence set forth in SEQ ID NO: 10. In some aspects, the CAR comprises an amino acid sequence set forth in SEQ ID NO: 108. In some aspects, the CAR comprises an amino acid sequence set forth in SEQ ID NO: 109. In some aspects, the CAR comprises an amino acid sequence set forth in SEQ ID NO: 110. In some aspects, the CAR comprises an amino acid sequence set forth in SEQ ID NO: 111. In some aspects, the CAR comprises an amino acid sequence set forth in SEQ ID NO: 112. In some aspects, the CAR comprises an amino acid sequence set forth in SEQ ID NO: 113. In some aspects, the CAR comprises an amino acid sequence set forth in SEQ ID NO: 114. In some aspects, the CAR comprises an amino acid sequence set forth in SEQ ID NO: 115. In some aspects, the CAR comprises an amino acid sequence set forth in SEQ ID NO: 116. In some aspects, the CAR comprises an amino acid sequence set forth in SEQ ID NO: 118. In some aspects, the CAR comprises an amino acid sequence set forth in SEQ ID NO: 119.

I.D. Spacer/Hinge Domain

Disclosed herein are polynucleotides comprising a nucleotide sequence encoding a CAR, wherein the CAR comprises (i) an antigen-binding domain that binds an epitope on human STEAP2, (ii) an intracellular signaling domain, (iii) a transmembrane domain, and (iv) a hinge/spacer domain. Any hinge/spacer domain can be used in the compositions disclosed herein. In some aspects, the hinge/spacer domain comprises a human immunoglobulin hinge/spacer domain. In some aspects, the hinge/spacer domain comprises an IgG hinge domain. In some aspects, the hinge/spacer domain comprise an IgG1 hinge domain, and IgG2 hinge domain, an IgG3 hinge domain, or an IgG4 hinge domain. In some aspects, the hinge/spacer domain comprises an IgG4 hinge domain. In some aspects, the IgG hinge domain is a variant hinge domain. In some aspects, the IgG4 hinge domain is a variant IgG4 hinge domain. In some aspects, the variant IgG4 hinge domain comprises a S228P mutation. In some aspects, the IgG4 hinge domain comprises an amino acid sequence set forth in SEQ ID NO: 128.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) a 4-1BB costimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129 and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) a 4-1BB co-stimulatory domain comprising the amino acid sequence set forth in SEQ ID NO: 130; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising the amino acid sequence set forth in SEQ ID NO: 9; (ii) a 4-1BB co-stimulatory domain comprising the amino acid sequence set forth in SEQ ID NO: 130; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z and a CD28 co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z comprising the amino acid sequence set forth in SEQ ID NO: 131 and a CD28 co-stimulatory domain comprising the amino acid sequence set forth in SEQ ID NO: 133; (iii) a transmembrane comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; (iii) a trans-membrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising the amino acid sequence set forth in SEQ ID NO: 9; (ii) the intracellular domain of CD3z and a CD28 co-stimulatory domain; (iii) a transmembrane domain comprising the trans-membrane domain of CD28; and (iv) an IgG hinge domain.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z and a 4-1BB co-stimulatory domain; (iii) a transmembrane domain comprising the trans-membrane domain of CD28; and (iv) an IgG hinge domain.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:130; (iii) a trans-membrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising the amino acid sequence set forth in SEQ ID NO: 9; (ii) the intracellular domain of CD3z and a 4-1BB co-stimulatory domain; (iii) a transmembrane domain comprising the trans-membrane domain of CD28; and (iv) an IgG hinge domain.

In some aspects, the CAR comprises (i) an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; (ii) the intracellular domain of CD3z, a CD28 co-stimulatory domain, and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a trans-membrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 7 and a VL comprising the amino acid sequence set forth in SEQ ID NO: 8; (ii) the intracellular domain of CD3z, a CD28 co-stimulatory domain, and a 4-1BB co-stimulatory domain; (iii) a transmembrane domain comprising the transmembrane domain of CD28; and (iv) an IgG hinge domain.

In some aspects, the CAR comprises (i) an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:130; (iii) a trans-membrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:128. In some aspects, the CAR comprises (i) an antigen-binding domain comprising the amino acid sequence set forth in SEQ ID NO: 9; (ii) the intracellular domain of CD3z, a CD28 co-stimulatory domain, and a 4-1BB co-stimulatory domain; (iii) a trans-membrane domain comprising the transmembrane domain of CD28; and (iv) an IgG hinge domain.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) a 4-1BB costimu-latory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain com-prising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:128. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) a 4-1BB co-stimulatory domain comprising the amino acid sequence set forth in SEQ ID NO: comprising the amino acid sequence set forth in SEQ ID NO: 131; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z and a CD28 co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i)

an antigen-binding domain comprising a VH comprising the amino acid sequence set forth in SEQ ID NO: 17 and a VL comprising the amino acid sequence set forth in SEQ ID NO: 18; (ii) the intracellular domain of CD3z comprising the amino acid sequence set forth in SEQ ID NO: 131 and a CD28 co-stimulatory domain comprising the amino acid sequence set forth in SEQ ID NO: 133; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:128. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) the intracellular domain of CD3z and a 4-1BB co-stimulatory domain; (iii) a transmembrane domain comprising the transmembrane domain of CD28; and (iv) an IgG hinge domain.

In some aspects, the CAR comprises (i) an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; (ii) the intracellular domain of CD3z, a CD28 co-stimulatory domain, and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 17 and a VL comprising the amino acid sequence set forth in SEQ ID NO: 18; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; (iii) a transmembrane comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) a 4-1BB costimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO:130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) a 4-1BB co-stimulatory domain comprising the amino acid sequence set forth in SEQ ID NO: 130; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z and a CD28 co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z comprising the amino acid sequence set forth in SEQ ID NO: 131 and a CD28 co-stimulatory domain comprising the amino acid sequence set forth in SEQ ID NO: 133; (iii) a transmembrane domain comprising the transmembrane domain of CD28 comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131 and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z comprising the amino acid sequence set forth in SEQ ID NO: 131 and a 4-1BB co-stimulatory domain comprising the amino acid sequence set forth in SEQ ID NO: 130; (iii) a transmembrane domain comprising the amino acid sequence set forth in SEQ ID NO: 129; and (iv) an IgG hinge domain comprising the amino acid sequence set forth in SEQ ID NO: 128.

In some aspects, the CAR comprises (i) an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; (ii) the intracellular domain of CD3z, a CD28 co-stimulatory domain, and a 4-1BB co-stimulatory domain; (iii) a transmembrane domain comprising the transmembrane domain of CD28; and (iv) an IgG hinge domain. In some aspects, the CAR comprises (i) an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; (ii) the intracellular domain of CD3z comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 131, a CD28 co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 133, and a 4-1BB co-stimulatory domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 130; (iii) a transmembrane domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 129; and (iv) an IgG hinge domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 128. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z comprising the amino acid sequence set forth in SEQ ID NO: 131, a CD28 co-stimulatory domain comprising the amino acid sequence set forth in SEQ ID NO: 133, and a 4-1BB co-stimulatory domain comprising the amino acid sequence set forth in SEQ ID NO: 130; (iii) a transmembrane domain comprising the amino acid sequence set forth in SEQ ID NO: 129; and (iv) an IgG hinge domain comprising the amino acid sequence set forth in SEQ ID NO:128. In some aspects, the CAR comprises (i) an antigen-binding domain comprising a VH comprising the amino acid sequence set forth in SEQ ID NO: 97 and a VL comprising the amino acid sequence set forth in SEQ ID NO: 98; (ii) the intracellular domain of CD3z, a CD28 co-stimulatory domain, and a 4-1BB co-stimulatory domain; (iii) a transmembrane domain comprising the transmembrane domain of CD28; and (iv) an IgG hinge domain.

In some aspects, the nucleotide sequence encoding the CAR has at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 101. In some aspects, the nucleotide sequence encoding the CAR comprises the nucleotide sequence set forth in SEQ ID NO: 101.

In some aspects, the nucleotide sequence encoding the CAR has at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 102. In some aspects, the nucleotide sequence encoding the CAR comprises the nucleotide sequence set forth in SEQ ID NO: 102.

In some aspects, the nucleotide sequence encoding the CAR has at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 103. In some aspects, the nucleotide sequence encoding the CAR comprises the nucleotide sequence set forth in SEQ ID NO: 103.

I.E. Armoring Molecule

Disclosed herein are polynucleotides comprising (a) a nucleotide sequence encoding a CAR, wherein the CAR comprises an antigen-binding domain that binds an epitope on human STEAP2, and (b) a nucleotide sequence encoding an armoring molecule. One approach to making CAR-T cells that are more resistant to tumor-associated immunosuppression is called "armoring." Armoring is the molecular manipulation of a CAR-T cell to express one or more "armoring molecules" that can counter immunosuppression. For example, investigators reported modifying CAR-T cells to secrete PD-1-blocking single-chain variable fragments (scFv), which improved CAR-T cell anti-tumor activity in mouse models of PD-L1+ hematologic and solid tumors (Rafiq, S., Yeku, O., Jackson, H. et al. Targeted delivery of a PD-1-blocking scFv by CAR-T cells enhances anti-tumor efficacy in vivo. Nat Biotechnol 36, 847-856 (2018)). Others studies have demonstrated the effectiveness of armoring T cells with a dominant-negative TGF-β receptor type 2 (TGFβRIIDN) armoring molecule to neutralize the suppressive effects of TGF-β on T cells (Bollard et al., Tumor-Specific T-Cells Engineered to Overcome Tumor Immune Evasion Induce Clinical Responses in Patients With Relapsed Hodgkin Lymphoma, J Clin Oncol 36(11):1128-1139 (2018)). Currently, at least one clinical study is investigating the effectiveness of armoring anti-PSMA-CAR-T cells with a TGFβRIIDN armoring molecule for treating castrate-resistant prostate cancer (NCT03089203).

In some aspects, the armoring molecule comprises a dominant-negative TGF-β receptor type 2 (TGFβRIIDN). In some aspects, the armoring molecule comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the armoring molecule comprises the amino acid sequence set forth in SEQ ID NO: 105.

In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising the amino acid sequence set forth in SEQ ID NO: 105.

In some aspects, the armoring molecule comprises a dominant-negative TGF-β receptor type 2 (TGFβRIIDN). In some aspects, the armoring molecule comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the armoring molecule comprises the amino acid sequence set forth in SEQ ID NO: 105.

In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising the amino acid sequence set forth in SEQ ID NO: 105.

In some aspects, the polynucleotide comprises (a) a nucleotide sequence encoding a CAR, wherein the CAR comprises an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99; and (b) a nucleotide sequence encoding a TGFβRIIDN. In some aspects, the polynucleotide comprises (a) a nucleotide sequence encoding a CAR, wherein the CAR comprises an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 108; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 108; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 108; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 109; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 109; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 109; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 110; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 110; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 110; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 111; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 111; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 111; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 112; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 112; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 112; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 113; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 113; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 113; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 114; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 114; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 114; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 115; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 115; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 115; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 116; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 116; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 116; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 118; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 118; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 118; and (b) an armoring molecule comprising the amino acid sequence set forth in SEQ ID NO: 105.

In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 119; and (b) a nucleotide sequence encoding a TGFβRIIDN. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 119; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 119; and (b) an armoring molecule comprising the amino acid sequence set forth in SEQ ID NO: 105.

In some aspects, the polynucleotide comprises (a) a nucleotide sequence encoding a CAR comprising the nucleotide sequence set forth in SEQ ID NO: 101; and (b) a nucleotide sequence encoding an armoring molecule comprising the nucleotide sequence set forth in SEQ ID NO: 104.

In some aspects, the polynucleotide comprises (a) a nucleotide sequence encoding a CAR comprising the nucleotide sequence set forth in SEQ ID NO: 102; and (b) a nucleotide sequence encoding an armoring molecule comprising the nucleotide sequence set forth in SEQ ID NO: 104.

In some aspects, the polynucleotide comprises (a) a nucleotide sequence encoding a CAR comprising the nucleotide sequence set forth in SEQ ID NO: 103; and (b) a nucleotide sequence encoding an armoring molecule comprising the nucleotide sequence set forth in SEQ ID NO: 104.

In some aspects, the polynucleotide comprises (a) a nucleotide sequence encoding a CAR comprising the nucleotide sequence set forth in SEQ ID NO: 101; and (b) a nucleotide sequence encoding an armoring molecule comprising the amino acid sequence set forth in SEQ ID NO: 105.

In some aspects, the polynucleotide comprises (a) a nucleotide sequence encoding a CAR comprising the nucleotide sequence set forth in SEQ ID NO: 102; and (b) a nucleotide sequence encoding an armoring molecule comprising the amino acid sequence set forth in SEQ ID NO: 105.

In some aspects, the polynucleotide comprises (a) a nucleotide sequence encoding a CAR comprising the nucleotide sequence set forth in SEQ ID NO: 103; and (b) a nucleotide sequence encoding an armoring molecule comprising the amino acid sequence set forth in SEQ ID NO: 105.

In some aspects, the nucleotide encoding the CAR and the nucleotide encoding the armoring molecule are linked by a third nucleotide sequence, wherein the third nucleotide sequence encodes a cleavable peptide linker. In some aspects, the cleavable peptide linker comprises a T2A peptide. In some aspects, the cleavable peptide linker comprises SEQ ID NO: 126.

In some aspects, the polynucleotide comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 107. In some aspects, the polynucleotide comprises the nucleotide sequence set forth in SEQ ID NO: 107.

II. Anti-STEAP2 Antibodies of the Present Disclosure

Some aspects of the present disclosure are directed to antibodies or antigen-binding portions thereof that specifically binds human STEAP2. In some aspects, the antibody or antigen-binding portion thereof comprises a variable heavy chain region (VH) and a variable light chain region (VL), wherein the VH comprises a VH complementarity determining region (CDR) 1, a VH-CDR2, a VH-CDR3; and wherein the VL comprises a VL-CDR1, a VL-CDR2, and VL-CDR3. In some aspects, the antibody or antigen-binding portion thereof comprises a VH-CDR3 comprising an amino acid sequence selected from SEQ ID NOs: 6, 16, 26, 36, 46, and 96. In some aspects, the antibody or antigen-binding portion thereof comprises a VH-CDR2 comprising an amino acid sequence selected from SEQ ID NOs: 5, 15, 25, 35, 45, and 95. In some aspects, the antibody or antigen-binding portion thereof comprises a VH-CDR1 comprising an amino acid sequence selected from SEQ ID NOs: 4, 14, 24, 34, and 44, and 94.

In some aspects, the antibody or antigen-binding portion thereof comprises a VL-CDR3 comprising an amino acid sequence selected from SEQ ID NOs: 3, 13, 23, 33, 43, and 93. In some aspects, the antibody or antigen-binding portion thereof comprises a VL-CDR2 comprising an amino acid sequence selected from SEQ ID NOs: 2, 12, 22, 32, 42, and 92. In some aspects, the antibody or antigen-binding portion thereof comprises a VL-CDR1 comprising an amino acid sequence selected from SEQ ID NOs: 1, 11, 21, 31, 41, and 91.

In some aspects, the antibody or antigen-binding portion thereof comprises a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6.

In some aspects, the antibody or antigen-binding portion thereof comprises a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16.

In some aspects, the antibody or antigen-binding portion thereof comprises a VL-CDR1 comprising the amino acid sequence set forth in SEQ ID NO: 21, a VL-CDR2 comprising the amino acid sequence set forth in SEQ ID NO: 22, a VL-CDR3 comprising the amino acid sequence set forth in SEQ ID NO: 23, a VH-CDR1 comprising the amino acid sequence set forth in SEQ ID NO: 24, a VH-CDR2 comprising the amino acid sequence set forth in SEQ ID NO: 25, a VH-CDR3 comprising the amino acid sequence set forth in SEQ ID NO: 26.

In some aspects, the antibody or antigen-binding portion thereof comprises a VL-CDR1 comprising the amino acid sequence set forth in SEQ ID NO: 31, a VL-CDR2 comprising the amino acid sequence set forth in SEQ ID NO: 32, a VL-CDR3 comprising the amino acid sequence set forth in SEQ ID NO: 33, a VH-CDR1 comprising the amino acid sequence set forth in SEQ ID NO: 34, a VH-CDR2 comprising the amino acid sequence set forth in SEQ ID NO: 35, a VH-CDR3 comprising the amino acid sequence set forth in SEQ ID NO: 36.

In some aspects, the antibody or antigen-binding portion thereof comprises a VL-CDR1 comprising the amino acid sequence set forth in SEQ ID NO: 41, a VL-CDR2 comprising the amino acid sequence set forth in SEQ ID NO: 42, a VL-CDR3 comprising the amino acid sequence set forth in SEQ ID NO: 43, a VH-CDR1 comprising the amino acid sequence set forth in SEQ ID NO: 44, a VH-CDR2 comprising the amino acid sequence set forth in SEQ ID NO: 45, a VH-CDR3 comprising the amino acid sequence set forth in SEQ ID NO: 46.

In some aspects, the antibody or antigen-binding portion thereof comprises the VL-CDR1, VL-CDR2, and VL-CDR3 present in the VL region having the amino acid sequence set forth in SEQ ID NO: 58; and the VH-CDR1, VH-CDR2, and VH-CDR3 present in the VH region having the amino acid sequence set forth in SEQ ID NO: 57.

In some aspects, the antibody or antigen-binding portion thereof comprises the VL-CDR1, VL-CDR2, and VL-CDR3 present in the VL region having the amino acid sequence set forth in SEQ ID NO: 68; and the VH-CDR1, VH-CDR2, and VH-CDR3 present in the VH region having the amino acid sequence set forth in SEQ ID NO: 67.

In some aspects, the antibody or antigen-binding portion thereof comprises the VL-CDR1, VL-CDR2, and VL-CDR3 present in the VL region having the amino acid sequence set forth in SEQ ID NO: 78; and the VH-CDR1, VH-CDR2, and VH-CDR3 present in the VH region having the amino acid sequence set forth in SEQ ID NO: 77.

In some aspects, the antibody or antigen-binding portion thereof comprises the VL-CDR1, VL-CDR2, and VL-CDR3 present in the VL region having the amino acid sequence set forth in SEQ ID NO: 88; and the VH-CDR1, VH-CDR2, and VH-CDR3 present in the VH region having the amino acid sequence set forth in SEQ ID NO: 87.

In some aspects, the antibody or antigen-binding portion thereof comprises the VL-CDR1, VL-CDR2, and VL-CDR3 present in the VL region having the amino acid sequence set forth in SEQ ID NO: 98; and the VH-CDR1, VH-CDR2, and VH-CDR3 present in the VH region having the amino acid sequence set forth in SEQ ID NO: 97.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 7, 17, 27, 37, 47, 57, 67, 77, 87, and 97. In some aspects, the antibody or antigen-binding portion thereof comprises a VH comprising an amino acid sequence selected from SEQ ID NOs: 7, 17, 27, 37, 47, 57, 67, 77, 87, and 97.

In some aspects, the antibody or antigen-binding portion thereof comprises a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to an amino acid sequence selected from SEQ ID NOs: 8, 18, 28, 38, 48, 58, 68, 78, 88, and 98. In some aspects, the antibody or antigen-binding portion thereof comprises a VL comprising an amino acid sequence selected from SEQ ID NOs: 8, 18, 28, 38, 48, 58, 68, 78, 88, and 98.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the antibody or antigen-binding portion thereof comprises a VH comprising the amino acid sequence set forth in SEQ ID NO: 7, and a VL comprising the amino acid sequence set forth in SEQ ID NO: 8.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the antibody or antigen-binding portion thereof comprises a VH comprising the amino acid sequence set forth in SEQ ID NO: 17, and a VL comprising the amino acid sequence set forth in SEQ ID NO: 18.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28. In some aspects, the antibody or antigen-binding portion thereof comprises a VH comprising the amino acid sequence set forth in SEQ ID NO: 27, and a VL comprising the amino acid sequence set forth in SEQ ID NO: 28.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38. In some aspects, the antibody or antigen-binding portion thereof comprises a VH comprising the amino acid sequence set forth in SEQ ID NO: 37, and a VL comprising the amino acid sequence set forth in SEQ ID NO: 38.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48. In some aspects, the antibody or antigen-binding portion thereof comprises a VH comprising the amino acid sequence set forth in SEQ ID NO: 47, and a VL comprising the amino acid sequence set forth in SEQ ID NO: 48.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58. In some aspects, the antibody or antigen-binding portion thereof comprises a VH comprising the amino acid sequence set forth in SEQ ID NO: 57, and a VL comprising the amino acid sequence set forth in SEQ ID NO: 58.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68. In some aspects, the antibody or antigen-binding portion thereof comprises a VH comprising the amino acid sequence set forth in SEQ ID NO: 67, and a VL comprising the amino acid sequence set forth in SEQ ID NO: 68.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78. In some aspects, the antibody or antigen-binding portion thereof comprises a VH comprising the amino acid sequence set forth in SEQ ID NO: 77, and a VL comprising the amino acid sequence set forth in SEQ ID NO: 78.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88. In some aspects, the antibody or antigen-binding portion thereof comprises a VH comprising the amino acid sequence set forth in SEQ ID NO: 87, and a VL comprising the amino acid sequence set forth in SEQ ID NO: 88.

In some aspects, the antibody or antigen-binding portion thereof comprises a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the antibody or antigen-binding portion thereof comprises a VH comprising the amino acid sequence set forth in SEQ ID NO: 97, and a VL comprising the amino acid sequence set forth in SEQ ID NO: 98.

In some aspects, the antibody or antigen-binding portion thereof comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 9. In some aspects, the antibody or antigen-binding portion thereof comprises the amino acid sequence set forth in SEQ ID NO: 9.

In some aspects, the antibody or antigen-binding portion thereof comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 99. In some aspects, the antibody or antigen-binding portion thereof comprises the amino acid sequence set forth in SEQ ID NO: 99.

In some aspects, the antibody or antigen-binding portion thereof cross competes for binding to human STEAP2 with an antibody or antigen-binding portion thereof disclosed herein. In some aspects, the antibody or antigen-binding portion thereof binds the same epitope on human STEAP2 as an antibody or antigen-binding portion thereof disclosed herein. In some aspects, the antibody or antigen-binding portion thereof binds on overlapping epitope on human STEAP2 as an antibody or antigen-binding portion thereof disclosed herein.

III. Cells of the Disclosure

Some aspects of the present disclosure are directed to cells comprising a polynucleotide or a polypeptide disclosed herein. Some aspects of the present disclosure are directed to a cell comprising (i) a polynucleotide encoding a chimeric antigen receptor (CAR) that binds human STEAP2. In some aspects, the cell further comprises (ii) a polynucleotide encoding an armoring molecule. In some aspects, the cell is an immune cell. In some aspects, the cell is selected from the group consisting of a T cell, a Natural Killer (NK) cell, a cytotoxic T lymphocyte (CTL), a regulatory T cell, a tumor infiltrating lymphocyte, and any combination thereof. In some aspects, the cell is a mammalian cell. In some aspects, the cell is a human cell.

The cell of the present disclosure can be obtained through any source. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain aspects, the cells collected by apheresis are washed to remove the plasma fraction, and placed in an appropriate buffer or media for subsequent processing. In some aspects, the cells are washed with PBS. As will be appreciated, a washing step can be used, such as by using a semiautomated flowthrough centrifuge, e.g., the COBE™ 2991 cell processor, the Baxter CYTOMATE™, or the like. In some aspects, the washed cells are resuspended in one or more biocompatible buffers, or other saline solution with or without buffer. In certain aspects, the undesired components of the apheresis sample are removed. Additional methods of isolating T cells for a T cell therapy are disclosed in U.S. Patent Publication No. 2013/0287748, which is herein incorporated by references in its entirety.

In certain aspects, T cells are isolated from PBMCs by lysing the red blood cells and depleting the monocytes, e.g., by using centrifugation through a PERCOLL™ gradient. In some aspects, a specific subpopulation of T cells, such as CD28+, CD4+, CD8+, CD45RA+, and CD45RO+ T cells is further isolated by positive or negative selection techniques known in the art. For example, enrichment of a T cell population by negative selection can be accomplished with a combination of antibodies directed to surface markers unique to the negatively selected cells. In some aspects, cell sorting and/or selection via negative magnetic immunoadherence or flow cytometry that uses a cocktail of monoclonal antibodies directed to cell surface markers present on the cells negatively selected can be used. For example, to enrich for CD4+ cells by negative selection, a monoclonal antibody cocktail typically includes antibodies to CD14, CD20, CD11b, CD16, HLA-DR, and CD8. In certain aspects, flow cytometry and cell sorting are used to isolate cell populations of interest for use in the present disclosure.

In some aspects, PBMCs are used directly for genetic modification with the immune cells (such as CARs) using methods as described herein. In certain aspects, after isolating the PBMCs, T lymphocytes are further isolated, and both cytotoxic and helper T lymphocytes are sorted into naive, memory, and effector T cell subpopulations either before or after genetic modification and/or expansion.

In some aspects, CD8+ cells are further sorted into naive, central memory, and effector cells by identifying cell surface antigens that are associated with each of these types of CD8+ cells. In some aspects, the expression of phenotypic markers of central memory T cells includes CD45RO, CD62L, CCR7, CD28, CD3, and CD127 and are negative for granzyme B. In some aspects, central memory T cells are CD45RO+, CD62L+, CD8+ T cells. In some aspects, effector T cells are negative for CD62L, CCR7, CD28, and CD127 and positive for granzyme B and perforin. In certain aspects, CD4+ T cells are further sorted into subpopulations. For example, CD4+ T helper cells can be sorted into naive, central memory, and effector cells by identifying cell populations that have cell surface antigens.

In some aspects, the immune cells, e.g., T cells, are genetically modified following isolation using known methods, or the immune cells are activated and expanded (or differentiated in the case of progenitors) in vitro prior to being genetically modified. In another aspect, the immune cells, e.g., T cells, are genetically modified with the CARs described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other aspects, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In certain aspects, the T cells are obtained from a donor subject. In some aspects, the donor subject is human patient afflicted with a cancer or a tumor. In other aspects, the donor subject is a human patient not afflicted with a cancer or a tumor.

In some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6.

In some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16.

some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6.

In some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16.

In some aspects, the cell comprises a polynucleotide comprising a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96. In some aspects, the polynucleotide comprises a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18.

In some aspects, the cell comprises a polynucleotide comprising a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98. In some aspects, the polynucleotide comprises a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising the amino acid sequence set forth in SEQ ID NO: 105.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising a nucleic acid sequence having at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 104. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6; and (b) an armoring molecule comprising the nucleic acid sequence set forth in SEQ ID NO: 104.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising a nucleic acid sequence having at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 104. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16; and (b) an armoring molecule comprising the nucleic acid sequence set forth in SEQ ID NO: 104.

In some aspects, the cell comprises a polynucleotide comprising (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) a nucleotide sequence encoding a TGFβRIIDN. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising a nucleic acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 104. In some aspects, the polynucleotide comprises (a) a nucleotide sequence encoding a CAR, wherein the CAR comprises an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96; and (b) an armoring molecule comprising the nucleic acid sequence set forth in SEQ ID NO: 104.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising nucleic acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 104. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8; and (b) an armoring molecule comprising the nucleic acid sequence set forth in SEQ ID NO: 104.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising a nucleic acid sequence having at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 104. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18; and (b) an armoring molecule comprising the nucleic acid sequence set forth in SEQ ID NO: 104.

In some aspects, the cell comprises a polynucleotide comprising (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) a nucleotide sequence encoding a TGFβRIIDN. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising a nucleic acid sequence having at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 104. In some aspects, the polynucleotide comprises (a) a nucleotide sequence encoding a CAR, wherein the CAR comprises an antigen-binding domain comprising a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97 and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98; and (b) an armoring molecule comprising the nucleic acid sequence set forth in SEQ ID NO: 104.

In some aspects, the cell comprises a polynucleotide comprising (a) a nucleotide sequence encoding a CAR comprising the nucleotide sequence set forth in SEQ ID NO: 101; and (b) a nucleotide sequence encoding an armoring molecule comprising the nucleotide sequence set forth in SEQ ID NO: 104.

In some aspects, the cell comprises a polynucleotide comprising (a) a nucleotide sequence encoding a CAR comprising the nucleotide sequence set forth in SEQ ID NO:

102; and (b) a nucleotide sequence encoding an armoring molecule comprising the nucleotide sequence set forth in SEQ ID NO: 104.

In some aspects, the cell comprises a polynucleotide comprising (a) a nucleotide sequence encoding a CAR comprising the nucleotide sequence set forth in SEQ ID NO: 103; and (b) a nucleotide sequence encoding an armoring molecule comprising the nucleotide sequence set forth in SEQ ID NO: 104.

In some aspects, the cell comprises a polynucleotide comprising (a) a nucleotide sequence encoding a CAR comprising the nucleotide sequence set forth in SEQ ID NO: 101; and (b) a nucleotide sequence encoding an armoring molecule comprising the amino acid sequence set forth in SEQ ID NO: 105.

In some aspects, the cell comprises a polynucleotide comprising (a) a nucleotide sequence encoding a CAR comprising the nucleotide sequence set forth in SEQ ID NO: 102; and (b) a nucleotide sequence encoding an armoring molecule comprising the amino acid sequence set forth in SEQ ID NO: 105.

In some aspects, the cell comprises a polynucleotide comprising (a) a nucleotide sequence encoding a CAR comprising the nucleotide sequence set forth in SEQ ID NO: 103; and (b) a nucleotide sequence encoding an armoring molecule comprising the amino acid sequence set forth in SEQ ID NO: 105.

In some aspects, the cell comprises a polynucleotide comprising a nucleotide sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleotide sequence set forth in SEQ ID NO: 107. In some aspects, the polynucleotide comprises the nucleotide sequence set forth in SEQ ID NO: 107.

In some aspects, the cell comprises a polynucleotide comprising a nucleotide sequence encoding a polypeptide comprising an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 106. In some aspects, the polypeptide comprises the amino acid sequence set forth in SEQ ID NO: 106.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 117. In some aspects, the polypeptide comprises the amino acid sequence set forth in SEQ ID NO: 117.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 120. In some aspects, the polypeptide comprises the amino acid sequence set forth in SEQ ID NO: 120.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 121. In some aspects, the polypeptide comprises the amino acid sequence set forth in SEQ ID NO: 121.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 122. In some aspects, the polypeptide comprises the amino acid sequence set forth in SEQ ID NO: 122.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 123. In some aspects, the polypeptide comprises the amino acid sequence set forth in SEQ ID NO: 123.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 124. In some aspects, the polypeptide comprises the amino acid sequence set forth in SEQ ID NO: 124.

In some aspects, the cell comprises a polynucleotide comprising a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 125. In some aspects, the polypeptide comprises the amino acid sequence set forth in SEQ ID NO: 125.

In some aspects, the cell comprises a CAR comprising an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6.

In some aspects, the cell comprises a CAR comprising an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16.

In some aspects, the cell comprises a CAR comprising an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

In some aspects, the cell comprises a polypeptide that comprises (i) a CAR comprising an antigen-binding domain comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6 and (ii) an amino acid sequence set forth in SEQ ID NO: 105.

In some aspects, the cell comprises a polypeptide that comprises (i) a CAR comprising an antigen-binding domain comprising a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16 and (ii) an amino acid sequence set forth in SEQ ID NO: 105.

In some aspects, the cell comprises a polypeptide that comprises (i) a CAR comprising an antigen-binding domain comprising a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96 and (ii) an amino acid sequence set forth in SEQ ID NO: 105.

In some aspects, the cell comprises a CAR comprising an amino acid set forth in SEQ ID NO: 10 and an armoring molecule comprising an amino acid set forth in SEQ ID NO: 105. In some aspects, the cell comprises a CAR comprising an amino acid set forth in SEQ ID NO: 108 and an armoring molecule comprising an amino acid set forth in SEQ ID NO: 105. In some aspects, the cell comprises a CAR comprising an amino acid set forth in SEQ ID NO: 109 and an armoring molecule comprising an amino acid set forth in SEQ ID NO: 105. In some aspects, the cell comprises a CAR comprising an amino acid set forth in SEQ ID NO: 110 and an armoring molecule comprising an amino acid set forth in SEQ ID NO: 105. In some aspects, the cell comprises a CAR comprising an amino acid set forth in SEQ ID NO: 111 and an armoring molecule comprising an amino acid set forth in SEQ ID NO: 105. In some aspects, the cell comprises a CAR comprising an amino acid set forth in SEQ ID NO: 112 and an armoring molecule comprising an amino acid set forth in SEQ ID NO:

105. In some aspects, the cell comprises a CAR comprising an amino acid set forth in SEQ ID NO: 113 and an armoring molecule comprising an amino acid set forth in SEQ ID NO: 105. In some aspects, the cell comprises a CAR comprising an amino acid set forth in SEQ ID NO: 114 and an armoring molecule comprising an amino acid set forth in SEQ ID NO: 105. In some aspects, the cell comprises a CAR comprising an amino acid set forth in SEQ ID NO: 115 and an armoring molecule comprising an amino acid set forth in SEQ ID NO: 105. In some aspects, the cell comprises a CAR comprising an amino acid set forth in SEQ ID NO: 116 and an armoring molecule comprising an amino acid set forth in SEQ ID NO: 105.

IV. Vectors, Host Cells, and Pharmaceutical Compositions of the Disclosure

In some aspects, the polynucleotide of the present disclosure is present in a vector. As such, provided herein are vectors comprising a polynucleotide of the present disclosure. In some aspects, the present disclosure is directed to a vector or a set of vectors comprising a polynucleotide encoding a CAR, as described herein. In other aspects, the present disclosure is directed to a vector or a set of vectors comprising a polynucleotide encoding an antibody or an antigen binding molecule thereof that specifically binds to STEAP2, as disclosed herein.

In some aspects, the set of vectors comprises a first vector and a second vector, wherein the first vector comprises a nucleic acid sequence encoding a CAR disclosed herein, and the second vector comprises a nucleic acid sequence encoding an armoring molecule disclosed herein.

Any vector known in the art can be suitable for the present disclosure. In some aspects, the vector is a viral vector. In some aspects, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are host cells comprising a polynucleotide or a vector of the present disclosure. In some aspects, the present disclosure is directed to host cells, e.g., in vitro cells, comprising a polynucleotide encoding a CAR or a TCR, as described herein. In some aspects, the present disclosure is directed to host cells, e.g., in vitro cells, comprising a polynucleotide encoding an antibody or an antigen binding molecule thereof that specifically binds to STEAP2, as disclosed herein. In other aspects, the present disclosure is directed to in vitro cells comprising a polypeptide encoded by a polynucleotide encoding a CAR—That specifically binds to STEAP2. In other aspects, the present disclosure is directed to cells, in vitro cells, comprising a polypeptide encoded by a polynucleotide encoding an antibody or an antigen binding molecule thereof that specifically binds to STEAP2, as disclosed herein.

Any cell may be used as a host cell for the polynucleotides, the vectors, or the polypeptides of the present disclosure. In some aspects, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Kleb-siella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some aspects, the cell is a human cell.

Other aspects of the present disclosure are directed to compositions comprising a polynucleotide described herein, a vector described herein, a polypeptide described herein, or cell described herein. In some aspects, the composition comprises a pharmaceutically acceptable carrier, diluent, solubilizer, emulsifier, preservative and/or adjuvant. In some aspects, the composition comprises an excipient. In one aspect, the composition comprises a polynucleotide encoding a CAR, wherein the CAR comprises an antigen binding molecule that specifically binds to STEAP2. In another aspect, the composition comprises a CAR encoded by a polynucleotide of the present disclosure, wherein the CAR comprises an antigen binding molecule that specifically binds to STEAP2. In another aspect, the composition comprises a T cell comprising a polynucleotide encoding a CAR, wherein the CAR comprises an antigen binding molecule that specifically binds to STEAP2. In another aspect, the composition comprises an antibody or an antigen binding molecule thereof that specifically binds STEAP2, as described herein. In another aspect, the composition comprises a cell (e.g., a T cell, e.g., a CAR-T cell) comprising a polynucleotide encoding CAR comprising an antigen binding domain that specifically binds STEAP2, as disclosed herein.

In other aspects, the composition is formulated for parenteral delivery, for inhalation, or for delivery through the digestive tract, such as orally. The preparation of such pharmaceutically acceptable compositions is within the ability of one skilled in the art. In certain aspects, buffers are used to maintain the composition at physiological pH or at a slightly lower pH, typically within a pH range of from about 5 to about 8. In certain aspects, when parenteral administration is contemplated, the composition is in the form of a pyrogen-free, parenterally acceptable aqueous solution comprising a desired antigen binding molecule to BCMA, with or without additional therapeutic agents, in a pharmaceutically acceptable vehicle. In certain aspects, the vehicle for parenteral injection is sterile distilled water in which an antigen binding molecule to BCMA, with or without at least one additional therapeutic agent, is formulated as a sterile, isotonic solution, properly preserved. In certain aspects, the preparation involves the formulation of the desired molecule with polymeric compounds (such as polylactic acid or polyglycolic acid), beads or liposomes, that provide for the controlled or sustained release of the product, which are then be delivered via a depot injection. In certain aspects, implantable drug delivery devices are used to introduce the desired molecule.

VI. Methods of the Disclosure

Certain aspects of the present disclosure are directed to methods of treating a disease or condition in a subject in need thereof, comprising administering to the subject a composition disclosed herein. In some aspects, the disease or condition comprises a cancer. In some aspects, the cancer is prostate cancer. In some aspects, the cancer comprises a tumor derived from a prostate cancer (e.g., a tumor arising from the metastasis of a prostate cancer). In some aspects, the cancer (e.g., the prostate cancer) is locally progressed. In some aspects, the cancer (e.g., the prostate cancer) is meta-static. In some aspects, the cancer (e.g., the prostate cancer) is recurrent. In some aspects, the cancer (e.g., the prostate cancer) is relapsed.

The compositions disclosed herein, e.g. a T-cell comprising a polynucleotide encoding a CAR disclosed herein, can be used in combination with other anti-cancer therapies, including one or more additional immunotherapies. In some aspects, the compositions disclosed herein are administered concurrently with the additional anti-cancer agent. In some aspects, the compositions disclosed herein and the additional anti-cancer agent are administered sequentially (e.g., on the same day or on different days).

In some aspects, the additional anti-cancer agent comprises an antimetabolites (including, without limitation, folic acid antagonists, pyrimidine analogs, purine analogs and adenosine deaminase inhibitors). In some aspects, the additional anti-cancer agent comprises methotrexate, 5-fluorouracil, floxuridine, cytarabine, 6-mercaptopurine, 6-thioguanine, fludarabine phosphate, pentostatine, gemcitabine, and any combination thereof.

In some aspects, the additional anti-cancer agent comprises a taxane, paclitaxel (e.g., TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone Bl, [17]-dehydrodesoxyepothilone B, dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone BIO, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, a microtubuline stabilizing, and any combination thereof.

TABLE 1

Sequences.

| SEQ ID | Description | Sequences |
|---|---|---|
| 1 | STEAP2 VL CDR1 (40A3) | RASQSVNSNLA |
| 2 | STEAP2 VL CDR2 | GASTRAT |
| 3 | STEAP2 VL CDR3 | QQYNNWPFT |
| 4 | STEAP2 VH CDR1 | RNSAVWN |
| 5 | STEAP2 VH CDR2 | RTYYRSKWYNDYAVSVKS |
| 6 | STEAP2 VH CDR3 | GLLQNNFYYYMDV |
| 7 | STEAP2 VH | QVQLQQSGPGLVKPSQTLSLTCAISGDSVSRNSAVWNWIRQS PSRGLEWLGRTYYRSKWYNDYAVSVKSRITINPDTSKNQFSL QVNSVTPEDTAVYYCARGLLQNNFYYYMDVWGKGTTVTVSS |
| 8 | STEAP2 VL | EIVMTQSPATLSVSPGERATLSCRASQSVNSNLAWYQQKPGQ APRLLIYGASTRATGIPARFSGSGSGTEFTLTISSLQSEDFA VYYCQQYNNWPFTFGPGTKVDIK |
| 9 | STEAP2 scFv amino acid sequence | EIVMTQSPATLSVSPGERATLSCRASQSVNSNLAWYQQKPGQ APRLLIYGASTRATGIPARFSGSGSGTEFTLTISSLQSEDFA VYYCQQYNNWPFTFGPGTKVDIKGGGGSGGGGSGGGGSGGGG SQVQLQQSGPGLVKPSQTLSLTCAISGDSVSRNSAVWNWIRQ SPSRGLEWLGRTYYRSKWYNDYAVSVKSRITINPDTSKNQFS LQVNSVTPEDTAVYYCARGLLQNNFYYYMDVWGKGTTVTVSS |
| 10 | STEAP2 BZ CAR amino acid sequence | MLLLVTSLLLCELPHPAFLLIPEIVMTQSPATLSVSPGERAT LSCRASQSVNSNLAWYQQKPGQAPRLLIYGASTRATGIPARF SGSGSGTEFTLTISSLQSEDFAVYYCQQYNNWPFTFGPGTKV DIKGGGGSGGGGSGGGGSGGGGSQVQLQQSGPGLVKPSQTLS LTCAISGDSVSRNSAVWNWIRQSPSRGLEWLGRTYYRSKWYN DYAVSVKSRITINPDTSKNQFSLQVNSVTPEDTAVYYCARGL LQNNFYYYMDVWGKGTTVTVSSGSESKYGPPCPPCPFWVLVV VGGVLACYSLLVTVAFIIFWVKRGRKKLLYIFKQPFMRPVOT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR |

TABLE 1-continued

Sequences.

| SEQ ID | Description | Sequences |
|---|---|---|
| 11 | STEAP2-3 VL CDR1 (40A3GL-LO7) | RASQSVSSNLA |
| 12 | STEAP2-3 VL CDR2 | GASTRAT |
| 13 | STEAP2-3 VL CDR3 | QQYNNWPFT |
| 14 | STEAP2-3 VH CDR1 | RNSAVWN |
| 15 | STEAP2-3 VH CDR2 | RTYYRSKWYNDYAVSVKS |
| 16 | STEAP2-3 VH CDR3 | GLLQNQFYYYMDV |
| 17 | STEAP2-3 VH | QVQLQQSGPGLVKPSQTLSLTCAISGDSVSRNSAVWNWIRQS PSRGLEWLGRTYYRSKWYNDYAVSVKSRITINPDTSKNQFSL QLNSVTPEDTAVYYCARGLLQNQFYYYMDVWGKGTTVTVSS |
| 18 | STEAP2-3 VL | EIVMTQSPATLSVSPGERATLSCRASQSVSSNLAWYQQKPGQ APRLLIYGASTRATGIPARFSGSGSGTEFTLTISSLQSEDFA VYYCQQYNNWPFTFGPGTKVDIK |
| 21 | STEAP2-2 VL CDR1 (mm 30D12) | RSSQSVVHSNGNTYLE |
| 22 | STEAP2-2 VL CDR2 | KVSNRFS |
| 23 | STEAP2-2 VL CDR3 | FQGSHVPYT |
| 24 | STEAP2-2 VH CDR1 | SYGMS |
| 25 | STEAP2-2 VH CDR2 | TISSGGSYTFYPDIMKG |
| 26 | STEAP2-2 VH CDR3 | RGYGTIYTFSFDS |
| 27 | STEAP2-2 VH | EVQLVESGGDLVKPGGSLKLSCAASGFSFSSYGMSWVRQTPD KRLEWVATISSGGSYTFYPDIMKGRFTISRDNAMNTLYLQMS SLKSEDSAMYYCARRGYGTIYTFSFDSWGQGTTLTVSS |
| 28 | STEAP2-2 VL | DVLMTQTPLSLPVSLGDQASISCRSSQSVVHSNGNTYLEWYL QKPGQSPKLLIYKVSNRFSGVPDRFSGSGSGTDFTLKISRVE AEDLGVYYCFQGSHVPYTFGGGTKLEIK |
| 31 | STEAP2-2 Humanized1 VL CDR1 | RSSQSVVHSNANTYLE |
| 32 | STEAP2-2 Humanized1 VL CDR2 | KVSNRFS |
| 33 | STEAP2-2 Humanized1 VL CDR3 | FQGSHVPYT |

TABLE 1-continued

| | | Sequences. | |

| SEQ ID | Description | Sequences |
| --- | --- | --- |
| 34 | STEAP2-2 Humanized1 VH CDR1 | SYGMS |
| 35 | STEAP2-2 Humanized1 VH CDR2 | TISSGGSYTFYPDIMKG |
| 36 | STEAP2-2 Humanized1 VH CDR3 | RGYGTIYTFSFDA |
| 37 | STEAP2-2 Humanized1 VH | EVQLVESGGGLVKPGGSLRLSCAASGFTFSSYGMSWVRQAPG KRLEWVATISSGGSYTFYPDIMKGRFTISRDNSKNTLYLQMN SLRAEDTAVYYCARRGYGTIYTFSFDAWGQGTTLTVSS |
| 38 | STEAP2-2 Humanized1 VL | DVVMTQSPLSLPVTLGQPASISCRSSQSVVHSNANTYLEWYL QKPGQSPQLLIYKVSNRFSGVPDRFSGSGSGTDFTLKISRVE AEDVGVYYCFQGSHVPYTFGQGTKLEIK |
| 41 | STEAP2-2 Humanized2 VL CDR1 | RSSQSVVHSNANTYLE |
| 42 | STEAP2-2 Humanized2 VL CDR2 | KVSNRFS |
| 43 | STEAP2-2 Humanized2 VL CDR3 | FQGSHVPYT |
| 44 | STEAP2-2 Humanized2 VH CDR1 | SYGMS |
| 45 | STEAP2-2 Humanized2 VH CDR2 | TISSGGSYTFYPDIMKG |
| 46 | STEAP2-2 Humanized2 VH CDR3 | RGYGTIYTFSFDA |
| 47 | STEAP2-2 Humanized2 VH | EVQLLESGGGLVQPGGSLRLSCAASGFTFSSYGMSWVRQAPG KRLEWVSTISSGGSYTFYPDIMKGRFTISRDNSKNTLYLQMN SLRAEDTAVYYCARRGYGTIYTFSFDAWGQGTTLTVSS |
| 48 | STEAP2-2 Humanized VL | DVVMTQSPLSLPVTLGQPASISCRSSQSVVHSNANTYLEWYL QKPGQSPQLLIYKVSNRFSGVPDRFSGSGSGTDFTLKISRVE AEDVGVYYCFQGSHVPYTFGQGTKLEIK |
| 57 | STEAP2-4 VH (40A1) | EVQLVESGGGLVQPGGSLRLSCAASGFTFSSFAMTWVRQAPG KGLEWVSVITYSGGRTYYADSVKGRFTISRDNSKNTLYLQMN SLRAEDTAVYFCAKDRIAAVGPFDYWGQGTLVTVSS |
| 58 | STEAP2-4 VL | DIQLTQSPSFLSASVGDRVTITCRASQGISVYLAWYQQEPGK APKLLIYAASTLQSGVPSRFSGSGSGTEFTLTISSLQPEDFA TYYCQQLNSYPRTFGQGTKVEIK |
| 67 | STEAP2-5 VH (34C1) | QVQLVQSGAEVKKPGASVKVSCKASGYTFTSYGISWVRQAPG QGLEWMGWISGYTGNTNYAQKLQGRVTMTADTSTSTAYMELR SLRSDDTAVYYCARGGSYFDYWGQGTLVTVSS |

TABLE 1-continued

Sequences.

| SEQ ID | Description | Sequences |
|---|---|---|
| 68 | STEAP2-5 VL | DIQMTQSPSTLSASVGDRVTITCRASQSISRWLAWYQQKPGK APKLLIYKASSLESGVPSRFSGSGSGTEFTLTISSLQPDDFA TYYCQQFNSFSPITFGQGTRLEIK |
| 77 | STEAP2-6 VH (6E10) | QVQLQQPGAELVKPGASVKLSCKASGYTFTSYWMEWVKQRPG QGLEWIGMIHPNSGITNYNERFKNKATLTVDKSSSTAYMQLS SLTSEDSAVYYCARDHYYILAYWGQGTLVTVSA |
| 78 | STEAP2-6 VL | DVLMTQTPLSLPVSLGDQASISCRSSQSVVHSNGNTYLEWYL QKPGQSPKLLIYKVSNRFSGVPDRFSGSGSGTDFTLKISRVE AEDLGVYYCFQGSHVPYTFGGGTKLEIK |
| 87 | STEAP2-7 VH (22F3) | QVQLQQPGADLVKPGASVKMSCKASGHTFTNYWVTWVKQRPG QGLEWIGNFYPGSGIIKYNENFRSKATLTVDISSSTAYMQLS SLTSEDSAVYYCARSKLGDSFYFDYWGQGTTLTVSS |
| 88 | STEAP2-7 VL | DVVMTQTPLSLPVSLGNQASISCRSSQSLVHSNGNTYLHWYL QKPGQSPKLLIYKVSNRFSGVPDRFSGSGSGTDFTLKISRVE AEDLGVYFCSQSTHVPLTFGAGTKLEIK |
| 91 | STEAP2-8 40A3GL-L014) VL CDR1 | RASQSVASNLA |
| 92 | STEAP2-8 VL CDR2 | GASTRAT |
| 93 | STEAP2-8 VL CDR3 | QQYNNWPFT |
| 94 | STEAP2-8 VH CDR1 | RNSAVWN |
| 95 | STEAP2-8 VH CDR2 | RTYYRSKWYNDYAPSVKS |
| 96 | STEAP2-8 VH CDR3 | GLRQNQFYYYMDV |
| 97 | STEAP2-8 VH | QVQLQQSGPGLVKPSQTLSLTCAISGDSVSRNSAVWNWIRQS PSRGLEWLGRTYYRSKWYNDYAPSVKSRITINPDTSKNQFSL QLNSVTPEDTAVYYCARGLRQNQFYYYMDVWGKGTTVTVSS |
| 98 | STEAP2-8 VL | EIVMTQSPATLSVSPGERATLSCRASQSVASNLAWYQQKPGQ APRLLIYGASTRATGIPARFSGSGSGTEFTLTISSLQSEDFA VYYCQQYNNWPFTFGPGTKVDIK |
| 99 | STEAP2-8 scFv | EIVMTQSPATLSVSPGERATLSCRASQSVASNLAWYQQKPGQ APRLLIYGASTRATGIPARFSGSGSGTEFTLTISSLQSEDFA VYYCQQYNNWPFTFGPGTKVDIKGGGGSGGGGSGGGGSGGGG SQVQLQQSGPGLVKPSQTLSLTCAISGDSVSRNSAVWNWIRQ SPSRGLEWLGRTYYRSKWYNDYAPSVKSRITINPDTSKNQFS LQLNSVTPEDTAVYYCARGLRQNQFYYYMDVWGKGTTVTVSS |
| 101 | STEAP2 scFv nucleic acid sequence | GAGATTGTGATGACCCAGAGCCCTGCAACTCTGAGCGTGTCA CCCGGAGAAAGGGCCACTCTGTCGTGTCGAGCATCGCAGTCC GTGAACTCCAATCTCGCCTGGTACCAGCAGAAGCCTGGGCAG GCCCCGAGGCTGCTCATCTACGGTGCCTCCACGAGAGCCACG GGAATTCCAGCGCGCTTTAGCGGATCCGGCTCGGGAACCGAG TTCACCCTTACCATCTCATCGCTGCAATCCGAAGATTTCGCC GTGTATTACTGTCAACAGTACAACAACTGGCCGTTCACCTTT GGCCCGGGAACTAAGGTCGACATCAAGGGCGGCGGGGGCTCT GGGGGTGGCGGAAGCGGCGGCGGCGGATCCGGTGGCGGCGGA AGCCAAGTGCAGCTGCAGCAGTCCGGACCCGGACTCGTGAAG CCGTCCCAGACTCTGTCCCTGACTTGCGCGATTTCCGGCGAT TCCGTGTCCCGCAACTCCGCTGTGTGGAACTGGATCCGGCAG TCGCCTTCGAGAGGACTGGAGTGGCTGGGACGGACCTACTAC CGCTCAAAATGGTATAACGACTATGCTGTGTCCGTCAAGAGC CGCATCACCATTAACCCCGATACCTCCAAGAACCAGTTCAGT CTGCAAGTCAACAGCGTGACTCCTGAGGACACCGCCGTGTAC TACTGCGCCCGGGGTCTGCTGCAAAACAACTTCTACTACTAC ATGGACGTCTGGGGAAAGGGAACTACTGTGACCGTGTCCTCC |

TABLE 1-continued

Sequences.

| SEQ ID | Description | Sequences |
|---|---|---|
| 102 | STEAP2 BZ CAR nucleic acid sequence | ATGCTGCTCCTTGTCACATCACTGCTGCTCTGCGAACTGCCC<br>CACCCTGCATTCCTCCTGATCCCCGAGATTGTGATGACCCAG<br>AGCCCTGCAACTCTGAGCGTGTCACCCGGAGAAAGGGCCACT<br>CTGTCGTGTCGAGCATCGCAGTCCGTGAACTCCAATCTCGCC<br>TGGTACCAGCAGAAGCCTGGGCAGGCCCCGAGGCTGCTCATC<br>TACGGTGCCTCCACGAGAGCCACGGGAATTCCAGCGCGCTTT<br>AGCGGATCCGGCTCGGGAACCGAGTTCACCCTTACCATCTCA<br>TCGCTGCAATCCGAAGATTTCGCCGTGTATTACTGTCAACAG<br>TACAACAACTGGCCGTTCACCTTTGGCCCGGGAACTAAGGTC<br>GACATCAAGGGCGGCGGGGGCTCTGGGGGTGGCGGAAGCGGC<br>GGCGGCGGATCCGGTGGCGGCGGAAGCCAAGTGCAGCTGCAG<br>CAGTCCGGACCCGGACTCGTGAAGCCGTCCCAGACTCTGTCC<br>CTGACTTGCGCGATTTCCGGCGATTCCGTGTCCCGCAACTCC<br>GCTGTGTGGAACTGGATCCGGCAGTCGCCTTCGAGAGGACTG<br>GAGTGGCTGGGACGGACCTACTACCGCTCAAAATGGTATAAC<br>GACTATGCTGTGTCCGTCAAGAGCCGCATCACCATTAACCCC<br>GATACCTCCAAGAACCAGTTCAGTCTGCAAGTCAACAGCGTG<br>ACTCCTGAGGACACCGCCGTGTACTACTGCGCCCGGGGTCTG<br>CTGCAAAACAACTTCTACTACTACATGGACGTCTGGGGAAAG<br>GGAACTACTGTGACCGTGTCCTCCGGCTCCGAATCAAAATAC<br>GGTCCGCCATGCCCACCGTGCCCCTTCTGGGTGCTCGTGGTC<br>GTCGGAGGGGTTCTGGCCTGCTACTCCCTGCTGGTCACCGTG<br>GCGTTTATCATCTTCTGGGTGAAGCGGGGAAGGAAGAAGCTA<br>CTGTACATTTTCAAGCAGCCTTTCATGCGGCCTGTGCAGACC<br>ACCCAGGAAGAGGACGGCTGTTCCTGCCGGTTCCCCGAGGAA<br>GAGGAAGGGGGTTGCGAGCTGCGCGTGAAGTTCAGCAGGAGC<br>GCTGATGCCCCAGCGTACCAACAGGGGCAAAACCAGTTGTAC<br>AACGAACTGAACCTTGGTCGGCGCGAAGAGTACGACGTGCTT<br>GACAAGCGCCGCGGCAGAGATCCCGAGATGGGTGGAAAGCCG<br>CGGCGGAAGAATCCGCAGGAAGGGCTCTACAACGAGCTCCAG<br>AAGGACAAGATGGCCGAAGCCTACAGCGAAATCGGGATGAAG<br>GGCGAAAGACGCCGGGGAAAAGGACACGACGGACTGTACCAG<br>GGGTTGTCGACCGCGACCAAGGACACCTACGACGCCCTGCAT<br>ATGCAAGCCTTGCCGCCGAGATGA |
| 103 | STEAP2-2 scFv nucleic acid sequence | GATGTTTTGATGACCCAAACTCCTCTCTCCCTGCCTGTCAGT<br>CTTGGAGATCAAGCCTCCATCTCTTGCAGATCTAGTCAGAGT<br>GTTGTACATAGTAATGGAAACACCTATTTAGAATGGTACCTG<br>CAGAAACCAGGCCAGTCTCCAAAGCTCCTGATCTACAAAGTT<br>TCCAACCGATTTTCTGGGGTCCCAGACAGGTTCAGTGGCAGT<br>GGATCAGGGACAGATTTCACACTCAAGATCAGCAGAGTGGAG<br>GCTGAGGATCTGGGAGTTTATTACTGCTTTCAAGGTTCACAT<br>GTTCCGTACACGTTCGGAGGGGGGACCAAGCTGGAAATAAAA<br>GGAGGCGGAGGATCTGGTGGTGGTGGATCTGGCGGCGGAGGA<br>AGTGGTGGCGGAGGCTCTGAGGTGCAGCTGGTGGAGTCTGGG<br>GGAGACTTAGTGAAGCCTGGAGGGTCCCTGAAACTCTCCTGT<br>GCCGCCTCTGGATTCTCTTTCTCCTCTTATGGCATGTCTTGG<br>GTTCGCCAGACTCCAGACAAGAGGCTGGAATGGGTCGCAACC<br>ATTAGTAGTGGTGGTAGTTACACCTTCTATCCCGACATTATG<br>AAGGGGCGATTCACCATCTCCAGAGACAATGCCATGAACACC<br>CTGTACCTGCAAATGAGCAGTCTGAAGTCTGAGGACTCAGCC<br>ATGTATTACTGTGCAAGACGGGGCTACGGTACTATCTACACG<br>TTTTCCTTTGACTCCTGGGGCCAAGGCACCACTCTCACAGTC<br>TCCAGC |
| 104 | Dominant-negative TGF-β receptor type 2 nucleic acid sequence | ATGGGACGCGGGCTGCTTCGAGGACTCTGGCCACTTCATATC<br>GTGTTGTGGACTCGCATCGCTTCAACCATTCCGCCGCACGTG<br>CAGAAGTCCGTGAACAATGACATGATCGTGACCGACAACAAC<br>GGTGCAGTGAAGTTCCCACAGCTGTGTCAAGTTCTGCGATGTC<br>AGATTCAGCACTTGCGACAACCAGAAGTCCTGCATGTCAAAC<br>TGCTCCATCACCTCCATCTGCGAGAAGCCTCAAGAGGTCTGC<br>GTGGCCGTGTGGCGGAAGAACGACGAGAACATCACCCTGGAA<br>ACCGTGTGCCACGATCCGAAGCTGCCTTATCACGACTTCATT<br>CTGGAAGATGCCGCCTCGCCCAAGTGTATCATGAAAGAAAAG<br>AAAAAGCCCGGAGAAACGTTCTTCATGTGCTCGTGTAGCTCC<br>GACGAGTGCAACGACAACATTATCTTTAGCGAAGAGTACAAC<br>ACTTCCAACCCTGACCTCCTGCTCGTGATTTTTCAAGTCACC<br>GGCATTTCCCTGCTGCCCCCGCTGGGCGTGGCGATCTCGGTG<br>ATCATTATCTTCTACTGTTACCGGGTCAATAGGCAG |

TABLE 1-continued

Sequences.

| SEQ ID | Description | Sequences |
|---|---|---|
| 105 | Dominant-negative TGF-β receptor type 2 amino acid sequence | MGRGLLRGLWPLHIVLWTRIASTIPPHVQKSVNNDMIVTDNN GAVKFPQLCKFCDVRFSTCDNQKSCMSNCSITSICEKPQEVC VAVWRKNDENITLETVCHDPKLPYHDFILEDAASPKCIMKEK KKPGETFFMCSCSSDECNDNIIESEEYNTSNPDLLLVIFQVT GISLLPPLGVAISVIIIFYCYRVNRQ |
| 106 | STEAP2 BZ CAR-T2A-Dominant-negative TGF-β receptor type 2 amino acid sequence | MLLLVTSLLLCELPHPAFLLIPEIVMTQSPATLSVSPGERAT LSCRASQSVNSNLAWYQQKPGQAPRLLIYGASTRATGIPARF SGSGSGTEFTLTISSLQSEDFAVYYCQQYNNWPFTFGPGTKV DIKGGGGSGGGGSGGGGSGGGGSQVQLQQSGPGLVKPSQTLS LTCAISGDSVSRNSAVWNWIRQSPSRGLEWLGRTYYRSKWYN DYAVSVKSRITINPDTSKNQFSLQVNSVTPEDTAVYYCARGL LQNNFYYYMDVWGKGTTVTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPRGSGEGRGSLLTCGDVEENPGPMGRGLLRGLWPLHI VLWTRIASTIPPHVQKSVNNDMIVTDNNGAVKFPQLCKFCDV RFSTCDNQKSCMSNCSITSICEKPQEVCVAVWRKNDENITLE TVCHDPKLPYHDFILEDAASPKCIMKEKKKPGETFFMCSCSS DECNDNIIFSEEYNTSNPDLLLVIFQVTGISLLPPLGVAISV IIIFYCYRVNRQ |
| 107 | STEAP2 BZ CAR-T2A-Dominant-negative TGF-β receptor type 2 nucleic acid sequence | ATGCTGCTCCTTGTCACATCACTGCTGCTCTGCGAACTGCCC CACCCTGCATTCCTCCTGATCCCCGAGATTGTGATGACCCAG AGCCCTGCAACTCTGAGCGTGTCACCCGGAGAAAGGGCCACT CTGTCGTGTCGAGCATCGCAGTCCGTGAACTCCAATCTCGCC TGGTACCAGCAGAAGCCTGGGCAGGCCCCGAGGCTGCTCATC TACGGTGCCTCCACGAGAGCCACGGGAATTCCAGCGCGCTTT AGCGGATCCGGCTCGGGAACCGAGTTCACCCTTACCATCTCA TCGCTGCAATCCGAAGATTTCGCCGTGTATTACTGTCAACAG TACAACAACTGGCCGTTCACCTTTGGCCCGGGAACTAAGGTC GACATCAAGGGCGGCGGGGGCTCTGGGGGTGGCGGAAGCGGC GGCGGCGGATCCGGTGGCGGCGGAAGCCAAGTGCAGCTGCAG CAGTCCGGACCCGGACTCGTGAAGCCGTCCCAGACTCTGTCC CTGACTTGCGCGATTTCCGGCGATTCCGTGTCCCGCAACTCC GCTGTGTGGAACTGGATCCGGCAGTCGCCTTCGAGAGGACTG GAGTGGCTGGGACGGACCTACTACCGCTCAAAATGGTATAAC GACTATGCTGTGTCCGTCAAGAGCCGCATCACCATTAACCCC GATACCTCCAAGAACGAGTTCAGTCTGCAAGTCAACAGCGTG ACTCCTGAGGACACCGCCGTGTACTACTGCGCCCGGGGTCTG CTGCAAAACAACTTCTACTACTACATGGACGTCTGGGGAAAG GGAACTACTGTGACCGTGTCCTCCGGCTCCGAATCAAAATAC GGTCCGCCATGCCCACCGTGCCCCTTCTGGGTGCTCGTGGTC GTCGGAGGGGTTCTGGCCTGCTACTCCCTGCTGGTCACCGTG GCGTTTATCATCTTCTGGGTGAAGCGGGGAAGGAAGAAGCTA CTGTACATTTTCAAGCAGCCTTTCATGCGGCCTGTGCAGACC ACCCAGGAAGAGGACGGCTGTTCCTGCCGGTTCCCCGAGGAA GAGGAAGGGGGTTGCGAGCTGCGCGTGAAGTTCAGCAGGAGC GCTGATGCCCCAGCGTACCAACAGGGGCAAAACCAGTTGTAC AACGAACTGAACCTTGGTCGGCGCGAAGAGTACGACGTGCTT GACAAGCGCCGCGGCAGAGATCCCGAGATGGGTGGAAAGCCG CGGCGGAAGAATCCGCAGGAAGGGCTCTACAACGAGCTCCAG AAGGACAAGATGGCCGAAGCCTACAGCGAAATCGGGATGAAG GGCGAAAGACGCCGGGGAAAAGGACACGACGGACTGTACCAG GGGTTGTCGACCGCGACCAAGGACACCTACGACGCCCTGCAT ATGCAAGCCTTGCCGCCGAGAGGATCCGGAGAGGGGAGGGGA AGCCTCCTCACTTGCGGCGATGTGGAGGAAAACCCGGGTCCT ATGGGACGCGGGCTGCTTCGAGGACTCTGGCCACTTCATATC GTGTTGTGGACTCGCATCGCTTCAACCATTCCGCCGCACGTG CAGAAGTCCGTGAACAATGACATGATCGTGACCGACAACAAC GGTGCAGTGAAGTTCCCACAGCTGTGCAAGTTCTGCGATGTC AGATTCAGCACTTGCGACAACCAGAAGTCCTGCATGTCAAAC TGCTCCATCACCTCCATCTGCGAGAAGCCTCAAGAGGTCTGC GTGGCCGTGTGGCGGAAGAACGACGAGAACATCACCCTGGAA ACCGTGTGCCACGATCCGAAGCTGCCTTATCACGACTTCATT CTGGAAGATGCCGCCTCGCCCAAGTGTATCATGAAAGAAAAG |

TABLE 1-continued

Sequences.

| SEQ ID | Description | Sequences |
|---|---|---|
| | | AAAAAGCCCGGAGAAACGTTCTTCATGTGCTCGTGTAGCTCC |
| | | GACGAGTGCAACGACAACATTATCTTTAGCGAAGAGTACAAC |
| | | ACTTCCAACCCTGACCTCCTGCTCGTGATTTTTCAAGTCACC |
| | | GGCATTTCCCTGCTGCCCCCGCTGGGCGTGGCGATCTCGGTG |
| | | ATCATTATCTTCTACTGTTACCGGGTCAATAGGCAG |
| 108 | STEAP2-2 BZ CAR amino acid sequence | MLLLVTSLLLCELPHPAFLLIPDVLMTQTPLSLPVSLGDQAS ISCRSSQSVVHSNGNTYLEWYLQKPGQSPKLLIYKVSNRFSG VPDRFSGSGSGTDFTLKISRVEAEDLGVYYCFQGSHVPYTFG GGTKLEIKGGGGSGGGGSGGGGSGGGGSEVQLVESGGDLVKP GGSLKLSCAASGFSFSSYGMSWVRQTPDKRLEWVATISSGGS YTFYPDIMKGRFTISRDNAMNTLYLQMSSLKSEDSAMYYCAR RGYGTIYTFSFDSWGQGTTLTVSSGSESKYGPPCPPCPFWVL VVVGGVLACYSLLVTVAFIIFWVKRGRKKLLYIFKQPFMRPV QTTQEEDGCSCRFPEEEEGGCELRVKFSRSADAPAYQQGQNQ LYNELNLGRREEYDVLDKRRGRDPEMGGKPRRKNPQEGLYNE LQKDKMAEAYSEIGMKGERRRGKGHDGLYQGLSTATKDTYDA LHMQALPPR |
| 109 | STEAP2-2 Humanized1 BZ CAR amino acid sequence | MLLLVTSLLLCELPHPAFLLIPDVVMTQSPLSLPVTLGQPAS ISCRSSQSVVHSNANTYLEWYLQKPGQSPQLLIYKVSNRFSG VPDRFSGSGSGTDFTLKISRVEAEDVGVYYCFQGSHVPYTFG QGTKLEIKGGGGSGGGGSGGGGSGGGGSEVQLVESGGGLVKP GGSLRLSCAASGFTFSSYGMSWVRQAPGKRLEWVATISSGGS YTFYPDIMKGRFTISRDNSKNTLYLQMNSLRAEDTAVYYCAR RGYGTIYTFSFDAWGQGTTLTVSSGSESKYGPPCPPCPFWVL VVVGGVLACYSLLVTVAFIIFWVKRGRKKLLYIFKQPFMRPV QTTQEEDGCSCRFPEEEEGGCELRVKFSRSADAPAYQQGQNQ LYNELNLGRREEYDVLDKRRGRDPEMGGKPRRKNPQEGLYNE LQKDKMAEAYSEIGMKGERRRGKGHDGLYQGLSTATKDTYDA LHMQALPPR |
| 110 | STEAP2-2 Humanized2 BZ CAR amino acid sequence | MLLLVTSLLLCELPHPAFLLIPDVVMTQSPLSLPVTLGQPAS ISCRSSQSVVHSNANTYLEWYLQKPGQSPQLLIYKVSNRFSG VPDRFSGSGSGTDFTLKISRVEAEDVGVYYCFQGSHVPYTFG QGTKLEIKGGGGSGGGGSGGGGSGGGGSEVQLLESGGGLVQP GGSLRLSCAASGFTFSSYGMSWVRQAPGKRLEWVSTISSGGS YTFYPDIMKGRFTISRDNSKNTLYLQMNSLRAEDTAVYYCAR RGYGTIYTFSFDAWGQGTTLTVSSGSESKYGPPCPPCPFWVL VVVGGVLACYSLLVTVAFIIFWVKRGRKKLLYIFKQPFMRPV QTTQEEDGCSCRFPEEEEGGCELRVKFSRSADAPAYQQGQNQ LYNELNLGRREEYDVLDKRRGRDPEMGGKPRRKNPQEGLYNE LQKDKMAEAYSEIGMKGERRRGKGHDGLYQGLSTATKDTYDA LHMQALPPR |
| 111 | STEAP2-3 BZ CAR amino acid sequence | MLLLVTSLLLCELPHPAFLLIPEIVMTQSPATLSVSPGERAT LSCRASQSVSSNLAWYQQKPGQAPRLLIYGASTRATGIPARF SGSGSGTEFTLTISSLQSEDFAVYYCQQYNNWPFTFGPGTKV DIKGGGGSGGGGSGGGGSGGGGSQVQLQQSGPGLVKPSQTLS LTCAISGDSVSRNSAVWNWIRQSPSRGLEWLGRTYYRSKWYN DYAVSVKSRITINPDTSKNQFSLQLNSVTPEDTAVYYCARGL LQNQFYYYMDVWGKGTTVTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR |
| 112 | STEAP2-4 BZ CAR amino acid sequence | MLLLVTSLLLCELPHPAFLLIPDIQLTQSPSFLSASVGDRVT ITCRASQGISVYLAWYQQEPGKAPKLLIYAASTLQSGVPSRF SGSGSGTEFTLTISSLQPEDFATYYCQQLNSYPRTFGQGTKV EIKGGGGSGGGGSGGGGSGGGGSEVQLVESGGGLVQPGGSLR LSCAASGFTFSSFAMTWVRQAPGKGLEWVSVITYSGGRTYYA DSVKGRFTISRDNSKNTLYLQMNSLRAEDTAVYFCAKDRIAA VGPFDYWGQGTLVTVSSGSESKYGPPCPPCPFWVLVVVGGVL ACYSLLVTVAFIIFWVKRGRKKLLYIFKQPFMRPVQTTQEED GCSCRFPEEEEGGCELRVKFSRSADAPAYQQGQNQLYNELNL GRREEYDVLDKRRGRDPEMGGKPRRKNPQEGLYNELQKDKMA EAYSEIGMKGERRRGKGHDGLYQGLSTATKDTYDALHMQALP PR |
| 113 | STEAP2-5 BZ CAR amino acid | MLLLVTSLLLCELPHPAFLLIPDIQMTQSPSTLSASVGDRVT ITCRASQSISRWLAWYQQKPGKAPKLLIYKASSLESGVPSRF SGSGSGTEFTLTISSLQPDDFATYYCQQFNSFSPITFGQGTR LEIKGGGGSGGGGSGGGGSGGGGSQVQLVQSGAEVKKPGASV |

TABLE 1-continued

Sequences.

| SEQ ID | Description | Sequences |
|---|---|---|
| | sequence | KVSCKASGYTFTSYGISWVRQAPGQGLEWMGWISGYTGNTNY AQKLQGRVTMTADTSTSTAYMELRSLRSDDTAVYYCARGGSY FDYWGQGTLVTVSSGSESKYGPPCPPCPFWVLVVVGGVLACY SLLVTVAFIIFWVKRGRKKLLYIFKQPFMRPVQTTQEEDGCS CRFPEEEEGGCELRVKFSRSADAPAYQQGQNQLYNELNLGRR EEYDVLDKRRGRDPEMGGKPRRKNPQEGLYNELQKDKMAEAY SEIGMKGERRRGKGHDGLYQGLSTATKDTYDALHMQALPPR |
| 114 | STEAP2-6 BZ CAR amino acid sequence | MLLLVTSLLLCELPHPAFLLIPDVLMTQTPLSLPVSLGDQAS ISCRSSQSVVHSNGNTYLEWYLQKPGQSPKLLIYKVSNRFSG VPDRFSGSGSGTDFTLKISRVEAEDLGVYYCFQGSHVPYTFG GGTKLEIKGGGGSGGGGSGGGGSGGGGSQVQLQQPGAELVKP GASVKLSCKASGYTFTSYWMEWVKQRPGQGLEWIGMIHPNSG ITNYNERFKNKATLTVDKSSSTAYMQLSSLTSEDSAVYYCAR DHYYILAYWGQGTLVTVSAGSESKYGPPCPPCPFWVLVVVGG VLACYSLLVTVAFIIFWVKRGRKKLLYIFKQPFMRPVQTTQE EDGCSCRFPEEEEGGCELRVKFSRSADAPAYQQGQNQLYNEL NLGRREEYDVLDKRRGRDPEMGGKPRRKNPQEGLYNELQKDK MAEAYSEIGMKGERRRGKGHDGLYQGLSTATKDTYDALHMQA LPPR |
| 115 | STEAP2-7 BZ CAR amino acid sequence | MLLLVTSLLLCELPHPAFLLIPDVVMTQTPLSLPVSLGNQAS ISCRSSQSLVHSNGNTYLHWYLQKPGQSPKLLIYKVSNRFSG VPDRFSGSGSGTDFTLKISRVEAEDLGVYFCSQSTHVPLTFG AGTKLEIKGGGGSGGGGSGGGGSGGGGSQVQLQQPGADLVKP GASVKMSCKASGHTFTNYWVTWVKQRPGQGLEWIGNFYPGSG 11KYNENFRSKATLTVDISSSTAYMQLSSLTSEDSAVYYCAR SKLGDSFYFDYWGQGTTLTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR |
| 116 | STEAP2-8 BZ CAR amino acid sequence | MLLLVTSLLLCELPHPAFLLIPEIVMTQSPATLSVSPGERAT LSCRASQSVASNLAWYQQKPGQAPRLLIYGASTRATGIPARF SGSGSGTEFTLTISSLQSEDFAVYYCQQYNNWPFTGPGTKV DIKGGGGSGGGGSGGGGSGGGGSQVQLQQSGPGLVKPSQTLS LTCAISGDSVSRNSAVWNWIRQSPSRGLEWLGRTYYRSKWYN DYAPSVKSRITINPDTSKNQFSLQLNSVTPEDTAVYYCARGL RQNQFYYYMDVWGKGTTVTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR |
| 117 | STEAP2-2 BZ CAR-T2A-Dominant-negative TGF-β receptor type 2 amino acid sequence | MLLLVTSLLLCELPHPAFLLIPDVLMTQTPLSLPVSLGDQAS ISCRSSQSVVHSNGNTYLEWYLQKPGQSPKLLIYKVSNRFSG VPDRFSGSGSGTDFTLKISRVEAEDLGVYYCFQGSHVPYTFG GGTKLEIKGGGGSGGGGSGGGGSGGGGSEVQLVESGGDLVKP GGSLKLSCAASGFSFSSYGMSWVRQTPDKRLEWVATISSGGS YTFYPDIMKGRFTISRDNAMNTLYLQMSSLKSEDSAMYYCAR RGYGTIYTFSFDSWGQGTTLTVSSGSESKYGPPCPPCPFWVL VVVGGVLACYSLLVTVAFIIFWVKRGRKKLLYIFKQPFMRPV QTTQEEDGCSCRFPEEEEGGCELRVKFSRSADAPAYQQGQNQ LYNELNLGRREEYDVLDKRRGRDPEMGGKPRRKNPQEGLYNE LQKDKMAEAYSEIGMKGERRRGKGHDGLYQGLSTATKDTYDA LHMQALPPRGSGEGRGSLLTCGDVEENPGPMGRGLLRGLWPL HIVLWTRIASTIPPHVQKSVNNDMIVTDNNGAVKFPQLCKFC DVRFSTCDNQKSCMSNCSITSICEKPQEVCVAVWRKNDENIT LETVCHDPKLPYHDFILEDAASPKCIMKEKKKPGETFFMCSC SSDECNDNIIFSEEYNTSNPDLLLVIFQVTGISLLPPLGVAI SVIIIFYCYRVNRQ |
| 118 | STEAP2-2 Humanized1 BZ CAR amino acid sequence | MLLLVTSLLLCELPHPAFLLIPDVVMTQSPLSLPVTLGQPAS ISCRSSQSVVHSNANTYLEWYLQKPGQSPQLLIYKVSNRFSG VPDRFSGSGSGTDFTLKISRVEAEDVGVYYCFQGSHVPYTFG QGTKLEIKGGGGSGGGGSGGGGSGGGGSEVQLVESGGGLVKP GGSLRLSCAASGFTFSSYGMSWVRQAPGKRLEWVATISSGGS YTFYPDIMKGRFTISRDNSKNTLYLQMNSLRAEDTAVYYCAR RGYGTIYTFSFDAWGQGTTLTVSSGSESKYGPPCPPCPFWVL VVVGGVLACYSLLVTVAFIIFWVKRGRKKLLYIFKQPFMRPV QTTQEEDGCSCRFPEEEEGGCELRVKFSRSADAPAYQQGQNQ LYNELNLGRREEYDVLDKRRGRDPEMGGKPRRKNPQEGLYNE |

TABLE 1-continued

Sequences.

| SEQ ID | Description | Sequences |
|---|---|---|
| | | LQKDKMAEAYSEIGMKGERRRGKGHDGLYQGLSTATKDTYDA<br>LHMQALPPRGSGEGRGSLLTCGDVEENPGPMGRGLLRGLWPL<br>HIVLWTRIASTIPPHVQKSVNNDMIVTDNNGAVKFPQLCKFC<br>DVRFSTCDNQKSCMSNCSITSICEKPQEVCVAVWRKNDENIT<br>LETVCHDPKLPYHDFILEDAASPKCIMKEKKKPGETFFMCSC<br>SSDECNDNIIFSEEYNTSNPDLLLVIFQVTGISLLPPLGVAI<br>SVIIIFYCYRVNRQ |
| 119 | STEAP2-2<br>Humanized2<br>BZ<br>CAR<br>amino<br>acid<br>sequence | MLLLVTSLLLCELPHPAFLLIPDVVMTQSPLSLPVTLGQPAS<br>ISCRSSQSVVHSNANTYLEWYLQKPGQSPQLLIYKVSNRFSG<br>VPDRFSGSGSGTDFTLKISRVEAEDVGVYYCFQGSHVPYTFG<br>QGTKLEIKGGGGSGGGGSGGGGSGGGGSEVQLLESGGGLVQP<br>GGSLRLSCAASGFTFSSYGMSWVRQAPGKRLEWVSTISSGGS<br>YTFYPDIMKGRFTISRDNSKNTLYLQMNSLRAEDTAVYYCAR<br>RGYGTIYTFSFDAWGQGTTLTVSSGSESKYGPPCPPCPFWVL<br>VVVGGVLACYSLLVTVAFIIFWVKRGRKKLLYIFKQPFMRPV<br>QTTQEEDGCSCRFPEEEEGGCELRVKFSRSADAPAYQQGQNQ<br>LYNELNLGRREEYDVLDKRRGRDPEMGGKPRRKNPQEGLYNE<br>LQKDKMAEAYSEIGMKGERRRGKGHDGLYQGLSTATKDTYDA<br>LHMQALPPRGSGEGRGSLLTCGDVEENPGPMGRGLLRGLWPL<br>HIVLWTRIASTIPPHVQKSVNNDMIVTDNNGAVKFPQLCKFC<br>DVRFSTCDNQKSCMSNCSITSICEKPQEVCVAVWRKNDENIT<br>LETVCHDPKLPYHDFILEDAASPKCIMKEKKKPGETFFMCSC<br>SSDECNDNIIFSEEYNTSNPDLLLVIFQVTGISLLPPLGVAI<br>SVIIIFYCYRVNRQ |
| 120 | STEAP2-3<br>BZ CAR-<br>T2A-<br>Dominant-<br>negative<br>TGF-β<br>receptor<br>type 2<br>amino<br>acid<br>sequence | MLLLVTSLLLCELPHPAFLLIPEIVMTQSPATLSVSPGERAT<br>LSCRASQSVSSNLAWYQQKPGQAPRLLIYGASTRATGIPARF<br>SGSGSGTEFTLTISSLQSEDFAVYYCQQYNNWPFTFGQGTKV<br>DIKGGGGSGGGGSGGGGSGGGGSQVQLQQSGPGLVKPSQTLS<br>LTCAISGDSVSRNSAVWNWIRQSPSRGLEWLGRTYYRSKWYN<br>DYAVSVKSRITINPDTSKNQFSLQLNSVTPEDTAVYYCARGL<br>LQNQFYYYMDVWGKGTTVTVSSGSESKYGPPCPPCPFWVLVV<br>VGGVLACYSLLVTVAFIIFWVKRGRKKLLYIFKQPFMRPVQT<br>TQEEDGCSCRFPEEEEGGCELRVKFSRSADAPAYQQGQNQLY<br>NELNLGRREEYDVLDKRRGRDPEMGGKPRRKNPQEGLYNELQ<br>KDKMAEAYSEIGMKGERRRGKGHDGLYQGLSTATKDTYDALH<br>MQALPPRGSGEGRGSLLTCGDVEENPGPMGRGLLRGLWPLHI<br>VLWTRIASTIPPHVQKSVNNDMIVTDNNGAVKFPQLCKFCDV<br>RFSTCDNQKSCMSNCSITSICEKPQEVCVAVWRKNDENITLE<br>TVCHDPKLPYHDFILEDAASPKCIMKEKKKPGETFFMCSCSS<br>DECNDNIIFSEEYNTSNPDLLLVIFQVTGISLLPPLGVAISV<br>IIIFYCYRVNRQ |
| 121 | STEAP2-4<br>BZ CAR-<br>T2A-<br>Dominant-<br>negative<br>TGF-β<br>receptor<br>type 2<br>amino<br>acid<br>sequence | MLLLVTSLLLCELPHPAFLLIPDIQLTQSPSFLSASVGDRVT<br>ITCRASQGISVYLAWYQQEPGKAPKLLIYAASTLQSGVPSRF<br>SGSGSGTEFTLTISSLQPEDFATYYCQQLNSYPRTFGQGTKV<br>EIKGGGGSGGGGSGGGGSGGGGSEVQLVESGGGLVQPGGSLR<br>LSCAASGFTFSSFAMTWVRQAPGKGLEWVSVITYSGGRTYYA<br>DSVKGRFTISRDNSKNTLYLQMNSLRAEDTAVYFCAKDRIAA<br>VGPFDYWGQGTLVTVSSGSESKYGPPCPPCPFWVLVVVGGVL<br>ACYSLLVTVAFIIFWVKRGRKKLLYIFKQPFMRPVQTTQEED<br>GCSCRFPEEEEGGCELRVKFSRSADAPAYQQGQNQLYNELNL<br>GRREEYDVLDKRRGRDPEMGGKPRRKNPQEGLYNELQKDKMA<br>EAYSEIGMKGERRRGKGHDGLYQGLSTATKDTYDALHMQALP<br>PRGSGEGRGSLLTCGDVEENPGPMGRGLLRGLWPLHIVLWTR<br>IASTIPPHVQKSVNNDMIVTDNNGAVKFPQLCKFCDVRFSTC<br>DNQKSCMSNCSITSICEKPQEVCVAVWRKNDENITLETVCHD<br>PKLPYHDFILEDAASPKCIMKEKKKPGETFFMCSCSSDECND<br>NIIFSEEYNTSNPDLLLVIFQVTGISLLPPLGVAISVIIIFY<br>CYRVNRQ |
| 122 | STEAP2-5<br>BZ CAR-<br>T2A-<br>Dominant-<br>negative<br>TGF-β<br>receptor<br>type 2<br>amino<br>acid<br>sequence | MLLLVTSLLLCELPHPAFLLIPDIQMTQSPSTLSASVGDRVT<br>ITCRASQSISRWLAWYQQKPGKAPKLLIYKASSLESGVPSRF<br>SGSGSGTEFTLTISSLQPDDFATYYCQQFNSFSPITFGQGTR<br>LEIKGGGGSGGGGSGGGGSGGGGSQVQLVQSGAEVKKPGASV<br>KVSCKASGYTFTSYGISWVRQAPGQGLEWMGWISGYTGNTNY<br>AQKLQGRVTMTADTSTSTAYMELRSLRSDDTAVYYCARGGSY<br>FDYWGQGTLVTVSSGSESKYGPPCPPCPFWVLVVVGGVLACY<br>SLLVTVAFIIFWVKRGRKKLLYIFKQPFMRPVQTTQEEDGCS<br>CRFPEEEEGGCELRVKFSRSADAPAYQQGQNQLYNELNLGRR<br>EEYDVLDKRRGRDPEMGGKPRRKNPQEGLYNELQKDKMAEAY<br>SEIGMKGERRRGKGHDGLYQGLSTATKDTYDALHMQALPPRG<br>SGEGRGSLLTCGDVEENPGPMGRGLLRGLWPLHIVLWTRIAS<br>TIPPHVQKSVNNDMIVTDNNGAVKFPQLCKFCDVRFSTCDNQ |

US 12,686,707 B2

127 128

TABLE 1-continued

Sequences.

| SEQ ID | Description | Sequences |
|---|---|---|
| | | KSCMSNCSITSICEKPQEVCVAVWRKNDENITLETVCHDPKL PYHDFILEDAASPKCIMKEKKKPGETFFMCSCSSDECNDNI1 FSEEYNTSNPDLLLVIFQVTGISLLPPLGVAISVIIIFYCYR VNRQ |
| 123 | STEAP2-6 BZ CAR-T2A-Dominant-negative TGF-β receptor type 2 amino acid sequence | MLLLVTSLLLCELPHPAFLLIPDVLMTQTPLSLPVSLGDQAS ISCRSSQSVVHSNGNTYLEWYLQKPGQSPKLLIYKVSNRFSG VPDRFSGSGSGTDFTLKISRVEAEDLGVYYCFQGSHVPYTFG GGTKLEIKGGGGSGGGGSGGGGSGGGGSQVQLQQPGAELVKP GASVKLSCKASGYTFTSYWMEWVKQRPGQGLEWIGMIHPNSG ITNYNERFKNKATLTVDKSSSTAYMQLSSLTSEDSAVYYCAR DHYYILAYWGQGTLVTVSAGSESKYGPPCPPCPFWVLVVVGG VLACYSLLVTVAFIIFWVKRGRKKLLYIFKQPFMRPVQTTQE EDGCSCRFPEEEEGGCELRVKFSRSADAPAYQQGQNQLYNEL NLGRREEYDVLDKRRGRDPEMGGKPRRKNPQEGLYNELQKDK MAEAYSEIGMKGERRRGKGHDGLYQGLSTATKDTYDALHMQA LPPRGSGEGRGSLLTCGDVEENPGPMGRGLLRGLWPLHIVLW TRIASTIPPHVQKSVNNDMIVTDNNGAVKFPQLCKFCDVRFS TCDNQKSCMSNCSITSICEKPQEVCVAVWRKNDENITLETVC HDPKLPYHDFILEDAASPKCIMKEKKKPGETFFMCSCSSDEC NDNIIFSEEYNTSNPDLLLVIFQVTGISLLPPLGVAISVIII FYCYRVNRQ |
| 124 | STEAP2-7 BZ CAR-T2A-Dominant-negative TGF-β receptor type 2 amino acid sequence | MLLLVTSLLLCELPHPAFLLIPDVVMTQTPLSLPVSLGNQAS ISCRSSQSLVHSNGNTYLHWYLQKPGQSPKLLIYKVSNRFSG VPDRFSGSGSGTDFTLKISRVEAEDLGVYFCSQSTHVPLTFG AGTKLEIKGGGGSGGGGSGGGGSGGGGSQVQLQQPGADLVKP GASVKMSCKASGHTFTNYWVTWVKQRPGQGLEWIGNFYPGSG IIKYNENFRSKATLTVDISSSTAYMQLSSLTSEDSAVYYCAR SKLGDSFYFDYWGQGTTLTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPRGSGEGRGSLLTCGDVEENPGPMGRGLLRGLWPLHI VLWTRIASTIPPHVQKSVNNDMIVTDNNGAVKFPQLCKFCDV RFSTCDNQKSCMSNCSITSICEKPQEVCVAVWRKNDENITLE TVCHDPKLPYHDFILEDAASPKCIMKEKKKPGETFFMCSCSS DECNDNIIFSEEYNTSNPDLLLVIFQVTGISLLPPLGVAISV IIIFYCYRVNRQ |
| 125 | STEAP2-8 BZ CAR-T2A-Dominant-negative TGF-β receptor type 2 amino acid sequence | MLLLVTSLLLCELPHPAFLLIPEIVMTQSPATLSVSPGERAT LSCRASQSVASNLAWYQQKPGQAPRLLIYGASTRATGIPARF SGSGSGTEFTLTISSLQSEDFAVYYCQQYNNWPFTFGPGTKV DIKGGGGSGGGGSGGGGSGGGGSQVQLQQSGPGLVKPSQTLS LTCAISGDSVSRNSAVWNWIRQSPSRGLEWLGRTYYRSKWYN DYAPSVKSRITINPDTSKNQFSLQLNSVTPEDTAVYYCARGL RQNQFYYYMDVWGKGTTVTVSSGSESKYGPPCPPCPFWVLVV VGGVLACYSLLVTVAFIIFWVKRGRKKLLYIFKQPFMRPVQT TQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPRGSGEGRGSLLTCGDVEENPGPMGRGLLRGLWPLHI VLWTRIASTIPPHVQKSVNNDMIVTDNNGAVKFPQLCKFCDV RFSTCDNQKSCMSNCSITSICEKPQEVCVAVWRKNDENITLE TVCHDPKLPYHDFILEDAASPKCIMKEKKKPGETFFMCSCSS DECNDNIIFSEEYNTSNPDLLLVIFQVTGISLLPPLGVAISV IIIFYCYRVNRQ |
| 126 | T2A Peptide | GSGEGRGSLLTCGDVEENPGP |
| 127 | Signal Peptide | MLLLVTSLLLCELPHPAFLLIP |
| 128 | IgG4P Hinge (S228P) | ESKYGPPCPPCP |
| 129 | CD28 Transmembrane Domain | FWVLVVVGGVLACYSLLVTVAFIIFWV |

TABLE 1-continued

Sequences.

| SEQ ID | Description | Sequences |
|---|---|---|
| 130 | 4-1BB Activation Domain (B domain) | KRGRKKLLYIFKQPFMRPVQTTQEEDGCSCRFPEEEEGGCEL |
| 131 | CD3zeta Domain (z domain) | RVKFSRSADAPAYQQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR |
| 132 | Bz Domain | KRGRKKLLYIFKQPFMRPVQTTQEEDGCSCRFPEEEEGGCEL RVKFSRSADAPAYQQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR |
| 133 | CD28 Co-stimulatory Domain | RSKRSRLLHSDYMNMTPRRPGPTRKHYQPYAPPRDFAAYRS |

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

The following examples are offered by way of illustration and not by way of limitation.

EXAMPLES

Example 1: Generation and Characterization of Anti-STEAP2 CARs

STEAP2 is a metalloreductase that reduces iron and copper to facilitate cellular uptake, metabolism, and proliferation, which is predominantly expressed in prostate cancer, with little to no expression in healthy tissue outside the prostate or in other cancer types (FIGS. 1A-1C). STEAP2 expression was analyzed by quantitative real-time PCR analysis of normal tissue and prostate cancer cDNA arrays. cDNA generated from CRPC FFPE patient samples was also included. GAPDH was utilized as a normalization control (FIG. 1B). STEAP2 has high, homogeneous cell surface expression across all disease stages, including metastases and CRPC (FIG. 1B), with a limited tissue sink and toxicity risk due to normal human tissue expression profile: prostate and minimal expression in kidney cortex (FIGS. 1A-1C). We performed cDNA array analyses, ISH, and IHC across a wide range of tumor types as well as prostate cancers throughout disease progression to confirm that the protein is overexpressed and present at the cell surface in prostate cancer compared to normal prostate (FIG. 1C).

IHC was performed on tissue microarrays containing primary prostate cancer, castrate-resistant prostate cancer (CRPC), and prostate lymph node metastases as well as decalcified full face sections of prostate cancer bone metastases for STEAP2 membrane expression (FIG. 1D). High expression of STEAP2 was found on CRPC (FIG. 1E) and in bone metastases (FIG. 1F). STEAP2 IHC and ISH performed in a normal human tissue microarray demonstrated absent or low STEAP2 in most normal tissues (FIG. 1G) and high STEAP 2 protein levels in normal prostate tissue (FIG. 1H).

Multiple anti-STEAP2 antigen-binding constructs were generated and assayed for binding specificity. In vitro binding assays were performed to assess the specificity for STEAP2 (FIG. 2A) and on-cell binding affinities of candidate scFv-Fc's using antigen-positive and -negative cell lines (FIGS. 2B-2F). Clone 40A3 showed strong on-target binding to human, cyno, and murine/rat STEAP2 heterologously expressed by Ad293 cells (FIGS. 2A, 2E, and 2F), with little to no binding to control Ad293 cells (FIGS. 2A and 2D) or Ad293 cells expressing other STEAP family members (FIG. 2A). Clone 40A3 further bound LNCaP cells (androgen-sensitive human prostate adenocarcinoma cells), both as a scFv-Fc CAR construct and as an IgG1 antibody; binding which was lost in the STEAP2 knock-out LNCaP cells (FIG. 2B).

The antigen-binding domain of clone 40A3 was used to generate a CAR construct, referred to herein as 40A3Bz, by fusing the 40A3 antigen-binding domain to a 4-1BB costimulatory domain and a CD3 zeta signaling domain (FIG. 3A. top). To further enhance CAR-T efficacy in vivo, the CAR-encoding sequence was placed upstream of a sequence encoding a dominant negative TGFβRII (dnTGFβRII), linked by a viral T2A peptide-coding sequence (FIG. 3A, bottom). The T2A peptide allows for expression of two separate proteins from the same promoter, ensuring equimolar expression of both proteins. Lentiviral transduction was then used to express the CAR constructs with high efficiency (FIGS. 3B-3D). CAR-T cells were generated using CD3/CD28 bead activated donor T cells via lentiviral transduction. CAR-T cells were expanded in CAR-T culture conditions for 10 days prior to flow cytometry assessment of cell surface CAR expression compared to untransduced donor T cells. A paratope antibody recognizing 40A3Bz was utilized in conjunction with a TGFβRII antibody to evaluate the cell surface localization of 40A3Bz and 40A3Bz dnTGFβRII in untransduced (FIG. 3B), 40A3Bz (FIG. 3C), and 40A3Bz dnTGFβRII (FIG. 3D) transduced cell populations at day 10.

To provide functional validation of the dnTGFβRII armoring, CAR positive cells (40A3Bz STEAP2 CAR and 403Bz dnTGFβRII STEAP2 CAR-T cells) were purified to >97% purity through FACS at Day 4 post transduction. These cells were expanded to Day 15, starved in X VIVO™ 15 media for 17 hours prior to being stimulated with 1 ng/mL recombinant human TGFβ. Analysis of the acute signaling downstream of the native TGFβRII was compared between the armored and unarmored CAR-T cells in western blots for pSMAD 2/3, total SMAD 2/3, and β-actin (FIG. 3E). A significant abrogation of TGFβ-mediated signaling in the dnTGFβRII (40A3Bz) CAR-T cells compared to 40A3Bz CAR or Untransduced cells alone was confirmed (FIG. 3E).

Phenotypic characterization was performed on (40A3Bz) STEAP2 CAR and dnTGFβRII (40A3Bz) STEAP2 CAR-T cells expanded from 2 healthy donors. T cells from all conditions were shown to have predominately a naive/central memory phenotype at the end of the expansion process at Day 10 as determined by staining with CD62L and CD45RO antibodies (FIGS. 4F-4K). Expanded CAR-T cells were also assessed for expression of differentiation and exhaustion markers (e.g., CD45RA, CD69, KLRG1, CD127, PD 1, and LAG-3; data not shown). Overall, the data showed that CAR and dnTGFβRII armoring can be expressed in T cells. Furthermore, it showed that the introduction of the dnTGFβRII armoring into the CAR constructs did not appear to substantially affect the cell phenotype at the end of culture.

Transduced 40A3Bz STEAP2 CAR and 40A3Bz dnTGFβRII STEAP2 CAR-T cells showed robust expansion (FIG. 4A). Phenotypic characterization was performed on 40A3Bz STEAP2 CAR and 40A3Bz dnTGFβRII STEAP2 CAR-T cells expanded from 2 healthy donors. T cells from all conditions were shown to have predominately a naïve/stem-like phenotype (FIGS. 4B-4K). Expanded CAR-T cells were also assessed for expression of differentiation and exhaustion markers (e.g., CD45RA, CD69, KLRG1, CD127, PD 1, and LAG-3; data not shown). Further, 40A3Bz STEAP2 CAR and 40A3Bz dnTGFβRII STEAP2 CAR-T cells maintained a mixed CD4:CD8 ratio (FIGS. 4L-4N). And 40A3Bz dnTGFβRII STEAP2 CAR-T cells were able to kill C4-2 target cells in the presence of 30 ng/ml TGFβ (FIG. 4O). 40A3Bz STEAP2 CAR and 40A3Bz dnTGFβRII STEAP2 CAR-T were pretreated with 30 ng/mL recombinant TGFβ for 6 days to suppress CAR-T function and then utilized in a co-culture assay with C4-2 cells stably expressing mKate red fluorescent protein at a 1:4 E:T ratio. Cytotoxicity was imaged using an Incucyte® live cell imaging system over time by the presence of RFP positive cells in co-culture over 120 hours. The results showed the improved potency of the dnTGFβRII armored CAR in vitro following exposure to immunosuppressive TGFβ.

A range of tumor cell lines was profiled by FACS with an anti-STEAP2 antibody-alexa fluor 647 conjugate for antibody binding capacity using the Bang's beads quantum simply cellular kit. STEAP2 cell surface IHC was performed on these cell lines and quantified (FIG. 4P, left panel). Further, these cell lines were included in 40A3Bz dnTGFβRII CAR-T co-culture assays at an E:T ratio of 1:1 and the media were sampled at 24 hours to analyze the levels of IFNγ release from the CAR-T cells. 40A3Bz dnTGFβRII CAR-T displayed specific cytotoxicity against C4-2, LNCaP, VCAP, 22RV1 cell lines (FIG. 4P, right panel).

STEAP2 CAR's specific cytotoxicity over time was also determined. STEAP2 CAR-T cells were cytotoxic against LNCaP cells (FIGS. 5A-5C) and Ad293 cells that exogenously express human STEAP2 (FIG. 5G) but not against STEAP2 knock out LNCaP cells (FIG. 5D-5F) or control Ad293 cells (FIG. 5H). Dominant-negative TGFβRII 40A3Bz STEAP2 CAR-T cells expanded in human T-cell media (AIM V™ media supplemented with 5% Human AB Heat Inactivated Serum and 300 U/mL IL-2) for 10 days were shown to kill antigen-positive target cells in a similar fashion to unarmored STEAP2 CAR-T cells (FIGS. 5C, 5F, and 5G-5H). In addition, 40A3Bz and 40A3Bz dnTGFβRII STEAP2 CAR-T cells were shown to release pro-inflammatory cytokines after 24 hours of co culture (FIGS. 5I-5K). No cytotoxic activity and release of pro-inflammatory cytokines was observed following co-culture of armored STEAP2 CAR-T cells with antigen-negative targets. This indicates that T-cell activity is STEAP2 antigen-dependent with no evidence of tonic CAR signaling. STEAP2 CAR-T had minimal on-target, off-tumor activity (FIG. 6).

Example 2: In Vivo Efficacy of Anti-STEAP2 CARs in a Mouse Model

Mice were implanted with STEAP2 positive tumor cells and administered untransduced (UT) T cells or T cells transduced with a GPC3-G08-Bz negative control, a 14N positive control, or 3, 7, or 21 million 40A3Bz CAR-T cells (FIGS. 7A-7F). In vivo proof-of-concept studies were conducted using 2 prostate cancer cell lines, C4-2 and 22RV1 shown to express STEAP2 (FIGS. 7C and 7F). The data revealed control of C4-2 tumor in NSG mice following infusion of 40A3Bz STEAP2 CAR-T cells at 3 different doses (FIG. 7A). No adverse changes in mouse body weight were observed with all 3 CAR-T cell doses during the study (FIG. 7B). These data are relevant from a safety perspective given that the 40A3 scFv can cross-react with murine STEAP2. In the 22RV1 xenograft model that contains a lower STEAP2 receptor density and proportion of expression compared to C4-2, control of the tumor was only evident at the highest dose ($21\times10^6$) of 40A3Bz STEAP2 CAR-T cells (FIG. 7D). Partial responses were seen with the $7\times10^6$ dose, and no effect on tumor cell growth was observed with the lowest $3\times10^6$ T-cell dose. Similar to the C4-2 model, mice engrafted with the 22RV1 cell line and then administered with 3 concentration levels of STEAP2 CAR-T cells showed no adverse change in body weight during the study (FIG. 7E).

Mice from the 22RV1 xenograft study were bled on Days 4, 7, 14, and 21 following CAR-T cell infusion to evaluate the kinetics of cytokine production. Human IFNγ, IL-2, and TNFα levels were elevated in serum, peaking at Day 4 or Day 7 for most CAR-T cell doses before reducing at Days 14 and 21 (FIG. 7G). These data confirm tumor recognition by STEAP2 CAR-T cells following challenge with tumor cell lines expressing various levels of STEAP2 antigen in vivo. STEAP2 expression 10 days post infusion was evaluated via ISH, with dose dependent focal infiltration and no signs of damage (FIGS. 7I-7K).

STEAP2 CAR-T administration showed no evidence of CD3+ CAR-T infiltration into nerves at the base of the heart (FIGS. 7L-7M) and no evidence of CD3+ CAR-T infiltration into peripheral subcutaneous nerves (FIGS. 7N-7O). However, two small intact and non-infiltrated peripheral nerves entrapped within the dense CAR-T infiltrate were observed (FIG. 7P; arrows). Several small blood vessels were also observed within the tumor with minimal to mild STEAP2 staining (FIG. 7R; arrow). Despite very dense CD3+ CAR-T infiltrate (FIG. 7Q), the nerves are intact and did not appear to be affected.

STEAP2 CAR-T showed increased persistence relative to untransduced T cells. Following 5 rounds of serial killing (FIG. 8A), 40A3Bz dnTGFβRII CAR-T cells showed consistent cytolysis and continuing IFN-γ production (FIGS. 8E-8G) in the presence of antigen positive cells, while maintaining a predominantly $T_{CM}$ and $T_{EM}$ differentiation status (FIG. 8B). 40A3Bz and 40A3Bz dnTGFβRII CAR-T cells dosed at 3 concentrations (0.5, 2.5, 5×e6 CAR positive cells) by tail vein injection in NSG mice implanted with TGFβ overexpressing C4-2 tumor cells showed reduced tumor volumes (FIG. 8E) and maintained body weights (FIG. 8F) out to 60 days post tumor implantation. Reduction in tumor volume (FIG. 8E) and cytokine release (FIGS. 8D and 8G) were further enhanced by dnTGFβRII armoring. Complete responders (CR) were defined as mice with a tumor volume of 0 mm3 for two successive measurements.

NSG mice were implanted in the intratibial space with C4-2 luciferase expressing cells and the luciferase signal was monitored. When the tumor flux reached 4.04e8 photons/sec, the animals were injected with 1×10⁶, 1×10⁵, 5×10⁵ or 1×10⁶ 40A3Bz CAR-T cells or 40A3Bz dnTGFβRII CAR-T cells per mouse. Tumor volume and body weights were monitored for 22 days post dose, and dose dependent tumor growth inhibition was evident with greater inhibition seen with the 40A3Bz dnTGFβRII CAR-T compared to 40A3Bz (FIG. 8H). No adverse change in body weight during the study was observed (FIG. 8I).

In some aspects, 40A3Bz dnTGFβRII CAR-T cells were manufactured according to the SMART process and CAR positivity, activation, and phenotypes of the cells were evaluated at expansion Day 4 and compared to untransduced T cells from the same donor (FIG. 9A). 40A3Bz dnTGFβRII SMART CAR-T cells were dosed at 4 concentrations (0.3, 1, 3, 6×10⁶ CAR positive cells) by tail vein injection in NSG MHC class 1 class 2 knockout mice implanted with 22Rv1 cells overexpressing TGFβ. Tumor volumes and body weights were measured out to 50 days post tumor implantation (FIG. 9B). Tumor volumes were effectively reduced in all 40A3Bz dnTGFβRII SMART CAR-T cell treated mice (FIG. 9B, top) with no adverse effects on body weight (FIG. 9B, bottom).

Further, NSG class 1 class 2 knockout mice were implanted with PDX fragments from frozen stocks of CTG-3610 prostate cancer cells and randomized when tumor volumes ranged from 125-250 mm³. The IHC intensity scores of CTB-3610 cells for membrane STEAP2 and TGFβ were 2+ and the proportion scores were 5 for STEAP2 and 2 for TGFβ (FIG. 9C). Mice were dosed with 0.5×10⁶ or 5×10⁶ 40A3Bz dnTGFβRII SMART CAR-T cells and compared to 5×10⁶ UT SMART controls. At both doses, the 40A3Bz dnTGFβRII SMART CAR-T cells efficiently suppressed tumor growth (FIG. 9C, top) with no adverse effect on body weight (FIG. 9C, bottom).

NSG class 1 class 2 knockout mice were implanted with PDX fragments from frozen stocks of CTG-2440 prostate cancer cells and randomized when tumor volumes ranged from 125-250 mm3. The IHC intensity scores for membrane STEAP2 and TGFβ were 2+ and the proportion scores were 5 for STEAP2 and 2 for TGFβ (FIG. 9D). Mice were dosed with 0.5×10⁶ or 5×10⁶ 40A3Bz dnTGFβRII SMART CAR-T cells and compared to 5×10⁶ UT SMART controls. The 40A3Bz dnTGFβRII SMART CAR-T cells suppressed tumor growth dose-dependently (FIG. 9D, top) with no adverse effect on body weight (FIG. 9D, bottom).

NSG class 1 class 2 knockout mice were implanted with PDX fragments from frozen stocks of Lucap 147 prostate cancer cells and randomized when tumor volumes ranged from 125-250 mm³. The IHC intensity score for membrane STEAP2 was 1+ and the proportion score for membrane STEAP2 was 5 (FIG. 9E). Mice were dosed with 0.5×10⁶ or 5×10⁶ 40A3Bz dnTGFβRII SMART CAR-T cells and compared to 5×10⁶ UT SMART controls. The 40A3Bz dnTGFβRII SMART CAR-T cells suppressed tumor growth dose-dependently (FIG. 9E, top) with no adverse effect on body weight (FIG. 9E, bottom).

NSG class 1 class 2 knockout mice were implanted with PDX fragments from frozen stocks of Lucap 73 prostate cancer cells and randomized when tumor volumes ranged from 125-250 mm³. The IHC intensity score for membrane STEAP2 was 1+ and the proportion score for membrane STEAP2 was 3 (FIG. 9F). Mice were dosed with 0.5×10⁶ or 5×10⁶ 40A3Bz dnTGFβRII SMART CAR-T cells and compared to 5×10⁶ UT SMART controls. The 40A3Bz dnTGFβRII SMART CAR-T cells suppressed tumor growth dose-dependently (FIG. 9F, top) with no adverse effect on body weight (FIG. 9F, bottom).

Co-cultures were setup with the LNCaP tumor cell line and 40A3Bz dnTGFβRII CAR-T cells at E:T ratio of 0.3:1 and blocking anti-STEAP2 antibodies were administered to the culture (0.2, 2, 20, or 200 μg/ml) (FIG. 10A). Co-cultures were also setup with the LNCaP tumor cell line and 40A3Bz dnTGFβRII CAR-T cells at E:T ratios of 0.3:1 and 1:1 in the presence of blocking anti-STEAP2 antibodies or isotype control blocking antibodies (0.2, 2, 20, or 200 μg/ml) and IFNγ levels were determined in the media (FIG. 10B). 40A3Bz dnTGFβRII CAR-T cells efficiently inhibited cell growth of LNCaP cells in the presence of low concentrations of blocking anti-STEAP2 antibodies. However, the highest concentration of anti-STEAP2 prevented the growth inhibition of LNCaP cells by 40A3Bz dnTGFβRII CAR-T cells (FIG. 10A). Similarly, IFNγ levels were induced dose-dependently by 40A3Bz dnTGFβRII CAR-T cells in the presence of low, but not high, concentrations of blocking STEAP2 antibodies, while isotype control blocking antibodies had no effect on IFNγ levels (FIG. 10B).

Co-cultures of LNCaP STEAP2 CRISPR cells with 40A3Bz dnTGFβRII CAR-T cells at E:T ratio of 0.3:1 in the presence of blocking anti-STEAP2 antibodies (0.2, 2, 20, or 200 μg/ml) showed similar cell growth of LNCaP STEAP2 CRISPR cells in the presence of 40A3Bz dnTGFβRII CAR-T cells as in the presence of untransduced T cells (FIG. 10C) and no secretion of IFNγ into the culture medium (FIG. 10D).

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

All publications, patents, and patent applications disclosed herein are incorporated by reference to the same extent as if each individual publication, patent or patent application was specifically and individually indicated to be incorporated by reference.

---

What is claimed:

1. A polynucleotide comprising a nucleotide sequence encoding a chimeric antigen receptor (CAR), the CAR comprising (i) an antigen-binding domain that binds an epitope on human six transmembrane epithelial antigen of prostate-2 (STEAP2);

(ii) a transmembrane domain; and (iii) an intracellular domain, wherein the antigen-binding domain comprises:

(a) a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6;

(b) a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16;

(c) a VL-CDR1 comprising the amino acid sequence set forth in SEQ ID NO: 21, a VL-CDR2 comprising the amino acid sequence set forth in SEQ ID NO: 22, a VL-CDR3 comprising the amino acid sequence set forth in SEQ ID NO: 23, a VH-CDR1 comprising the amino acid sequence set forth in SEQ ID NO: 24, a VH-CDR2 comprising the amino acid sequence set forth in SEQ ID NO: 25, a VH-CDR3 comprising the amino acid sequence set forth in SEQ ID NO: 26;

(d) a VL-CDR1 comprising the amino acid sequence set forth in SEQ ID NO: 31, a VL-CDR2 comprising the amino acid sequence set forth in SEQ ID NO: 32, a VL-CDR3 comprising the amino acid sequence set forth in SEQ ID NO: 33, a VH-CDR1 comprising the amino acid sequence set forth in SEQ ID NO: 34, a VH-CDR2 comprising the amino acid sequence set forth in SEQ ID NO: 35, a VH-CDR3 comprising the amino acid sequence set forth in SEQ ID NO: 36;

(e) a VL-CDR1 comprising the amino acid sequence set forth in SEQ ID NO: 41, a VL-CDR2 comprising the amino acid sequence set forth in SEQ ID NO: 42, a VL-CDR3 comprising the amino acid sequence set forth in SEQ ID NO: 43, a VH-CDR1 comprising the amino acid sequence set forth in SEQ ID NO: 44, a VH-CDR2 comprising the amino acid sequence set forth in SEQ ID NO: 45, a VH-CDR3 comprising the amino acid sequence set forth in SEQ ID NO: 46; or (f) a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

2. The polynucleotide of claim 1, wherein the antigen-binding domain comprises:

(a) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8;

(b) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18;

(c) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28;

(d) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38;

(e) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48; or (f) a VH comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and a VL comprising an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

3. The polynucleotide of claim 1, wherein the antigen-binding domain comprises:

(a) a VH comprising the amino acid sequence set forth in SEQ ID NO: 7, and a VL comprising the amino acid sequence set forth in SEQ ID NO: 8;

(b) a VH comprising the amino acid sequence set forth in SEQ ID NO: 17, and a VL comprising the amino acid sequence set forth in SEQ ID NO: 18;

(c) a VH comprising the amino acid sequence set forth in SEQ ID NO: 27, and a VL comprising the amino acid sequence set forth in SEQ ID NO: 28;

(d) a VH comprising the amino acid sequence set forth in SEQ ID NO: 37, and a VL comprising the amino acid sequence set forth in SEQ ID NO: 38;

(e) a VH comprising the amino acid sequence set forth in SEQ ID NO: 47, and a VL comprising the amino acid sequence set forth in SEQ ID NO: 48;

(f) a VH comprising the amino acid sequence set forth in SEQ ID NO: 57, and a VL comprising the amino acid sequence set forth in SEQ ID NO: 58;

(g) a VH comprising the amino acid sequence set forth in SEQ ID NO: 67, and a VL comprising the amino acid sequence set forth in SEQ ID NO: 68;

(h) a VH comprising the amino acid sequence set forth in SEQ ID NO: 77, and a VL comprising the amino acid sequence set forth in SEQ ID NO: 78;

(i) a VH comprising the amino acid sequence set forth in SEQ ID NO: 87, and a VL comprising the amino acid sequence set forth in SEQ ID NO: 88; or (j) a VH comprising the amino acid sequence set forth in SEQ ID NO: 97, and a VL comprising the amino acid sequence set forth in SEQ ID NO: 98.

4. The polynucleotide of claim 1, wherein the intracellular domain comprises a costimulatory domain selected from the group consisting of the intracellular domain of CD3z, a CD28 co-stimulatory domain, a CD27 co-stimulatory domain, a 4-1BB co-stimulatory domain, an ICOS co-stimulatory domain, an OX-40 co-stimulatory domain, a GITR co-stimulatory domain, a CD2 co-stimulatory domain, an IL-2Rβ co-stimulatory domain, an MyD88/CD40a CD28 co-stimulatory domain, and any combination thereof.

5. The polynucleotide of claim 1, wherein the CAR comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10.

6. The polynucleotide of claim 1, which further encodes an armoring molecule, wherein the armoring molecule counters immunosuppression of a cell in a tumor microenvironment when expressed on a surface of the cell.

7. The polynucleotide of claim 6, wherein the armoring molecule comprises a dominant-negative TGF-β receptor type 2 (TGFβRIIDN), and wherein the armoring molecule comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 105.

8. A vector or a set of vectors comprising the polynucleotide of claim 7.

9. A cell comprising the polynucleotide of claim 7.

10. A cell comprising (i) a polynucleotide encoding a chimeric antigen receptor (CAR) that binds human STEAP2 and (ii) a polynucleotide encoding an armoring molecule, wherein the CAR comprises an antigen-binding domain comprising a VH and a VL, wherein the VH comprises a VH-CDR1, a VH-CDR2, a VH-CDR3, and wherein the VL comprises a VL-CDR1, a VL-CDR2, and VL-CDR3; and wherein (a) the VL-CDR1 comprises the amino acid sequence set forth in SEQ ID NO: 1, the VL-CDR2 comprises the amino acid sequence set forth in SEQ ID NO: 2, the VL-CDR3 comprises the amino acid sequence set forth in SEQ ID NO: 3, the VH-CDR1 comprises the amino acid sequence set forth in SEQ ID NO: 4, the VH-CDR2 comprises the amino acid sequence set forth in SEQ ID NO: 5, and the VH-CDR3 comprises the amino acid sequence set forth in SEQ ID NO: 6;

(b) the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 14, the VH-CDR2 comprises the amino acid sequence set forth in SEQ ID NO: 15, and the VH-CDR3 comprises the amino acid sequence set forth in SEQ ID NO: 16;

(c) the VL-CDR1 comprises the amino acid sequence set forth in SEQ ID NO: 21, the VL-CDR2 comprises the amino acid sequence set forth in SEQ ID NO: 22, the VL-CDR3 comprises the amino acid sequence set forth in SEQ ID NO: 23, the VH-CDR1 comprises the amino acid sequence set forth in SEQ ID NO: 24, the VH-CDR2 comprises the amino acid sequence set forth in SEQ ID NO: 25, and the VH-CDR3 comprises the amino acid sequence set forth in SEQ ID NO: 26;

(d) the VL-CDR1 comprises the amino acid sequence set forth in SEQ ID NO: 31, the VL-CDR2 comprises the amino acid sequence set forth in SEQ ID NO: 32, the VL-CDR3 comprises the amino acid sequence set forth in SEQ ID NO: 33, the VH-CDR1 comprises the amino acid sequence set forth in SEQ ID NO: 34, the VH-CDR2 comprises the amino acid sequence set forth in SEQ ID NO: 35, and the VH-CDR3 comprises the amino acid sequence set forth in SEQ ID NO: 36;

(e) the VL-CDR1 comprises the amino acid sequence set forth in SEQ ID NO: 41, the VL-CDR2 comprises the amino acid sequence set forth in SEQ ID NO: 42, the VL-CDR3 comprises the amino acid sequence set forth in SEQ ID NO: 43, the VH-CDR1 comprises the amino acid sequence set forth in SEQ ID NO: 44, the VH-CDR2 comprises the amino acid sequence set forth in SEQ ID NO: 45, and the VH-CDR3 comprises the amino acid sequence set forth in SEQ ID NO: 46; or (f) the VL-CDR1 comprises the amino acid sequence set forth in SEQ ID NO: 91, the VL-CDR2 comprises the amino acid sequence set forth in SEQ ID NO: 92, the VL-CDR3 comprises the amino acid sequence set forth in SEQ ID NO: 93, the VH-CDR1 comprises the amino acid sequence set forth in SEQ ID NO: 94, the VH-CDR2 comprises the amino acid sequence set forth in SEQ ID NO: 95, and the VH-CDR3 comprises the amino acid sequence set forth in SEQ ID NO: 96.

11. The cell of claim 10, wherein (a) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8;

(b) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18;

(c) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28;

(d) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38;

(e) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48;

(f) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58;

(g) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68;

(h) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78;

(i) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88; or (j) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

12. The cell of claim 10, wherein the CAR comprises an antigen-binding domain that comprises the amino acid sequence of SEQ ID NO: 9.

13. The cell of claim 12, wherein the armoring molecule comprises a dominant-negative TGF-β receptor type 2 (TGFβRIIDN), and wherein, the armoring molecule comprises an amino acid sequence having at least about 70%, at least about 75%, at least about 80%, at least about 85%, at least about 90%, at least about 95%, at least about 96%, at least about 97%, at least about 98%, at least about 99%, or 100% sequence identity to the amino acid sequence set forth in SEQ ID NO: 105.

14. A cell comprising a chimeric antigen receptor (CAR) that binds human STEAP2, wherein the CAR comprises an antigen-binding domain that comprises:

a) a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6;

b) a VL-CDR1 comprising the amino acid sequence set forth in SEQ ID NO: 11, a VL-CDR2 comprising the amino acid sequence set forth in SEQ ID NO: 12, a VL-CDR3 comprising the amino acid sequence set forth in SEQ ID NO: 13, a VH-CDR1 comprising the amino acid sequence set forth in SEQ ID NO: 14, a VH-CDR2 comprising the amino acid sequence set forth in SEQ ID NO: 15, a VH-CDR3 comprising the amino acid sequence set forth in SEQ ID NO: 16;

c) a VL-CDR1 comprising the amino acid sequence set forth in SEQ ID NO: 21, a VL-CDR2 comprising the amino acid sequence set forth in SEQ ID NO: 22, a VL-CDR3 comprising the amino acid sequence set forth in SEQ ID NO: 23, a VH-CDR1 comprising the amino acid sequence set forth in SEQ ID NO: 24, a VH-CDR2 comprising the amino acid sequence set forth in SEQ ID NO: 25, a VH-CDR3 comprising the amino acid sequence set forth in SEQ ID NO: 26;

d) a VL-CDR1 comprising the amino acid sequence set forth in SEQ ID NO: 31, a VL-CDR2 comprising the amino acid sequence set forth in SEQ ID NO: 32, a VL-CDR3 comprising the amino acid sequence set forth in SEQ ID NO: 33, a VH-CDR1 comprising the amino acid sequence set forth in SEQ ID NO: 34, a VH-CDR2 comprising the amino acid sequence set forth in SEQ ID NO: 35, a VH-CDR3 comprising the amino acid sequence set forth in SEQ ID NO: 36; or e) a VL-CDR1 comprising the amino acid sequence set forth in SEQ ID NO: 41, a VL-CDR2 comprising the amino acid sequence set forth in SEQ ID NO: 42, a VL-CDR3 comprising the amino acid sequence set forth in SEQ ID NO: 43, a VH-CDR1 comprising the amino acid sequence set forth in SEQ ID NO: 44, a VH-CDR2 comprising the amino acid sequence set forth in SEQ ID NO: 45, a VH-CDR3 comprising the amino acid sequence set forth in SEQ ID NO: 46; or f) a VL-CDR1 comprising the amino acid sequence set forth in SEQ ID NO: 91, a VL-CDR2 comprising the amino acid sequence set forth in SEQ ID NO: 92, a VL-CDR3 comprising the amino acid sequence set forth in SEQ ID NO: 93, a VH-CDR1 comprising the amino acid sequence set forth in SEQ ID NO: 94, a VH-CDR2 comprising the amino acid sequence set forth in SEQ ID NO: 95, a VH-CDR3 comprising the amino acid sequence set forth in SEQ ID NO: 96.

15. An antibody or an antigen-binding portion thereof that specifically binds human STEAP2, comprising a variable heavy chain region (VH) and a variable light chain region (VL), wherein the VH comprises a VH complementarity determining region 1 (VH-CDR1), a VH-CDR2, a VH-CDR3; and wherein the VL comprises a VL-CDR1, a VL-CDR2, and VL-CDR3, wherein:

(a) the VL-CDR1 comprises the amino acid sequence set forth in SEQ ID NO: 1, the VL-CDR2 comprises the amino acid sequence set forth in SEQ ID NO: 2, the VL-CDR3 comprises the amino acid sequence set forth in SEQ ID NO: 3, the VH-CDR1 comprises the amino acid sequence set forth in SEQ ID NO: 4, the VH-CDR2 comprises the amino acid sequence set forth in SEQ ID NO: 5, and the VH-CDR3 comprises the amino acid sequence set forth in SEQ ID NO: 6;

(b) the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 14, the VH-CDR2 comprises the amino acid sequence set forth in SEQ ID NO: 15, and the VH-CDR3 comprises the amino acid sequence set forth in SEQ ID NO: 16;

(c) the VL-CDR1 comprises the amino acid sequence set forth in SEQ ID NO: 21, the VL-CDR2 comprises the amino acid sequence set forth in SEQ ID NO: 22, the VL-CDR3 comprises the amino acid sequence set forth in SEQ ID NO: 23, the VH-CDR1 comprises the amino acid sequence set forth in SEQ ID NO: 24, the VH-CDR2 comprises the amino acid sequence set forth in SEQ ID NO: 25, and the VH-CDR3 comprises the amino acid sequence set forth in SEQ ID NO: 26;

(d) the VL-CDR1 comprises the amino acid sequence set forth in SEQ ID NO: 31, the VL-CDR2 comprises the amino acid sequence set forth in SEQ ID NO: 32, the VL-CDR3 comprises the amino acid sequence set forth in SEQ ID NO: 33, the VH-CDR1 comprises the amino acid sequence set forth in SEQ ID NO: 34, the VH-CDR2 comprises the amino acid sequence set forth in SEQ ID NO: 35, and the VH-CDR3 comprises the amino acid sequence set forth in SEQ ID NO: 36;

(e) the VL-CDR1 comprises the amino acid sequence set forth in SEQ ID NO: 41, the VL-CDR2 comprises the amino acid sequence set forth in SEQ ID NO: 42, the VL-CDR3 comprises the amino acid sequence set forth in SEQ ID NO: 43, the VH-CDR1 comprises the amino acid sequence set forth in SEQ ID NO: 44, the VH-CDR2 comprises the amino acid sequence set forth in SEQ ID NO: 45, and the VH-CDR3 comprises the amino acid sequence set forth in SEQ ID NO: 46; or (f) the VL-CDR1 comprises the amino acid sequence set forth in SEQ ID NO: 91, the VL-CDR2 comprises the amino acid sequence set forth in SEQ ID NO: 92, the VL-CDR3 comprises the amino acid sequence set forth in SEQ ID NO: 93, the VH-CDR1 comprises the amino acid sequence set forth in SEQ ID NO: 94, the VH-CDR2 comprises the amino acid sequence set forth in SEQ ID NO: 95, and the VH-CDR3 comprises the amino acid sequence set forth in SEQ ID NO: 96.

16. The antibody or an antigen-binding portion thereof of claim 15, wherein:

(a) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 7, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 8;

(b) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 17, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 18;

(c) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 27, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 28;

(d) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 37, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 38;

(e) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 47, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 48;

(f) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 57, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 58;

(g) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 67, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 68;

(h) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 77, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 78;

(i) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 87, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 88; or (j) the VH comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 97, and the VL comprises an amino acid sequence having at least about 70%, at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 98.

17. A pharmaceutical composition comprising the cell of claim 13 and a pharmaceutically acceptable excipient.

18. A method of treating a cancer in a subject in need thereof, comprising administering to the subject the cell of claim 13.

19. A polynucleotide comprising a nucleotide sequence encoding a chimeric antigen receptor (CAR), the CAR comprising:

(i) an antigen-binding domain that binds an epitope on human six transmembrane epithelial antigen of prostate-2 (STEAP2) comprising a VL-CDR1 comprising the amino acid sequence set forth in SEQ ID NO: 1, a VL-CDR2 comprising the amino acid sequence set forth in SEQ ID NO: 2, a VL-CDR3 comprising the amino acid sequence set forth in SEQ ID NO: 3, a VH-CDR1 comprising the amino acid sequence set forth in SEQ ID NO: 4, a VH-CDR2 comprising the amino acid sequence set forth in SEQ ID NO: 5, a VH-CDR3 comprising the amino acid sequence set forth in SEQ ID NO: 6;

(ii) a transmembrane domain; and (iii) an intracellular domain.

20. The polynucleotide of claim 19, wherein the antigen-binding domain comprises a VH comprising the amino acid sequence set forth in SEQ ID NO: 7, and a VL comprising the amino acid sequence set forth in SEQ ID NO: 8.

21. The polynucleotide of claim 19, wherein the CAR comprises the amino acid sequence as set forth in SEQ ID NO: 10.

22. The polynucleotide of claim 19, wherein the CAR comprises the amino acid sequence set forth in SEQ ID NO: 106.

23. The polynucleotide of claim 19, comprising nucleotide sequence set forth in SEQ ID NO: 107.

24. The cell of claim 12, wherein the CAR comprises the amino acid sequence of SEQ ID NO: 10.

25. The cell of claim 12, wherein the armoring molecule comprises an amino acid sequence of SEQ ID NO: 105.

26. The cell of claim 14, wherein the antigen-binding domain comprises a VH comprising the amino acid sequence set forth in SEQ ID NO: 7, and a VL comprising the amino acid sequence set forth in SEQ ID NO: 8.

27. The cell of claim 26, wherein the antigen-binding domain that comprises the amino acid sequence of SEQ ID NO: 9.

28. The cell of claim 27, wherein the CRA comprises the amino acid sequence of SEQ ID NO: 10.

29. The cell of claim 27, wherein the CAR comprises the amino acid sequence of SEQ ID NO: 106.

30. The cell of claim 14, comprising the nucleotide sequence set forth in SEQ ID NO: 107.

31. A method of treating a cancer in a subject in need thereof, comprising administering to the subject the cell of claim 25.

32. A method of treating a cancer in a subject in need thereof, comprising administering to the subject the cell of claim 28.

33. The polynucleotide of claim 1, wherein the CAR comprises the amino acid sequence set forth in SEQ ID NO: 10.

34. A pharmaceutical composition comprising the cell of claim 24 and a pharmaceutically acceptable excipient.

35. A method of treating a cancer in a subject in need thereof, comprising administering to the subject the cell of claim 24.

36. A pharmaceutical composition comprising the cell of claim 29 and a pharmaceutically acceptable excipient.

37. A method of treating a cancer in a subject in need thereof, comprising administering to the subject the cell of claim 29.

38. A vector comprising the polynucleotide of claim 23.

39. A cell comprising the vector of claim 38.

40. A chimeric antigen receptor (CAR) that binds human STEAP2 comprising the amino acid sequence of SEQ ID NO: 10 or SEQ ID NO: 106.

* * * * *

```
                            SEQUENCE LISTING

Sequence total quantity: 133
SEQ ID NO: 1              moltype = AA  length = 11
FEATURE                   Location/Qualifiers
source                    1..11
                          mol_type = protein
                          organism = synthetic construct
REGION                    1..11
                          note = STEAP2 VL CDR1 (40A3)
SEQUENCE: 1
RASQSVNSNL A                                                        11

SEQ ID NO: 2              moltype = AA  length = 7
FEATURE                   Location/Qualifiers
source                    1..7
                          mol_type = protein
                          organism = synthetic construct
REGION                    1..7
                          note = STEAP2 VL CDR2
SEQUENCE: 2
GASTRAT                                                             7

SEQ ID NO: 3              moltype = AA  length = 9
FEATURE                   Location/Qualifiers
REGION                    1..9
                          note = STEAP2 VL CDR3
source                    1..9
                          mol_type = protein
                          organism = synthetic construct
SEQUENCE: 3
QQYNNWPFT                                                           9

SEQ ID NO: 4              moltype = AA  length = 7
FEATURE                   Location/Qualifiers
REGION                    1..7
                          note = STEAP2 VH CDR1
source                    1..7
                          mol_type = protein
                          organism = synthetic construct
SEQUENCE: 4
RNSAVWN                                                             7

SEQ ID NO: 5              moltype = AA  length = 18
FEATURE                   Location/Qualifiers
REGION                    1..18
                          note = STEAP2 VH CDR2
source                    1..18
                          mol_type = protein
                          organism = synthetic construct
SEQUENCE: 5
RTYYRSKWYN DYAVSVKS                                                 18

SEQ ID NO: 6              moltype = AA  length = 13
FEATURE                   Location/Qualifiers
REGION                    1..13
                          note = STEAP2 VHCDR3
source                    1..13
                          mol_type = protein
                          organism = synthetic construct
SEQUENCE: 6
GLLQNNFYYY MDV                                                      13

SEQ ID NO: 7              moltype = AA  length = 125
FEATURE                   Location/Qualifiers
```

-continued

```
REGION                    1..125
                          note = STEAP2 VH
source                    1..125
                          mol_type = protein
                          organism = synthetic construct
SEQUENCE: 7
QVQLQQSGPG LVKPSQTLSL TCAISGDSVS RNSAVWNWIR QSPSRGLEWL GRTYYRSKWY    60
NDYAVSVKSR ITINPDTSKN QFSLQVNSVT PEDTAVYYCA RGLLQNNFYY YMDVWGKGTT   120
VTVSS                                                              125

SEQ ID NO: 8              moltype = AA   length = 107
FEATURE                   Location/Qualifiers
REGION                    1..107
                          note = STEAP2 VL
source                    1..107
                          mol_type = protein
                          organism = synthetic construct
SEQUENCE: 8
EIVMTQSPAT LSVSPGERAT LSCRASQSVN SNLAWYQQKP GQAPRLLIYG ASTRATGIPA    60
RFSGSGSGTE FTLTISSLQS EDFAVYYCQQ YNNWPFTFGP GTKVDIK               107

SEQ ID NO: 9              moltype = AA   length = 252
FEATURE                   Location/Qualifiers
REGION                    1..252
                          note = STEAP2 scFv amino acid sequence
source                    1..252
                          mol_type = protein
                          organism = synthetic construct
SEQUENCE: 9
EIVMTQSPAT LSVSPGERAT LSCRASQSVN SNLAWYQQKP GQAPRLLIYG ASTRATGIPA    60
RFSGSGSGTE FTLTISSLQS EDFAVYYCQQ YNNWPFTFGP GTKVDIKGGG GSGGGGSGGG   120
GSGGGGSQVQ LQQSGPGLVK PSQTLSLTCA ISGDSVSRNS AVWNWIRQSP SRGLEWLGRT   180
YYRSKWYNDY AVSVKSRITI NPDTSKNQFS LQVNSVTPED TAVYYCARGL LQNNFYYYMD   240
VWGKGTTVTV SS                                                      252

SEQ ID NO: 10             moltype = AA   length = 469
FEATURE                   Location/Qualifiers
REGION                    1..469
                          note = STEAP2 BZ CAR amino acid sequence
source                    1..469
                          mol_type = protein
                          organism = synthetic construct
SEQUENCE: 10
MLLLVTSLLL CELPHPAFLL IPEIVMTQSP ATLSVSPGER ATLSCRASQS VNSNLAWYQQ    60
KPGQAPRLLI YGASTRATGI PARFSGSGSG TEFTLTISSL QSEDFAVYYC QQYNNWPFTF   120
GPGTKVDIKG GGGSGGGGSG GGGSGGGGSQ VQLQQSGPGL VKPSQTLSLT CAISGDSVSR   180
NSAVWNWIRQ SPSRGLEWLG RTYYRSKWYN DYAVSVKSRI TINPDTSKNQ FSLQVNSVTP   240
EDTAVYYCAR GLLQNNFYYY MDVWGKGTTV TVSSGSESKY GPPCPPCPFW VLVVVGGVLA   300
CYSLLVTVAF IIFWVKRGRK KLLYIFKQPF MRPVQTTQEE DGCSCRFPEE EEGGCELRVK   360
FSRSADAPAY QQGQNQLYNE LNLGRREEYD VLDKRRGRDP EMGGKPRRKN PQEGLYNELQ   420
KDKMAEAYSE IGMKGERRRG KGHDGLYQGL STATKDTYDA LHMQALPPR             469

SEQ ID NO: 11             moltype = AA   length = 11
FEATURE                   Location/Qualifiers
REGION                    1..11
                          note = STEAP2-3 VL CDR1 (40A3GL-LO7)
source                    1..11
                          mol_type = protein
                          organism = synthetic construct
SEQUENCE: 11
RASQSVSSNL A                                                        11

SEQ ID NO: 12             moltype = AA   length = 7
FEATURE                   Location/Qualifiers
REGION                    1..7
                          note = STEAP2-3 VL CDR2
source                    1..7
                          mol_type = protein
                          organism = synthetic construct
SEQUENCE: 12
GASTRAT                                                             7

SEQ ID NO: 13             moltype = AA   length = 9
FEATURE                   Location/Qualifiers
REGION                    1..9
                          note = STEAP2-3 VL CDR3
source                    1..9
                          mol_type = protein
                          organism = synthetic construct
```

-continued

```
SEQUENCE: 13
QQYNNWPFT                                                                  9

SEQ ID NO: 14              moltype = AA   length = 7
FEATURE                    Location/Qualifiers
REGION                     1..7
                           note = STEAP2-3 VH CDR1
source                     1..7
                           mol_type = protein
                           organism = synthetic construct
SEQUENCE: 14
RNSAVWN                                                                    7

SEQ ID NO: 15              moltype = AA   length = 18
FEATURE                    Location/Qualifiers
REGION                     1..18
                           note = STEAP2-3 VH CDR2
source                     1..18
                           mol_type = protein
                           organism = synthetic construct
SEQUENCE: 15
RTYYRSKWYN DYAVSVKS                                                        18

SEQ ID NO: 16              moltype = AA   length = 13
FEATURE                    Location/Qualifiers
REGION                     1..13
                           note = STEAP2-3 VH CDR3
source                     1..13
                           mol_type = protein
                           organism = synthetic construct
SEQUENCE: 16
GLLQNQFYYY MDV                                                             13

SEQ ID NO: 17              moltype = AA   length = 125
FEATURE                    Location/Qualifiers
REGION                     1..125
                           note = STEAP2-3 VH
source                     1..125
                           mol_type = protein
                           organism = synthetic construct
SEQUENCE: 17
QVQLQQSGPG LVKPSQTLSL TCAISGDSVS RNSAVWNWIR QSPSRGLEWL GRTYYRSKWY         60
NDYAVSVKSR ITINPDTSKN QFSLQLNSVT PEDTAVYYCA RGLLQNQFYY YMDVWGKGTT        120
VTVSS                                                                    125

SEQ ID NO: 18              moltype = AA   length = 107
FEATURE                    Location/Qualifiers
REGION                     1..107
                           note = STEAP2-3 VL
source                     1..107
                           mol_type = protein
                           organism = synthetic construct
SEQUENCE: 18
EIVMTQSPAT LSVSPGERAT LSCRASQSVS SNLAWYQQKP GQAPRLLIYG ASTRATGIPA         60
RFSGSGSGTE FTLTISSLQS EDFAVYYCQQ YNNWPFTFGP GTKVDIK                      107

SEQ ID NO: 19              moltype =    length =
SEQUENCE: 19
000

SEQ ID NO: 20              moltype =    length =
SEQUENCE: 20
000

SEQ ID NO: 21              moltype = AA   length = 16
FEATURE                    Location/Qualifiers
REGION                     1..16
                           note = STEAP2-2 VL CDR1(mm30D12)
source                     1..16
                           mol_type = protein
                           organism = synthetic construct
SEQUENCE: 21
RSSQSVVHSN GNTYLE                                                          16

SEQ ID NO: 22              moltype = AA   length = 7
FEATURE                    Location/Qualifiers
REGION                     1..7
                           note = STEAP2-2 VL CDR2
source                     1..7
```

-continued

```
                              mol_type = protein
                              organism = synthetic construct
SEQUENCE: 22
KVSNRFS                                                                    7

SEQ ID NO: 23          moltype = AA   length = 9
FEATURE                Location/Qualifiers
REGION                 1..9
                       note = STEAP2-2 VL CDR3
source                 1..9
                       mol_type = protein
                       organism = synthetic construct
SEQUENCE: 23
FQGSHVPYT                                                                  9

SEQ ID NO: 24          moltype = AA   length = 5
FEATURE                Location/Qualifiers
REGION                 1..5
                       note = STEAP2-2 VH CDR1
source                 1..5
                       mol_type = protein
                       organism = synthetic construct
SEQUENCE: 24
SYGMS                                                                      5

SEQ ID NO: 25          moltype = AA   length = 17
FEATURE                Location/Qualifiers
REGION                 1..17
                       note = STEAP2-2 VH CDR2
source                 1..17
                       mol_type = protein
                       organism = synthetic construct
SEQUENCE: 25
TISSGGSYTF YPDIMKG                                                         17

SEQ ID NO: 26          moltype = AA   length = 13
FEATURE                Location/Qualifiers
REGION                 1..13
                       note = STEAP2-2 VH CDR3
source                 1..13
                       mol_type = protein
                       organism = synthetic construct
SEQUENCE: 26
RGYGTIYTFS FDS                                                             13

SEQ ID NO: 27          moltype = AA   length = 122
FEATURE                Location/Qualifiers
REGION                 1..122
                       note = STEAP2-2 VH
source                 1..122
                       mol_type = protein
                       organism = synthetic construct
SEQUENCE: 27
EVQLVESGGD LVKPGGSLKL SCAASGFSFS SYGMSWVRQT PDKRLEWVAT ISSGGSYTFY    60
PDIMKGRFTI SRDNAMNTLY LQMSSLKSED SAMYYCARRG YGTIYTFSFD SWGQGTTLTV   120
SS                                                                   122

SEQ ID NO: 28          moltype = AA   length = 112
FEATURE                Location/Qualifiers
REGION                 1..112
                       note = STEAP2-2 VL
source                 1..112
                       mol_type = protein
                       organism = synthetic construct
SEQUENCE: 28
DVLMTQTPLS LPVSLGDQAS ISCRSSQSVV HSNGNTYLEW YLQKPGQSPK LLIYKVSNRF    60
SGVPDRFSGS GSGTDFTLKI SRVEAEDLGV YYCFQGSHVP YTFGGGTKLE IK           112

SEQ ID NO: 29          moltype =    length =
SEQUENCE: 29
000

SEQ ID NO: 30          moltype =    length =
SEQUENCE: 30
000

SEQ ID NO: 31          moltype = AA   length = 16
FEATURE                Location/Qualifiers
REGION                 1..16
```

-continued

```
                              note = STEAP2-2 Humanized1 VL CDR1
source                        1..16
                              mol_type = protein
                              organism = synthetic construct
SEQUENCE: 31
RSSQSVVHSN ANTYLE                                                           16

SEQ ID NO: 32      moltype = AA  length = 7
FEATURE            Location/Qualifiers
REGION             1..7
                   note = STEAP2-2 Humanized1 VL CDR2
source             1..7
                   mol_type = protein
                   organism = synthetic construct
SEQUENCE: 32
KVSNRFS                                                                     7

SEQ ID NO: 33      moltype = AA  length = 9
FEATURE            Location/Qualifiers
REGION             1..9
                   note = STEAP2-2 Humanized1 VL CDR3
source             1..9
                   mol_type = protein
                   organism = synthetic construct
SEQUENCE: 33
FQGSHVPYT                                                                   9

SEQ ID NO: 34      moltype = AA  length = 5
FEATURE            Location/Qualifiers
REGION             1..5
                   note = STEAP2-2 Humanized1 VH CDR1
source             1..5
                   mol_type = protein
                   organism = synthetic construct
SEQUENCE: 34
SYGMS                                                                       5

SEQ ID NO: 35      moltype = AA  length = 17
FEATURE            Location/Qualifiers
REGION             1..17
                   note = STEAP2-2 Humanized1 VH CDR2
source             1..17
                   mol_type = protein
                   organism = synthetic construct
SEQUENCE: 35
TISSGGSYTF YPDIMKG                                                          17

SEQ ID NO: 36      moltype = AA  length = 13
FEATURE            Location/Qualifiers
REGION             1..13
                   note = STEAP2-2 Humanized1 VH CDR3
source             1..13
                   mol_type = protein
                   organism = synthetic construct
SEQUENCE: 36
RGYGTIYTFS FDA                                                              13

SEQ ID NO: 37      moltype = AA  length = 122
FEATURE            Location/Qualifiers
REGION             1..122
                   note = STEAP2-2 Humanized1 VH
source             1..122
                   mol_type = protein
                   organism = synthetic construct
SEQUENCE: 37
EVQLVESGGG LVKPGGSLRL SCAASGFTFS SYGMSWVRQA PGKRLEWVAT ISSGGSYTFY    60
PDIMKGRFTI SRDNSKNTLY LQMNSLRAED TAVYYCARRG YGTIYTFSFD AWGQGTTLTV   120
SS                                                                        122

SEQ ID NO: 38      moltype = AA  length = 112
FEATURE            Location/Qualifiers
REGION             1..112
                   note = STEAP2-2 Humanized1 VL
source             1..112
                   mol_type = protein
                   organism = synthetic construct
SEQUENCE: 38
DVVMTQSPLS LPVTLGQPAS ISCRSSQSVV HSNANTYLEW YLQKPGQSPQ LLIYKVSNRF    60
SGVPDRFSGS GSGTDFTLKI SRVEAEDVGV YYCFQGSHVP YTFGQGTKLE IK           112
```

-continued

```
SEQ ID NO: 39            moltype =    length =
SEQUENCE: 39
000

SEQ ID NO: 40            moltype =    length =
SEQUENCE: 40
000

SEQ ID NO: 41            moltype = AA   length = 16
FEATURE                  Location/Qualifiers
REGION                   1..16
                         note = STEAP2-2 Humanized2 VL CDR1
source                   1..16
                         mol_type = protein
                         organism = synthetic construct
SEQUENCE: 41
RSSQSVVHSN ANTYLE                                                             16

SEQ ID NO: 42            moltype = AA   length = 7
FEATURE                  Location/Qualifiers
REGION                   1..7
                         note = STEAP2-2 Humanized2 VL CDR2
source                   1..7
                         mol_type = protein
                         organism = synthetic construct
SEQUENCE: 42
KVSNRFS                                                                        7

SEQ ID NO: 43            moltype = AA   length = 9
FEATURE                  Location/Qualifiers
REGION                   1..9
                         note = STEAP2-2 Humanized2 VL CDR3
source                   1..9
                         mol_type = protein
                         organism = synthetic construct
SEQUENCE: 43
FQGSHVPYT                                                                      9

SEQ ID NO: 44            moltype = AA   length = 5
FEATURE                  Location/Qualifiers
REGION                   1..5
                         note = STEAP2-2 Humanized2 VH CDR1
source                   1..5
                         mol_type = protein
                         organism = synthetic construct
SEQUENCE: 44
SYGMS                                                                          5

SEQ ID NO: 45            moltype = AA   length = 17
FEATURE                  Location/Qualifiers
REGION                   1..17
                         note = STEAP2-2 Humanized2 VH CDR2
source                   1..17
                         mol_type = protein
                         organism = synthetic construct
SEQUENCE: 45
TISSGGSYTF YPDIMKG                                                            17

SEQ ID NO: 46            moltype = AA   length = 13
FEATURE                  Location/Qualifiers
REGION                   1..13
                         note = STEAP2-2 Humanized2 VH CDR3
source                   1..13
                         mol_type = protein
                         organism = synthetic construct
SEQUENCE: 46
RGYGTIYTFS FDA                                                                13

SEQ ID NO: 47            moltype = AA   length = 122
FEATURE                  Location/Qualifiers
REGION                   1..122
                         note = STEAP2-2 Humanized2 VH
source                   1..122
                         mol_type = protein
                         organism = synthetic construct
SEQUENCE: 47
EVQLLESGGG LVQPGGSLRL SCAASGFTFS SYGMSWVRQA PGKRLEWVST ISSGGSYTFY  60
PDIMKGRFTI SRDNSKNTLY LQMNSLRAED TAVYYCARRG YGTIYTFSFD AWGQGTTLTV  120
```

-continued

SS                                                                                                          122

SEQ ID NO: 48                    moltype = AA   length = 112
FEATURE                          Location/Qualifiers
REGION                           1..112
                                 note = STEAP2-2 Humanized2 VL
source                           1..112
                                 mol_type = protein
                                 organism = synthetic construct
SEQUENCE: 48
DVVMTQSPLS LPVTLGQPAS ISCRSSQSVV HSNANTYLEW YLQKPGQSPQ LLIYKVSNRF   60
SGVPDRFSGS GSGTDFTLKI SRVEAEDVGV YYCFQGSHVP YTFGQGTKLE IK          112

SEQ ID NO: 49                    moltype =    length =
SEQUENCE: 49
000

SEQ ID NO: 50                    moltype =    length =
SEQUENCE: 50
000

SEQ ID NO: 51                    moltype =    length =
SEQUENCE: 51
000

SEQ ID NO: 52                    moltype =    length =
SEQUENCE: 52
000

SEQ ID NO: 53                    moltype =    length =
SEQUENCE: 53
000

SEQ ID NO: 54                    moltype =    length =
SEQUENCE: 54
000

SEQ ID NO: 55                    moltype =    length =
SEQUENCE: 55
000

SEQ ID NO: 56                    moltype =    length =
SEQUENCE: 56
000

SEQ ID NO: 57                    moltype = AA   length = 120
FEATURE                          Location/Qualifiers
REGION                           1..120
                                 note = STEAP2-4 VH (40A1)
source                           1..120
                                 mol_type = protein
                                 organism = synthetic construct
SEQUENCE: 57
EVQLVESGGG LVQPGGSLRL SCAASGFTFS SFAMTWVRQA PGKGLEWVSV ITYSGGRTYY   60
ADSVKGRFTI SRDNSKNTLY LQMNSLRAED TAVYFCAKDR IAAVGPFDYW GQGTLVTVSS  120

SEQ ID NO: 58                    moltype = AA   length = 107
FEATURE                          Location/Qualifiers
REGION                           1..107
                                 note = STEAP2-4 VL
source                           1..107
                                 mol_type = protein
                                 organism = synthetic construct
SEQUENCE: 58
DIQLTQSPSF LSASVGDRVT ITCRASQGIS VYLAWYQQEP GKAPKLLIYA ASTLQSGVPS   60
RFSGSGSGTE FTLTISSLQP EDFATYYCQQ LNSYPRTFGQ GTKVEIK               107

SEQ ID NO: 59                    moltype =    length =
SEQUENCE: 59
000

SEQ ID NO: 60                    moltype =    length =
SEQUENCE: 60
000

SEQ ID NO: 61                    moltype =    length =
SEQUENCE: 61
000

-continued

```
SEQ ID NO: 62           moltype =    length =
SEQUENCE: 62
000

SEQ ID NO: 63           moltype =    length =
SEQUENCE: 63
000

SEQ ID NO: 64           moltype =    length =
SEQUENCE: 64
000

SEQ ID NO: 65           moltype =    length =
SEQUENCE: 65
000

SEQ ID NO: 66           moltype =    length =
SEQUENCE: 66
000

SEQ ID NO: 67           moltype = AA  length = 116
FEATURE                 Location/Qualifiers
REGION                  1..116
                        note = STEAP2-5 VH (34C1)
source                  1..116
                        mol_type = protein
                        organism = synthetic construct
SEQUENCE: 67
QVQLVQSGAE VKKPGASVKV SCKASGYTFT SYGISWVRQA PGQGLEWMGW ISGYTGNTNY   60
AQKLQGRVTM TADTSTSTAY MELRSLRSDD TAVYYCARGG SYFDYWGQGT LVTVSS       116

SEQ ID NO: 68           moltype = AA  length = 108
FEATURE                 Location/Qualifiers
REGION                  1..108
                        note = STEAP2-5 VL
source                  1..108
                        mol_type = protein
                        organism = synthetic construct
SEQUENCE: 68
DIQMTQSPST LSASVGDRVT ITCRASQSIS RWLAWYQQKP GKAPKLLIYK ASSLESGVPS   60
RFSGSGSGTE FTLTISSLQP DDFATYYCQQ FNSFSPITFG QGTRLEIK              108

SEQ ID NO: 69           moltype =    length =
SEQUENCE: 69
000

SEQ ID NO: 70           moltype =    length =
SEQUENCE: 70
000

SEQ ID NO: 71           moltype =    length =
SEQUENCE: 71
000

SEQ ID NO: 72           moltype =    length =
SEQUENCE: 72
000

SEQ ID NO: 73           moltype =    length =
SEQUENCE: 73
000

SEQ ID NO: 74           moltype =    length =
SEQUENCE: 74
000

SEQ ID NO: 75           moltype =    length =
SEQUENCE: 75
000

SEQ ID NO: 76           moltype =    length =
SEQUENCE: 76
000

SEQ ID NO: 77           moltype = AA  length = 117
FEATURE                 Location/Qualifiers
REGION                  1..117
                        note = STEAP2-6 VH (6E10)
source                  1..117
```

```
                              mol_type = protein
                              organism = synthetic construct
SEQUENCE: 77
QVQLQQPGAE LVKPGASVKL SCKASGYTFT SYWMEWVKQR PGQGLEWIGM IHPNSGITNY    60
NERFKNKATL TVDKSSSTAY MQLSSLTSED SAVYYCARDH YYILAYWGQG TLVTVSA       117

SEQ ID NO: 78        moltype = AA  length = 112
FEATURE              Location/Qualifiers
REGION               1..112
                     note = STEAP2-6 VL
source               1..112
                     mol_type = protein
                     organism = synthetic construct
SEQUENCE: 78
DVLMTQTPLS LPVSLGDQAS ISCRSSQSVV HSNGNTYLEW YLQKPGQSPK LLIYKVSNRF    60
SGVPDRFSGS GSGTDFTLKI SRVEAEDLGV YYCFQGSHVP YTFGGGTKLE IK           112

SEQ ID NO: 79        moltype =    length =
SEQUENCE: 79
000

SEQ ID NO: 80        moltype =    length =
SEQUENCE: 80
000

SEQ ID NO: 81        moltype =    length =
SEQUENCE: 81
000

SEQ ID NO: 82        moltype =    length =
SEQUENCE: 82
000

SEQ ID NO: 83        moltype =    length =
SEQUENCE: 83
000

SEQ ID NO: 84        moltype =    length =
SEQUENCE: 84
000

SEQ ID NO: 85        moltype =    length =
SEQUENCE: 85
000

SEQ ID NO: 86        moltype =    length =
SEQUENCE: 86
000

SEQ ID NO: 87        moltype = AA  length = 120
FEATURE              Location/Qualifiers
REGION               1..120
                     note = STEAP2-7 VH (22F3)
source               1..120
                     mol_type = protein
                     organism = synthetic construct
SEQUENCE: 87
QVQLQQPGAD LVKPGASVKM SCKASGHTFT NYWVTWVKQR PGQGLEWIGN FYPGSGIIKY    60
NENFRSKATL TVDISSSTAY MQLSSLTSED SAVYYCARSK LGDSFYFDYW GQGTTLTVSS   120

SEQ ID NO: 88        moltype = AA  length = 112
FEATURE              Location/Qualifiers
REGION               1..112
                     note = STEAP2-7 VL
source               1..112
                     mol_type = protein
                     organism = synthetic construct
SEQUENCE: 88
DVVMTQTPLS LPVSLGNQAS ISCRSSQSLV HSNGNTYLHW YLQKPGQSPK LLIYKVSNRF    60
SGVPDRFSGS GSGTDFTLKI SRVEAEDLGV YFCSQSTHVP LTFGAGTKLE IK           112

SEQ ID NO: 89        moltype =    length =
SEQUENCE: 89
000

SEQ ID NO: 90        moltype =    length =
SEQUENCE: 90
000
```

-continued

```
SEQ ID NO: 91          moltype = AA   length = 11
FEATURE                Location/Qualifiers
REGION                 1..11
                       note = STEAP2-840A3GL- LO14)VL CDR1
source                 1..11
                       mol_type = protein
                       organism = synthetic construct
SEQUENCE: 91
RASQSVASNL A                                                    11

SEQ ID NO: 92          moltype = AA   length = 7
FEATURE                Location/Qualifiers
REGION                 1..7
                       note = STEAP2-8 VL CDR2
source                 1..7
                       mol_type = protein
                       organism = synthetic construct
SEQUENCE: 92
GASTRAT                                                         7

SEQ ID NO: 93          moltype = AA   length = 9
FEATURE                Location/Qualifiers
REGION                 1..9
                       note = STEAP2-8 VL CDR3
source                 1..9
                       mol_type = protein
                       organism = synthetic construct
SEQUENCE: 93
QQYNNWPFT                                                       9

SEQ ID NO: 94          moltype = AA   length = 7
FEATURE                Location/Qualifiers
REGION                 1..7
                       note = STEAP2-8 VH CDR1
source                 1..7
                       mol_type = protein
                       organism = synthetic construct
SEQUENCE: 94
RNSAVWN                                                         7

SEQ ID NO: 95          moltype = AA   length = 18
FEATURE                Location/Qualifiers
REGION                 1..18
                       note = STEAP2-8 VH CDR2
source                 1..18
                       mol_type = protein
                       organism = synthetic construct
SEQUENCE: 95
RTYYRSKWYN DYAPSVKS                                             18

SEQ ID NO: 96          moltype = AA   length = 13
FEATURE                Location/Qualifiers
REGION                 1..13
                       note = STEAP2-8 VH CDR3
source                 1..13
                       mol_type = protein
                       organism = synthetic construct
SEQUENCE: 96
GLRQNQFYYY MDV                                                  13

SEQ ID NO: 97          moltype = AA   length = 125
FEATURE                Location/Qualifiers
REGION                 1..125
                       note = STEAP2-8 VH
source                 1..125
                       mol_type = protein
                       organism = synthetic construct
SEQUENCE: 97
QVQLQQSGPG LVKPSQTLSL TCAISGDSVS RNSAVWNWIR QSPSRGLEWL GRTYYRSKWY 60
NDYAPSVKSR ITINPDTSKN QFSLQLNSVT PEDTAVYYCA RGLRQNQFYY YMDVWGKGTT 120
VTVSS                                                          125

SEQ ID NO: 98          moltype = AA   length = 107
FEATURE                Location/Qualifiers
REGION                 1..107
                       note = STEAP2-8 VL
source                 1..107
                       mol_type = protein
                       organism = synthetic construct
```

```
SEQUENCE: 98
EIVMTQSPAT LSVSPGERAT LSCRASQSVA SNLAWYQQKP GQAPRLLIYG ASTRATGIPA    60
RFSGSGSGTE FTLTISSLQS EDFAVYYCQQ YNNWPFTFGP GTKVDIK                 107

SEQ ID NO: 99          moltype = AA  length = 252
FEATURE                Location/Qualifiers
REGION                 1..252
                       note = STEAP2-8 scFv
source                 1..252
                       mol_type = protein
                       organism = synthetic construct
SEQUENCE: 99
EIVMTQSPAT LSVSPGERAT LSCRASQSVA SNLAWYQQKP GQAPRLLIYG ASTRATGIPA    60
RFSGSGSGTE FTLTISSLQS EDFAVYYCQQ YNNWPFTFGP GTKVDIKGGG GSGGGGSGGG   120
GSGGGGSQVQ LQQSGPGLVK PSQTLSLTCA ISGDSVSRNS AVWNWIRQSP SRGLEWLGRT   180
YYRSKWYNDY APSVKSRITI NPDTSKNQFS LQLNSVTPED TAVYYCARGL RQNQFYYYMD   240
VWGKGTTVTV SS                                                       252

SEQ ID NO: 100         moltype =   length =
SEQUENCE: 100
000

SEQ ID NO: 101         moltype = DNA  length = 756
FEATURE                Location/Qualifiers
misc_feature           1..756
                       note = STEAP2 scFv nucleic acid sequence
source                 1..756
                       mol_type = other DNA
                       organism = synthetic construct
SEQUENCE: 101
gagattgtga tgacccagag ccctgcaact ctgagcgtgt cacccggaga aagggccact    60
ctgtcgtgtc gagcatcgca gtccgtgaac tccaatctcg cctggtacca gcagaagcct   120
gggcaggccc cgaggctgct catctacggt gcctccacga gagccacggg aattccagcg   180
cgctttagcg gatccggctc gggaaccgag ttcaccctta ccatctcatc gctgcaatcc   240
gaagatttcg ccgtgtatta ctgtcaacag tacaacaact ggccgttcac ctttggcccg   300
ggaactaagg tcgacatcaa gggcggcggg ggctctgggg gtggcggaag cggcggcggc   360
ggatccggtg gcggcggaag ccaagtgcag ctgcagcagt ccggaccggg actcgtgaag   420
ccgtcccaga ctctgtccct gacttgcgcg atttccggcg attccgtgtc cgcaactcc    480
gctgtgtgga actggatccg gcagtcgcct cgagagcag tggagtggct gggacggacc   540
tactaccgct caaaatggta taacgactat gctgtgtccg tcaagagccg catcaccatt   600
aaccccgata cctccaagaa ccagttcagt ctgcaagtca cagcgtgac tcctgaggac   660
accgccgtgt actactgcgc ccggggtctg ctgcaaaaca acttctacta ctacatggac   720
gtctggggaa agggaactac tgtgaccgtg tcctcc                            756

SEQ ID NO: 102         moltype = DNA  length = 1410
FEATURE                Location/Qualifiers
misc_feature           1..1410
                       note = STEAP2 BZ CAR nucleic acid sequence
source                 1..1410
                       mol_type = other DNA
                       organism = synthetic construct
SEQUENCE: 102
atgctgctcc ttgtcacatc actgctgctc tgcgaactgc cccaccctgc attcctcctg    60
atccccgaga ttgtgatgac ccagagccct gcaactctga gcgtgtcacc cggagaaagg   120
gccactctgt cgtgtcgagc atcgcagtcc gtgaactcca atctcgcctg gtaccagcag   180
aagcctgggc aggccccgag gctgctcatc tacggtgcct ccacgagagc cacgggaatt   240
ccagcgcgct ttagcggatc cggctcggga accgagttca cccttaccat ctcatcgctg   300
caatccgaag atttcgccgt gtattactgt caacagtaca caactggcc gttcaccttt   360
ggcccgggaa ctaaggtcga catcaagggc ggcggggc ctggggggtgg cggaagcggc   420
ggcggcggat ccggtggcgg cggaagccaa gtgcagctgc agcagtcccg gaccgggact   480
gtgaagccgt cccagactct gtccctgact tgcgcgattt ccggcgattc cgtgtccgc   540
aactccgctg tgtggaactg gatccggcag tcgccttcga ggagctgga gtggctggga   600
cggacctact accgctcaaa atggtataac gactatgctg tgtccgtcaa gagccgcatc   660
accattaacc ccgataccct caagaaccag ttcagtctgc aagtcaacag cgtgactcct   720
gaggacaccg ccgtgtacta ctgcgcccgg ggtctgctgc aaaacaactt ctactactac   780
atggacgtct ggggaaaggg aactactgtg accgtgtcct ccggctccga tcaaaatac   840
ggtccgccat gcccaccgtg cccccttctg gtgctcgtgg tcgtcggagg ggttctggcc   900
tgctactccc tgctggtcac cgtggcgttt atcatcttct gggtgaagcg gggaaggaag   960
aagctactgt acatttttca gcagcctttc atgcggcctg tgcagaccac ccaggaagag  1020
gacggctgtt cctgccggtt ccccgaggaa gaggaagggg gttgcgagct gcgcgtgaag  1080
ttcagcagga gcgctgatgc cccagcgtac aacaggggc aaaaccagtt gtacaacgaa  1140
ctgaaccttg tcggcgcga agagtacgac gtgcttgaca gcgccgcgg cagagatccc  1200
gagatgggtg gaaagccgcg gcggaagaat ccgcaggaag ggctctacaa cgagctccag  1260
aaggacaaga tggccgaagc ctacagcgaa atcgggatga ggggcgaaag acgccgggga  1320
aaaggacacg acggactgta tcagggggttg tcgaccgcga ccaaggacac ctacgacgcc  1380
ctgcatatgc aagccttgcc gccgagatga                                  1410

SEQ ID NO: 103         moltype = DNA  length = 762
FEATURE                Location/Qualifiers
```

-continued

```
misc_feature      1..762
                  note = STEAP2-2 scFv nucleic acid sequence
source            1..762
                  mol_type = other DNA
                  organism = synthetic construct
SEQUENCE: 103
gatgttttga tgacccaaac tcctctctcc ctgcctgtca gtcttggaga tcaagcctcc   60
atctcttgca gatctagtca gagtgttgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc acatgttccg  300
tacacgttcg gaggggggac caagctggaa ataaaaggag gcggaggatc tggtggtggt  360
ggatctggcg gcggaggaag tggtggcgga ggctctgagg tgcagctggt ggagtctggg  420
ggagacttag tgaagcctgg agggtccctg aaactctcct gtgccgcctc tggattctct  480
ttctcctctt atggcatgtc ttgggttcgc cagactccag acaagaggct ggaatgggtc  540
gcaaccatta gtagtggtgg tagttacacc ttctatcccg acattatgaa ggggcgattc  600
accatctcca gagacaatgc catgaacacc ctgtacctgc aaatgagcag tctgaagtct  660
gaggactcag ccatgtatta ctgtgcaaga cgggggctacg gtactatcta cacgtttcc   720
tttgactcct ggggccaagg caccactctc acagtctcca gc                     762

SEQ ID NO: 104       moltype = DNA   length = 582
FEATURE              Location/Qualifiers
misc_feature         1..582
                     note = Dominant-negative TGF-? receptor type 2 nucleic acid
                     sequence
source               1..582
                     mol_type = other DNA
                     organism = synthetic construct
SEQUENCE: 104
atgggacgcg ggctgcttcg aggactctgg ccacttcata tcgtgttgtg gactcgcatc   60
gcttcaacca ttccgccgca cgtgcagaag tccgtgaaca atgacatgat cgtgaccgac  120
aacaacggtg cagtgaagtt cccacagctg tgcaagttct gcgatgtcag attcagcact  180
tgcgacaacc agaagtcctg catgtcaaac tgctccatca cctccatctg cgagaagcct  240
caagaggtct gcgtggccgt gtggcggaag aacgacgaga acatcaccct ggaaaccgtg  300
tgccacgatc cgaagctgcc ttatcacgac ttcattctgg aagatgccgc ctcgcccaag  360
tgtatcatga agaaaaagaa aaagcccgga gaaacgttct tcatgtgctc gtgtagctcc  420
gacgagtgca cgacaacat tatctttagc gaagagtaca acacttccaa ccctgacctc  480
ctgctcgtga ttttttcaagt caccggcatt tccctgctgc cccgctggg cgtggcgatc   540
tcggtgatca ttatcttcta ctgttaccgg gtcaataggc ag                     582

SEQ ID NO: 105       moltype = AA   length = 194
FEATURE              Location/Qualifiers
REGION               1..194
                     note = Dominant-negative TGF-B receptor type 2 amino acid
                     sequence
source               1..194
                     mol_type = protein
                     organism = synthetic construct
SEQUENCE: 105
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQ                                                    194

SEQ ID NO: 106       moltype = AA   length = 684
FEATURE              Location/Qualifiers
REGION               1..684
                     note = STEAP2 BZ CAR-T2A-Dominant-negative TGF-B receptor
                     type 2aminoacid sequence
source               1..684
                     mol_type = protein
                     organism = synthetic construct
SEQUENCE: 106
MLLLVTSLLL CELPHPAFLL IPEIVMTQSP ATLSVSPGER ATLSCRASQS VNSNLAWYQQ   60
KPGQAPRLLI YGASTRATGI PARFSGSGSG TEFTLTISSL QSEDFAVYYC QQYNNWPFTF  120
GPGTKVDIKG GGGSGGGGSG GGGSGGGGSQ VQLQQSGPGL VKPSQTLSLT CAISGDSVSR  180
NSAVWNWIRQ SPSRGLEWLG RTYYRSKWYN DYAVSVKSRI TINPDTSKNQ FSLQVNSVTP  240
EDTAVYYCAR GLLQNNFYYY MDVWGKGTTV TVSSGSESKY GPPCPPCPFW VLVVVGGVLA  300
CYSLLVTVAF IIFWVKRGRK KLLYIFKQPF MRPVQTTQEE DGCSCRFPEE EEGGCELRVK  360
FSRSADAPAY QQGQNQLYNE LNLGRREEYD VLDKRRGRDP EMGGKPRRKN PQEGLYNELQ  420
KDKMAEAYSE IGMKGERRRG KGHDGLYQGL STATKDTYDA LHMQALPPRG SGEGRGSLLT  480
CGDVEENPGP MGRGLLRGLW PLHIVLWTRI ASTIPPHVQK SVNNDMIVTD NNGAVKFPQL  540
CKFCDVRFST CDNQKSCMSN CSITSICEKP QEVCVAVWRK NDENITLETV CHDPKLPYHD  600
FILEDAASPK CIMKEKKKPG ETFFMCSCSS DECNDNIIFS EEYNTSNPDL LLVIFQVTGI  660
SLLPPLGVAI SVIIIFYCYR VNRQ                                         684

SEQ ID NO: 107       moltype = DNA   length = 2052
FEATURE              Location/Qualifiers
misc_feature         1..2052
```

-continued

```
                        note = STEAP2 BZ CAR-T2A-Dominant-negative TGF-B receptor
                        type 2nucleic acid sequence
source                  1..2052
                        mol_type = other DNA
                        organism = synthetic construct
SEQUENCE: 107
atgctgctcc ttgtcacatc actgctgctc tgcgaactgc cccaccctgc attcctcctg  60
atccccgaga ttgtgatgac ccagagccct gcaactctga gcgtgtcacc cggagaaagg  120
gccactctgt cgtgtcgagc atcgcagtcc gtgaactcca atctcgcctg gtaccagcag  180
aagcctgggc aggccccgag gctgctcatc tacggtgcct ccacgagagc cacgggaatt  240
ccagcgcgct ttagcggatc cggctcggga accgagttca cccttaccat ctcatcgctg  300
caatccgaag atttcgccgt gtattactgt caacagtaca caactggcc gttcaccttt  360
ggcccgggaa ctaaggtcga catcaagggc ggcggggggc ctgggggtgg cggaagcggc  420
ggcggcggat ccggtggcgg cggaagccaa gtgcagctga gcagtccggg acccggactc  480
gtgaagccgt cccagactct gtccctgact tgcgcgattt ccggcgattc cgtgcccgc  540
aactccgctg tgtggaactg gatccggcag tcgccttcga gaggactgga gtggctggga  600
cggacctact accgctcaaa atggtataac gactatgctg tgtccgtcaa gagccgcatc  660
accattaacc ccgataccytc caagaaccag ttcagtctgc aagtcaacag cgtgactcct  720
gaggacaccg ccgtgtacta ctgcgcccgg ggtctgctgc aaaacaactt ctactactac  780
atggacgtct ggggaaaggg aactactgtg accgtgtcct ccggctccga atcaaaatac  840
ggtccgccat gcccaccgtg cccccttctgg gtgctcgtgg tcgtcggagg ggttctggcc  900
tgctactccc tgctggtcac cgtggcgttt atcatcttct ggtgaagcg ggaaaggaag  960
aagctactgt acattttcaa gcagcctttc atgcggcctg tgcagaccac ccaggaagag  1020
gacggctgtt cctgccggtt ccccgaggaa gaggaagggg gttgcgagct gcgcgtgaag  1080
ttcagcagga gcgctgatgc cccagcgtac aacaggggc aaaaccagtt gtacaacgaa  1140
ctgaaccttg gtcggcgcga agagtacgac gtgcttgaac aggccgcgg cagagatccc  1200
gagatgggtg aaagccgcg gcggaagaat ccgcaggaag ggctctacaa cgagctccag  1260
aaggacaaga tggccgaagc ctacagcgaa atcgggatga agggcgaaag acgccgggga  1320
aaaggacacg acggactgta ccaggggttg tcgaccgcga ccaaggacac ctacgacgcc  1380
ctgcatatgc aagccttgcc gccgagagga tccggagagg ggaggggaag cctcctcact  1440
tgcggcgatg tggaggaaaa cccgggtcct atgggacgcg ggctgcttcg aggactctga  1500
ccacttcata tcgtgttgtg gactcgcatc gcttcaacca ttccgccgca cgtgcagaag  1560
tccgtgaaca atgacatgat cgtgaccgac aacaacggtg cagtgaagtt cccacagctg  1620
tgcaagttct gcgatgtcag attcagcact tgcgacaacc agaagtcctg catgtcaaac  1680
tgctccatca cctccatctg cgagaagcct caagaggtct gcgtggccgt gtggcggaag  1740
aacgacgaga acatcaccct ggaaaccgtg tgccacgatc cgaagctgcc ttatcacgac  1800
ttcattctgg aagatgccgc ctcgcccaag tgtatcatga agaaaagaa aaagcccgga  1860
gaaacgttct tcatgtgctc gtgtagctcc gacgagtgca acgacaacat tatctttagc  1920
gaagagtaca acacttccaa ccctgacctc ctgctcgtga ttttcaagt caccggcatt  1980
tccctgctgc ccccgctggg cgtggcgatc tcggtgatca ttatcttcta ctgttaccgg  2040
gtcaataggc ag                                                        2052

SEQ ID NO: 108         moltype = AA  length = 471
FEATURE                Location/Qualifiers
REGION                 1..471
                       note = STEAP2-2 BZ CAR amino acid sequence
source                 1..471
                       mol_type = protein
                       organism = synthetic construct
SEQUENCE: 108
MLLLVTSLLL CELPHPAFLL IPDVLMTQTP LSLPVSLGDQ ASISCRSSQS VVHSNGNTYL  60
EWYLQKPGQS PKLLIYKVSN RFSGVPDRFS GSGSGTDFTL KISRVEAEDL GVYYCFQGSH  120
VPYTFGGGTK LEIKGGGGSG GGGSGGGGSG GGGSEVQLVE SGGDLVKPGG SLKLSCAASG  180
FSFSSYGMSW VRQTPDKRLE WVATISSGGS YTFYPDIMKG RFTISRDNAM NTLYLQMSSL  240
KSEDSAMYYC ARRGYGTIYT FSFDSWGQGT TLTVSSGGSS KYGPPCPPCP FWVLVVVGGV  300
LACYSLLVTV AFIIFWVKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R             471

SEQ ID NO: 109         moltype = AA  length = 471
FEATURE                Location/Qualifiers
REGION                 1..471
                       note = STEAP2-2Humanized1 BZ CAR amino acid sequence
source                 1..471
                       mol_type = protein
                       organism = synthetic construct
SEQUENCE: 109
MLLLVTSLLL CELPHPAFLL IPDVVMTQSP LSLPVTLGQP ASISCRSSQS VVHSNANTYL  60
EWYLQKPGQS PQLLIYKVSN RFSGVPDRFS GSGSGTDFTL KISRVEAEDV GVYYCFQGSH  120
VPYTFGQGTK LEIKGGGGSG GGGSGGGGSG GGGSEVQLVE SGGGLVKPGG SLRLSCAASG  180
FTFSSYGMSW VRQAPGKRLE WVATISSGGS YTFYPDIMKG RFTISRDNSK NTLYLQMNSL  240
RAEDTAVYYC ARRGYGTIYT FSFDAWGQGT TLTVSSGSES KYGPPCPPCP FWVLVVVGGV  300
LACYSLLVTV AFIIFWVKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R             471

SEQ ID NO: 110         moltype = AA  length = 471
FEATURE                Location/Qualifiers
REGION                 1..471
```

-continued

```
                         note = STEAP2-2 Humanized2 BZ CAR amino acid sequence
source                   1..471
                         mol_type = protein
                         organism = synthetic construct
SEQUENCE: 110
MLLLVTSLLL CELPHPAFLL IPDVVMTQSP LSLPVTLGQP ASISCRSSQS VVHSNANTYL  60
EWYLQKPGQS PQLLIYKVSN RFSGVPDRFS GSGSGTDFTL KISRVEAEDV GVYYCFQGSH  120
VPYTFGQGTK LEIKGGGGSG GGGSGGGGSG GGGSEVQLLE SGGGLVQPGG SLRLSCAASG  180
FTFSSYGMSW VRQAPGKRLE WVSTISSGGS YTFYPDIMKG RFTISRDNSK NTLYLQMNSL  240
RAEDTAVYYC ARRGYGTIYT FSFDAWGQGT TLTVSSGSES KYGPPCPPCP FWVLVVVGGV  300
LACYSLLVTV AFIIFWVKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R           471

SEQ ID NO: 111          moltype = AA   length = 469
FEATURE                 Location/Qualifiers
REGION                  1..469
                        note = STEAP2-3 BZ CAR amino acid sequence
source                  1..469
                        mol_type = protein
                        organism = synthetic construct
SEQUENCE: 111
MLLLVTSLLL CELPHPAFLL IPEIVMTQSP ATLSVSPGER ATLSCRASQS VSSNLAWYQQ  60
KPGQAPRLLI YGASTRATGI PARFSGSGSG TEFTLTISSL QSEDFAVYYC QQYNNWPFTF  120
GPGTKVDIKG GGGSGGGGSG GGGSGGGGSQ VQLQQSGPGL VKPSQTLSLT CAISGDSVSR  180
NSAVWNWIRQ SPSRGLEWLG RTYYRSKWYN DYAVSVKSRI TINPDTSKNQ FSLQLNSVTP  240
EDTAVYYCAR GLLQNQFYYY MDVWGKGTTV TVSSGSESKY GPPCPPCPPFW VLVVVGGVLA  300
CYSLLVTVAF IIFWVKRGRK KLLYIFKQPF MRPVQTTQEE DGCSCRFPEE EEGGCELRVK  360
FSRSADAPAY QQGQNQLYNE LNLGRREEYD VLDKRRGRDP EMGGKPRRKN PQEGLYNELQ  420
KDKMAEAYSE IGMKGERRRG KGHDGLYQGL STATKDTYDA LHMQALPPR              469

SEQ ID NO: 112          moltype = AA   length = 464
FEATURE                 Location/Qualifiers
REGION                  1..464
                        note = STEAP2-4 BZ CAR amino acid sequence
source                  1..464
                        mol_type = protein
                        organism = synthetic construct
SEQUENCE: 112
MLLLVTSLLL CELPHPAFLL IPDIQLTQSP SFLSASVGDR VTITCRASQG ISVYLAWYQQ  60
EPGKAPKLLI YAASTLQSGV PSRFSGSGSG TEFTLTISSL QPEDFATYYC QQLNSYPRTF  120
GQGTKVEIKG GGGSGGGGSG GGGSGGGGSE VQLVESGGGL VQPGGSLRLS CAASGFTFSS  180
FAMTWVRQAP GKGLEWVSVI TYSGGRTYYA DSVKGRFTIS RDNSKNTLYL QMNSLRAEDT  240
AVYFCAKDRI AAVGPPDYWG QGTLVTVSSG SESKYGPPCP PCPFWVLVVV GGVLACYSLL  300
VTVAFIIFWV KRGRKKLLYI FKQPFMRPVQ TTQEEDGCSC RFPEEEEGGC ELRVKFSRSA  360
DAPAYQQGQN QLYNELNLGR REEYDVLDKR RGRDPEMGGK PRRKNPQEGL YNELQKDKMA  420
EAYSEIGMKG ERRRGKGHDG LYQGLSTATK DTYDALHMQA LPPR                   464

SEQ ID NO: 113          moltype = AA   length = 461
FEATURE                 Location/Qualifiers
REGION                  1..461
                        note = STEAP2-5 BZ CAR amino acid sequence
source                  1..461
                        mol_type = protein
                        organism = synthetic construct
SEQUENCE: 113
MLLLVTSLLL CELPHPAFLL IPDIQMTQSP STLSASVGDR VTITCRASQS ISRWLAWYQQ  60
KPGKAPKLLI YKASSLESGV PSRFSGSGSG TEFTLTISSL QPDDFATYYC QQFNSFSPIT  120
FGQGTRLEIK GGGGSGGGGS GGGGSGGGGS QVQLVQSGAE VKKPGASVKV SCKASGYTFT  180
SYGISWVRQA PGQGLEWMGW ISGYTGNTNY AQKLQGRVTM TADTSTSTAY MELRSLRSDD  240
TAVYYCARGG SYFDYWGQGT LVTVSSGSES KYGPPCPPCP FWVLVVVGGV LACYSLLVTV  300
AFIIFWVKRG RKKLLYIFKQ PFMRPVQTTQ EEDGCSCRFP EEEEGGCELR VKFSRSADAP  360
AYQQGQNQLY NELNLGRREE YDVLDKRRGR DPEMGGKPRR KNPQEGLYNE LQKDKMAEAY  420
SEIGMKGERR RGKGHDGLYQ GLSTATKDTY DALHMQALPP R                      461

SEQ ID NO: 114          moltype = AA   length = 466
FEATURE                 Location/Qualifiers
REGION                  1..466
                        note = STEAP2-6 BZ CAR amino acid sequence
source                  1..466
                        mol_type = protein
                        organism = synthetic construct
SEQUENCE: 114
MLLLVTSLLL CELPHPAFLL IPDVLMTQTP LSLPVSLGDQ ASISCRSSQS VVHSNGNTYL  60
EWYLQKPGQS PKLLIYKVSN RFSGVPDRFS GSGSGTDFTL KISRVEAEDL GVYYCFQGSH  120
VPYTFGGGTK LEIKGGGGSG GGGSGGGGSG GGGSQVQLQQ PGAELVKPGA SVKLSCKASG  180
YTFTSYWMEW VKQRPGQGLE WIGMIHPNSG ITNYNERFKN KATLTVDKSS STAYMQLSSL  240
TSEDSAVYYC ARDHYYILAY WGQGTLVTVS AGSESKYGPP CPPCPFWVLV VVGGVLACYS  300
LLVTVAFIIF WVKRGRKKLL YIFKQPFMRP VQTTQEEDGC SCRFPEEEEG GCELRVKFSR  360
```

-continued

```
SADAPAYQQG QNQLYNELNL GRREEYDVLD KRRGRDPEMG GKPRRKNPQE GLYNELQKDK   420
MAEAYSEIGM KGERRRGKGH DGLYQGLSTA TKDTYDALHM QALPPR                    466

SEQ ID NO: 115          moltype = AA  length = 469
FEATURE                 Location/Qualifiers
REGION                  1..469
                        note = STEAP2-7 BZ CAR amino acid sequence
source                  1..469
                        mol_type = protein
                        organism = synthetic construct
SEQUENCE: 115
MLLLVTSLLL CELPHPAFLL IPDVVMTQTP LSLPVSLGNQ ASISCRSSQS LVHSNGNTYL   60
HWYLQKPGQS PKLLIYKVSN RFSGVPDRFS GSGSGTDFTL KISRVEAEDL GVYFCSQSTH   120
VPLTFGAGTK LEIKGGGGSG GGGSGGGGSG GGGSQVQLQQ PGADLVKPGA SVKMSCKASG   180
HTFTNYWVTW VKQRPGQGLE WIGNFYPGSG IIKYNENFRS KATLTVDISS STAYMQLSSL   240
TSEDSAVYYC ARSKLGDSFY FDYWGQGTTL TVSSGSESKY GPPCPPCPFW VLVVVGGVLA   300
CYSLLVTVAF IIFWVKRGRK KLLYIFKQPF MRPVQTTQEE DGCSCRFPEE EEGGCELRVK   360
FSRSADAPAY QQGQNQLYNE LNLGRREEYD VLDKRRGRDP EMGGKPRRKN PQEGLYNELQ   420
KDKMAEAYSE IGMKGERRRG KGHDGLYQGL STATKDTYDA LHMQALPPR               469

SEQ ID NO: 116          moltype = AA  length = 469
FEATURE                 Location/Qualifiers
REGION                  1..469
                        note = STEAP2-8 BZ CAR amino acid sequence
source                  1..469
                        mol_type = protein
                        organism = synthetic construct
SEQUENCE: 116
MLLLVTSLLL CELPHPAFLL IPEIVMTQSP ATLSVSPGER ATLSCRASQS VASNLAWYQQ   60
KPGQAPRLLI YGASTRATGI PARFSGSGSG TEFTLTISSL QSEDFAVYYC QQYNNWPFTF   120
GPGTKVDIKG GGGSGGGGSG GGGSGGGGSQ VQLQQSGPGL VKPSQTLSLT CAISGDSVSR   180
NSAVWNWIRQ SPSRGLEWLG RTYYRSKWYN DYAPSVKSRI TINPDTSKNQ FSLQLNSVTP   240
EDTAVYYCAR GLRQNQFYYY MDVWGKGTTV TVSSGSESKY GPPCPPCPFW VLVVVGGVLA   300
CYSLLVTVAF IIFWVKRGRK KLLYIFKQPF MRPVQTTQEE DGCSCRFPEE EEGGCELRVK   360
FSRSADAPAY QQGQNQLYNE LNLGRREEYD VLDKRRGRDP EMGGKPRRKN PQEGLYNELQ   420
KDKMAEAYSE IGMKGERRRG KGHDGLYQGL STATKDTYDA LHMQALPPR               469

SEQ ID NO: 117          moltype = AA  length = 686
FEATURE                 Location/Qualifiers
REGION                  1..686
                        note = STEAP2-2 BZ CAR-T2A-Dominant-negative TGF-? receptor
                         type 2amino acid sequence
source                  1..686
                        mol_type = protein
                        organism = synthetic construct
SEQUENCE: 117
MLLLVTSLLL CELPHPAFLL IPDVLMTQTP LSLPVSLGDQ ASISCRSSQS VVHSNGNTYL   60
EWYLQKPGQS PKLLIYKVSN RFSGVPDRFS GSGSGTDFTL KISRVEAEDL GVYYCFQGSH   120
VPYTFGGGTK LEIKGGGGSG GGGSGGGGSG GGGSEVQLVE SGGDLVKPGG SLKLSCAASG   180
FSFSSYGMSW VRQTPDKRLE WVATISSGGS YTFYPDIMKG RFTISRDNAM NTLYLQMSSL   240
KSEDSAMYYC ARRGYGTIYT FSFDSWGQGT TLTVSSGSES KYGPPCPPCP FWVLVVVGGV   300
LACYSLLVTV AFIIFWVKRG RKKLLYIFKQ PFMRPVQTTQ EEDGCSCRFP EEEEGGCELR   360
VKFSRSADAP AYQQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP RGSGEGRGSL   480
LTCGDVEENP GPMGRGLLRG LWPLHIVLWT RIASTIPPHV QKSVNNDMIV TDNNGAVKFP   540
QLCKFCDVRF STCDNQKSCM SNCSITSICE KPQEVCVAVW RKNDENITLE TVCHDPKLPY   600
HDFILEDAAS PKCIMKEKKK PGETFFMCSC SSDECNDNII FSEEYNTSNP DLLLVIFQVT   660
GISLLPPLGV AISVIIIFYC YRVNRQ                                        686

SEQ ID NO: 118          moltype = AA  length = 686
FEATURE                 Location/Qualifiers
REGION                  1..686
                        note = STEAP2-2Humanized1 BZ CAR amino acid sequence
source                  1..686
                        mol_type = protein
                        organism = synthetic construct
SEQUENCE: 118
MLLLVTSLLL CELPHPAFLL IPDVVMTQSP LSLPVTLGQP ASISCRSSQS VVHSNANTYL   60
EWYLQKPGQS PQLLIYKVSN RFSGVPDRFS GSGSGTDFTL KISRVEAEDV GVYYCFQGSH   120
VPYTFGQGTK LEIKGGGGSG GGGSGGGGSG GGGSEVQLVE SGGGLVKPGG SLRLSCAASG   180
FTFSSYGMSW VRQAPGKRLE WVATISSGGS YTFYPDIMKG RFTISRDNSK NTLYLQMNSL   240
RAEDTAVYYC ARRGYGTIYT FSFDAWGQGT TLTVSSGSES KYGPPCPPCP FWVLVVVGGV   300
LACYSLLVTV AFIIFWVKRG RKKLLYIFKQ PFMRPVQTTQ EEDGCSCRFP EEEEGGCELR   360
VKFSRSADAP AYQQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP RGSGEGRGSL   480
LTCGDVEENP GPMGRGLLRG LWPLHIVLWT RIASTIPPHV QKSVNNDMIV TDNNGAVKFP   540
QLCKFCDVRF STCDNQKSCM SNCSITSICE KPQEVCVAVW RKNDENITLE TVCHDPKLPY   600
HDFILEDAAS PKCIMKEKKK PGETFFMCSC SSDECNDNII FSEEYNTSNP DLLLVIFQVT   660
GISLLPPLGV AISVIIIFYC YRVNRQ                                        686
```

```
SEQ ID NO: 119          moltype = AA  length = 686
FEATURE                 Location/Qualifiers
REGION                  1..686
                        note = STEAP2-2 Humanized2 BZ CAR amino acid sequence
source                  1..686
                        mol_type = protein
                        organism = synthetic construct
SEQUENCE: 119
MLLLVTSLLL CELPHPAFLL IPDVVMTQSP LSLPVTLGQP ASISCRSSQS VVHSNANTYL  60
EWYLQKPGQS PQLLIYKVSN RFSGVPDRFS GSGSGTDFTL KISRVEAEDV GVYYCFQGSH  120
VPYTFGQGTK LEIKGGGGSG GGGSGGGGSG GGGSEVQLLE SGGGLVQPGG SLRLSCAASG  180
FTFSSYGMSW VRQAPGKRLE WVSTISSGGS YTFYPDIMKG RFTISRDNSK NTLYLQMNSL  240
RAEDTAVYYC ARRGYGTIYT FSFDAWGQGT TLTVSSGSES KYGPPCPPCP FWVLVVVGGV  300
LACYSLLVTV AFIIFWVKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP RGSGEGRGSL  480
LTCGDVEENP GPMGRGLLRG LWPLHIVLWT RIASTIPPHV QKSVNNDMIV TDNNGAVKFP  540
QLCKFCDVRF STCDNQKSCM SNCSITSICE KPQEVCVAVW RKNDENITLE TVCHDPKLPY  600
HDFILEDAAS PKCIMKEKKK PGETFFMCSC SSDECNDNII FSEEYNTSNP DLLLVIFQVT  660
GISLLPPLGV AISVIIIFYC YRVNRQ                                        686

SEQ ID NO: 120          moltype = AA  length = 684
FEATURE                 Location/Qualifiers
REGION                  1..684
                        note = STEAP2-3 BZ CAR-T2A-Dominant-negative TGF-B receptor
                         type 2amino acid sequence
source                  1..684
                        mol_type = protein
                        organism = synthetic construct
SEQUENCE: 120
MLLLVTSLLL CELPHPAFLL IPEIVMTQSP ATLSVSPGER ATLSCRASQS VSSNLAWYQQ  60
KPGQAPRLLI YGASTRATGI PARFSGSGSG TEFTLTISSL QSEDFAVYYC QQYNNWPFTF  120
GPGTKVDIKG GGGSGGGGSG GGGSGGGGSQ VQLQQSGPGL VKPSQTLSLT CAISGDSVSR  180
NSAVWNWIRQ SPSRGLEWLG RTYYRSKWYN DYAVSVKSRI TINPDTSKNQ FSLQLNSVTP  240
EDTAVYYCAR GLLQNQFYYY MDVWGKGTTV TVSSGSESKY GPPCPPCPFW VLVVVGGVLA  300
CYSLLVTVAF IIFWVKRGRK KLLYIFKQPF MRPVQTTQEE DGCSCRFPEE EEGGCELRVK  360
FSRSADAPAY QQGQNQLYNE LNLGRREEYD VLDKRRGRDP EMGGKPRRKN PQEGLYNELQ  420
KDKMAEAYSE IGMKGERRRG KGHDGLYQGL STATKDTYDA LHMQALPPRG SGEGRGSLLT  480
CGDVEENPGP MGRGLLRGLW PLHIVLWTRI ASTIPPHVQK SVNNDMIVTD NNGAVKFPQL  540
CKFCDVRFST CDNQKSCMSN CSITSICEKP QEVCVAVWRK NDENITLETV CHDPKLPYHD  600
FILEDAASPK CIMKEKKKPG ETFFMCSCSS DECNDNIIFS EEYNTSNPDL LLVIFQVTGI  660
SLLPPLGVAI SVIIIFYCYR VNRQ                                          684

SEQ ID NO: 121          moltype = AA  length = 679
FEATURE                 Location/Qualifiers
REGION                  1..679
                        note = STEAP2-4 BZ CAR-T2A-Dominant-negative TGF-B receptor
                         type 2amino acid sequence
source                  1..679
                        mol_type = protein
                        organism = synthetic construct
SEQUENCE: 121
MLLLVTSLLL CELPHPAFLL IPDIQLTQSP SFLSASVGDR VTITCRASQG ISVYLAWYQQ  60
EPGKAPKLLI YAASTLQSGV PSRFSGSGSG TEFTLTISSL QPEDFATYYC QQLNSYPRTF  120
GQGTKVEIKG GGGSGGGGSG GGGSGGGGSE VQLVESGGGL VQPGGSLRLS CAASGFTFSS  180
FAMTWVRQAP GKGLEWVSVI TYSGGRTYYA DSVKGRFTIS RDNSKNTLYL QMNSLRAEDT  240
AVYFCAKDRI AAVGPFDYWG QGTLVTVSSG SESKYGPPCP PCPFWVLVVV GGVLACYSLL  300
VTVAFIIFWV KRGRKKLLYI FKQPFMRPVQ TTQEEDGCSC RFPEEEEGGC ELRVKFSRSA  360
DAPAYQQGQN QLYNELNLGR REEYDVLDKR RGRDPEMGGK PRRKNPQEGL YNELQKDKMA  420
EAYSEIGMKG ERRRGKGHDG LYQGLSTATK DTYDALHMQA LPPRGSGEGR GSLLTCGDVE  480
ENPGPMGRGL LRGLWPLHIV LWTRIASTIP PHVQKSVNND MIVTDNNGAV KFPQLCKFCD  540
VRFSTCDNQK SCMSNCSITS ICEKPQEVCV AVWRKNDENI TLETVCHDPK LPYHDFILED  600
AASPKCIMKE KKKPGETFFM CSCSSDECND NIIFSEEYNT SNPDLLLVIF QVTGISLLPP  660
LGVAISVIII FYCYRVNRQ                                                679

SEQ ID NO: 122          moltype = AA  length = 676
FEATURE                 Location/Qualifiers
REGION                  1..676
                        note = STEAP2-5 BZ CAR-T2A-Dominant-negative TGF-B receptor
                         type 2amino acid sequence
source                  1..676
                        mol_type = protein
                        organism = synthetic construct
SEQUENCE: 122
MLLLVTSLLL CELPHPAFLL IPDIQMTQSP STLSASVGDR VTITCRASQS ISRWLAWYQQ  60
KPGKAPKLLI YKASSLESGV PSRFSGSGSG TEFTLTISSL QPDDFATYYC QQFNSFSPIT  120
FGQGTRLEIK GGGGSGGGGS GGGGSGGGGS QVQLVQSGAE VKKPGASVKV SCKASGYTFT  180
SYGISWVRQA PGQGLEWMGW ISGYTGNTNY AQKLQGRVTM TADTSTSTAY MELRSLRSDD  240
```

-continued

```
TAVYYCARGG SYFDYWGQGT LVTVSSGSES KYGPPCPPCP FWVLVVVGGV LACYSLLVTV  300
AFIIFWVKRG RKKLLYIFKQ PFMRPVQTTQ EEDGCSCRFP EEEEGGCELR VKFSRSADAP  360
AYQQGQNQLY NELNLGRREE YDVLDKRRGR DPEMGGKPRR KNPQEGLYNE LQKDKMAEAY  420
SEIGMKGERR RGKGHDGLYQ GLSTATKDTY DALHMQALPP RGSGEGRGSL LTCGDVEENP  480
GPMGRGLLRG LWPLHIVLWT RIASTIPPHV QKSVNNDMIV TDNNGAVKFP QLCKFCDVRF  540
STCDNQKSCM SNCSITSICE KPQEVCVAVW RKNDENITLE TVCHDPKLPY HDFILEDAAS  600
PKCIMKEKKK PGETFFMCSC SSDECNDNII FSEEYNTSNP DLLLVIFQVT GISLLPPLGV  660
AISVIIIFYC YRVNRQ                                                  676

SEQ ID NO: 123           moltype = AA  length = 681
FEATURE                  Location/Qualifiers
REGION                   1..681
                         note = STEAP2-6 BZ CAR-T2A-Dominant-negative TGF-B receptor
                          type 2amino acid sequence
source                   1..681
                         mol_type = protein
                         organism = synthetic construct
SEQUENCE: 123
MLLLVTSLLL CELPHPAFLL IPDVLMTQTP LSLPVSLGDQ ASISCRSSQS VVHSNGNTYL  60
EWYLQKPGQS PKLLIYKVSN RFSGVPDRFS GSGSGTDFTL KISRVEAEDL GVYYCFQGSH  120
VPYTFGGGTK LEIKGGGGSG GGGSGGGGGS GGGSQVQLQQ PGAELVKPGA SVKLSCKASG  180
YTFTSYWMEW VKQRPGQGLE WIGMIHPNSG ITNYNERFKN KATLTVDKSS STAYMQLSSL  240
TSEDSAVYYC ARDHYYILAY WGQGTLVTVS AGSESKYGPP CPPCPFWVLV VVGGVLACYS  300
LLVTVAFIIF WVKRGRKKLL YIFKQPFMRP VQTTQEEDGC SCRFPEEEEG GCELRVKFSR  360
SADAPAYQQG QNQLYNELNL GRREEYDVLD KRRGRDPEMG GKPRRKNPQE GLYNELQKDK  420
MAEAYSEIGM KGERRRGKGH DGLYQGLSTA TKDTYDALHM QALPPRGSGE GRGSLLTCGD  480
VEENPGPMGR GLLRGLWPLH IVLWTRIAST IPPHVQKSVN NDMIVTDNNG AVKFPQLCKF  540
CDVRFSTCDN QKSCMSNCSI TSICEKPQEV CVAVWRKNDE NITLETVCHD PKLPYHDFIL  600
EDAASPKCIM KEKKKPGETF FMCSCSSDEC NDNIIFSEEY NTSNPDLLLV IFQVTGISLL  660
PPLGVAISVI IIFYCYRVNR Q                                            681

SEQ ID NO: 124           moltype = AA  length = 684
FEATURE                  Location/Qualifiers
REGION                   1..684
                         note = STEAP2-7 BZ CAR-T2A-Dominant-negative TGF-B receptor
                          type 2amino acid sequence
source                   1..684
                         mol_type = protein
                         organism = synthetic construct
SEQUENCE: 124
MLLLVTSLLL CELPHPAFLL IPDVVMTQTP LSLPVSLGNQ ASISCRSSQS LVHSNGNTYL  60
HWYLQKPGQS PKLLIYKVSN RFSGVPDRFS GSGSGTDFTL KISRVEAEDL GVYFCSQSTH  120
VPLTFGAGTK LEIKGGGGSG GGGSGGGGGS GGGSQVQLQQ PGADLVKPGA SVKMSCKASG  180
HTFTNYWVTW VKQRPGQGLE WIGNFYPGSG IIKYNENFRS KATLTVDISS STAYMQLSSL  240
TSEDSAVYYC ARSKLGDSFY FDYWGQGTTL VSSGSESKY GPPCPPCPFW VLVVVGGVLA  300
CYSLLVTVAF IIFWVKRGRK KLLYIFKQPF MRPVQTTQEE DGCSCRFPEE EEGGCELRVK  360
FSRSADAPAY QQGQNQLYNE LNLGRREEYD VLDKRRGRDP EMGGKPRRKN PQEGLYNELQ  420
KDKMAEAYSE IGMKGERRRG KGHDGLYQGL STATKDTYDA LHMQALPPRG SGEGRGSLLT  480
CGDVEENPGP MGRGLLRGLW PLHIVLWTRI ASTIPPHVQK SVNNDMIVTD NNGAVKFPQL  540
CKFCDVRFST CDNQKSCMSN CSITSICEKP QEVCVAVWRK NDENITLETV CHDPKLPYHD  600
FILEDAASPK CIMKEKKKPG ETFFMCSCSS DECNDNIIFS EEYNTSNPDL LLVIFQVTGI  660
SLLPPLGVAI SVIIIFYCYR VNRQ                                         684

SEQ ID NO: 125           moltype = AA  length = 684
FEATURE                  Location/Qualifiers
REGION                   1..684
                         note = STEAP2-8 BZ CAR-T2A-Dominant-negative TGF-B receptor
                          type 2amino acid sequence
source                   1..684
                         mol_type = protein
                         organism = synthetic construct
SEQUENCE: 125
MLLLVTSLLL CELPHPAFLL IPEIVMTQSP ATLSVSPGER ATLSCRASQS VASNLAWYQQ  60
KPGQAPRLLI YGASTRATGI PARFSGSGSG TEFTLTISSL QSEDFAVYYC QQYNNWPFTF  120
GPGTKVDIKG GGGSGGGGSG GGGSGGGGSQ VQLQQSGPGL VKPSQTLSLT CAISGDSVSR  180
NSAVWNWIRQ SPSRGLEWLG RTYYRSKWYN DYAPSVKSRI TINPDTSKNQ FSLQLNSVTP  240
EDTAVYYCAR GLRQNFYYY MDVWGKGTTV TVSSGSESKY GPPCPPCPFW VLVVVGGVLA  300
CYSLLVTVAF IIFWVKRGRK KLLYIFKQPF MRPVQTTQEE DGCSCRFPEE EEGGCELRVK  360
FSRSADAPAY QQGQNQLYNE LNLGRREEYD VLDKRRGRDP EMGGKPRRKN PQEGLYNELQ  420
KDKMAEAYSE IGMKGERRRG KGHDGLYQGL STATKDTYDA LHMQALPPRG SGEGRGSLLT  480
CGDVEENPGP MGRGLLRGLW PLHIVLWTRI ASTIPPHVQK SVNNDMIVTD NNGAVKFPQL  540
CKFCDVRFST CDNQKSCMSN CSITSICEKP QEVCVAVWRK NDENITLETV CHDPKLPYHD  600
FILEDAASPK CIMKEKKKPG ETFFMCSCSS DECNDNIIFS EEYNTSNPDL LLVIFQVTGI  660
SLLPPLGVAI SVIIIFYCYR VNRQ                                         684

SEQ ID NO: 126           moltype = AA  length = 21
FEATURE                  Location/Qualifiers
REGION                   1..21
                         note = T2A Peptide
```

-continued

```
source                   1..21
                         mol_type = protein
                         organism = synthetic construct
SEQUENCE: 126
GSGEGRGSLL TCGDVEENPG P                                              21

SEQ ID NO: 127           moltype = AA  length = 22
FEATURE                  Location/Qualifiers
REGION                   1..22
                         note = Signal Peptide
source                   1..22
                         mol_type = protein
                         organism = synthetic construct
SEQUENCE: 127
MLLLVTSLLL CELPHPAFLL IP                                             22

SEQ ID NO: 128           moltype = AA  length = 12
FEATURE                  Location/Qualifiers
REGION                   1..12
                         note = IgG4P Hinge
source                   1..12
                         mol_type = protein
                         organism = synthetic construct
SEQUENCE: 128
ESKYGPPCPP CP                                                        12

SEQ ID NO: 129           moltype = AA  length = 27
FEATURE                  Location/Qualifiers
REGION                   1..27
                         note = CD28 Transmembrane Domain
source                   1..27
                         mol_type = protein
                         organism = synthetic construct
SEQUENCE: 129
FWVLVVVGGV LACYSLLVTV AFIIFWV                                        27

SEQ ID NO: 130           moltype = AA  length = 42
FEATURE                  Location/Qualifiers
REGION                   1..42
                         note = 4-1BB Activation Domain (B domain)
source                   1..42
                         mol_type = protein
                         organism = synthetic construct
SEQUENCE: 130
KRGRKKLLYI FKQPFMRPVQ TTQEEDGCSC RFPEEEEGGC EL                       42

SEQ ID NO: 131           moltype = AA  length = 112
FEATURE                  Location/Qualifiers
REGION                   1..112
                         note = CD3zeta Domain (z domain)
source                   1..112
                         mol_type = protein
                         organism = synthetic construct
SEQUENCE: 131
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR            112

SEQ ID NO: 132           moltype = AA  length = 154
FEATURE                  Location/Qualifiers
REGION                   1..154
                         note = Bz Domain
source                   1..154
                         mol_type = protein
                         organism = synthetic construct
SEQUENCE: 132
KRGRKKLLYI FKQPFMRPVQ TTQEEDGCSC RFPEEEEGGC ELRVKFSRSA DAPAYQQGQN    60
QLYNELNLGR REEYDVLDKR RGRDPEMGGK PRRKNPQEGL YNELQKDKMA EAYSEIGMKG    120
ERRRGKGHDG LYQGLSTATK DTYDALHMQA LPPR                                154

SEQ ID NO: 133           moltype = AA  length = 41
FEATURE                  Location/Qualifiers
source                   1..41
                         mol_type = protein
                         organism = synthetic construct
SEQUENCE: 133
RSKRSRLLHS DYMNMTPRRP GPTRKHYQPY APPRDFAAYR S                        41
```